United States Patent
Weiss et al.

(10) Patent No.: US 10,731,153 B2
(45) Date of Patent: Aug. 4, 2020

(54) RECOMBINASES AND TARGET SEQUENCES

(71) Applicants: Massachusetts Institute of Technology, Cambridge, MA (US); INRIA (French Institute for Research in Computer Science and Automation), Paris (FR)

(72) Inventors: Ron Weiss, Newton, MA (US); Xavier Cesar Duportet, Paris (FR); Gregory Batt, Saint Cyr l'ecole (FR); Yinqing Li, Cambridge, MA (US)

(73) Assignees: Massachusetts Institute of Technology, Cambridge, MA (US); INRIA (French Institute for Research in Computer Science and Automation), Paris (FR)

( * ) Notice: Subject to any disclaimer, the term of this patent is extended or adjusted under 35 U.S.C. 154(b) by 0 days.

(21) Appl. No.: 15/410,875

(22) Filed: Jan. 20, 2017

(65) Prior Publication Data

US 2017/0211061 A1    Jul. 27, 2017

Related U.S. Application Data

(60) Provisional application No. 62/281,435, filed on Jan. 21, 2016.

(51) Int. Cl.
| | |
|---|---|
| *C12N 15/00* | (2006.01) |
| *C12N 15/10* | (2006.01) |
| *C12N 15/85* | (2006.01) |
| *C12N 9/22* | (2006.01) |
| *C12N 15/52* | (2006.01) |
| *C12Q 1/02* | (2006.01) |
| *C12Q 1/6897* | (2018.01) |

(52) U.S. Cl.
CPC .......... *C12N 15/1086* (2013.01); *C12N 9/22* (2013.01); *C12N 15/10* (2013.01); *C12N 15/1034* (2013.01); *C12N 15/1093* (2013.01); *C12N 15/52* (2013.01); *C12N 15/85* (2013.01); *C12Q 1/025* (2013.01); *C12Q 1/6897* (2013.01); *C12N 2800/30* (2013.01)

(58) Field of Classification Search
None
See application file for complete search history.

(56) References Cited

U.S. PATENT DOCUMENTS

2006/0128020 A1 *  6/2006  Calos ................. C12N 15/8509
                                                                    435/456
2017/0183654 A1 *  6/2017  Wong .................. C12N 15/113

OTHER PUBLICATIONS

Duportet et al "A platform for rapid prototyping of synthetic gene networks in mammalian cells" Nucleic Acids Research, vol. 42, No. 21, Dec. 1, 2014, pp. 13440-13451. (Year: 2014).*
Singh et al Cross-talk between diverse serine integrases (J of Mol Biol Jan. 23, 2014 vol. 426, No. 2, pp. 318-331 (Year: 2014).*
Supplementary Material for Duportet et al "A platform for rapid prototyping of synthetic gene networks in mammalian cells" Nucleic Acids Research, vol. 42, No. 21, Dec. 1, 2014, pp. 13440-13451. (Year: 2014).*
0000 (Year: 0000).*
Duportet, Developing new tools and platforms for mammalian synthetic biology: From the assembly and chromosomal integeration of complex DNA circuits to the engineering of artificial intercellular communication systems. Universite Paris Diderot (Paris7) Ecole Doctorale Frontieres du vivant; Doctorat Discipline: Biologie de Synthese. Nov. 14, 2014. pp. 1-213. Retrieved from the Internet: URL:https://hal .archives-ouvertes.fr/tel-81108520 on Mar. 28, 2017.
Groth et al., Phage integrases: biology and applications. J Mol Biol. Jan. 16, 2004;335(3):667-78.
Guye et al., Rapid, modular and reliable construction of complex mammalian gene circuits. Nucleic Acids Res. Sep. 2013;41(16):e156. doi: 10.1093/nar/gkt605. Epub Jul. 11, 2013.
Rutherford et al., Attachment site recognition and regulation of directionality by the serine integrases. Nucleic Acids Res. 2013:41(17):8341-56.
Singh et al., Attachment site selection and identity in Bxb1 serine integrase-mediated site-specific recombination. PLoS Genet. May 2013;9(5):e1003490. doi: 10.1371/journal.pgen.1003490. Epub May 2, 2013.
Wang et al., Engineering modular and orthogonal genetic logic gates for robust digital-like synthetic biology. Nat Commun. Oct. 18, 2011;2:508. doi: 10.1038/ncomms1516.

* cited by examiner

*Primary Examiner* — Catherine S Hibbert
(74) *Attorney, Agent, or Firm* — Wolf, Greenfield & Sacks, P.C.

(57) ABSTRACT

The disclosure provides novel large serine recombinases and their respective recognition sites, as well as libraries of orthogonal recombinase recognition sites. Uses of the large serine recombinases, recognition sites, and libraries of orthogonal recombinase recognition sites also are provided.

14 Claims, 11 Drawing Sheets

Specification includes a Sequence Listing.

| Recombinases | Rey | bongo | Ahmid | benedict | theta | Hinder | (c)lared | sheen | Mundrea | Veractuz | rebeuca | G-ball | RSS/E8 | pattyp | Doom | Scowl | Lockley | switzer | bob3 | Trouble | Abrogate | Anglerfish | sarrie

FIG. 13
FIG. 14A
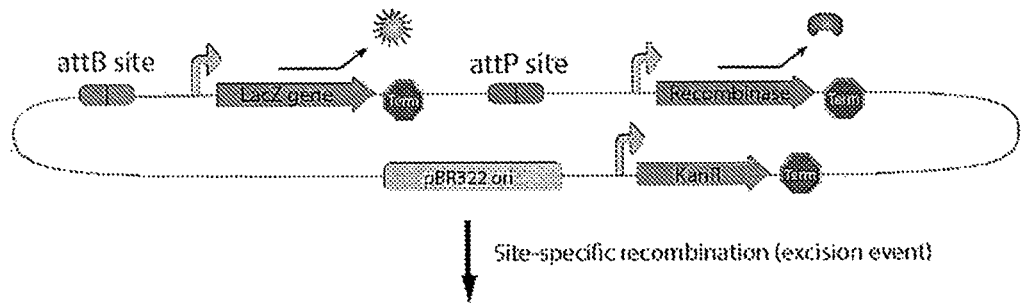
Site-specific recombination (excision event)
FIG. 14B
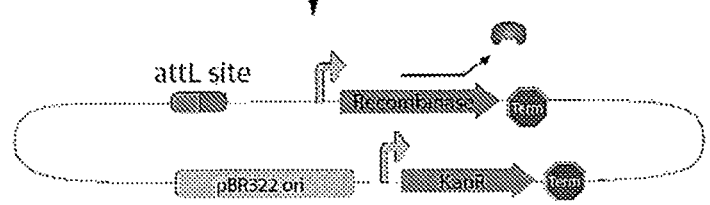

RECOMBINASES AND TARGET SEQUENCES

RELATED APPLICATION

This application claims the benefit under 35 U.S.C. § 119(e) of U.S. Provisional Application Ser. No. 62/281,435, filed on Jan. 21, 2016, the entire content of which is herein incorporated by reference.

GOVERNMENT INTEREST

This invention was made with Government support under Grant No. P50 GM098792 awarded by the National Institutes of Health. The Government has certain rights in the invention.

FIELD OF THE DISCLOSURE

Some aspects of this present disclosure relate to discovering novel large serine recombinases and their respective recognition sits.

BACKGROUND

Programming mammalian cells with large synthetic gene networks is expected to play a central role in helping elucidate complex regulatory cellular mechanisms (41, 42, 13, 43), implementing new useful biological functions (44, 14, 45) and accelerating the design of novel tailor-made therapeutic treatments (46, 47, 17). Complex, stable and heritable programming of mammalian cells by genomic engineering is limited by the requirement to pre-integrate a natural recombination site at single or multiple genomic (chromosomal) loci, thus necessitating the identification of programmable orthogonal (independently acting) recombinases that can be directly targeted sequentially or simultaneously to the endogenous sequences of choice in the mammalian genome.

SUMMARY

Provided herein are newly identified large serine recombinases from recently sequenced Mycobacteriophage genome and the characterization of their respective recombination sites (attP and attB). A number of these new large serine recombinases had a significantly different amino acid sequence than the well-characterized BxB1. In addition, the nucleotide sequences preceding the recombinase coding sequences were also significantly different compared to the sequence at the same location from BxB1, indicating that these recombinases would use different attP and attB sites than BxB1. A dedicated plasmid rescue system to was designed and used to discover the specific attB/attP recombination sites recognized by these recombinases. New attP/attB site pairs for Mycobacteriophages were identified. These sites are used by four of the newly identified large serine recombinases, Theia, Benedict, Veracruz and Rebeuca, to stably integrate their own genome into *M. smegmatis* chromosome. The functioning of the four above-mentioned recombinases in heterologous hosts *E. coli* and mammalian cells were validated. Libraries of orthogonal sites for each of these recombinases were created, which could be used in parallel at the same time, allowing multiplex integration of different genetic circuits into the host genome. These recombinases also provides basis for engineering cell lines step by step, or developing new DNA assembly methods.

Thus, in one aspect, methods for identifying a genomic insertion site of an integrated plasmid are provided. The methods include obtaining genomic DNA from bacteria that include an integrated plasmid, wherein the plasmid includes a promoter operably linked to a nucleotide sequence encoding a large serine recombinase, an attP site recognized by the large serine recombinase, a bacterial origin of replication, one recognition site for a DNA restriction enzyme, and a promoter operably linked to a nucleotide sequence encoding a selectable marker. The methods also include digesting the genomic DNA with the DNA restriction enzyme to obtain fragments of the genomic DNA, ligating the fragments of the genomic DNA to recircularize plasmid sequences, wherein the recircularized plasmid includes the selectable marker, the bacterial origin of replication, and genomic DNA flanking the genomic insertion site, transforming transformation-competent bacteria with the ligated fragments, culturing the transformed bacteria on media that selects for growth of bacteria transformed with the recircularized plasmid that includes the selectable marker, isolating the recircularized plasmid, and determining the sequence of the recircularized plasmid to identify the genomic insertion site.

In some embodiments, the DNA restriction enzyme is EcoRI. In some embodiments, the step of ligating the fragments of the genomic DNA is performed under conditions that favor intramolecular ligation. In some embodiments, the transformation-competent bacteria are transformation-competent *E. coli*. In some embodiments, the genomic insertion site is a chromosomal attB site. In some embodiments, the recognition site for the DNA restriction enzyme is located between the nucleotide sequence encoding a large serine recombinase and the attP site recognized by the large serine recombinase. In some embodiments, the methods also include identifying the attB and attP sites at the genomic insertion site.

According to another aspect, reporter plasmids for monitoring recombination events between large serine recombinase recognition sites are provided. The reporter plasmids include, in order, a predicted attB site sequence for a large serine recombinase, a gene cassette expressing a detectable marker, a predicted attP site sequence for the large serine recombinase, a gene cassette expressing the large serine recombinase, and a gene cassette expressing a selectable marker, wherein each gene cassette includes a promoter operably linked to a sequence encoding a polypeptide, followed by a terminator. In some embodiments, the detectable marker is a lacZ nucleotide sequence.

Another aspect provides methods for testing for function of predicted large serine recombinase recognition sites, including obtaining bacterial cells transformed with the reporter plasmid, culturing the bacterial cells on media that permits detection of expression of the detectable marker and to express the large serine recombinase, wherein if the predicted recombinase recognition sites are correct, then recombination between attP and attB sites results in excision of the gene cassette expressing the detectable marker, and wherein if the predicted recombinase recognition sites are not correct, then the gene cassette expressing the detectable marker is not excised. In some embodiments, detectable marker is a lacZ nucleotide sequence and the media that permits detection includes 5-bromo-4-chloro-3-indolyl-β-D-galactopyranoside (Xgal). In some embodiments, the bacteria are *E. coli*.

In another aspect, reporter systems are provided for testing intermolecular site-specific recombination capacity of a large serine recombinase in mammalian cells. A reporter system includes a first plasmid and a second plasmid. The first plasmid includes a gene cassette that includes a constitutive promoter operably linked to a nucleotide sequence encoding a first detectable marker, and an attB site of the large serine recombinase placed in between the constitutive promoter and the first detectable marker coding sequence. The second plasmid includes a promoter-less gene cassette that includes an attP site of the large serine recombinase followed by a nucleotide sequence encoding a second detectable marker, wherein the second detectable marker is not the same as the first detectable marker. In some embodiments, the reporter system also includes a plasmid expressing the recombinase. In some embodiments, the first detectable marker is a first detectable protein. In some embodiments, the first detectable protein is a first fluorescent protein. In some embodiments, the fluorescent protein is eGFP, eYFP, eCFP, mKate2, mCherry, mPlum, mGrape2, mRaspberry, mGrape1, mStrawberry, mTangerine, mBanana, or mHoneydew. In some embodiments, the constitutive promoter is a Hef1a promoter, a CMV promoter, or a SV40 promoter. In some embodiments, the second detectable marker is a second detectable protein. In some embodiments, the second detectable protein is a second fluorescent protein. In some embodiments, the second fluorescent protein is eGFP, eYFP, eCFP, mKate2, mCherry, mPlum, mGrape2, mRaspberry, mGrape1, mStrawberry, mTangerine, mBanana, or mHoneydew.

Another aspect provides methods for testing intermolecular site-specific recombination capacity of a large serine recombinase in mammalian cells. The methods include co-transfecting the first plasmid and the second plasmid together with a plasmid expressing the corresponding large serine recombinase, wherein intermolecular site-specific recombination between the attB and the attP sites results in fusion of the first plasmid and the second plasmid which results in the insertion of the coding sequence of the second detectable marker in frame with the constitutive promoter.

In another aspect, libraries of orthogonal large serine recombinase recognition site sequences, including pairs of attB site sequences and attP site sequences recognized by large serine recombinases, are provided. The attB site sequences in the libraries include a central dinucleotide sequence and at least 5 nucleotides upstream of the central dinucleotide sequence and at least 5 nucleotides downstream of the central dinucleotide sequence. The attP site sequences in the library include a central dinucleotide sequence, at least 5 nucleotides upstream of the central dinucleotide sequence and at least 5 nucleotides downstream of the central dinucleotide sequence. Each pair of attB site sequences and attP site sequences includes one attB site sequence for use in a host genome and one attP site sequence for use in an integrative vector. In the libraries disclosed herein, each pair of attP site sequences and attB site sequences share the same central dinucleotide, and crosstalk between the attB site sequences and the attP site sequences in the libraries is less than about 20%.

In some embodiments, the central dinucleotide is nonpalindromic. In some embodiments, the central dinucleotide is AA, TT, GG, CC, AG, GA, AC, CA, TG, GT, TC, or CT. In some embodiments, the sequences upstream and downstream of the central dinucleotide of the attB site include additional recognition sequences for the large serine recombinase. In some embodiments, the sequences upstream of the central dinucleotide of the attB sites are 5-50 nucleotides in length. In some embodiments, the sequences downstream of the central dinucleotide of the attB sites are 5-50 nucleotides in length. In some embodiments, the sequences upstream and downstream of the central dinucleotide of the attP site include additional recognition sequences for the recombinase. In some embodiments the sequences upstream of the central dinucleotide of the attP sites are 5-50 nucleotides in length. In some embodiments, the sequences downstream of the central dinucleotide of the attP sites are 5-50 nucleotides in length.

In some embodiments, the large serine recombinase, whose attP and attB sites are included in the libraries, is BxB1, Peaches, Veracruz, Rebeuca, Theia, Benedict, or PhiC31. In some embodiments, a of attB site sequences and attP site sequences can be: SEQ ID NO: 79 and SEQ ID NO: 79, SEQ ID NO: 80 and SEQ ID NO: 80, SEQ ID NO: 81 and SEQ ID NO: 81, SEQ ID NO: 82 and SEQ ID NO: 82, SEQ ID NO: 83 and SEQ ID NO: 83, SEQ ID NO: 84 and SEQ ID NO: 84, SEQ ID NO: 85 and SEQ ID NO: 91, SEQ ID NO: 86 and SEQ ID NO: 92, SEQ ID NO: 87 and SEQ ID NO: 93, SEQ ID NO: 88 and SEQ ID NO: 94, SEQ ID NO: 89 and SEQ ID NO: 95, SEQ ID NO: 90 and SEQ ID NO: 96, SEQ ID NO: 97 and SEQ ID NO: 103, SEQ ID NO: 98 and SEQ ID NO: 104, SEQ ID NO: 99 and SEQ ID NO: 105, SEQ ID NO: 100 and SEQ ID NO: 106, SEQ ID NO: 101 and SEQ ID NO: 107, SEQ ID NO: 102 and SEQ ID NO: 108, SEQ ID NO: 109 and SEQ ID NO: 115, SEQ ID NO: 110 and SEQ ID NO: 116, SEQ ID NO: 111 and SEQ ID NO: 117, SEQ ID NO: 112 and SEQ ID NO: 118, SEQ ID NO: 113 and SEQ ID NO: 119, SEQ ID NO: 114 and SEQ ID NO: 120, SEQ ID NO: 121 and SEQ ID NO: 127, SEQ ID NO: 122 and SEQ ID NO: 128, SEQ ID NO: 123 and SEQ ID NO: 129, SEQ ID NO: 124 and SEQ ID NO: 130, SEQ ID NO: 125 and SEQ ID NO: 131, SEQ ID NO: 126 and SEQ ID NO: 132, SEQ ID NO: 133 and SEQ ID NO: 139, SEQ ID NO: 134 and SEQ ID NO: 140, SEQ ID NO: 135 and SEQ ID NO: 141, SEQ ID NO: 136 and SEQ ID NO: 142, SEQ ID NO: 137 and SEQ ID NO: 143, SEQ ID NO: 144 and SEQ ID NO: 150, SEQ ID NO: 145 and SEQ ID NO: 151, SEQ ID NO: 146 and SEQ ID NO: 152, SEQ ID NO: 147 and SEQ ID NO: 153, SEQ ID NO: 148 and SEQ ID NO: 154, or SEQ ID NO: 149 and SEQ ID NO: 155.

Another aspect provides methods for site-specific recombination between specific attB and attP sites of a large serine recombinase. The methods include providing a nucleic acid molecule including an attB site from a pair of the attB and attP sites from the libraries, providing a nucleic acid molecule including an attP site from the same pair of the attB and attP sites from the library, and combining the nucleic acid molecules in the presence of the large serine recombinase. In some embodiments, the nucleic acid molecule includes an attP site is a bacteriophage genome or a plasmid. In some embodiments, the nucleic acid molecule includes an attB site is a bacterial genome or a mammalian genome.

In yet another aspect, cell lines comprising a plurality of landing pads integrated into the genomic DNA of a parental cell line are provided. Each landing pad includes a constitutive promoter operably linked to a nucleotide sequence encoding a detectable marker, followed by a nucleotide sequence encoding a first selectable marker, and an attB site of a large serine recombinase, wherein the attB site is between the promoter and the nucleotide sequence encoding the detectable protein. The attB sites in the plurality of landing pads are orthogonal to each other, and crosstalk between the attB site sequences is less than about 20%.

In some embodiments, the number of landing pads is 2, 3, 4, 5, 6, 7, 8, 9, 10, 11, or 12. In some embodiments, each landing pad is integrated into the genomic DNA of the cell line using a zinc-finger nuclease, TALEN or CRISPR-Cas system. In some embodiments, the attB site is SEQ ID NOs: 79-84, 85-90, 97-102, 109-114, 121-126, 133-138, and 144-148, or 149. In some embodiments, the detectable marker is a fluorescent protein. In some embodiments, the fluorescent protein is EYFP, eGFP, eYFP, eCFP, mKate2, mCherry, mPlum, mGrape2, mRaspberry, mGrape1, mStrawberry, mTangerine, mBanana, or mHoneydew. In some embodiments, the first selectable marker hydrolyzes a first drug. In some embodiments, first drug is puromycin, hygromycin, G418, neomycin, or bleomycin. In some embodiments, the large serine recombinase that recognizes the attB sites in the landing pads integrated into the cell lines is BxB1 (SEQ ID NO: 73), BxZ2 (SEQ ID NO: 77), PhiC31 (SEQ ID NO: 160), Peaches (SEQ ID NO: 75), Veracruz (SEQ ID NO: 69), Rebeuca (SEQ ID NO: 49), Theia (SEQ ID NO: 65), Benedict (SEQ ID NO: 27), PattyP (SEQ ID NO: 47), Trouble (SEQ ID NO: 67), KSSJEB (SEQ ID NO: 39), Lockley (SEQ ID NO: 71), Scowl (SEQ ID NO: 55), Switzer (SEQ ID NO: 63), Bob3 (SEQ ID NO: 29), Abrogate (SEQ ID NO: 21), Doom (SEQ ID NO: 41), ConceptII (SEQ ID NO: 33), Anglerfish (SEQ ID NO: 25), SkiPole (SEQ ID NO: 61), Museum (SEQ ID NO: 45), or Severus (SEQ ID NO: 57).

According to another aspect, methods of integrating a plurality of genetic sequences or circuits into a cell are provided. The methods include delivering into the cell line any one of claims E1-E8 a plurality of integrative vectors, each including an attP site, one or more genetic sequences or gene cassettes that express components of the genetic circuit, and a promoterless second selectable marker, wherein the cell expresses the large serine recombinase, and wherein each attP site is selected to allow site-specific recombination between the attB site in one of the landing pads and the attP site in the integrative vector, which results in the insertion of the coding sequence of the second selectable marker in frame with the constitutive promoter in the landing pad, and screening for cells with the integration of the genetic sequence or circuit in media including a drug to which the second selectable marker confers resistance.

In some embodiments, the one or more gene cassettes that express components of the genetic circuit include a promoter operably linked to a sequence encoding a polypeptide that is part of the genetic circuit. In some embodiments the integrative vector is introduced into the cell by CaPO$_4$ transfection, lipid transfection, electroporation, or lentiviral vector infection. In some embodiments wherein the drug in the media is puromycin, hygromycin, G418, neomycin, or bleomycin.

In some embodiments, the large serine recombinase used to integrate the genetic sequences or circuits into the landing pads is BxB1 (SEQ ID NO: 73), BxZ2 (SEQ ID NO: 77), PhiC31 (SEQ ID NO: 160), Peaches (SEQ ID NO: 75), Veracruz (SEQ ID NO: 69), Rebeuca (SEQ ID NO: 49), Theia (SEQ ID NO: 65), Benedict (SEQ ID NO: 27), PattyP (SEQ ID NO: 47), Trouble (SEQ ID NO: 67), KSSJEB (SEQ ID NO: 39), Lockley (SEQ ID NO: 71), Scowl (SEQ ID NO: 55), Switzer (SEQ ID NO: 63), Bob3 (SEQ ID NO: 29), Abrogate (SEQ ID NO: 21), Doom (SEQ ID NO: 41), ConceptII (SEQ ID NO: 33), Anglerfish (SEQ ID NO: 25), SkiPole (SEQ ID NO: 61), Museum (SEQ ID NO: 45), or Severus (SEQ ID NO: 57).

Another aspect provides methods for site-specific recombination between specific attB and attP sites of a large serine recombinase. The methods include providing a first nucleic acid molecule comprising an attB site, providing a second nucleic acid molecule comprising an attP site that selectively recombines with the attB site, and combining the nucleic acid molecules in the presence of a large serine recombinase, which can be: Veracruz (SEQ ID NO: 69), Rebeuca (SEQ ID NO: 49), Theia (SEQ ID NO: 65), Benedict (SEQ ID NO: 27), PattyP (SEQ ID NO: 47), Trouble (SEQ ID NO: 67), KSSJEB (SEQ ID NO: 39), Lockley (SEQ ID NO: 71), Scowl (SEQ ID NO: 55), Switzer (SEQ ID NO: 63), Bob3 (SEQ ID NO: 29), Abrogate (SEQ ID NO: 21), Doom (SEQ ID NO: 41), ConceptII (SEQ ID NO: 33), Anglerfish (SEQ ID NO: 25), SkiPole (SEQ ID NO: 61), Museum (SEQ ID NO: 45), Severus (SEQ ID NO: 57), Sarfire (SEQ ID NO: 53), Rey (SEQ ID NO: 51), Bongo (SEQ ID NO: 31), Airmid (SEQ ID NO: 23), Hinder (SEQ ID NO: 35), ICleared (SEQ ID NO: 37), Sheen (SEQ ID NO: 59), or Mundrea (SEQ ID NO: 43).

BRIEF DESCRIPTION OF THE DRAWINGS

FIG. 2A: When both loxP sites are in opposite orientation on the same DNA strand, the sequence located between the sites is constantly inversed by the Cre recombinase. FIG. 2B: When both loxP sites are in the same orientation, the Cre recombinase mediates the excision of the insert. Because the reaction is non-directional, the circular excised insert can be re-linearized, though the intermolecular reaction is less favored compared to intramolecular recombination.

FIG. 10 shows a summary of functional recombinases in M. smegmatis.

FIG. 11A: The genome sequence of M. smegmatis carries multiple cleavage sites for EcoRI (arrows), while the linearized integrated vector carries a single EcoRI restriction site. FIG. 11B: Genomic DNA is extracted from a resistant clone and digested with EcoRI, leading to fragments of linearized DNA pieces, among which one contains both part of the M. smegmatis genome and part of the integration vector with the origin of replication and the gene cassette encoding the selective marker. FIG. 11C: Ligation of the fragments results in the re-circularization of the linearized DNA sequences. FIG. 11D: Transformation of the re-circularized DNA into competent E. coli cells and selection of the bacteria containing the re-circularized DNA containing the pBR322 origin of replication and the gene cassette encoding the selective marker (from the integrative vector) and the attB site sequence (from E. coli genome DNA). FIG. 11E: Sequencing of the ligated vector reveals the sequence of the recombination site.

FIG. 13 shows sequences of the attB and attP sites for Veracruz, Rebeuca, Benedict, and Theia. Central dinucleotides are bolded in gray. Homologies between the attP sites are shown with dots between the sequences. Inverted repeats are represented by gray arrows for attB sites. This figure depicts SEQ ID NOs: 9 through 20 from top to bottom, respectively.

FIGS. 14A-14B show an intramolecular site-specific recombination reporter system.

FIG. 15A: The reporter system is composed of 2 plasmids: 1 plasmid harboring the attP site followed by the mKate2 coding sequence and 1 plasmid carrying the Hef1a promoter followed by the corresponding attB site and the EYFP coding sequence. A third vector to constitutively express the recombinase was also created. FIG. 15B: After co-transfection of these 3 plasmids in mammalian cells, intermolecular site-specific recombination between the plasmids carrying attB and attP site should result in the constitutive expression of mKate2. Depending on the recombination efficiency, some plasmids may still express EYFP a few hours after transfection.

FIG. 16A: Co-transfection of both the reporter system and the vector expressing the recombinase leads to efficient intermolecular recombination between the 2 plasmids of the reporter system as depicted by expression of mKate2. FIG. 16B: Negative control of the same experiment: only the 2 plasmids of the reporter system were transfected without the vector expressing the recombinase.

FIG. 17 shows crosstalk of different large serine recombinases. Efficient site-specific recombination between attB/attP pair is represented by light gray rectangles. On the opposite side, rectangles in dark gray illustrate a non-functional recombinase for the corresponding attB/attP site pair.

FIG. 18 shows a library of orthogonal recombination sites for 7 large serine-recombinases.

DETAILED DESCRIPTION

Figure 1:
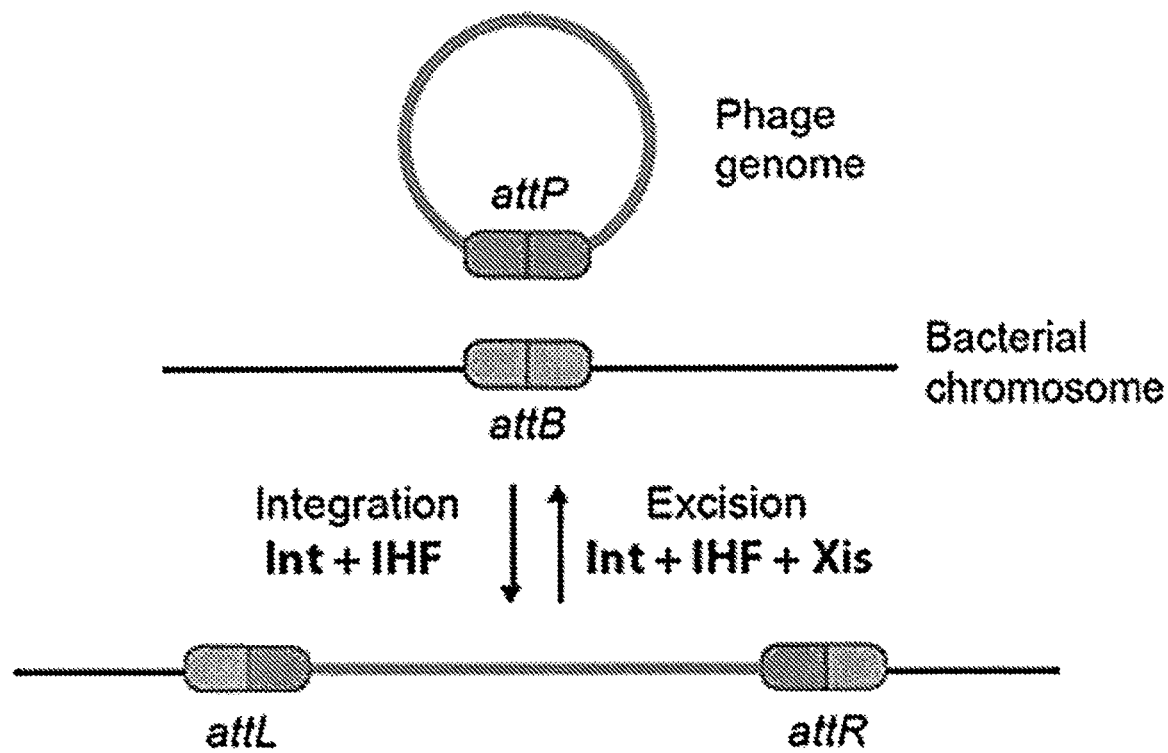
FIG. 1 shows Lambda phage integration and excision. Integration of the circular phage genome into the bacterial genome is mediated by the Lambda phage integrase Int, which interacts with endogenous Integration Host Factor (IHT). Site-specific recombination between the phage designated site (attP) and the bacterial designated site (attB) results in the creation of attL and attR sites flanking the linearized phage genome within the bacterial genome. The reverse reaction happens when Int and Xis are expressed at the same time.

Provided herein are new large serine recombinases identified from recently sequenced Mycobacteriophage genomes and recombinase recognition sites therefore, and a dedicated plasmid rescue system to identify the specific attB/attP recombination sites recognized by these recombinases. New attP/attB site pairs for Mycobacteriophages Theia, Benedict, Veracruz, and Rebeuca were identified and used to stably integrate their own genome into the M. smegmatis chromosome. The present disclosure further provides that, Benedict and Theia recombinases use the same attB site within the 2-nitropropane dioxygenase CDS; and Rebeuca and Veracruz use the same attB site within the TmrH RNA methyltransferase CDS. While the attB site specificity for these two pairs of recombinases is extremely high, the attP specificity is less stringent as Theia can use Benedict's attP site and vice-versa; and Rebeuca can use Veracruz's attP site and vice-versa.

Also provided herein are procedures to identify new serine recombinases and discover their attB/attP sites, which can also be used for newly sequenced isolated mycobacteriophages in order to extend the toolbox of available recombinases. The present discloses further provides methods for using the newly discovered large serine recombinases and their recognition sites in heterologous hosts. Also provided herein is a library of orthogonal sites that could be used in parallel at the same time and therefore broaden the spectrum of applications. Programming mammalian cells with large synthetic gene networks can significantly facilitate elucidating complex regulatory cellular mechanisms (41, 42, 13, 43), implementing new useful biological functions (44, 14, 45) and accelerating the design of novel tailor-made therapeutic treatments (46, 47, 17). For example, transcriptional and post-transcriptional regulatory networks may be integrated into a mammalian genome using the methods disclosed herein, to explore how these networks fine tune mammalian gene expression. In yet another example, trigger-controlled transcription factors, which independently control gene expression, and RNA-binding proteins that inhibit the translation of transcripts harboring specific RNA target motifs maybe included in a set of synthetic transcription-translation control devices that could be rewired in a plug-and-play manner, which can then be integrated into mammalian cells using the methods disclosed herein, and allow the cells to execute input-triggered genetic instructions with precision, robustness and computational logic reminiscent of electronic circuits. In some embodiments, an inducible positive or negative feedback loop maybe integrated into a mammalian cell using the methods disclosed herein, allowing the monitoring and modeling of cellular behavior. In yet another embodiment, therapeutic peptides, RNAs, proteins maybe integrated into cells using the methods disclosed herein, allowing continuing and controlled expression of these therapeutic agents.

Also provided herein, are methods for integrating complex genetic circuits into mammalian chromosomes using landing pads comprising the recognition sites for large serine recombinases, wherein the genetic circuits to be integrated comprise attP sites that are orthogonal to the large serine recombinase.

While intramolecular site-specific recombination has proven useful for excision of constructs integrated in mammalian genomes, intermolecular site-specific recombination can be used to integrate complex circuits into mammalian chromosomes. The ability of multiplex integration by using orthogonal sites could help to integrate a variety of different sequences, including circuits containing more than one sequence each, at different locations within a genome, which is helpful in preventing interference between circuits or attaining higher levels of expression (with a lower coefficient of variation) by integrating the same construct in multiple copies. The method of sequential integration allows engineering cell lines step by step, integrating one circuit after the other so as to incrementally increase the complexity. Such genomic modifications can also be performed in a simultaneous multiplex ("one shot") procedure, providing savings in time and facilitating inter-related or compensatory modifications which must be synchronized in time.

Further provided herein is the use of multiple serine recombinases with orthogonal sites to develop new DNA assembly methods. For instance, a system can be created based on the Gateway assembly methodology, by flanking each part to be assembled with either an attB on its 5' end and an attP on its 3' end. Having six orthogonal sites for one recombinase would allow assembling five parts per reaction, i.e. enough for many mammalian transcription units. The assembled vectors could carry sites from another recombinase, and following the same principle, could be used to assemble five transcription units together. Such strategy could be used to assemble even larger constructs with more orthogonal recombinases. As site-specific recombination with serine recombinases is extremely efficient, fast and reliable, such an assembly method would be extremely convenient.

The present disclosure also provides reliable methods for gene transfer via recombinase-mediated cassette exchange (RMCE), wherein predictable expression patterns are achieved by the non-disruptive insertion of a gene cassette at a pre-characterized genomic insertion site. In some embodiments, the genomic insertion site is marked by a recognition sequence, e.g., the attB site of a large serine recombinase disclosed herein, at the flanks of a selection marker. Providing an integrative vector comprising a gene cassette encoding the gene of interest and the attP site of the corresponding large serine recombinase, can cleanly replace the resident cassette under the influence of a site-specific recombinase.

Recombinases

A "recombinase," as used herein, is a site-specific enzyme that recognizes short DNA sequence(s), which sequence(s) are typically between about 30 base pairs (bp) and 40 bp, and that mediates the recombination between these recombinase recognition sequences, which results in the excision, inversion, or exchange of DNA fragments between the recombinase recognition sequences. Recombinases can be classified into two distinct families: serine recombinases (e.g., resolvases and invertases) and tyrosine recombinases (e.g., integrases), based on the conserved nucleophilic amino acid residue that they use to attack the DNA and which becomes covalently linked to it during strand exchange.

Large serine recombinases are the most efficient, directional, and specific recombinases for DNA integration in mammalian cells. Examples of large serine recombinases provided herein or useful in the products and methods disclosed herein include, but are not limited to, KSSJEB, PattyP, Doom, Scowl, Lockley, Switzer, Bob3, Trouble, Abrogate, Anglerfish, Sarfire, SkiPole, ConceptII, Museum, Severus, Rey, Bongo, Airmid, Benedict, Theia, Hinder, ICleared, Sheen, Mundrea, Veracruz, and Rebeuca, from the recently sequenced Mycobacteriophage, and the previously characterized Bxb1, Peaches, PhiC31, and BxZ2. These large serine recombinases can be used individually, or in combination, such as to integrate complex genetic circuits into a host genome.

In some aspects, a large serine recombinase is required for site-specific recombination, wherein DNA strand exchange takes place between segments possessing attB and attP sites, and wherein the recombinase rearranges DNA segments by recognizing and binding to the attB and attP sites, at which they cleave the DNA backbone, exchange the two DNA helices involved and rejoin the DNA strands.

The recombinases that may be used include, without limitation, BxB1 (SEQ ID NO: 73), BxZ2 (SEQ ID NO: 77), PhiC31 (SEQ ID NO: 160), Peaches (SEQ ID NO: 75), Veracruz (SEQ ID NO: 69), Rebeuca (SEQ ID NO: 49), Theia (SEQ ID NO: 65), Benedict (SEQ ID NO: 27), PattyP (SEQ ID NO: 47), Trouble (SEQ ID NO: 67), KSSJEB (SEQ ID NO: 39), Lockley (SEQ ID NO: 71), Scowl (SEQ ID NO: 55), Switzer (SEQ ID NO: 63), Bob3 (SEQ ID NO: 29), Abrogate (SEQ ID NO: 21), Doom (SEQ ID NO: 41), ConceptII (SEQ ID NO: 33), Anglerfish (SEQ ID NO: 25), SkiPole (SEQ ID NO: 61), Museum (SEQ ID NO: 45), and Severus (SEQ ID NO: 57).

Recombinase Recognition Sites

Recombination sites are typically between 30 and 200 nucleotides in length and consist of two motifs with a partial inverted-repeat symmetry, which flank a central crossover sequence at which the recombination takes place (see FIG. 13, arrows above the nucleic acid sequence of attB sites). Recombinases bind to these inverted-repeated sequences, which are specific to each recombinase, and are herein referred to as "recombinase recognition sequences," "recombinase recognition sites," "attP sites," "attB sites" or "genomic insertion sites". Pairs of attB and attP sites share a certain degree of identity, such as at least 80%. In some embodiments, pairs of attB and attP sites share an identify of at least 81%, 82%, 83%, 84%, 85%, 86%, 87%, 88%, 89%, 90%, 91%, 92%, 93%, 94%, 95%, 96%, 97%, 98%, 99%, or even 100%. In some embodiments, an attB site is present in the genomic DNA sequence and an attP site is present in the DNA sequence integrated into the genomic DNA sequence.

In some embodiments, an attB site is in the genomic DNA of bacteria and an attP site is in the DNA sequence of the respective bacteriophage.

During recombination, crossover occurs at the central dinucleotide of the attB/attP sites. The sequence of the central dinucleotide is the sole determinant of the directionality of the recombination. For the recombination to be directional, the central dinucleotide needs to be nonpalindomic. For example, the central dinucleotide sequence found in the attB/attP sites for large serine recombinases, which are strictly directional, can be AA, TT, GG, CC, AG, GA, AC, CA, TG, GT, TC, or CT.

The outcome of recombination depends, in part, on the location and orientation of two short repeated DNA sequences that are to be recombined, typically less than 30 bp long. For example, inversion recombination happens between two short, inverted, repeated DNA sequences. A DNA loop formation, assisted by DNA bending 5 proteins, brings the two repeat sequences together, at which point DNA cleavage and ligation occur. This reaction is ATP independent and requires supercoiled DNA. The end result of such an inversion recombination event is that the stretch of DNA between the repeated site inverts (i.e., the stretch of DNA reverses orientation) such that what was the coding strand is now the non-coding strand and vice versa. In such reactions, the DNA is conserved with no net gain or no loss of DNA. Conversely, integration (excision) recombination occurs between two short, repeated DNA sequences that are oriented in the same direction. In this case, the intervening DNA is excised/removed.

Methods for Identifying Recognition Sites

The present disclosure provides, in some aspects, methods for characterizing the recombination sites of large serine recombinases. In some embodiments, the method comprises using a nucleic acid construct designated an "integrative plasmid." The "integrative plasmid", as defined herein, comprises a promoter operably linked to a nucleotide sequence encoding a large serine recombinase, an attP site recognized by the large serine recombinase, a bacterial origin of replication, one single recognition site for a DNA restriction enzyme, and a promoter operably linked to a nucleotide sequence encoding a selectable marker. The integrative plasmid is transformed into a cell in which the large serine recombinase is expressed, such as a M. smegmatis cell, and the integrative plasmid is inserted (i.e., integrated) into the cell's genomic DNA at the genomic insertion site.

The methods provided herein further include digesting the genomic DNA containing the integrated plasmid with a DNA restriction enzyme. In some embodiments of the present disclosure, the recognition and cleavage site of the DNA restriction enzyme is only present at one single location in the integrated plasmid, e.g., between the nucleotide sequence encoding a large serine recombinase and the attP site recognized by the large serine recombinase. Recognition and cleavage sites are usually present throughout cell genomes. In some embodiments, digesting the genomic DNA containing the integrated plasmid results in DNA fragments, among which one species of fragments contains the sequences of the integrated plasmid and a segment of the genomic sequence where the recombinase recognition site can be found. Once obtained from restriction digestion of the genomic DNA, the DNA fragments are recircularized, delivered into bacteria, and bacteria are selected that can grow on selective media based on the presence of the selectable marker. In some embodiments, the way of delivering the recircularized DNA into bacteria is by transforming transformation-competent bacteria. Only bacteria that are transformed with the recircularized plasmid containing sequences from the integrated plasmid, which contains the bacteria origin of replication and the selectable marker, can grow on the selective media. Then the recircularized plasmid is isolated from the bacteria and the sequence of the recircularized plasmid is determined to identify the genomic insertion site of the integrated plasmid.

Figure 11A:
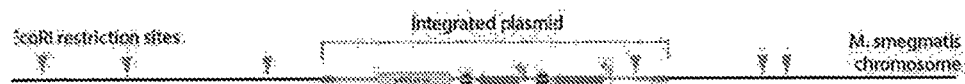
FIGS. 11A-11E show the plasmid-rescue workflow.
Figure 11B:
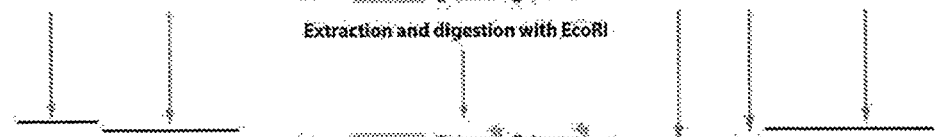
Figure 11D:
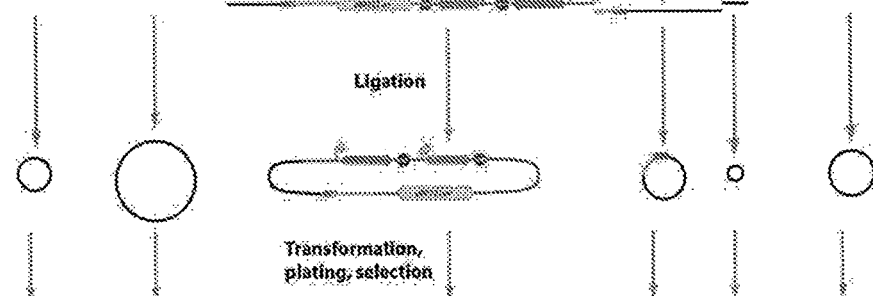
Figure 11E:
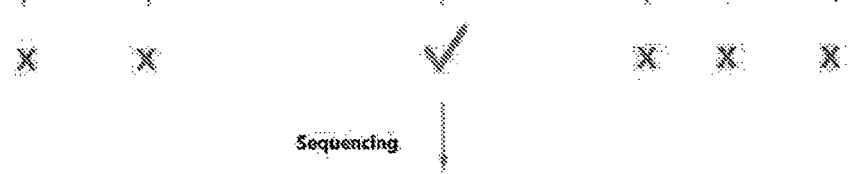
Figures 11C, 12:
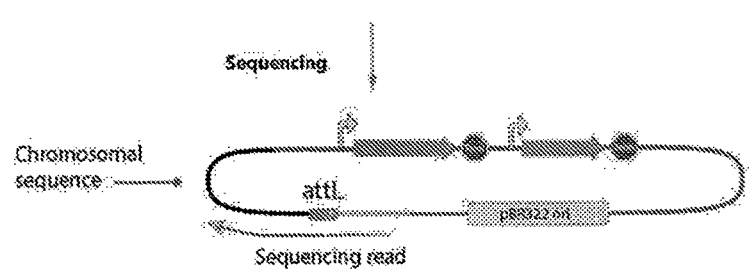
FIG. 12 shows the localization of the attB sites for different large site-specific recombinases from Mycobacteriophages.

Using this method, recognition sites in the M. smegmatis genome for the exemplary large serine recombinases were identified, which are provided herein. Fifteen of the exemplary large serine recombinases integrated into the same genomic attB site as BxB1 (in the groEL coding sequence), two integrated in the TmrH RNA methyltransferase coding sequence (Rebeuca and Veracruz) and two others integrated into the 2-nitropropane dioxygenase coding sequence (FIG. 12). The recognition sequences at the attP and attB sites are disclosed herein. For the recombinases that integrated into the groEL coding sequence, the attP and attB sites are totally homologous to the one recognized by BxB1 recombinase. However, for Rebeuca and Veracruz, even though integration happens in the same attB site, the attP site recognized by Rebeuca is slightly different from the attP site recognized by Veracruz. Similarly, for Theia and Benedict, even though integration happens in the same attB site, the attP site recognized by Theia is slightly different from the attP site recognized by Benedict (FIG. 13).

The recombinases provided herein are not meant to be exclusive examples of recombinases that can be used in certain embodiments.

Testing the Site-Specific Recombinase Activity

The ability of a large serine recombinase to function with its predicted recombination sites in a heterologous host allows the possibility to use these recombinases to engineer the genetic composition of an organism. For example, such recombination events may be used in human cells to allow the precise integration and excision of DNA at a predetermined chromosomal locus, thus facilitating the analysis of gene regulation in a particular chromosomal, physiological, or disease related context. Examples of testing the functionality of the new large serine recombinases and its respective recognition sites include, without limitation, reporter plasmids or reporter systems that monitor the recombinase activities in heterologous hosts.

Reporter Plasmid

Provided herein are reporter plasmids for monitoring recombination events between large serine recombinase recognition sites comprising, in order, a predicted attB sequence for a large serine recombinase, a gene cassette expressing a detectable marker, a predicted attP site sequence for the large serine recombinase, a gene cassette expressing the large serine recombinase, and a gene cassette expressing a selectable marker, wherein each gene cassette comprises a promoter operably linked to a sequence encoding a polypeptide, followed by a terminator (FIG. 14). The reporter plasmid, when delivered into an appropriate, e.g., E. coli, results in the expression of the large serine recombinase. When the attB and attP sites provided on the reporter plasmid are correct sites for the particular large serine recombinase, intramolecular recombination of the reporter plasmid between the attP and attB sites is triggered, leading to the excision of the gene cassette expressing the detectable marker. In one example, LacZ is the detectable marker, and the loss of LacZ gene can be monitored by plating the E. coli on media including 5-bromo-4-chloro-3-indolyl-β-D-galactopyranoside (Xgal) and checking for white colonies. Other detectable markets are described elsewhere herein.

In some embodiments, a plasmid having similar features as the reporter plasmid disclosed herein may also be used for exerting precise control over the expression of a gene of interest. For example, a gene of interest can replace the LacZ gene cassette in the reporter plasmid. Without limitation, such gene of interest may be a gene encoding a protein or variants whereof, a gene of a non-coding RNA such as a siRNA, or a ribosomal RNA or variants whereof. Wherein such gene of interest encodes a protein, the protein may be, for example, a detectable marker, a selectable marker, a therapeutic protein, a regulatory protein, or an enzyme.

In yet another embodiment, the excision of the gene of interest can be timed by manipulating the promoter under which the expression of the large serine recombinase is controlled. For example, the gene of the large serine recombinase can be put under the control of an inducible promoter. At a desired time, the expression of the large serine recombinase is induced and only then will intramolecular recombination occur, excising the gene of interest.

In some aspects, the reporter plasmid provided herein can be modified to have attP and attB site sequences of different lengths. Recombination will only occur when the lengths of the attP and attB sites are sufficiently long for the large serine recombination, thus identifying the minimal sequence required for attP and attB sites for the large serine recombinase to function. For example, the lengths of the attP and attB sites can be: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, or more base pairs.

Reporter System

The present disclosure also provides a reporter system for testing intermolecular site-specific recombination capacity of a large serine recombinase in mammalian cells. The reporter system, defined herein, comprises a first plasmid, a second plasmid, and a plasmid express the recombinase.

In some embodiments, the first plasmid comprises a gene cassette that comprises a constitutive promoter operably linked to a nucleotide sequence encoding a first detectable marker, and an attB site of the large serine recombinase placed in between the constitutive promoter and the detectable maker coding sequence. The second plasmid comprises a promoter-less gene cassette that comprises an attP site of the large serine recombinase followed by a nucleotide sequence encoding a second detectable marker, wherein the second detectable marker is not the same as the first detectable marker. In some embodiments, the first detectable marker is a first detectable protein. The first detectable protein can be, for example, a fluorescent protein chosen from the group consisting of: eGFP, eYFP, eCFP, mKate2, mCherry, mPlum, mGrape2, mRaspberry, mGrape1, mStrawberry, mTangerine, mBanana, and mHoneydew. The constitutive promoter in the first plasmid may be, for example, a Hef1a promoter, a CMV promoter, or a SV40 promoter. The second detectable protein can be a second detectable protein. For example, the second detectable marker can be a second fluorescent protein chosen from the group consisting of: eGFP, eYFP, eCFP, mKate2, mCherry, mPlum, mGrape2, mRaspberry, mGrape1, mStrawberry, mTangerine, mBanana, and mHoneydew. In some embodiments, the first detectable maker and/or the second detectable marker is an RNA molecule, or an enzyme such as beta-galactosidase (encoded by LacZ), horseradish peroxidase, or luciferase.

Figure 15A:
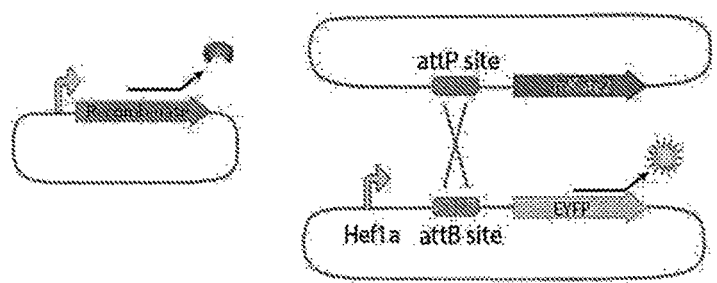
FIGS. 15A-15B show an intermolecular site-specific recombination mammalian reporter system.
Figure 15B:
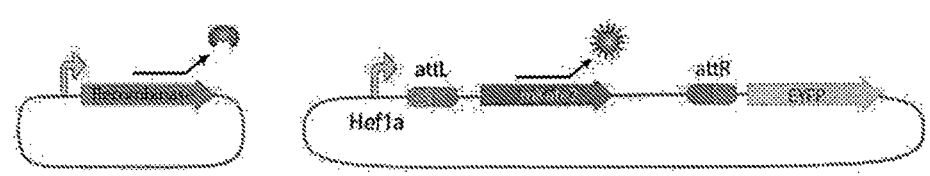

Also provided herein, is the use of the of the reporter system to test intermolecular site-specific recombination capacity of a large serine recombinase, wherein the first plasmid, the second plasmid, and the plasmid expressing the corresponding large serine recombinase are co-transfected into mammalian cells. The constitutive or induced expression of the recombination leads to the intermolecular recombination of the first plasmid and the second plasmid, further leading to the insertion of the second detectable marker after the constitute promoter in the first plasmid (and the first detectable marker is promoter-less) (FIG. 15). In some embodiments, the recombinase is under the control of a constitutive promoter. In some embodiments, the recombinase is under the control of a inducible promoter to provide control of when the recombination occurs. Similar to the reporter plasmid described above, the reporter system disclosed herein can also be used to control the expression of one or more exogenous proteins in the host cell, such as when the recombinase is placed under an inducible promoter. In some embodiments, the large serine recombinases whose activity is tested in mammalian cells using the reporter system is Veracruz, Rebeuca, Benedict or Theia. In other embodiments, the large serine recombinase used is any large serine recombinase disclosed herein. In other embodiments, the large serine recombinase is Bxb1, Peaches, PhiC31, or BxZ2.

Host organisms in which the recombinase activity can be tested using the reporter systems provided herein or in which gene expression can be manipulated using the recombinases and recombinase recognition sites encompass prokaryotes and eukaryotes, unicellular organisms and multi-cellular organisms. A prokaryote, as defined herein, a single-celled organism that lacks a membrane-bound nucleus, mitochondria, or any other membrane-bound organelle. A eukaryote is any organism whose cells contain a nucleus and other organelles enclosed within membranes, which may be a unicellular organism or a multicellular organism. Examples of a prokaryote that may be used include but are not limited to all bacteria species and their variants, e.g., *Yersinia* spp., *Escherichia* spp., *Klebsiella* spp., *Bordetella* spp., *Neisseria* spp., *Aeromonas* spp., 10 *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Stremtomyces* spp. In some embodiments, the bacterial cells are *Staphylococcus aureus, Bacillus subtilis, Clostridium butyricum, Brevibacterium* 15 *lactofermentum, Streptococcus agalactiae, Lactococcus lactis, Leuconostoc lactis, Streptomyces, Actinobacillus actinobycetemcomitans, Bacteroides, cyanobacteria, Escherichia coli, Helobacter pylori, Selnomonas ruminatium, Shigella sonnei, Zymomonas mobilis, Mycoplasma mycoides, Treponema denticola, Bacillus thuringiensis, Staphlococcus lugdunensis, Leuconostoc oenos, Corynebacterium xerosis, Lactobacillus planta rum,* 20 *Streptococcus faecalis, Bacillus coagulans, Bacillus ceretus, Bacillus popillae, Synechocystis* strain PCC6803, *Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Zymomonas mobilis, Streptomyces phaechromogenes, Streptomyces ghanaenis,* or *Halobacterium* strain GRB. Examples of eukaryotic cells that maybe used include but are not limited to mammalian cells, insect cells, yeast cells (e.g., *Saccharomyces cerevisiae*) and plant cells. In some embodiments, a eukaryotic cell is a vertebrate cell. Examples of vertebrate cells include, without limitation, reproductive cells including sperm, ova and embryonic cells, and non-reproductive cells, including kidney, lung, spleen, lymphoid, cardiac, gastric, intestinal, pancreatic, muscle, bone, neural, brain and epithelial cells. Stem cells, including embryonic stem cells, can also be used. In some embodiments, a non-cellular system or an in vitro system may be used.

Libraries of Orthogonal Large Serine Recombinase Recognition Sites

Also provided herein are libraries of orthogonal attB and attP sequences (SEQ ID NOs: 79-155) A recombinase recognition site is "orthogonal" when it does not significantly recognize the recognition site or nucleotide sequence of a recombinase. Thus, one attB site of a recombinase can be orthogonal to an attB site of a different recombinase. In addition, one pair of attB and attP sites of a recombinase can be orthogonal to another pair of attB and attP sites recognized by the same recombinase. A pair of recombinases are considered orthogonal to each other, as defined herein, when the recognition of each other's attB or attP site sequences. The lack of recognition of recombinase recognitions sites or pairs of sites by the same recombinase or a different recombinase (also referred to herein as "crosstalk") is less than about 20%. The crosstalk can be less than 19%, 18%, 17%, 16%, 15%, 14%, 13%, 12%, 11%, 10%, 9%, 8%, 7%, 6%, 5%, 4%, 3%, 2%, or 1%, or even 0%.

In some embodiments, the attB and/or attP site sequences in the library comprise a central dinucleotide sequence and at least 5 nucleotides upstream and downstream of the central dinucleotide. For example, the sequence upstream of the central dinucleotide in the attP and/attB site sequences can be 5-50 nucleotides. In some embodiments, the sequence upstream of the central dinucleotide in the attP and/attB site sequences are at least 10 nucleotides, 15 nucleotides, 20 nucleotides, 25 nucleotides, 30 nucleotides, 35 nucleotides, 40 nucleotides, or 45 nucleotides. In some embodiments, the sequence upstream of the central dinucleotide in the attP and/attB site sequences are 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides. Likewise, the sequence downstream of the central dinucleotide in the attP and/or attB site sequences can be 5-50 nucleotides. In some embodiments, the sequence downstream of the central dinucleotide in the attP and/attB site sequences are at least 10 nucleotides, 15 nucleotides, 20 nucleotides, 25 nucleotides, 30 nucleotides, 35 nucleotides, 40 nucleotides, or 45 nucleotides. In some embodiments, the sequence downstream of the central dinucleotide in the attP and/attB site sequences are 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides. In some embodiments, the sequence upstream and downstream of the attB sites provide additional recognition sequence for the corresponding large serine recombinase. In some embodiments, the sequence upstream and downstream of the attP sites provide additional recognition sequence for the corresponding large serine recombinase. In some embodiments, the attB and attP sites in the library are selected from SEQ ID NOs: 79-155.

A "pair of an attB site sequence and an attP site sequence," and like terms, refers to attB and attP site sequences that share the same central dinucleotide. In some embodiments, the central dinucleotide is nonpalindromic. In some embodiments, the central dinucleotide is selected from the group consisting of: AA, TT, GG, CC, AG, GA, AC, CA, TG, GT, TC, and CT. In some embodiments, a pair of an attB site sequence and an attP site sequence are used in a recombination event, wherein the attB site sequence is used in a host genome and the attP site sequence for use in an integrative vector. In some embodiments, in a pair of an attB site sequence and an attP site sequence, the sequences upstream and downstream of the central dinucleotide in the attB site share 100% homology with that of the attP site. In some embodiments, in a pair of an attB site sequence and an attP site sequence, the sequences upstream and downstream of the central dinucleotide in the attB site vary from that of the attP site, e.g., 99%, 98%, 97%, 96%, 95%, 94%, 93%, 92%, 91%, 91%, 89%, 88%, 87%, 86%, 85%, 84%, 83%, 82%, 81%, or 80% identical in sequence.

An integrative vector, as defined herein, is a nucleotide sequence that is exogenous to a host DNA sequence and is to be inserted into the host DNA sequence via site-directed recombination, wherein the integrative vector comprises an attP site recognized by the respective large serine recombinase and any additional sequence features it comprises. The integrative vector maybe, without limitation, a bacteriophage DNA, a plasmid, a linear DNA fragment, or a synthetic nucleic acid sequence. A host genome that contains the attB site recognized by the respective large serine recombinase, without limitation, maybe a bacteria genome, an insect cell genome, a mammalian cell genome, or a human cell genome.

In some embodiments, the attP and attB site sequences are recognized by a large serine recombinase, such as BxB1, Peaches, Veracruz, Rebeuca, Theia, Benedict, or PhiC31.

Further provided herein, is a method for site-specific recombination between specific attB and attP sites of a large serine recombinase, wherein a pair of an attB site sequence and an attP site sequence are used in two different nucleic acid molecules, and wherein the two nucleic acid molecules are combined in the presence of a large serine recombinase. In some embodiments, the large serine recombinase is BxB1, Peaches, Veracruz, Rebeuca, Theia, Benedict, or PhiC31. In some embodiments, the attB and attP sites in the library are selected from SEQ ID NOs: 79-155. In some embodiments, the nucleic acid including the attP site is, without limitation, a bacteriophage genome or a plasmid. In some embodiments, the nucleic acid including the attB site is, without limitation, a bacterial genome or a mammalian genome.

Use of the Libraries of Orthogonal attB and attP Sites

The libraries of orthogonal attB and attP sites described herein have a variety of uses. For example, a cell line comprising a plurality of landing pads integrated into the genomic DNA of a parental cell line can be constructed. The parental cell line may be a wild type cell line, or a cell line with existing genomic modification. In the latter, the cell line would be "parental" to the cell line generated from further modification of its genomic DNA. A "landing pad," is an exogenous DNA sequence integrated into a location of the host genome that includes an attB site of a large serine recombinase. In some instances, the exogenous DNA sequence includes an attB site of a large serine recombinase, a constitutive promoter operably linked to a nucleotide sequence encoding a detectable marker, followed by a nucleotide sequence encoding a first selectable market. In certain types of landing pads, the attB site is between the promoter and the nucleotide sequence encoding the detectable protein. When there are more than one landing pads used in a given cell, it is preferred that an attB site of one landing pad is orthogonal to an attB site of the same large serine recombinase in any other landing pad. The landing pad is used for further genetic engineering and integration of a nucleic acid molecule of interest via site-specific recombination. The landing pad can be integrated into the parental genome using any method known in the art, such as by using a zinc finger nuclease, TALEN, or the CRISPR-Cas9 system. In some embodiments, the number of landing pads integrated into a cell line is 2, 3, 4, 5, 6, 7, 8, 9, 10, 11, or 12. In some embodiments, the attB site in the landing pad is selected from SEQ ID NOs: 79-84, 85-90, 97-102, 109-114, 121-126, 133-138, and 144-149. In some embodiments, the detectable marker in the landing pad is a fluorescent protein, such as, eGFP, eYFP, eCFP, mKate2, mCherry, mPlum, mGrape2, mRaspberry, mGrape1, mStrawberry, mTangerine, mBanana, and mHoneydew, luciferase, or LacZ. In some embodiments, a selectable marker hydrolyzes a drug, such as, puromycin, hygromycin, G418, neomycin, or bleomycin.

Further provided herein, is a method of integrating a genetic circuit, or multiple genetic circuits, into a cell comprising a plurality of landing pads. In some embodiments, one genetic circuit is integrated into the cell line. In some embodiments, 2, 3, 4, 5, 6, 7, 8, 9, 10, 11, 12 or more circuits may be integrated into the cell line, provided that the number of the landing pads in the cell line is sufficient to accommodate the number of genetic circuits that are to be integrated into the cell line. In some instances, it may be preferred that the number of landing pads is at least the number of genetic sequences or circuits to be integrated. In other instances, a single landing pad can include multiple circuits under the control of different promoters. A genetic circuit, as used herein, is a rationally designed artificial gene regulatory networks with robust function, comprising primary genetic elements, i.e., building blocks. The primary genetic elements maybe, without limitation, insulators, promoters, ribosome binding sites, transcriptional activators and repressors, gene coding sequences, 5'UTRs, 3'UTRs, polyA signals, and terminators. Independent modules of a genetic circuit can be built using the primary genetic elements. Methods of building these genetic circuits are known to those of skill in the art. A library of these independent modules are available for bacterial systems, e.g., switches, time-delayed circuits, cascades, pulse generators, logic gates, spatial patterning and memory devices (33-40). In some aspects, a plurality of landing pads may be integrated into different locations of the genome, allowing modification at multiple loci of the genome via site-specific recombination.

To integrate a genetic sequence or circuit into a cell, one can obtain a cell line with pre-integrated landing pads, deliver into the cells of the cell line an integrative vector comprising an attP site, the genetic sequence or circuit or interest, and an promoter-less second selectable marker. In some embodiments, the attP site used in the integrative vector is selected from SEQ ID NOs: 79-84, 91-96, 103-108, 115-120, 127-132 and 150-155. In some embodiments, the cell also expresses a large serine recombinase that recognizes the attB site sequences in the landing pads and the attP site sequences in the integrative vector. The site-specific recombination mediated by the large serine recombinase between the landing pad and the integrative vector results in the insertion of the coding sequence of the second selectable maker in frame with the constitutive promoter in the landing pad, thereby allowing expression of the second selectable marker. Cells with the integrative vector incorporated into the genomic DNA may be selected using media including a drug to which the second selectable marker confers resistance. Examples of the drug to which the second selectable marker confers resistance include puromycin, hygromycin, G418, neomycin, or bleomycin. In some embodiments, the large serine recombinase maybe BxB1 (SEQ ID NO: 73), BxZ2 (SEQ ID NO: 77), PhiC31 (SEQ ID NO: 160), Peaches (SEQ ID NO: 75), Veracruz (SEQ ID NO: 69), Rebeuca (SEQ ID NO: 49), Theia (SEQ ID NO: 65), Benedict (SEQ ID NO: 27), PattyP (SEQ ID NO: 47), Trouble (SEQ ID NO: 67), KSSJEB (SEQ ID NO: 39), Lockley (SEQ ID NO: 71), Scowl (SEQ ID NO: 55), Switzer (SEQ ID NO: 63), Bob3 (SEQ ID NO: 29), Abrogate (SEQ ID NO: 21), Doom (SEQ ID NO: 41), ConceptII (SEQ ID NO: 33), Anglerfish (SEQ ID NO: 25), SkiPole (SEQ ID NO: 61), Museum (SEQ ID NO: 45), or Severus (SEQ ID NO: 57).

Gene Cassette

A gene cassette, as defined herein, is a nucleic acid sequence that comprises genetic elements necessary for the expression of a gene. In some embodiments, a gene cassette comprises a promoter, wherein the promoter is operably linked to the nucleic acid encoding a protein, and a terminator. In come embodiments, a gene cassette comprises a nucleic acid encoding a protein and a terminator.

Promoter

A "promoter" refers to a control region of a nucleic acid at which initiation and rate of transcription of the remainder of a nucleic acid sequence are controlled. A promoter drives transcription of the nucleic acid sequence that it regulates, thus, it is typically located at or near the transcriptional start site of a gene. A promoter may have, for example, a length of 100 to 1000 nucleotides.

In some embodiments, a promoter is operably linked to a nucleic acid, or a sequence of a nucleic acid (nucleotide sequence). A promoter is considered to be "operably linked" to a sequence of nucleic acid that it regulates when the promoter is in a correct functional location and orientation relative to the sequence such that the promoter regulates (e.g., to control ("drive") transcriptional initiation and/or expression of) that sequence.

The promoters that can be used include constitutive promoters or inducible promoters. In some embodiments, a promoter is a "constitutive" promoter. A constitutive promoter refers to an unregulated promoter that allows for continual transcription of its associated gene. In some embodiments of the present disclosure, a gene is "promoter-less". A promoter-less gene is not transcribed and does not express.

In some embodiments of the present disclosure, a gene is placed under an "inducible promoter". An "inducible promoter" may be conditioned to endogenous factors or to environmental conditions and external stimuli that can be artificially controlled. Within this group, there are promoters modulated by abiotic factors such as light, oxygen levels, heat, cold and wounding. Since some of these factors are difficult to control outside an experimental setting, promoters that respond to chemical compounds, not found naturally in the organism of interest, are of particular interest. Along those lines, promoters that respond to antibiotics, copper, alcohol, steroids, and herbicides, among other compounds, have been adapted and refined to allow the induction of gene activity at will and independently of other biotic or abiotic factors. The promoters that can be used include, without limitation, the promoters disclosed in (30), the entire contents of which hereby incorporated by reference, and the promoters disclosed in (31); the entire contents of which also incorporated by reference.

In some embodiments, the promoters used herein may be, without limitation, a Hef1a promoter, a CMV promoter, an SV40 promoter, a luxI promoter, an Hsp70 promoter, a UREX promoter, a LacZ promoter, or a T7 promoter.

Terminator

Provided herein are terminator sequences for use in some embodiments. A "terminator" or "terminator sequence," as used herein, is a nucleic acid sequence that causes transcription to stop. A terminator may be unidirectional or bidirectional. It is comprised of a DNA sequence involved in specific termination of an RNA transcript by an RNA polymerase. A terminator sequence prevents transcriptional activation of downstream nucleic acid sequences by upstream promoters. The most commonly used type of terminator is a forward terminator. When placed downstream of a nucleic acid sequence that is usually transcribed, a forward transcriptional terminator will cause transcription to abort. In prokaryotic systems, terminators usually fall into two categories (1) rho-independent terminators and (2) rho-dependent terminators. Rho-independent terminators are generally composed of palindromic sequence that forms a stem loop rich in G-C base pairs followed by several T bases. Without wishing to be bound by theory, the conventional model of transcriptional termination is that the stem loop causes RNA polymerase to pause, and transcription of the poly-A tail causes the RNA:DNA duplex to unwind and dissociate from RNA polymerase. In eukaryotic systems, the terminator region may comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in some embodiments involving eukaryotes, a terminator may comprise a signal for the cleavage of the RNA. In some embodiments, the terminator signal promotes polyadenylation of the message. The terminator and/or polyadenylation site elements may serve to enhance output nucleic acid levels and/or to minimize read through between nucleic acids. Terminators include any terminator of transcription described herein or known to one of ordinary skill in the art.

Examples of terminators include, without limitation, the termination sequences of genes such as, for example, the bovine growth hormone terminator, and viral termination sequences such as, for example, the SV40 terminator, spy, yejM, secG-leuU, thrLABC, rrnB T1, hisLGDCBHAFI, metZWV, rrnC, xapR, aspA and arcA terminator. In some embodiments, the termination signal may be a sequence that cannot be transcribed or translated, such as those resulting from a sequence truncation.

Selectable Marker

As used herein, a selectable marker is a gene introduced into a cell, especially a bacterium or to cells in culture, that confers a trait suitable for artificial selection. In some embodiments, a selectable marker is a gene that confers resistance to bacteria against an antibiotic, including but not limited to, ampicillin, amphotericin B, carbenicillin, chloramphenicol, erythromycin, kanamycin, gentamycin, neomycin, nystarin, rifampicin, streptomycin, or tetracycline. In some embodiments, a selectable marker is a gene that confers resistance to a drug to eukaryotic cells, including but not limited to puromycin, hygromycin, G418, neomycin, or bleomycin.

Detectable Marker

As used herein, a reporter refers to a protein that can be used to measure gene expression and generally produce a measurable signal such as fluorescence, luminescence or color. The presence of a reporter in a cell or organism is readily observed. For example, fluorescent proteins (e.g., GFP) cause a cell to fluoresce when excited with light of a particular wavelength, luciferases or horseradish peroxidase cause a cell to catalyze a reaction that produces light, and enzymes such as galactosidase convert a substrate to a colored product. Reporters include any reporter described herein or known to one of ordinary skill in the art. In some embodiments, the detectable marker is a fluorescent protein, including, without limitation, eGFP, eYFP, eCFP, mKate2, mCherry, mPlum, mGrape2, mRaspberry, mGrape1, mStrawberry, mTangerine, mBanana, or mHoneydew.

Insulator

An insulator, as defined herein, is a control element which insulates the transcription of genes placed within its range of action. In its natural position, the chromatin insulator element presumably buffers the genes and the regulatory machinery of one domain from the cis-acting influence(s) of the chromatin structure and the regulatory machinery of an adjacent domain. An insulator can be a "pure" insulator from higher eukaryotes, which on its own, does not perturb gene expression, either positively or negatively, and which serves to insulate the expression of a given gene. An insulator can be incorporated into a genetic circuit of the present disclosure to prevent or reduce epigenetic chromatin silencing, and/or to significantly reduce promoter interference between the integrated transgene's promoter and the surrounding endogenous promoters from the integration locus. The insulator of the present disclosure can be cis-acting or trans-acting. In some embodiments, the insulator is a nucleic acid sequence. In some embodiments, the insulator can be the cHS4 sequence (48). In some embodiments of the present disclosure, the presence of insulators in a procedure for integrating multiple genetic circuits into the cell line containing a plurality of landing pads can providing savings in time and facilitate inter-related or compensatory modifications which must be synchronized in time.

Plasmid

A plasmid is a small DNA molecule within a cell that is physically separated from a chromosomal DNA and can replicate independently. They are most commonly found in bacteria as small, circular, double-stranded DNA molecules; however, plasmids are sometimes present in archaea and eukaryotic organisms.

Bacterial Origin of Replication

A bacterial origin of replication herein refers to a bacterial plasmid origin of replication. It is a particular sequence in a genome at which replication is initiated. The specific structure of the origin of replication varies somewhat from species to species, but all share some common characteristics such as high AT content (repeats of adenine and thymine are easier to separate because their base stacking interactions are not as strong as those of guanine and cytosine. The origin of replication binds the pre-replication complex, a protein complex that recognizes, unwinds, and begins to copy DNA. The bacteria origin of replication that may be used in the present disclosure include, without limitation, pBR322 and pUC.

Ligation

Ligation refers to the joining of two nucleic acid fragments through the action of an enzyme, most commonly done using DNA ligase, such as T4 DNA ligase. The ends of DNA fragments are joined together by the formation of phosphodiester bonds between the 3'-hydroxyl of one DNA terminus with the 5'-phosphoryl of another. A co-factor is generally involved in the reaction, and this is usually ATP or NAD+. Factors that affect an enzyme-mediated chemical reaction would naturally affect a ligation reaction, such as the concentration of enzyme and the reactants, as well as the temperature of reaction and the length of time of incubation. Ligation is complicated by the fact that the desired ligation products for most ligation reactions should be between two different DNA molecules and the reaction involves both inter- and intra-molecular reactions, and that an additional annealing step is necessary for efficient ligation.

In some embodiments of the present disclosure, ligation is carried out under conditions that favor intra-molecular ligation, wherein the two ends of one linear DNA molecule joins to form a circularized molecule. The conditions that favor intramolecular ligation comprises, without limitation, using low concentration of linear DNAs and/or carrying out the ligation reaction in the absence of cations or polyamines, and in 6.0% to 10% PEG 6,000 solutions (32).

Restriction Enzyme and Restriction Sites

A restriction enzyme or restriction endonuclease is an enzyme that cuts DNA at or near specific recognition nucleotide sequences known as restriction sites. Restriction enzymes are commonly classified into three types, which differ in their structure and whether they cut their DNA substrate at their recognition site, or if the recognition and cleavage sites are separate from one another. To cut DNA, all restriction enzymes make two incisions, once through each sugar-phosphate backbone (i.e. each strand) of the DNA double helix.

These enzymes are found in bacteria and archaea and provide a defense mechanism against invading viruses. Inside a prokaryote, the restriction enzymes selectively cut up foreign DNA in a process called restriction; meanwhile, host DNA is protected by a modification enzyme (a methyltransferase) that modifies the prokaryotic DNA and blocks cleavage. Together, these two processes form the restriction modification system.

The restriction enzymes that may be used include, without limitation, AatII, MfeI, Acc65I, AccI, MscI, AclI, MspA1I, AatII, MfeI, Acc65I, MluI, AccI, MscI, AclI, MspA1, AfeI, NaeI, AflII, NarI, AgeI, NcoI, ApaI, NdeI, ApaLI, NgoMIV, ApoI, NheI, AscI, NotI, AseI, NruI, AsiSI, NsiI, AvrII, NspI, BamHI, PacI, BclI, PciI, BglII, PmeI, Bme1580I, PmlI, BmtI, PsiI, BsaHI, PspOMI, BsiEI PstI, BsiWI, PvuI, BspEI, PvuII, BspHI, SacI, BsrGI, SacII, BssHII SalI, BstBI, SbfI, BstZ17I, ScaI, BtgI, SfcI, ClaI, SfoO, DraI, SgrAI, EaeI, SmaI, EagI, SmlI, EcoRI, SnaBI, EcoRV, SpeI, FseI, SphI, FspI, SspI, HaeII, StuI, HincII, SwaI, HindIII, XbaI, HpaI, XhoI, KasI, XmaI, and KpnI.

EXAMPLES

Example 1: Expanding the Site-Specific Recombinase Toolbox for Mammalian Synthetic Biology Site-specific recombination systems mediate recombination reactions between two specific DNA sequences termed recombination sites. While most site-specific recombination systems occur in bacteria and their viruses, many of the characterized site-specific recombinases function in heterologous systems, which can be extremely useful to manipulate or engineer their genome via integration, excision or inversion events as demonstrated in many other studies (1-7). To streamline the engineering of mammalian cells, one would benefit from having a programmable recombinase that could be directly targeted to the endogenous sequence of choice in the mammalian genome. This would eliminate the requirement to pre-integrate a natural recombination site. To be useful, the integration reaction would still have to be highly specific and efficient.

Based on amino acid sequence homology, site-specific recombinases fall into one of two mechanistically distinct families: the tyrosine and the serine recombinases(8, 9). The names come from the conserved nucleophilic amino acid residue that they use to attack the DNA, which becomes covalently linked to it during strand exchange.

The better characterized members of the tyrosine recombinase family are the integrases from coliphage I and from prophage lambda (10, 11) which are used either to integrate or excise the phage genome from their bacterial host. The integrase recognize a specific attachment on the phage genome, attP, and its counterpart on the bacterial genome, attB, between which it catalyzes a single DNA crossover (Table 1; SEQ ID NOs: 79-155). The circular phage genome is therefore linearized upon integration and the hybrid attachment sites formed that flank it are called attL and attR (FIG. 1). The integration reaction also requires an accessory protein, the Integration Host Factor (IHF), which is specific to bacteria and helps folding the DNA molecule in the appropriate way for recombination to happen (12). When and only when an additional protein (Xis) is expressed together with Int and IHF, the excision reaction is triggered.

This system ensures that the integration events are directional and therefore not reversible in the absence of the Xis protein.

A major drawback of these systems that limits their use for mammalian genome engineering is the required intervention of the IHF for recombination to occur. IHF is indeed not naturally expressed in mammalian cells and even though scientists have engineered a mammalian version of IHF, the efficiency of both intra- and intermolecular reactions remained extremely low in mammalian cells (13, 1).

Figure 2A:
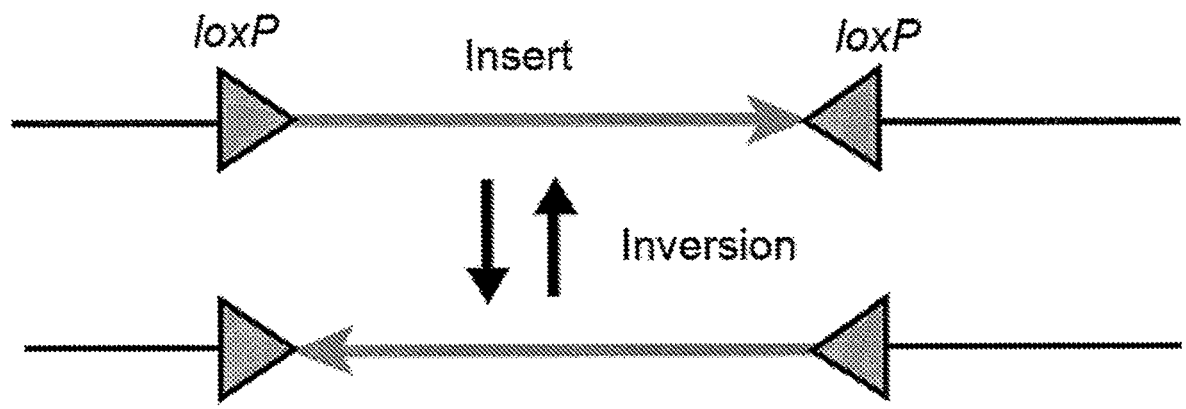
FIGS. 2A-2B show recombination events mediated by Cre recombinase.
Figure 2B:
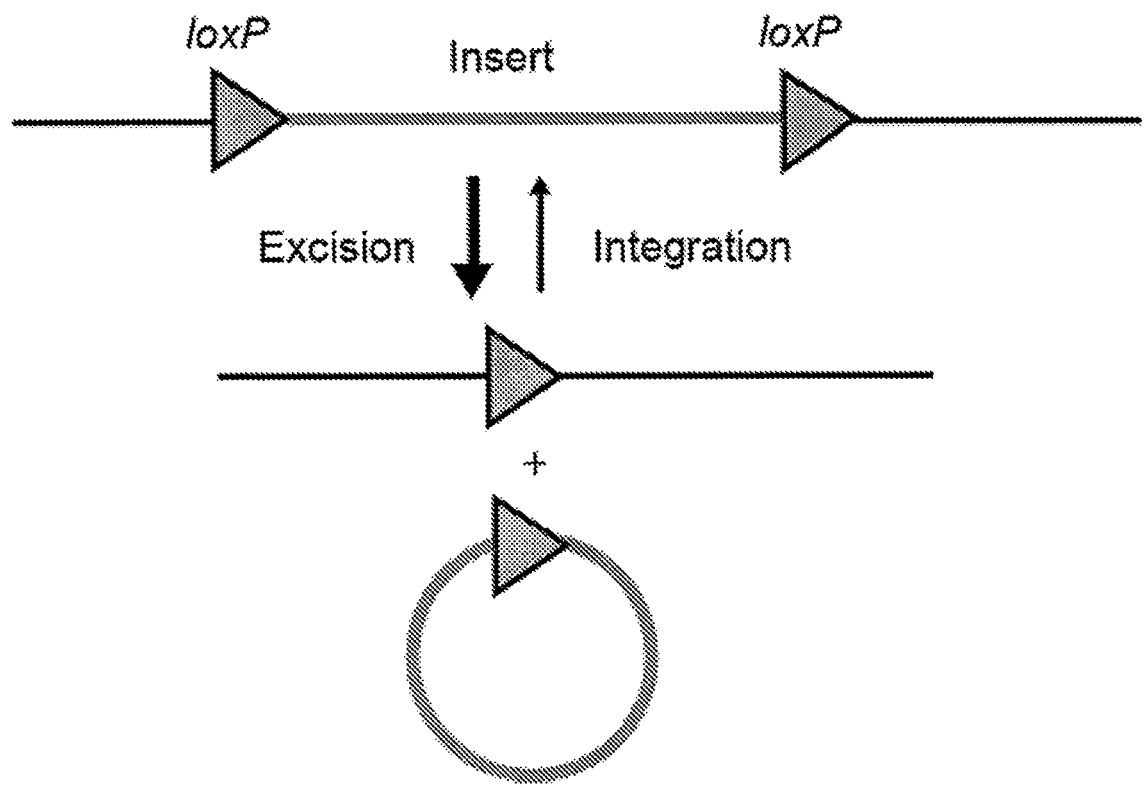

The tyrosine recombinase family also includes many members such as Cre (8), Flp (14,10) and Dre (15, 13) that catalyze non-directional and therefore reversible site-specific recombination reactions between two identical sites of approximately 35 bp in length in the absence of accessory proteins. These recombination systems, in particular the widely used Cre-loxP and Flp-frt, demonstrated highly efficient deletion of DNA located between two directly repeated substrates inserted into the genomes of many higher eukaryotes (16, 17). As the recombination sites are regenerated after Cre-loxP or FLP-frt recombination, efficient and stable integration of DNA is greatly compromised by the tendency of the integrated DNA to immediately excise, therefore favoring the deletion reaction (FIGS. 2A and 2B). To overcome the reversibility of these systems, some recombination with a few base pair mutation sites have been created that prevent results in hybrid recombination sites after the integration events, not recognized anymore by the recombinase (15, 14). Although these tricks improved the integration efficiency of DNA in the genomes of heterologous hosts, it stayed significantly lower than what has been achieved with serine recombinases.

The serine recombinase family is composed of multiple structural groups represented by the resolvase/invertases, the large serine recombinases (Table 1; SEQ ID NOs: 21-78) and the transposases (FIG. 3) (18). They all mediate site-specific recombination reactions with strictly controlled directionality, in the absence of an accessory protein (Xis or recombination directionality factor, RDF), and are therefore of great interest for mammalian genome engineering (19, 15, 18).

In their native contexts, serine resolvases and invertases selectively recombine target sites within the same DNA molecule. Although directional, they are poorly suited for accurate genomic recombination because the recognition motifs of their DNA binding domain (DBD) are short (4-6 bp) and degenerate. Recent studies have demonstrated that the DBD of a serine resolvase can be replaced with a zinc finger protein of higher affinity and specificity (20, 15). This substitution retargets recombination to sequences flanked by zinc finger binding sites (ZFBS). However, these zinc finger-recombinases (RecZFs) retain a second, complementary specificity. The serine catalytic domain indeed imposes its own sequence requirements on the interior of the RecZF target site (20-bp core). Functional RecZF recombination sites must then contain sequences compatible with both the zinc finger DNA-binding protein and recombinase catalytic domain. Even though such hybrid recombinases can offer broader targeting capabilities, their low efficacy for DNA integration is still a bottleneck.

To date, the most efficient, directional and specific recombinases are the large serine recombinases, widely used for DNA integration in mammalian cells (19). The integrases from the Streptomyces temperate phage PhiC31 (21, 20) or from the Mycobacteriophage BxB1(22, 21) were shown to mediate unidirectional and highly specific recombination between relatively small recombination substrates, attP and attB (<50 bp). The domains that compose large serine recombinases are, however, not as modular as with the resolvases. It remains unclear how to retarget these recombinases towards new recombination site sequences. To date, a very limited number of highly efficient large serine recombinases have been characterized. As they have been discovered in phage genomes, it is very probable that they are yet many others to discover given the large diversity of phages that exist on the planet.

The identification and characterization of new large serine recombinases would not only help better understand the relation between their structure and their function and therefore give more insight on how to reprogram them, but it would also expand the current toolbox scientists have at their disposal for the engineering of heterologous hosts genomes and for the manipulation of synthetic genetic circuits.

Figure 4:
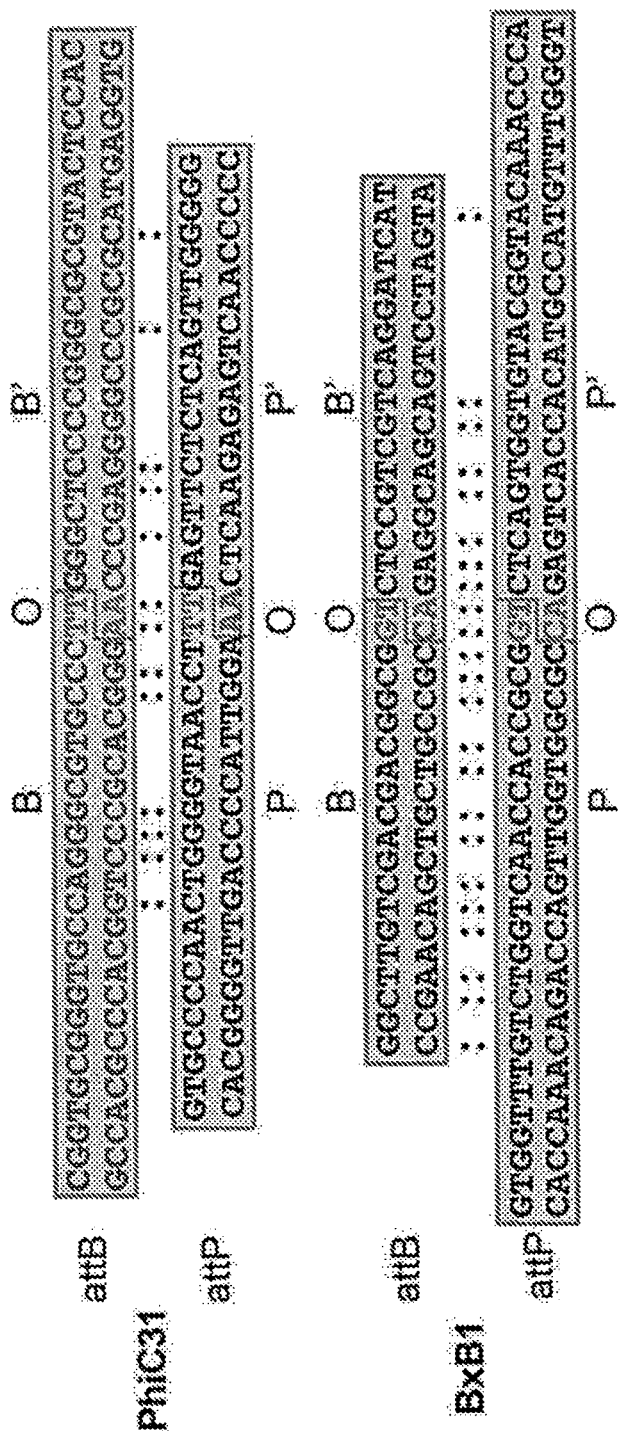
FIG. 4 shows sequences of PhiC31 and BxB1 attachment sites. For each recombinase, the attB and attP attachment sites share a common central dinucleotide sequence (in gray) that is used for the strand exchange reaction during site-specific recombination. This central dinucleotide sequence ensures the directionality of the reaction. Homologies between the sites are shown with dots between the sequences. This figure depicts SEQ ID NOs: 1 through 8 from top to bottom, respectively.

Described here is the discovery of new large serine recombinases from recently sequenced Mycobacteriophages (FIG. 4) and the characterization of their respective attachment sites. After having identified putative large serine recombinase from genome sequences, their function in their natural host, *Mycobacterium smegmatis*, was validated and a plasmid rescue strategy was used to infer their respective attachment sites, which was then validated in *E. coli*. It was then demonstrated that these systems could be used in mammalian cells and libraries of orthogonal site-pairs for each of these recombinases were then created.

Example 2: Identification of Large Serine Recombinases

Among the few large serine recombinases already identified, 3 of them have been discovered from Mycobacteriophage genomes: BxB1 (23, 21), Peaches and BxZ2 (24, 22, 25). BxB1 recombinase has been demonstrated to be the most efficient to integrate DNA into the genome of mammalian cells (19).

Peaches and BxZ2 have yet never been tested in eukaryotic cells. To extend the limited toolbox of large serine recombinases available for the manipulation of mammalian genomes, putative recombinase sequences among the very recently sequenced 400 new Mycobacteriophages genomes, were analyzed (26, 23).

Figure 3:
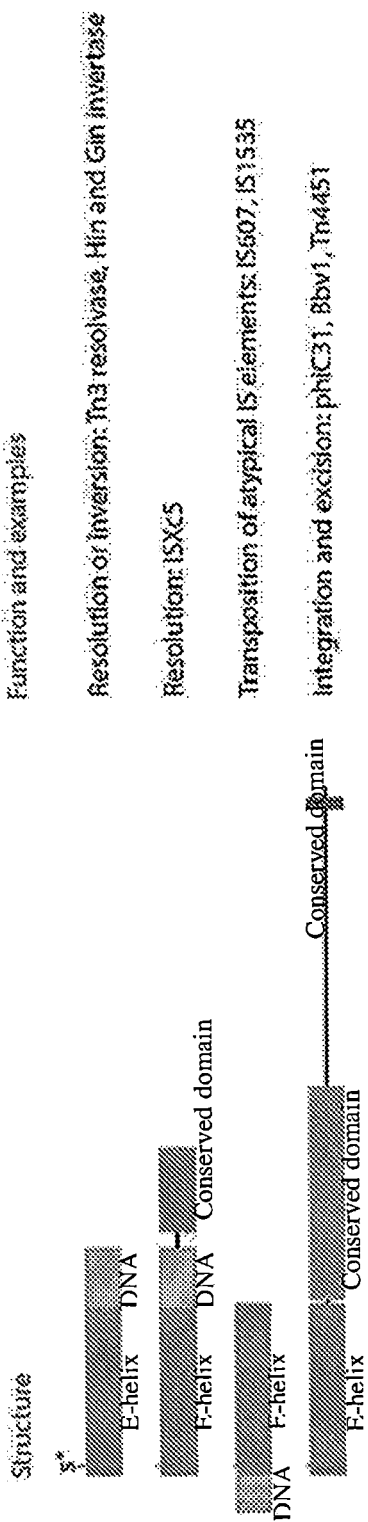
FIG. 3 shows an overview of the structural and functional variation in the serine recombinases. This figure shows the catalytic domain and E-helix, with S* showing the position of the serine nucleophile; the DNA-binding domain containing a recognizable helix-turn-helix (H-T-H) motif, and conserved domains of unknown function found in subsets of recombinases.
Figure 5:
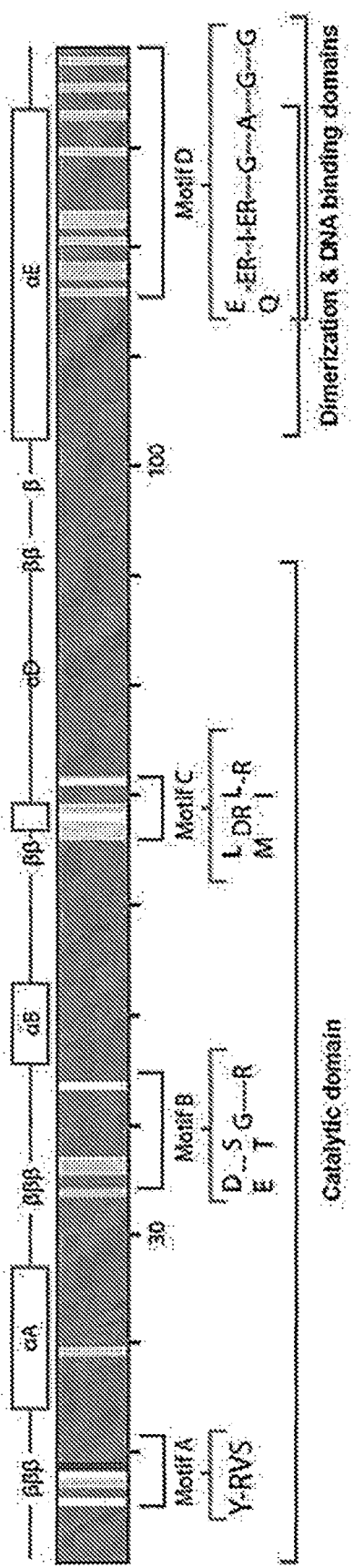
FIG. 5 shows conserved motifs within the catalytic domain and dimerization helix (αE) of large serine recombinases. Motifs A and C contain the critical active site residues of the recombinase. Motif D, contained within the C-terminal portion of the E-helix plus a few residues beyond, is mostly involved with binding the DNA in the region abutting the cleavage site. Motif B forms a rather mobile loop whose function remains unknown despite the remarkable conservation of the Ser-39, Gly-40, and Arg-45 residues. This figure depicts SEQ ID NOs: 156-159 from left to right, respectively.

An algorithm was created to scan through all putative protein sequences from these genomes and extract the ones that contain conserved motifs typical of large serine recombinases. Compared to other serine recombinases, many features and motifs are specific to large serine recombinases (FIG. 3). Not only all known large serine recombinases are constituted of more than 400 amino acids, but they also carry very specific conserved residues in their catalytic and dimerization domains (FIG. 5).

Figure 6:
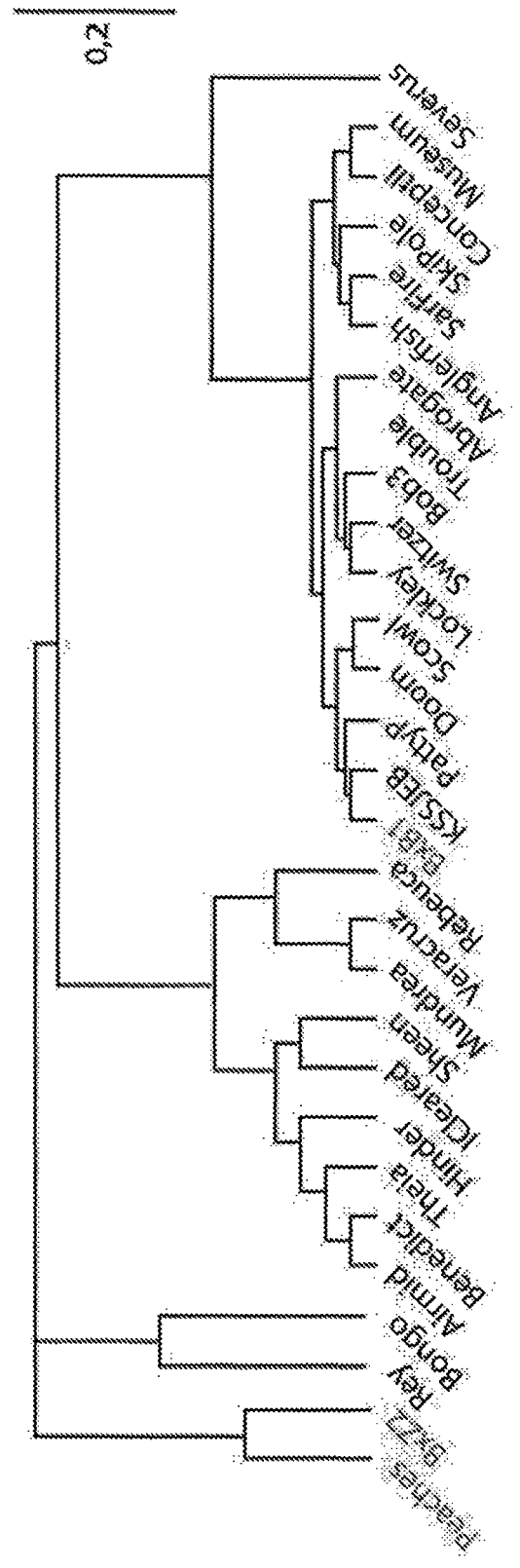
FIG. 6 shows a phylogenic tree of identified large serine recombinase sequences, including the 26 recombinases together with Peaches and BxZ2. The scale bar indicates a difference of 2 amino acids.

Taking into account these specificities, the algorithm identified that 26 genomes carried a large serine recombinase (out of the 400 genomes). The 374 other genomes carried a tyrosine recombinase. By comparing the amino-acid sequences of the 26 identified serine recombinases to the ones of BxB1, Peaches and BxZ2, two new clusters emerged, significantly distant from the Peaches and BxZ2 cluster and the BxB1 cluster (FIG. 6). While none of the 26 recombinases was grouped with Peaches and BxZ2, one third of them shared a high degree of homology with the well-characterized BxB1 recombinase: KSSJEB, PattyP, Doom, Scowl, Lockley, Switzer, Bob3, Trouble, Abrogate, Anglerfish, Sarfire, SkiPole, ConceptII, Museum and Severus. The first new cluster contains both Rey and Bongo recombinases; and the second one contains Airmid, Benedict, Theia, Hinder, ICleared, Sheen, Mundrea, Veracruz and Rebeuca recombinases.

Different amino acid sequences likely result in different tertiary protein structure and therefore different DNA recognition and binding activities.

Example 3: Creation of Integrative Vectors for *Mycobacterium* Species

Figure 7:
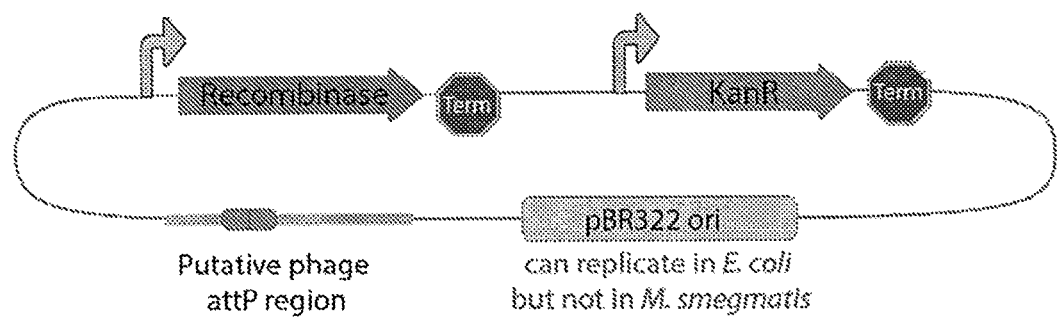
FIG. 7 shows details of the integrative vector architecture. The vector is composed of three main components: the recombinase, the gene cassette encoding the selective marker, and a sequence carrying the attP sequence. The pBR322 ori has been chosen so that the vector can replicate in E. coli but not in M. smegmatis.

When a mycobacteriophage infects *M. smegmatis*, its recombinase is expressed to mediate the integration of the phage genome into the *M. smegmatis* via site-specific recombination between the phage attachment site (attP) and the bacterial chromosomal attachment site (attB). Therefore, in order to validate the integration capacity of the 26 putative recombinases identified with the algorithm, a synthetic vector was created mimicking the mycobacteriophage genome and designed in a way such that integration events could be easily monitored (FIG. 7).

This vector carried three essential components: an attP site, a gene cassette to constitutively express the recombinase and a selection marker to enable selection of integrants. While it is almost impossible to predict the exact sequence of the attP site, it is however possible to predict its approximate location on the phage genome. When looking into phage biology, it appears that the attP site is most often located close to the start codon of the recombinase coding sequence. This evolutionary strategy allows the recombinase expression to be under the control of bacterial promoter once the phage has integrated into its host genome. Because the physical DNA of the 26 mycobacteriophages identified for the presence of a large serine recombinase was not available, the DNA region that was potentially carrying the attP site was synthesized (from 750 bp before to 50 bp after the start codon of the putative recombinase).

For the recombinase cassette, the Golden Gate assembly method was used to assemble the strong Hsp70 constitutive promoter together with a codon-optimized coding sequence of the recombinase followed by an efficient transcription terminator. Again, the coding sequence of the recombinase was synthesized given that the physical DNA of the corresponding phage was not available. The coding sequence was codon-optimized for an efficient expression in mammalian cells since the end goal was to test these recombinases in mammalian cells.

To be able to screen for integration events of the synthetic vector into the chromosome of *M. smegmatis*, a selection marker was added constitutively expressed both in *E. coli* and *M. smegmatis*.

Finally, the origin of replication pBR322 was used to allow for efficient replication of the plasmid in *E. coli* for cloning purpose. However, pBR322 cannot be replicated in *M. smegmatis*.

Figure 8:
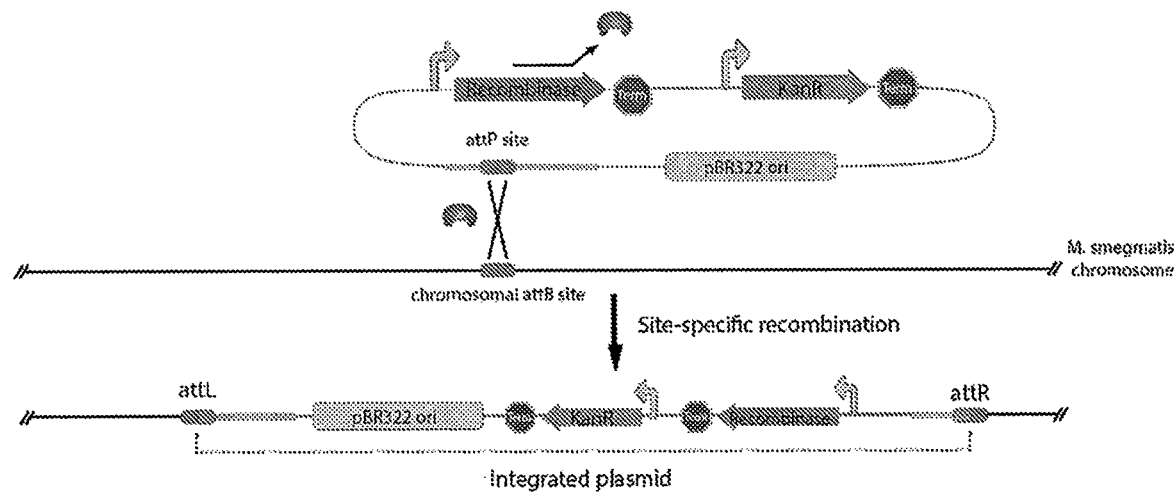
FIG. 8 shows the integration of the integrative vector into M. smegmatis genome. After transformation of the integrative vector in M. smegmatis, the putative serine recombinase is expressed and mediates site-specific recombination between the attP site located on the integrative vector and its counterpart, the attB site on the M. smegmatis genome, resulting in the linearization of the integrative vector and its stable integration into the genome of M. smegmatis, which then becomes resistant to Kanamycin.

Due to this specificity, transformation of *M. smegmatis* with the integrative vector would result in resistant cells only if the expressed recombinase would mediate site-specific recombination between the plasmidic attP and the chromosomal endogenous attB (FIG. 8). This would indeed lead to the stable integration of the vector and therefore to the stable expression of the resistance marker. If the vector cannot self-integrate into *M. smegmatis* genome (either because the recombinase is not functional or because the attP sequence is not present on the vector), then the non-replicative vector would be diluted among the population of cell.

Example 4: Transformation of *M. smegmatis* with the Integrative Vectors

Each of the 27 integrative vectors (26 new recombinases+ BxB1 as a positive control) was transformed in wild type *M. smegmatis* and plated the transformed bacteria on a selective media. Out of the 27 integrative vectors tested, 23 led to the growth of resistant clones, which were then picked 4 days after transformation and expanded for further testing.

Figure 9:
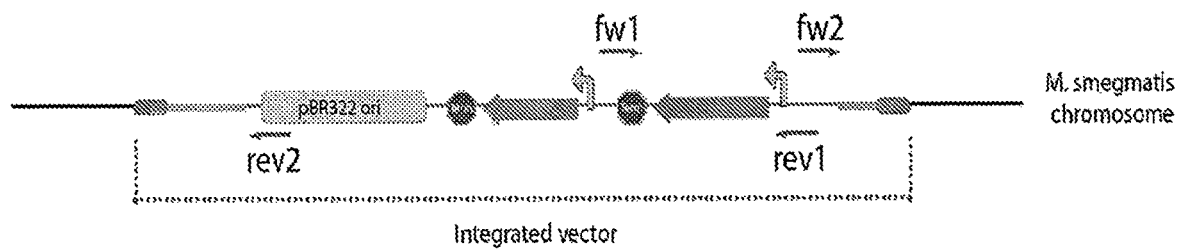
FIG. 9 shows the representation of the primers used to check chromosomal integration of the vector. Fw1 and rev1 primer pair was used to confirm the presence of the Kanamycin resistance gene. Fw2 and rev2 primer pair was used to confirm that integration of the vector mediated by site-specific recombination occurred at an attP site within the predicted attP region sequence carried by the vector.

To confirm the stable integration of the vector into the chromosome of the resistant clones, their chromosomal DNA was extracted and a PCR was performed with primers flanking the resistance cassette (FIG. 9). The PCRs were positive for each of the 3 clones picked for the 23 functional recombinases.

To verify that stable integration into the chromosome was the result of the plasmid linearization via site-specific recombination from a sequence carried by the putative attP region on the plasmid, this attP region with primers flanking the sequence carried by the original integration vector was amplified. While the amplification worked on all 23 integration vectors, it did not work when using the extracted chromosomal DNA as a template.

These first results were encouraging as they meant that both the identified recombinases were functional and that the attP sequences were indeed located in the phage genome region predicted, somewhere close to the start codon of these recombinases.

Example 5: Identification of the Integration Site in *M. smegmatis* Genome

The plasmid rescue method was used to discover the exact location of the insertion site of the integrative vector in the *M. smegmatis* genome (FIG. 11). This method allowed for the identification of the genomic sequences flanking the integrative vectors insertion site.

First, the extracted genomic DNA was digested from the resistant clones with EcoRI restriction enzyme. This restriction digest reaction would normally result in 1199 independent fragments. However, only one EcoRI site was intentionally inserted in the integrative vector sequence, in between the putative attP region and the recombinase cassette. Restriction digest of the genomic DNA from the resistant clones would therefore result in 1200 independent fragments.

All the fragments were ligated together and *E. coli* were transformed with the reaction mix and plated on selective media. While the majority of the ligation products would not be able to replicate in *E. coli*, this method allows the ligated fragment that contains both the resistance gene cassette and the origin of replication from the integrative vector to replicate in *E. coli*, conferring the resistance to Kanamycin in the bacteria. Because the integrative vector contained a single EcoRI restriction site, the recircularized product also contains some chromosomal sequences from *M. smegmatis* flanking the insertion site.

Therefore, the resistant clones that grew on selective media were expanded, miniprepped and the extracted vectors sequenced. The sequencing results unveiled the sequence flanking the insertion site and allowed for the inference of the sequence of the attB site.

Out of the 23 putative recombinases tested, 15 of them integrated into the same genomic attB site as BxB1 (groEL CDS), two integrated in the TmrH RNA methyltransferase CDS (Rebeuca and Veracruz) and two others integrated in the 2-nitropropane dioxygenase CDS (FIG. 12). No information concerning the importance of these genes in the growth regulation or metabolism of *M. smegmatis* was found. However, the resistant clones that were expanded to prepare the plasmid-rescue workflow grew at a normal rate and with a normal phenotype.

Based on the sequencing results, the point of strand exchange of the site-specific recombination reaction was deduced and then the approximate attB and attP sites sequences were predicted.

For the recombinases that integrated into the groEL CDS, the attP and attB sites were total homologs to the one recognized by BxB1 recombinase.

Although integration happens in the same attB site for Rebeuca and Veracruz, the attP site recognized by Rebeuca is slightly different from the attP site recognized by Veracruz (FIG. 13). This case is actually similar for Theia and Benedict recombinases and such differences had already been observed with the BxZ2/Peaches pair (22).

Example 6: Validation of Functional attB/attP Recombination Sites

To verify that the predicted attP and attB sites were correct and could be recombined by their putative large serine recombinase in a heterologous host, a reporter system to monitor recombination events between the predicted att sites in *E. coli* was created (FIG. 14). The reporter system consists of a plasmid carrying 1) the predicted attB sequence followed by 2) a lacZ gene cassette followed by 3) the predicted attP sequence, 4) a gene cassette expressing the recombinase and 5) a gene cassette expressing a resistance marker. After transformation in *E. coli* cells, the expressed recombinase would mediate the excision of the LacZ cassette after the recognition and site-specific recombination between the predicted attP and attB sites. Efficient recombination between attP and attB sites would result in the development of white colonies (LacZ negative) in an Xgal screen. If the sites were not correct, recombination could not allow for the excision of the lacZ cassette and the colonies would be blue (LacZ positive).

The vectors in E. coli were transformed, plated on selective media and incubated the plates overnight. Given that pBR322 is a relatively low copy plasmid, excision of the lacZ gene from all the copies within a cell should be achieved relatively rapidly. Blue or white colonies were screened for the next morning and for all 4 recombinase, more than 99% of the obtained resistant clones were LacZ negative, validating the exactitude of the attP and attB sites.

To further validate that the non-expression of LacZ was due to the excision of the LacZ cassette and not a consequence of instability of the construct, the plasmids miniprepped from white clones were sequenced. The results were positive as the sequencing showed the presence of the expected deletion and the attL site created by site-specific recombination between attB and attP site.

In some embodiments the exact minimal sequence required for the att sites to enable site-specific recombination is performed. In some embodiments, a library of att sites is synthesized with different lengths and the experiment described above is then repeated. In some embodiments, when the att site tested is be too short, resistant clones should all express the LacZ gene even after an extended period of time.

Example 7: Assessment of Intermolecular Recombination

Because both the activity of these recombinases for intramolecular site-specific recombination in E. coli and the correct sequences of their attB and attP sites were confirmed, further testing was performed to confirm whether they could also be used for the manipulation of DNA sequences in mammalian cells. Therefore, a reporter system was created based on two separate plasmids to test their intermolecular site-specific recombination capacity in mammalian cells (FIG. 15). The first plasmid carried a gene cassette allowing the constitutive expression of EYFP. The attB site was placed in between the Hef1a constitutive promoter and the EYFP coding sequence. The second plasmid carried a promoter-less gene cassette composed of the attP site followed by the mKate2 coding sequence. When co-transfecting these two plasmids together with a plasmid expressing the corresponding recombinase, intermolecular site-specific recombination between the attB and the attP sites would result in the fusion of the two plasmids and therefore in the insertion of the promoterless mKate2 coding sequence in frame with the Hef1a promoter. This recombination event would therefore trigger the constitutive expression of mKate2 and interrupt the expression of EYFP as it becomes promoterless.

These two plasmids were con-transfected together with a third plasmid to express the recombinase and assessed the intermolecular recombination events based on the fluorescence output. If the recombinase mediates site-specification recombination between the separated attB and attP sites, the two plasmids fuse together and the mKate2 coding sequence is placed just after the Hef1a promoter while the EYFP coding sequence becomes promoterless.

Figure 16A:
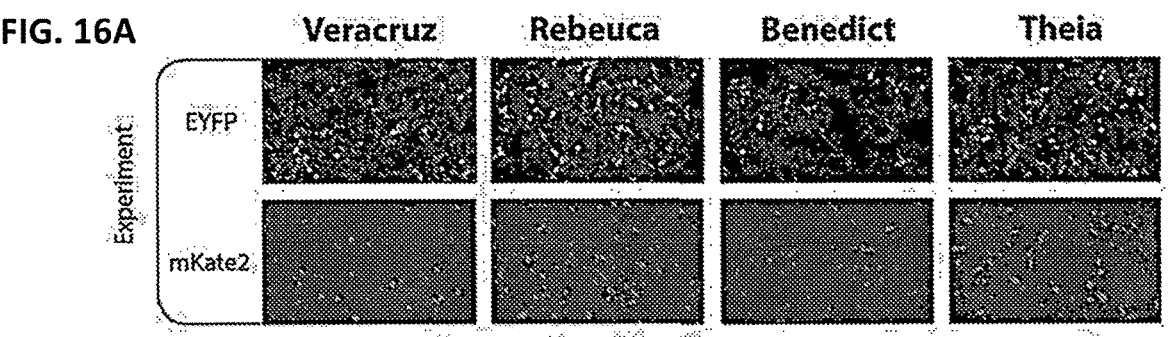
FIGS. 16A-16B show fluorescent microscopy images of mammalian cells 36 h after transfection of the intermolecular site-specific recombination reporter system.
Figure 16B:
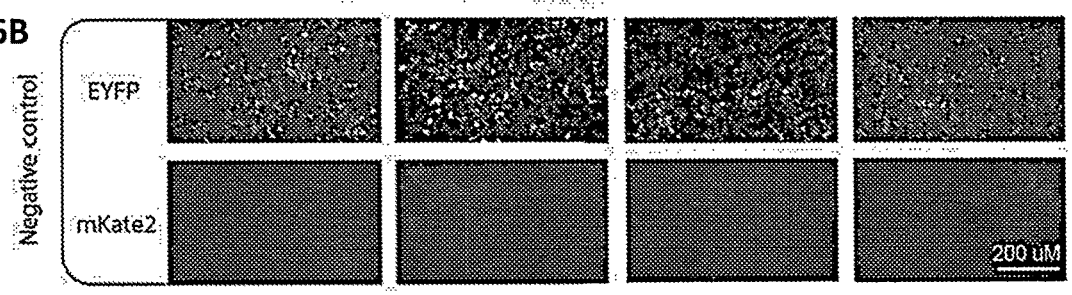

As depicted in FIG. 16, the 4 new recombinases could mediate intermolecular recombination in mammalian cells.

Example 8: Assessment of Recombination Crosstalk

To test whether these recombinases were orthogonal to each other, i.e. could only mediate site specific recombination between their own attB and attP sites identified in previous experiments, each of the recombinase expression vectors were co-transfected with the reporter systems corresponding to all recombinases. The recombinases that had different attB sites were completely orthogonal to each other (no mKate2 expression). However, the recombinases, which shared the same attB but a different attP site, could mediate site-specific recombination using both attP sites (significant mKate2 expression). The results are summarized in FIG. 17.

Example 9: Creation of a Library of Orthogonal Sites

The nonpalindromic central dinucleotide at the center of attP and attB sites is the sole determinant of the prophage orientation (27), and a single base pair substitution in the two sites inhibits recombination. However, when identical central dinucleotide mutations are in both attP and attB partners, recombination is restored, as demonstrated for BxB1 and PhiC31 in bacterial cells (27, 28). Moreover, for the directionality of the reaction to be retained, these two central dinucleotides have to be non-palindromic.

Based on these requirements, 6 different variants of the central dinucleotide sequence were synthesized for each attP and attB partners that were non-palindromic and tested against each other in transient transfections to see whether they were orthogonal in mammalian cells.

Figures 17, 18:
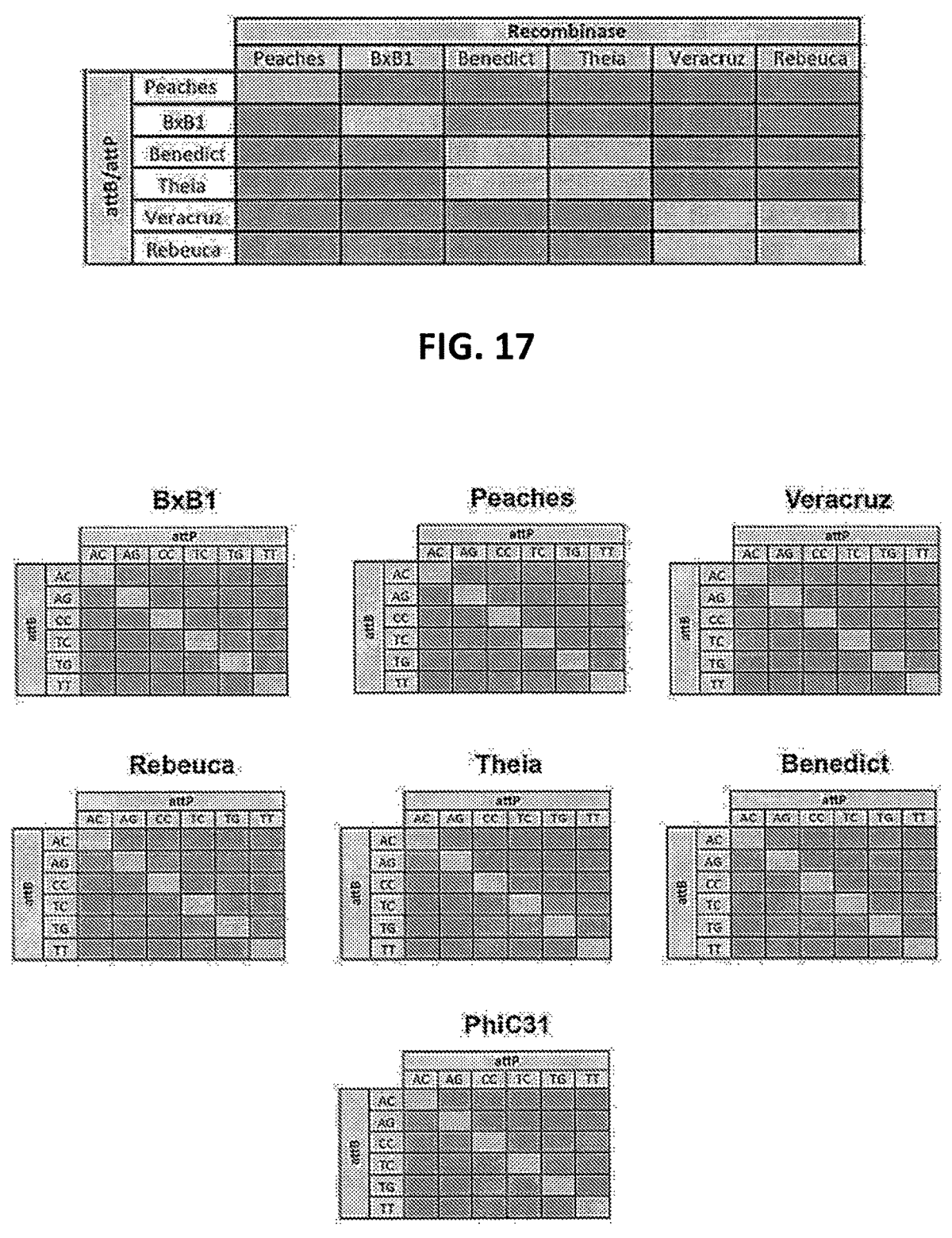

As predicted, only attP and attB that shared the exact same central dinucleotide sequence could recombine for all 7 recombinases tested (i.e. 42 orthogonal sites) (FIG. 18).

For this purpose, a stable cell line with two landing pads was created, each one carrying one BxB1 attB site orthogonal to the other. The integration of a circuit in the landing pad of choice depending on the attP site carried by the integrative circuits was then performed (results not shown).

Example 10: Streamlined Identification of attP/attB Sites

A deeper analysis of these sites could help shorten the pace of att site identification by skipping the required experiments in the natural host M. smegmatis. Indeed, all these sites share common features such as 6 to 8 base pair homologies between attB and attP sites core sequence and numerous inverted repeats in the flanking sequences. It could therefore become useful to develop an algorithm to 1) itemize all possible large serine recombinases within sequenced mycobacteriophage genomes, 2) itemize all putative attP sites within 200 bp flanking the start codon of these recombinases, 3) scan mycobacterium genomes to itemize all putative attB sites sharing an homologous core sequence flanked by numerous inverted repeats.

Example 11: Multiplexed Integration of Genetic Circuits

While intramolecular site-specific recombination has proven useful for excision of constructs integrated in mammalian genomes, intermolecular site-specific recombination can be used to integrate complex circuits into mammalian chromosomes. The ability to multiplex integrations by using orthogonal sites could help to integrate a variety of different circuits at different locations within a genome. This could be very helpful to prevent interference between circuits or attain higher levels of expression (with a lower coefficient of variation) by integrating the same construct in multiple copies. This could also allow engineering cell lines step by step, integrating one circuit after the other so as to incrementally increase the complexity.

To integrate multiple genetic circuits into mammalian genome, multiple landing pads containing attB sites orthogonal to the corresponding large serine recombinase are integrated first. Each genetic circuit to be integrated is provided on a integrative vector, together with a unique attP site that only recombines with one landing pad in the mammalian genome, allowing specific integration of each genetic circuit into its desired target location. The multiple genetic circuits may be inserted into a central location in a mammalian genome or into different locations in a mammalian genome. The multiple genetic circuits can also be integrated sequentially or simultaneously to the endogenous sequences of choice in the mammalian genome.

Example 12: New DNA Assembly Methods

The use of multiple serine recombinases with orthogonal sites could also lead to the development of new DNA assembly methods. Based on the Gateway principle, a system may be created flanking each DNA fragment to be assembled with either an attB on its 5' end and an attP on its 3'. Having 6 orthogonal sites for one recombinase would allow assembling 5 parts per reaction, i.e. enough for a mammalian transcription unit. The assembled vectors could carry sites from another recombinase, and following the same principle, could be used to assemble 5 transcription units together. Such strategy could be used to assemble even larger constructs with 6 orthogonal recombinases. As site-specific recombination with serine recombinases is extremely efficient, fast and reliable, such an assembly method would be extremely convenient.

Materials and Methods

In-Silico Identification of Large Serine Recombinases

Scripts were written and run with Matlab2013a.

Expression Units and Plasmids Assembly

All expression units and plasmids were assembled with the Golden Gate framework and are listed in the Annexes. For all Golden Gate assembly reactions, used were: 0.4 µl of Type IIS enzyme (either BsaI from NEB, or BpiI from Fermentas), 0.2 µl of T4 Ligase HC+1 µl of T4 Ligase HC buffer (Promega), 1 µl of 10×BSA (NEB), 40 fmol for all vectors used in the reaction, ddH20 up to a final total volume of 10 µl. The thermocycler program used for all assemblies included: 1 step of 15 min at 37° C.; then 50 cycles of [2 min at 37° C. followed by 5 min at 16° C.]; 1 step of 15 min at 37° C., 1 step of 5 min at 50° C. and 1 final step of 5 min at 80° C.

Bacterial Cell Cultures

Liquid cultures of *E. coli* MG1655 were grown in LB Medium (Difco) at 37° C. When appropriate, antibiotics were added as follows: spectinomycin (100 µg/mL), ampicillin (100 µg/mL) and kanamycin (25 µg/mL). For blue/white screening, we used X-gal at a final concentration of 40 µg/mL.

For liquid cultures, *M. smegmatis* was grown in Difco 7H9 liquid medium supplemented with 0.5% glycerol, 0.5% Tween 80 and 10% albumin-dextrose complex (ADC). Carbenicillin and cycloheximide were added to all cultures at concentrations of 50 mg ml-1 and 10 mg ml-1 respectively. When necessary, the following antibiotics were also added; kanamycin (8 mg ml-1), Hygromycin (50 mg ml-1) and tetracycline (0.5 mg ml-1). For solid cultures, *M. smegmatis* was grown on Difco 7H10 agar supplemented with 0.5% glycerol and 10% ADC.

Mammalian Cell Culture and Transfections

HEK293FT cell line was purchased from Invitrogen. HEK293FT cells were maintained in Dulbecco's modified Eagle medium (DMEM, Cellgro) supplemented with 10% FBS (PAA), 0.045 g/mL penicillin/streptomycin and non-essential amino acids (HyClone) at 37° C., 100% humidity and 5% CO2. HEK293FT transfections were carried out in 24-well plates using Attractene reagent (Qiagen), 200000 cells and 200-300 ng total DNA per well (plasmid ratio 1:1:1). Media was changed 24 hours after transfection.

Microscope Measurements and Image Processing

Fluorescence microscopy images of live cells were taken in glass-bottom dishes or 12-well plates using Zeiss Axiovert 200 microscope and Plan-Neofluar 10×/0.30 Ph1 objective. The imaging settings for the fluorophores were S430/25x (excitation) and S470/30m (emission) filters for EYFP, and S565/25x (excitation) and S650/70m (emission) for mKate2. Data collection and processing were performed using AxioVision software (Zeiss).

TABLE 1

Amino-acid and Nucleotide Sequences

| SEQ ID NO: | Species | Sequence |
|---|---|---|
| 21 | Abrogate | MRALVVIRLSRVTDATTSPERQLESCQQLCAQRGWDVVGVAEDLDVSGAVD<br>PFDRRRRPNLARWLAFEEQPFDVIVAYRVDRLTRSIRHLQQLVHWAEDHKKL<br>VVSATEAHFDTTTPFAAVVIALMGTVAQMELEAIKERNRSAAHFNIRAGKYRG<br>SLPPWGYLPTRVDGEWRLVPDPVQRERILEVYHRVVDNHEPLHLVAHDLNRR<br>GVLSPKDYFAKLQGREPRGREWSATALKRSLISEAMLGYATLNGKTVRDDDG<br>APLVRAEPILTREQLEALRAELVKTDRAKPSVSTPSMLLRVLFCAVCGEPAYKFT<br>GGGRKNARYRCRSWGWAQRCGNGTVAMAEWDSFCEEQVLDLLGDSERLE<br>KVWVAGSDSAVELAEVNAELVDLTSLIGSPAYRAGSPQREALDARIAALAARQ<br>EELEGLEARPSGWEWRETGQRFGDWWREQDTAGKNTWLRSMNVRLTFDV<br>RGGLTRTIDFGDLQEYEQHLRLGSVVERLHAGMS |
| 22 | Abrogate | ATGAGAGCACTGGTAGTGATCCGACTGTCCCGCGTCACCGATGCTACGACT<br>TCACCGGAGCGCCAGCTGGAGTCTTGCCAGCAGCTCTGCGCCCAGCGCGG<br>GTGGGACGTCGTCGGGGTAGCAGAGGATCTGGACGTCTCCGGAGCAGTC<br>GATCCGTTCGACCGGAGGCGCAGACCGAACCTGGCCCGGTGGCTAGCGTT<br>CGAGGAGCAACCGTTCGACGTGATCGTGGCGTACCGGGTAGACCGGCTGA<br>CCCGATCAATCCGGCATCTGCAGCAGCTGGTCCACTGGGCCGAGGACCAC<br>AAGAAGCTGGTCGTCTCCGCGACCGAAGCGCACTTCGACACGACAACGCC<br>GTTCGCGGCGGTCGTCATCGCGCTTATGGGAACGGTGGCGCAGATGGAAT |

TABLE 1-continued

Amino-acid and Nucleotide Sequences

| SEQ ID NO: | Species | Sequence |
|---|---|---|
| | | TAGAAGCGATCAAAGAGCGGAACCGATCGGCGGCGCATTTCAATATCCGC<br>GCCGGTAAATACCGAGGTTCCCTGCCGCCGTGGGGTTACCTGCCTACGCGC<br>GTGGACGGGGAGTGGCGGCTGGTGCCGGACCCGGTGCAGCGAGAGCGC<br>ATCCTCGAGGTGTATCACCGCGTCGTCGACAACCACGAGCCGCTGCACCTG<br>GTGGCACACGACCTGAACCGGCGTGGTGTCCTGTCGCCTAAGGACTACTTC<br>GCAAAGCTGCAAGGTCGGGAGCCGCGGGGCCGGGAGTGGTCGGCTACCG<br>CGCTGAAGCGCTCGCTGATCTCCGAGGCGATGCTCGGGTACGCGACTCTG<br>AACGGTAAGACCGTCCGAGACGACGACGGAGCTCCGCTGGTGCGGGCTG<br>AGCCGATCCTGACCCGTGAGCAGCTGGAGGCGCTGCGCGCCGAGCTCGTC<br>AAGACCGACCGGGCAAAGCCATCGGTGTCGACTCCGTCGATGTTGCTGCG<br>GGTGTTGTTCTGCGCAGTGTGCGGGGAGCCCGCATACAAGTTCACCGGGG<br>GCGGTAGGAAGAACGCACGATACCGCTGCCGGTCGTGGGGCTGGGCACA<br>GCGGTGCGGCAACGGCACGGTCGCAATGGCAGAGTGGGACTCGTTCTGC<br>GAGGAGCAGGTGCTGGATCTGCTCGGGGACTCGGAGCGCCTGGAGAAAG<br>TCTGGGTAGCAGGCTCGGACTCCGCAGTCGAACTCGCGGAGGTGAACGCG<br>GAGCTGGTGGACCTGACGTCGCTGATCGGCTCCCCGGCCTACCGGGCCGG<br>TTCTCCGCAGCGCGAAGCGCTGGATGCTCGTATTGCGGCGCTGGCAGCAC<br>GGCAGGAGGAGCTGGAGGGTCTAGAGGCACGCCCGTCGGGTTGGGAGTG<br>GCGCGAGACTGGGCAGCGGTTCGGGGACTGGTGGCGGGAGCAGGACACC<br>GCGGGTAAGAACACCTGGCTTCGGTCGATGAACGTTCGGCTGACGTTCGA<br>CGTCCGCGGCGGGCTGACTCGCACGATCGACTTCGGGGATCTGCAGGAGT<br>ACGAGCAGCACCTCAGGCTCGGCAGCGTGGTCGAACGACTACACGCCGGG<br>ATGTCGTAG |
| 23 | Airmid | MRVLGRIRLSRVMEESTSVERQREIIETWARQNDHEIIGWAEDLDVSGSVDPF<br>ETPALGPWLTDHRKHEWDILVAWKLDRLSRRAIPMNKLFGWVMENDKTLVC<br>VSENLDLSTWIGRMIANVIAGVAEGELEARERTKGSQKKLRELGRWGGGKPY<br>YGYRAQEREDAAGWELVPDEHASKVLLSIIEKVLEGQSTESIARELNERGELSPS<br>DYLRHRAGKPTRGGKWSNAHIRQQLRSKTLLGYSTHNGETIRDERGIAVRKGP<br>ALVSQDVFDRLQAALDSRSFKVTNRSAKASPLLGVLVCRVCERPMHLRQHHN<br>KKRGKTYRYYQCVGGVEKTHPANLTNADQMEQLVEESFLAELGDRKIQERVYI<br>PAESHRAELDEAVRAVEEITPLLGTVTSDTMRKRLLDQLSALDARISELEKLPES<br>EARWEYREGDETYAEAWNRGDAEARRQLLLKSGITAAAEMKGREARVNPGV<br>LHFDLRIPEDILERMSA |
| 24 | Airmid | ATGCGAGTTCTTGGAAGAATACGACTCTCGCGGGTCATGGAGGAAT<br>CGACATCGGTCGAGAGGCAGCGAGAGATATCGAGACGTGGGCGC<br>GTCAGAACGACCACGAGATCATCGGCTGGGCTGAGGACCTCGACGT<br>GTCTGGATCGGTCGATCCGTTCGAGACGCCAGCCTTGGGTCCGTGG<br>CTTACCGACCACCGGAAGCACGAGTGGGACATCCTCGTGGCATGGA<br>AGCTCGACCGGCTGTCCAGGCGAGCTATCCCGATGAACAAACTCTTC<br>GGCTGGGTCATGGAGAACGACAAGACCCTCGTCTGCGTGTCGGAGA<br>ATCTGGACCTGTCGACGTGGATCGGTCGGATGATCGCCAACGTCATC<br>GCTGGCGTGGCAGAAGGTGAGTTGGAGGCGATACGAGAGAGGACC<br>AAGGGCTCTCAGAAGAAGCTACGTGAGCTTGGCCGCTGGGGAGGA<br>GGCAAGCCCTATTACGGCTACCGCGCGAAGAGCGTGAGGACGCTG<br>CTGGGTGGGAGCTGGTGCCTGACGAGCACGCCTCGAAGGTCCTGCT<br>CTCGATCATCGAGAAGGTCCTCGAAGGGCAGTCGACGGAGTCGATA<br>GCTCGTGAGCTGAACGAGAGGGAGAGCTGTCCCCGTCTGACTACC<br>TTCGGCACAGGGCTGGTAAGCCGACCAGAGGCGGTAAGTGGAGCA<br>ACGCGCACATCCGTCAGCAGCTCCGCTCCAAGACTCTCCTGGGTTAC<br>TCCACGCATAACGGCGAAACCATCCGAGACGAGCGGGGGATCGCG<br>GTACGCAAAGGGCCGGCGCTGGTTTCCCAGGACGTGTTCGACCGCC<br>TCCAGGCGGCGCTTGATTCTCGATCCTTCAAGGTGACGAACAGGTCA<br>GCGAAAGCGTCGCCGTTGCTCGGCGTCCTCGTCTGCCGGGTGTGCG<br>AACGACCGATGCACCTGCGTCAGCACCACAACAAGAAGCGCGGCAA<br>GACCTACCGCTACTACCAGTGCGTGGGCGGTGTTGAAAAGACCCAC<br>CCTGCCAATCTCACCAACGCCGATCAGATGGAGCAGTTGGTCGAAG<br>AGTCCTTCCTTGCTGAACTCGGTGACCGGAAGATCCAAGAGAGGGT<br>TTACATCCCTGCGGAGTCACATCGAGCCGAGTTGGACGAGGCTGTA<br>CGGGCCGTTGAGGAGATAACCCCTCTGCTGGGCACCGTCACGTCGG<br>ACACCATGCGAAAGCGTCTCCTGGATCAGCTGAGCGCGTTAGATGC<br>TCGTATCTCCGAGCTGGAGAAGCTGCCCGAGTCCGAAGCTCGGTGG<br>GAGTACCGAGAAGGCGACGAAACCTACGCCGAGGCGTGGAACCGG<br>GGTGACGCGGAAGCCCGTCGACAGCTCCTGCTCAAGTCGGGGATCA<br>CGGCGGCTGCTGAGATGAAGGGCAGAGAGGCCCGAGTCAACCCGG<br>GGGTCTTACACTTCGACCTACGAATACCGGAGGACATCTTAGAAAG<br>GATGAGCGCGTGA |
| 25 | Anglerfish | MRALVVIRLSRVTDATTSPERQLESCRQLCAQRGWEVVGVAEDLDVSGAVDP<br>FDRKRRPNLARWLAFEEQPFDVIVAYRVDRLTRSIRHLQQLVHWAEDHKKLV<br>VSATEAHFDTTTPFAAVVIALMGTVAQMELESIKERNRSAAHFNIRAGKYRGS<br>LPPWGYLPTRVDGEWRLVPDPVQRERILEVYHRVVDNHEPLHLVAHDLNRR<br>GVLSPKDYFAKLQGREPQGRAWSATALKRSLISEAMLGYTTLNGKTVRDDDG |

TABLE 1-continued

Amino-acid and Nucleotide Sequences

| SEQ ID NO: | Species | Sequence |
|---|---|---|
| | | APLVRAEPILTREQLEALRAELVKTDRTKPAVSTPSLLLRVLFCAVCGEPAYKFD<br>AGRKIPRYRCRSFGFAQRCGNGTIPIAEWDAFCEEQVLDLLGDSERLEKVWVA<br>GSDSAVELAEVNAELVDLTSLIGSPAYRVGSPQREALDARIAALAARQEELEGL<br>EARPSGWEWRETGQRFGDWWRDQDTAGKNTWLRSMNVRLTFDVRGGLT<br>RTIDFGDLQEYEQHLRLGSALDLVNAEKPPTGR |
| 26 | Anglerfish | ATGAGAGCACTGGTAGTGATCCGACTGTCCCGCGTCACCGATGCTACGACC<br>TCCCCGGAGCGTCAGCTGGAGTCTTGCCGGCAGCTCTGCGCCCAGCGCGG<br>CTGGGAGGTGGTCGGGGTAGCAGAGGATCTGGACGTCTCCGGAGCAGTC<br>GATCCGTTCGACCGGAAGCGCAGACCGAACCTGGCCCGGTGGCTAGCGTT<br>CGAGGAGCAACCGTTCGACGTGATCGTGGCGTACCGGGTAGACCGACTGA<br>CCCGATCGATCCGTCATCTGCAGCAGCTGGTCCACTGGGCCGAGGACCAC<br>AAGAAGCTGGTCGTTTCCGCGACCGAAGCCCACTTCGATACGACGACGCC<br>GTTCGCGGCGGTCGTCATCGCGCTTATGGGAACTGTGGCGCAGATGGAAT<br>TAGAATCGATCAAAGAGCGGAACCGATCGGCGGCGCATTTCAATATCCGC<br>GCCGGTAAATACCGCGGTTCCCTGCCGCCGTGGGGCTACCTGCCCACGCG<br>CGTGGACGGGGAGTGGAGGCTGGTGCCTGACCCGGTGCAGCGCGAGCGC<br>ATCCTCGAGGTGTATCACCGCGTCGTCGACAACCACGAGCCGCTGCACCTG<br>GTGGCACACGACCTGAACCGGCGTGGTGTCCTGTCGCCGAAGGACTACTT<br>CGCAAAGCTGCAGGGTCGGGAGCCGCAGGGGCGGGCGTGGTCAGCCACC<br>GCGCTGAAGCGCTCGCTGATCTCTGAGGCGATGCTCGGGTATACGACGCT<br>GAACGGCAAGACCGTCCGAGACGACGACGGGGCTCCGCTGGTGCGGGCT<br>GAGCCGATCCTGACCCGCGAGCAGCTGGAGGCGCTGCGCGCCGAGCTCGT<br>CAAGACCGACCGGACGAAGCCCGCGGTGTCGACGCCGTCGCTGCTGCTGC<br>GGGTGTTGTTCTGCGCGGTGTGCGGGGAGCCTGCCTACAAGTTCGACGCA<br>GGCCGGAAGATCCCCCGCTACCGCTGCAGGTCGTTCGGGTTCGCACAGCG<br>CTGCGGGAACGGCACCATACCGATCGCAGAGTGGGACGCATTCTGCGAGG<br>AGCAGGTGCTGGATCTGCTCGGGGACTCGGAGCGTCTGGAGAAAGTCTG<br>GGTAGCAGGCTCGGACTCGGCGGTCGAACTCGCGGAGGTGAACGCGGAG<br>CTGGTGGACCTGACGTCGTTGATCGGCTCTCCGGCCTACCGGGTCGGTTCT<br>CCGCAGCGCGAAGCACTGGATGCTCGTATTGCGGCGCTGGCCGCGCGGCA<br>GGAGGAGCTGGAAGGGCTAGAGGCTCGCCCGTCGGGTTGGGAGTGGCGC<br>GAAACCGGTCAGAGGTTCGGTGACTGGTGGCGGGATCAGGACACCGCGG<br>GTAAGAACACCTGGCTCCGGTCGATGAACGTTCGGCTGACGTTCGACGTCC<br>GCGGCGGGCTGACTCGCACGATCGACTTCGGGGATCTGCAGGAGTATGAG<br>CAGCATCTGAGGCTGGGCTCGGCTCTGGACCTCGTAAACGCAGAAAAGCC<br>CCCTACGGGCCGCTAG |
| 27 | Benedict | MRVLGRIRLSRVMEESTSVERQREIIETWARQNDHEIIGWAEDLDVSGSVDPF<br>ETPALGPWLTDHRKHEWDILVAWKLDRLSRRAIPMNKLFGWVMENDKTLVC<br>VSENLDLSTWIGRMIANVIAGVAEGELEAIRERTKGSQKKLRELGRWGGGKPY<br>YGYRAQEREDAAGWELVPDEHASAVLLSIIEKVLEGQSTESIARELNERGELSPS<br>DYLRHRAGKPTRGGKWSNAHIRQQLRSKTLLGYSTHNGETIRDERGIAVRKGP<br>ALVSQDVFDRLQAALDSRSFKVTNRSAKASPLLGVLICRVCERPMHLRQHHNK<br>KRGKTYRYYQCVGGVEKTHPANLTNADQMEQLVEESFLAELGDRKIQERVYIP<br>AESHRAELDEAVRAVEEITPLLGTVTSDTMRKRLLDQLSALDARISELEKLPESE<br>ARWEYREGDETYAEAWNRGDAEARRQLLLKSGITAAAEMKGREARVNPGVL<br>HFDLRIPEDILERMSA |
| 28 | Benedict | ATGCGAGTTCTTGGAAGAATACGACTCTCGCGGGTCATGGAAGAATCGAC<br>ATCGGTCGAGAGGCAGCGAGAGATCATCGAAACCTGGGCGCGTCAGAAC<br>GACCACGAGATCATCGGCTGGGCTGAAGACCTAGACGTGTCTGGATCGT<br>CGATCCGTTCGAGACGCCAGCCTTGGGTCCGTGGCTTACCGACCACCGGA<br>AGCACGAGTGGGACATCCTCGTGGCGTGGAAGCTCGACCGGCTGTCCAGG<br>CGAGCTATCCCGATGAACAAACTCTTCGGCTGGGTCATGGAGAACGACAA<br>GACCCTCGTCTGCGTGTCGGAGAATCTGGACCTGTCGACATGGATCGGTC<br>GGATGATCGCCAACGTCATCGCTGGCGTGGCAGAGGGGGAGTTGGAGGC<br>GATACGAGAGAGGACCAAGGGCTCTCAGAAGAAGCTACGTGAGCTTGGC<br>CGCTGGGGAGGAGGCAAGCCCTACTACGGCTACCGCGCGCAAGAGCGTG<br>AGGACGCTGCTGGGTGGGAGCTGGTGCCCGACGAGCACGCCTCGGCGGT<br>CCTGCTCTCCATCATCGAGAAGGTCCTCGAAGGGCAGTCGACGGAGTCGA<br>TAGCTCGTGAGCTGAACGAGAGAGGAGAGCTGTCCCCTTCTGACTACCTTC<br>GGCACAGGGCCGGTAAGCCGACCAGGGGCGGTAAGTGGAGCAACGCGCA<br>CATCCGTCAGCAGCTCCGCTCCAAGACTCTCCTGGGTTACTCCACGCATAAC<br>GGCGAAACCATCCGAGACGAGCGGGGGATCGCGGTACGCAAAGGGCCGG<br>CGCTGGTTTCCCAGGACGTGTTCGACCGCCTCCAGGCGGCGCTTGATTCTC<br>GATCCTTCAAGGTGACGAACAGGTCAGCGAAAGCGTCGCCGTTGCTCGGC<br>GTCCTCATCTGCCGGGTGTGCGAACGACCGATGCACCTGCGTCAGCACCAC<br>AACAAGAAGCGCGGCAAGACCTACCGCTACTACCAGTGCGTGGCGGTGT<br>TGAAAAGACCCACCCTGCCAATCTCACCAACGCCGATCAGATGGAGCAGTT<br>GGTCGAAGAGTCCTTCCTTGCTGAACTCGGTGACCGGAAGATCCAAGAGA<br>GGGTGTACATCCCTGCGGAGTCACATCGGGCCGAGTTGGACGAGGCTGTA<br>CGGGCCGTTGAGGAGATAACCCCACTGCTGGGCACCGTCACATCGGACAC<br>CATGCGAAAGCGTCTCCTGGATCAGCTGAGCGCGTTAGATGCTCGTATCTC |

TABLE 1-continued

Amino-acid and Nucleotide Sequences

| SEQ ID NO: | Species | Sequence |
|---|---|---|
| | | CGAGCTGGAGAAGCTGCCCGAGTCCGAAGCTCGGTGGGAGTATCGAGAA
GGCGACGAAACCTACGCCGAGGCGTGGAACCGGGGTGACGCGGAAGCGC
GTCGACAGCTCCTGCTCAAGTCGGGGATCACGGCGGCTGCTGAGATGAAG
GGCAGAGAGGCCCGAGTCAACCCGGGGGTCTTACACTTCGACCTACGAAT
ACCGGAGGACATCTTAGAAAGGATGAGCGCGTGA |
| 29 | Bob3 | MRALVVIRLSRVTDATTSPERQLESCQQLCAQRGWDVVGVAEDLDVSGAVD
PFDRKRRPNLARWLAFEEQPFDVIVAYRVDRLTRSIRHLQQLVHWAEDHKKLI
VSATEAHFDTTTPFAAVVIALMGTVAQMELEAIKERNRSAAHFNIRAGKYRGS
LPPWGYMPARVDGEWRLLVDPVQRERILEVYHRVVDNHEPLHLVAHDLNQR
GILSPKDYFAKLQGREPKGREWSATALKRSLISEAMLGYTTLNGKTVRDDDGA
PLVRAEPILTREQLESLRAELVKTDRTKPAVSTPSLLLRVLFCAVCGEPAYKFTGG
GRKNARYRCRSWGWAQRCGNGTVAMAEWDAFCEEQVLDLLGDAERLEKV
WVAGSDAAVELTELNAELVDLTSLIGSPAYRAGSPQREALDARIAALAARQEEL
EGLEARPSGWEWRETGQRFGDWWRDQDTAGKNTWLRSMNVRLTFDVRG
GLTRTIDFGDLQEYEQHLRLGSVVEQLHTGMS |
| 30 | Bob3 | ATGAGAGCACTGGTAGTCATCCGACTGTCCCGCGTCACCGATGCTACGACC
TCACCGGAGCGTCAGCTGGAGTCTTGCCAGCAGCTCTGCGCGCAGCGCGG
CTGGGACGTCGTCGGGGTAGCAGAGGATCTGGACGTCTCCGGAGCAGTC
GATCCGTTCGACCGGAAGCGCCGCCCGAACCTGGCCCGATGGCTAGCGTT
CGAGGAGCAACCGTTCGACGTCATCGTGGCGTACCGGGTGGACCGGTTGA
CCCGCTCGATCCGGCATCTGCAGCAGCTGGTGCACTGGGCCGAGGACCAC
AAGAAGCTGATCGTCTCCGCGACCGAAGCGCACTTCGATACGACGACGCC
GTTCGCGGCGGTCGTGATCGCGCTTATGGGAACGGTGGCGCAGATGGAAT
TAGAAGCGATCAAAGAGCGGAACCGTTCGGCTGCGCATTTCAACATCCGC
GCGGGTAAATACCGCGGTTCCCTGCCGCCGTGGGGTTACATGCCCGCACG
CGTTGACGGGGAGTGGAGGCTGCTCGTCGACCCCGTGCAGCGCGAACGC
ATCCTCGAGGTCTATCACCGCGTCGTCGACAACCACGAGCCTCTGCATCTG
GTCGCACACGACCTGAACCAGCGTGGTATCCTGTCGCCGAAGGACTACTTC
GCAAAGCTGCAGGGTCGAGAGCCCAAGGGCCGGAGTGGTCGGCTACCG
CGCTGAAGCGCTCGCTGATCTCGGAGGCGATGCTCGGGTATACGACGCTG
AACGGCAAGACCGTCCGAGACGACGACGGGGCTCCGCTGGTGCGGGCCG
AGCCGATCCTGACGCGCGAGCAGCTGGAATCGCTGCGGGCGGAACTGGTC
AAGACCGACCGGACCAAGCCCGCAGTGTCCACCCCGTCGCTGCTGCTGCG
GGTGCTGTTCTGCGCAGTGTGCGGGGAGCCCGCATACAAGTTCACCGGGG
GCGGCAGGAAGAACGCTCGCTACCGCTGCCGGTCGTGGGGCTGGGCGCA
GCGGTGCGGCAACGGCACGGTGGCAATGGCCGAGTGGGACGCATTCTGC
GAGGAGCAGGTGTTGGATCTGCTCGGGGACGCAGAGCGTCTGGAGAAAG
TCTGGGTAGCAGGCTCGGACGCTGCTGTGGAGCTGACGGAGCTCAACGCA
GAGCTGGTGGATCTGACGTCGCTGATCGGCTCCCCGGCATACCGGGCAGG
TTCTCCGCAGCGCGAGGCACTGGATGCTCGTATCGCAGCACTGGCAGCGC
GGCAGGAGGAGTTGGAAGGGCTAGAGGCACGCCCGTCGGGCTGGGAGT
GGCGCGAAACCGGGCAGAGGTTCGGGGACTGGTGGCGGGATCAGGACAC
CGCAGGTAAGAACACCTGGCTCCGGTCGATGAACGTTCGGCTGACGTTCG
ACGTCCGCGGCGGGCTGACTCGCACGATCGACTTCGGGGATCTGCAGGAG
TACGAGCAGCATCTCAGGCTCGGCAGCGTGGTCGAACAGCTACACACCGG
GATGTCGTAG |
| 31 | Bongo | MTATLETPPQVVAPPRLRAAVYLRMSTDKELGIDRQREDCVALCERLGWDPV
LYVDNDRSAVKENVRREAYEQMCEDIRDGRIDAIITWRSDRLYRKMKSLLPLID
LIQGVNKNGKRIPIETCQTGLIDLTTDAGRMTAKILAAVAENEGEVRTARQMR
AYEQIAESGRSLGAPAFGYTNDPKARVREIVPEEAAAIREGYDDVLAGCTLYSIA
KKWNDRGLKTPRGNAFVATVVGRILRNPRYAGLYRFRGEIIGEGDWEPIVDVE
TWAMATAVLDGKNTGPKGPRVRTTLLSGIVRCGHCGNRMSASKNSNGEPIY
KCKRYEVCNHGVTRVRKKVDKYVEARIVAKLEERKWVVGTKSDADQAKALHT
EAETLRARKASFTDALVDGTLTPAQVKEASDKVDAKLEEIERQLARLTKSRVYD
GLLGHDDLEAVWVGLPLDRKRAIIEQLCDKIVIRHVEITGRAAAKLPLGHNIDIY
WHKPSDD |
| 32 | Bongo | ATGACAGCAACCCTTGAAACCCCACCACAGGTCGTCGCGCCGCCCCGGCTG
AGGGCTGCGGTCTACCTCCGCATGTCCACCGACAAAGAGCTGGGCATCGA
CCGCCAACGCGAGGACTGCGTCGCCCTGTGCGAGCGCCTCGGCTGGGATC
CCGTGCTCTACGTCGACAACGACCGCAGCGCCGTCAAAGAGAACGTGCGC
CGCGAAGCGTACGAGCAGATGTGCGAGGACATCCGCGACGGCCGCATCG
ACGCCATCATCACGTGGCGCTCCGACCGGCTCTACCGCAAGATGAAGTCCC
TGCTGCCGCTCATCGACCTGATCCAGGGCGTCAACAAGAACGGCAAGCGG
ATCCCCATCGAGACGTGCCAGACAGGGCTCATCGATCTCACCACCGACGCA
GGCCGCATGACGGCTAAGATCCTGGCAGCCGTAGCGGAGAACGAGGGCG
AGGTCAGGACAGCCAGGCAGATGCGCGCATACGAGCAGATCGCAGAGAG
CGGCCGGTCACTGGGGGCCCAGCGTTCGGCTACACCAACGACCCCAAGG
CCCGCGTGCGTGAGATCGTGCCCGAAGAAGCCGCCGCAATCCGCGAGGGC
TACGACGATGTGCTCGCCGGATGCACGTTGTACTCGATTGCGAAGAAGTG
GAACGACCGTGGACTCAAGACACCCCGCGGCAACGCGTTCGTCGCCACCG |

TABLE 1-continued

Amino-acid and Nucleotide Sequences

| SEQ ID NO: | Species | Sequence |
|---|---|---|
| | | TCGTCGGCCGCATCCTCAGGAACCCCCGCTATGCGGGCCTGTACCGCTTCA<br>GGGGCGAGATCATCGGTGAGGGCGACTGGGAGCCCATCGTGGACGTTGA<br>GACGTGGGCGATGGCCACAGCGGTCCTCGACGGCAAGAACACCGGCCCA<br>AAGGGGCCCCAGGGTGCGCACAACGCTGCTCTCGGGCATCGTCGGTGCGG<br>ACACTGCGGCAACCGGATGTCGGCCAGCAAGAACAGCAACGGCGAGCCG<br>ATCTACAAGTGCAAGCGCTACGAGGTCTGCAACCACGGTGTTACGCGAGT<br>ACGCAAGAAGGTCGACAAGTACGTCGAGGCGCGGATCGTGGCCAAGCTC<br>GAAGAGCGCAAGTGGGTTGTCGGCACCAAGTCCGACGCGGACCAAGCCA<br>AGGCCCTGCACACAGAGGCCGAGACGCTGCGGGCCCGCAAGGCTTCGTTC<br>ACCGACGCCCTGGTCGATGGCACCCTGACACCCGCACAGGTGAAGGAGGC<br>CAGCGACAAGGTCGACGCGAAGCTGGAGGAGATTGAACGCCAGCTAGCC<br>CGCCTCACCAAGTCTCGGGTGTATGACGGGCTGCTGGGTCACGACGACCT<br>GGAGGCCGTCTGGGTGGGGCTGCCGCTGGACCGCAAGCGGGCCATCATC<br>GAGCAGCTATGCGACAAGATCGTGATACGGCATGTCGAGATCACCGGCCG<br>TGCTGCCGCCAAGCTGCCGCTTGGCCACAACATCGACATCTACTGGCATAA<br>GCCCAGCGATGACTGA |
| 33 | ConceptII | MRALVVIRLSRVTDATTSPERQLESCQQLCAQRGWDVVGVAEDLDVSGAVD<br>PFDRKRRPNLARWLAFEEQPFDVIVAYRVDRLTRSIRHLQQLVHWAEDHKKL<br>VVSATEAHFDTTTPFAAVVIALMGTVAQMELEAIKERNRSAAHFNIRAGKYRG<br>SLPPWGYLPTRVDGEWRLVPDPVQRERILEVYHRVVDNHEPLHLVAHDLNQR<br>GVLSPKDYFAKLQGREPQGREWSATALKRSLISEAMLGYATLNGKTVRDDDG<br>APLVRAEPILTREQLEALRAELVKADRTKPAVSTPSLLLRVLFCAVCGEPAYKFT<br>GGGRKNARYRCRSWGWAQRCGNGTVAMAEWDAFCEEQVLDLLGDSERLE<br>KVWVAGSDSAVELAEVNAELVDLTSLIGSPAYRAGSPQREALDARIAALAARQ<br>EELEGLEARPSGWEWRETGQRFGDWWRDQDTAGKNAWLRSMNVRLTFD<br>VRGGLTRTIDFGDLQEYEQHLRLGSALDVLNAEKPPTGR |
| 34 | ConceptII | ATGAGAGCACTGGTAGTCATCCGCCTGTCCCGCGTCACCGATGCTACGACT<br>TCGCCGGAGCGTCAGCTGGAGTCTTGCCAGCAGCTCTGCGCCCAGCGCGG<br>TTGGGACGTCGTCGGTGTAGCAGAGGATCTGGACGTCTCCGGAGCGGTCG<br>ATCCGTTCGACCGGAAGCGCAGACCGAACCTGGCCCGGTGGCTAGCATTC<br>GAGGAGCAACCGTTCGATGTCATCGTGGCATACCGGGTAGACCGGCTGAC<br>CCGATCGATCCGGCATCTGCAGCAGCTGGTCCACTGGGCTGAGGACCATA<br>AGAAGCTGGTCGTCTCCGCAACCGAAGCCCACTTCGACACGACGACGCCG<br>TCGCAGCGGTCGTCATCGCGCTTATGGGAACGGTGGCGCAGATGGAATT<br>AGAAGCGATCAAAGAGCGGAACCGTTCGGCGGCGCATTTCAATATCCGCG<br>CCGGTAAATACCGTGGAAGCCTGCCGCCGTGGGGTTACCTGCCTACGCGC<br>GTGGACGGTGAGTGGCGGCTGGTGCCGGACCCGGTGCAGCGAGAGCGCA<br>TCCTCGAGGTGTATCACCGCGTCGTCGACAACCACGAGCCGCTGCACCTG<br>TGGCCCACGACCTGAACCAGCGCGGCGTCCTGTCGCCGAAGGACTACTTC<br>GCGAAGCTGCAAGGCCGCGAGCCGCAGGGCCGGGAGTGGTCGGCTACCG<br>CGCTGAAGCGCTCGCTGATCTCCGAGGCGATGCTCGGGTACGCGACTCTG<br>AACGGTAAGACCGTCCGAGACGACGACGGAGCCCCGCTGGTCGGGCTG<br>AGCCGATCCTGACCCGTGAGCAGCTGGAGGCGCTGCGCGCCGAGCTCGTG<br>AAGGCCGACCGGACCAAGCCCGCAGTGTCTACCCCGTCGCTGCTGCTGCG<br>GGTGCTGTTCTGCGCAGTGTGCGGTGAGCCCGCATACAAGTTCACCGGTG<br>GCGGTAGGAAGAACGCTCGCTACCGCTGCCGGTCGTGGGGTTGGGCACA<br>GCGGTGCGGTAACGGCACGGTGGCGATGGCAGAGTGGGACGCATTCTGC<br>GAGGAGCAGGTGTTGGATCTGCTCGGGGACTCGGAGCGTCTGGAGAAAG<br>TCTGGGTAGCAGGTTCGGACTCCGCAGTAGAACTCGCGGAGGTGAACGCG<br>GAGCTGGTGGACCTGACGTCGCTGATCGGCTCCCCGGCGTACCGGGCCGG<br>TTCTCCGCAGCGCGAGGCGCTGGATGCTCGTATCGCGGCGCTGGCCGCGC<br>GGCAGGAGGAGTTGGAAGGGCTAGAGGCTCGCCCGTCGGGTTGGGAGTG<br>GCGCGAAACCGGGCAGAGGTTCGGGGACTGGTGGCGGGATCAGGACACC<br>GCGGGTAAGAACGCGTGGCTCCGGTCGATGAACGTTCGGCTGACGTTCGA<br>CGTCCGCGGCGGGCTGACTCGCACGATCGACTTCGGGGATCTGCAGGAGT<br>ATGAGCAGCATCTGAGGCTGGGCTCGGCTCTGGACCTCGTAAACGCAGAA<br>AAGCCCCCTACGGGCCGCTAG |
| 35 | Hinder | MRVLGRIRLSRLSDESTSPERQREIIEGWAKSNDHTIVGWAEDLDVSGSVDPF<br>DTPALGPWLSEPKLHEWDILCAWKLDRLSRRAIPMNKLFGWVMDHDKTLVC<br>VNDNIDLSTWIGRMVANVIAGVAEGELEAIRERTTASHRKLRELGRWPGGRP<br>SYGYRAVEREDAAGWVLEPDPVSSVVLRSIIDWVLQGQSVESIAKDLTAMGE<br>VSPSDYVRQRAGEAPRGHPWHGRTIVKLLRSKTLLGYVTHNGTTVRDENGVP<br>VQKGPPLVDQDTFNRLQAALDDGSRPKTVNRTSKASPLLGVALCWDCEKPLY<br>SRRQTTAGKVYRYYHCRDGHTQSIPADDLQQLVEERFLNALGDQEVHEMVYL<br>PAESHQAELEEAQIAVQELTSALGRMKSNYAQQRIHTQLEALDKRIQELEGLPT<br>SEARSEMRPTGGLYKDAWEEADEQGRRELLIKSGITAKAKLEGRVPNQSGGAL<br>SFDLVVPEDLLARMSV |
| 36 | Hinder | ATGCGTGTTCTTGGGAGAATCAGGCTGTCCAGGCTCAGCGACGAATCTACC<br>AGTCCCGAGCGGCAGCGAGAGATCATCGAGGGTTGGGCAAAGTCCAACG<br>ACCACACCATCGTCGGTTGGGCAGAGGATCTGGACGTGTCCGGTTCCGTC |

TABLE 1-continued

Amino-acid and Nucleotide Sequences

| SEQ ID NO: | Species | Sequence |
|---|---|---|
| | | GACCCGTTCGACACCCCGGCCTTGGGTCCGTGGCTGTCGGAGCCGAAACT<br>GCACGAGTGGGACATCCTCTGCGCATGGAAGCTCGACCGCCTCTCGCGGC<br>GAGCGATCCCGATGAACAAACTCTTCGGTTGGGTGATGGATCACGACAAG<br>ACACTCGTATGCGTCAACGACAACATCGACCTCTCGACGTGGATCGGTCGC<br>ATGGTCGCAAACGTCATCGCTGGTGTGGCCGAGGGGGAGTTGGAGGCGA<br>TCCCGGGAGAGGACGACGGCCTCTCACCGGAAGCTCCGGGAGTTGGGCCG<br>GTGGCCGGGAGGCAGACCGTCCTACGGCTACCGCGCCGTCGAGCGCGAG<br>GACGCAGCAGGGTGGGTGTTGGAGCCTGACCCGGTGTCGTCGGTGGTCCT<br>CCGGTCGATCATCGACTGGGTCCTGCAGGGGCAGTCCGTCGAGTCGATAG<br>CCAAGGATCTGACCGCGATGGGAGAGGTGTCCCCGTCCGACTACGTCCGT<br>CAGCGGGCCGGTGAGGCCCCACGGGGACACCCGTGGCATGGCCGCACCA<br>TCGTCAAGCTGTTGCGGTCCAAGACCCTCCTGGGGTACGTCACGCACAACG<br>GGACGACCGTCCGGGACGAGAACGGTGTGCCGGTCCAGAAAGGCCCACC<br>GCTGGTCGACCAGGACACCTTCAACCGGCTGCAGGCCGCTCTCGATGACG<br>GCTCCAGACCCAAGACCGTCAACCGGACCTCGAAGGCGTCCCCGCTACTCG<br>GGGTCGCCCTGTGTTGGGACTGCGAGAAGCCGCTGTACTCCCGCCGCCAG<br>ACGACGGCGGGGAAGGTGTACCGGTACTACCACTGCCGCGACGGCCACAC<br>CCAGTCCATCCCCGCCGACGACCTACAACAACTCGTGGAGGAGCGGTTCCT<br>GAACGCACTCGGGGACCAGGAGGTCCACGAGATGGTTTACCTCCCAGCGG<br>AATCGCACCAGGCCGAGCTAGAGGAGGCTCAGATCGCCGTACAGGAGTTG<br>ACGAGCGCCCTCGGGAGGATGAAGTCCAACTACGCGCAGCAGCGCATCCA<br>CACGCAACTGGAGGCTCTGGACAAACGCATACAGGAGCTTGAGGGACTAC<br>CGACCTCCGAGGCCCGGTCGGAGATGCGCCCGACAGGTGGGCTGTACAA<br>GGACGCCTGGGAGGAGGCCGACGAGCAAGGTCGCCGGGAGCTTCTGATC<br>AAGTCAGGGATCACGGCCAAGGCCAAGCTGGAGGGCCGGGTGCCCAACC<br>AGTCCGGAGGGGCATTGTCGTTCGATCTCGTTGTGCCAGAGGATCTTCTGG<br>CACGAATGTCCGTGTAA |
| 37 | ICleared | MRVLGRLRISRATEESTSIERQRELVEQWAAAHEHEIVGWAVDQDVSGSVDP<br>FDAPALGPWLSDHRKHEWDILCAWKLDRLSRRAIPMNKLFGWMIDNDKTLV<br>CVSENLDLGTWVGRMIANVIAGVAEGELEAIRERTTASHKKLRELGRWAGGP<br>TYYGYVPKPRDGAGWELDIDLHAAGVLREIIEKTIAGQSTESIVVELNERGELSP<br>SDYHRKRSGKPIRGTKWNTSWLRTQLKSKTLLGHMTHNGETVYDDAGLPVQ<br>KGPALIDRDTYKQLQDALQSRGINRTKRRTGASPLLGVAVCDVCDGPLYYRQT<br>KNQKGTAMLRQYICKHGRYGNTKANGGEPYNIIQADLLEATVEELFLSKMGD<br>LPRVERVFIPGEGHQHELETAERAVEDLTSLLGTITQEGARKRLLAQLSAAHERL<br>AHLEELPSSEPRWETRETGETYREAWESATTEERRQILLKAGVTLKVQMKGRV<br>PRVHPGVIVANWIEPHDIEKRLAS |
| 38 | ICleared | ATGCGAGTTCTTGGAAGATTGCGAATCTCACGAGCCACTGAAGAATCTACC<br>AGCATCGAGCGGCAGCGCGAGTTGGTCGAGCAGTGGGCGGCGGCTCACG<br>AGCACGAGATCGTCGGCTGGGCCGTGGATCAGGACGTGTCCGGATCGGTC<br>GATCCGTTCGACGCGCCAGCACTTGGGCCCTGGCTGTCTGACCATCGGAAA<br>CACGAATGGGACATCCTGTGCGCCTGGAAGCTGGACCGCCTGTCGCGGCG<br>AGCGATCCCGATGAACAAGCTGTTCGGTTGGATGATCGACAACGACAAGA<br>CGCTCGTCTGCGTGTCGGAGAATCTGGACCTCGGGACGTGGGTCGGTCGC<br>ATGATCGCCAACGTCATCGCCGGGGTCGCAGAGGGTGAATTGGAGGCGAT<br>CCGGGAGCGGACGACTGCCTCGCACAAGAAGCTCAGGGAGCTGGGAAGG<br>TGGGCCGGTGGGCCCACGTACTACGGCTACGTGCCGAAGCCCCGCGACGG<br>CGCGGGGTGGGAGCTGGACATCGACCTGCACGCTGCGGGCGTGCTGAGG<br>GAGATCATCGAAAAGACCATCGCCGGTCAGTCGACCGAGTCCATCGTGGT<br>CGAGCTCAACGAGCGAGGGGAGCTGTCCCCGTCCGACTACCACCGGAAGC<br>GGAGCGGGAAGCCGATCCGGGGCACGAAGTGGAACACGTCGTGGCTGCG<br>GACGCAGCTCAAGTCCAAGACCCTGCTTGGTCACATGACCCACAACGGCG<br>AAACCGTCTACGACGACGCCGGCCTCCCCGTCCAGAAGGGCCCTGCGCTG<br>ATCGACCGGGACACCTACAAGCAACTGCAGGACGCACTGCAGAGTCGCGG<br>GATCAACCGGACCAAGCGCAGGACCGGGGCCTCGCCGCTGCTCGGTGTCG<br>CCGTCTGCGATGTCTGCGACGGGCCGCTGTACTACCGCCAGACCAAGAAC<br>CAGAAGGGCACGGCCATGCTGCGGCAGTACATCTGCAAGCACGGCCGCTA<br>CGGCAACACCAAGGCCAACGGCGGGGAGCCGTACAACATCATTCAGGCCG<br>ATCTATTGGAGGCCACAGTCGAAGAGCTGTTCCTCTCCAAGATGGGCGATC<br>TGCCCCGCGTCGAGCGGGTGTTCATCCCAGGCGAAGGACACCAGCATGAG<br>CTGGAAACGGCTGAGCGAGCCGTGGAGGACTTGACATCGCTTCTGGGCAC<br>GATCACCCAGGAGGGTGCGAGAAAGCGTCTCCTGGCGCAACTCTCAGCCG<br>CCCACGAACGGCTGGCCCACCTCGAGGAGCTCCCGAGCTCCGAGCCCCGC<br>TGGGAAACCCGAGAGACAGGGGAGACGTACCGCGAAGCGTGGGAGAGC<br>GCGACGACCGAGGAGCGTCGGCAGATTCTGCTCAAAGCCGGTGTGACACT<br>CAAGGTCCAGATGAAGGGCCGGGTGCCGAGAGTGCATCCCGGCGTCATC<br>GTCGCGAACTGGATCGAGCCGCACGACATCGAGAAGCGCCTGGCTTCCTG<br>A |
| 39 | KSSJEB | MRALVVIRLSRVTDATTSPERQLESCQQLCAQRGWDVVGVAEDLDVSGAVD<br>PFDRKRRPNLARWLAFEEQPFDVIVAYRVDRLTRSIRHLQQLVHWAEDHKKL<br>VVSATEAHFDTTTPFAAVVIALMGTVAQMELEAIKERNRSAAHFNIRAGKYRG |

TABLE 1-continued

Amino-acid and Nucleotide Sequences

| SEQ ID NO: | Species | Sequence |
|---|---|---|
| | | SLPPWGYLPTRVDGEWRLLVDPVQRERILEVYHRVVDNHEPLHLVAHDLNQR
GILSPKDYFAQLQGREPQGRAWSATALKRSLISEAMLGYATLNGKTVRDDDG
APLVRAEPILTREQLEALRAELVKTDRTKPAVSTPSLLLRVLFCAVCGEPAYKFA
GGGRKHPRYRCRSMGFPKHCGNGTVAMAEWDAFCEEQVLDLLGDAERLEK
VWVAGSDAAVELAELNAELVDLTSLIGSPAYRAGSPQREALDARIEALAARQE
ELEGLEARPSGWEWRETGQRFGDWWREQDTAAKNTWLRSMNVRLTFDVR
GGLTRTIDFGDLQEYEQHLRLGSVVERLHTGMS |
| 40 | KSSJEB | ATGAGAGCACTGGTAGTCATCCGCCTGTCCCGCGTCACCGATGCTACGACT
TCACCGGAGCGTCAGCTGGAGTCTTGCCAGCAGCTCTGCGCACAGCGCGG
TTGGGACGTCGTCGGTGTGGCGGAGGATCTGGACGTCTCCGGAGCAGTCG
ATCCGTTCGACCGGAAGCGCAGACCGAACCTGGCACGGTGGCTGGCATTC
GAGGAGCAACCGTTCGATGTGATCGTGGCGTACCGGGTAGACCGGTTGAC
CCGATCGATCCGGCATCTGCAGCAGCTGGTCCACTGGGCGGAGGACCACA
AGAAGCTGGTCGTCTCCGCGACCGAAGCGCACTTCGACACGACGACGCCG
TTCGCGGCGGTCGTGATCGCGCTTATGGGTACGGTGGCGCAGATGGAATT
AGAAGCGATCAAAGAGCGGAACCGTTCGGCTGCACATTTCAATATCCGCG
CCGGTAAATACCGAGGTTCCCTGCCGCCGTGGGGTTACCTGCCTACGCGCG
TGGACGGGGAGTGGAGGCTGCTCGTCGACCCCGTGCAACGAGAGCGCAT
CCTCGAGGTCTATCACCGCGTCGTCGACAACCACGAGCCGCTGCATCTGGT
CGCCCACGACCTGAACCAGCGCGGCATCCTGTCGCCCAAGGACTACTTCGC
GCAGCTGCAGGGCCGGGAGCCGCAGGGGCGGGCGTGGTCGGCTACCGCG
TTGAAGCGCTCGCTGATCTCCGAGGCGATGCTCGGGTACGCGACTCTGAA
CGGTAAGACCGTCCGAGACGACGACGGAGCTCCGCTGGTGCGGGCCGAG
CCGATCCTGACGCGAGAGCAGCTGGAGGCGCTGCGCGCCGAGCTCGTCAA
GACCGACCGGACCAAGCCCGCAGTGTCTACCCCGTCGCTGCTGCTGCGGG
TGCTGTTCTGCGCAGTGTGCGGGGAGCCCGCATACAAGTTCGCAGGGGGA
GGACGTAAGCACCCGCGCTACCGCTGCCGCTCGATGGGGTTCCCGAAGCA
CTGCGGGAACGGCACGGTCGCAATGGCAGAGTGGGACGCATTCTGCGAG
GAGCAGGTGCTGGATCTGCTCGGGGACGCAGAGCGGCTGGAGAAGGTAT
GGGTCGCAGGCTCGGACGCTGCTGTGGAGCTGGCAGAGCTCAACGCAGA
GCTGGTGGACCTGACGTCGCTGATCGGCTCCCCGGCATACCGCGCAGGTT
CCCCGCAGCGGGAGGCATTGGACGCACGTATCGAGGCTCTGGCTGCACGG
CAAGAGGAGTTGGAAGGGCTGGAGGCTCGCCCGTCGGGTTGGGAGTGGC
GCGAAACCGGGCAGCGGTTCGGTGACTGGTGGCGAGAGCAGGACACCGC
AGCAAAGAACACCTGGCTCCGGTCGATGAACGTCCGGCTGACGTTCGACG
TCCGCGGCGGGCTGACTCGCACGATCGACTTCGGGGATCTGCAGGAGTAC
GAGCAGCATCTCAGGCTCGGCAGCGTGGTCGAACGGCTACACACCGGGAT
GTCGTAG |
| 41 | Doom | MRALVVIRLSRVTDATTSPERQLESCQQLCAQRGWEVVGVAEDLDVSGAVD
PFDRKRRPNLARWLAFEEQPFDVIVAYRVDRLTRSIRHLQQLVHWAEDHKKL
VVSATEAHFDTTTPFAAVVIALMGTVAQMELEAIKERNRSAAHFNIRAGKYRG
SLPPWGYLPTRVDGEWRLVPDPVQRERILEVYHRVVDNHEPLHLVAHDLNRR
GVLSPKDYFAKLQGREPQGREWSATALKRSLISEAMLGYATLNGKTVRDDDG
APLVRAEPILTREQLEALRAELVKTDRAKPAVSTPSLLLRVLFCAVCGEPAYKFD
AGRKIPRYRCRSFGFAQRCGNGTVPIAEWDAFCEEQVLDLLGDSERLEKVWV
AGSDSAVELAEVNAELVDLTSLIGSPAYRVGSPQREALDARIAALAARQEELEG
LEARPSGWEWRETGQRFGDWWREQDTSAKNTWLRSMNVRLTFDVRGGLT
RTIDFGDLQEYEQHLRLGSVVEQLHAGMS |
| 42 | Doom | ATGAGAGCACTGGTAGTCATCCGCCTGTCCCGTGTCACCGATGCTACGACT
TCACCTGAGCGTCAGCTGGAGTCTTGCCAGCAGCTCTGCGCACAGCGCGG
TTGGGACGTCGTCGGTGTAGCGGAGGATCTGGACGTCTCCGGAGCAGTCG
ATCCGTTCGACCGGAAGCGCCGCCCGAACCTGGCACGGTGGCTGTCATTC
GAGGAGCAACCGTTCGATGTGATCGTGGCGTACCGGGTAGACCGGTTGAC
CCGCTCGATCCGGCATCTGCAGCAGCTGGTCCACTGGGCCGAGGACCACA
AGAAGCTGATCGTCTCCGCGACTGAATCGCACTTCGACACGACGTCGCCGT
TTGCGGCGGTCGTGATCGCGCTTATGGGAACGGTGGCGCAGATGGAGTTG
GAGGCGATCAAGGAGCGGAACCGCTCGGCAGCACACTTCAACATCCGCGC
CGGTAAGTACCGTGGTTCCCTGCCGCCGTGGGGTTACATGCCGTACACGCG
TGGACGGGGAGTGGCGGCTGGTGCCGGACCCGGTGCAGCGCGAGCGCAT
CCTCGAGGTGTATCACCGCGTCGTCGACAACCACGAGCCGCTGCACCTGGT
GGCACACGACCTGAACCGGCGTGGTGTCCTGTCGCCGAAGGACTACTTCG
CAAAGCTGCAAGGTCGCGAGCCGCGGGGTCGGGAGTGGTCGGCTACCGC
GCTGAAGCGCTCGCTGATCTCCGAGGCGATGCTCGGGTACGCGACTCTGA
ACGGTAAGACCGTCCGAGACGACGACGGAGCCCCGCTGGTGCGGGCTGA
GCCGATCCTGACCCGTGAGCAGCTGGAGGCGCTGCGCGCCGAGCTCGTCA
AGACCGACCGGACCAAGCCCGCAGTGTCCACCCCGTCGCTGCTGCGGG
GTGCTGTTCTGTGCAGTGTGTGGGGAGCCCGCATACAAGTTCGACGCCGG
CCGGAAGATCCCCCGCTACCGCTGTAGGCTCGTTCGGGTTCGCACAGCGCTG
TGGGAACGGCACCATACCGATCGCAGAGTGGGACGCATTCTGTGAGGAGC
AGGTGCTGGATCTGCTCGGGGACGCAGAGCGGCTGGAGAAGGTGTGGGT
CGCAGGCTCGGACGCAGCAGTGGAGCTGGCAGAGCTCAACGCGGAGCTG |

TABLE 1-continued

Amino-acid and Nucleotide Sequences

| SEQ ID NO: Species | Sequence |
|---|---|
| | GTGGATCTGACGTCGCTGATCGGCTCCCCGGCATACCGGGCAGGCTCTCC<br>GCAGCGCGAGGCACTGGACGCTCGTATCGCGGCGCTGGCCGCGCGGCAG<br>GAGGAGCTGGAAGGGCTAGAGGCTCGCCCGTCGGGCTGGGAGTGGCGCG<br>AAACCGGGCAGAGGTTCGGGGACTGGTGGCGAGAGCAGGACACCGCGGC<br>AAAGAACACCTGGCTTCGGTCGATGAACGTTCGGCTGACGTTCGACGTCC<br>GCGGCGGGCTGACTCGCACGATCGACTTCGGGGATCTGCAGGAGTACGA<br>GCAGCATCTCAGGCTCGGCAGCGTGGTCGAACAGCTACACACCGGGATGT<br>CGTAG |
| 43 Mundrea | MRVLGRLRISRATEESTSIERQREIVEQWASVNDHEIVGWAVDQDVSGSVDP<br>FDAPALGPWLSEHRKHEWDILVAWKLDRLSRRAIPMNKLFGWMIDNEKTLV<br>CVSENLDLGTWVGRMIANVIAGVAEGELEAIRERTTASHKKLRELGRWAGGP<br>TYYGYVPKPRDGAGWELDIDPHAAGVLTEIIEKTIAGQSTESIVVELNERGELAP<br>SDYHRKRNGKPIRGTKWSTSWLRSQLKSKTLLGHMTHNGETVYDDAGLPVQ<br>KGPALVDRDTYKQLQDALESRGINRTRRRTGASPLLGVAVCDVCEGPLYYRQT<br>KNAKGTAMLRQYICKHGRYGNTQANGGEPYNIIQADLLEATVEELFLSKMGD<br>LPRVERVFIPGEGHQHELETAERAVEDLTSLLGTITQESARKRLLAQLAAAHERL<br>AHLEELPSSEPRWETRETGETYREAWEGATVEERRQILLKAGVTLKVQMKDR<br>VPRVHPGVIVANWIEPHDIEKRLAS |
| 44 Mundrea | ATGCGAGTTCTTGGAAGATTGCGAATTTCCCGAGCCACTGAGGAATCTACC<br>AGCATCGAGCGGCAGCGCGAGATCGTGGAGCAGTGGGCGTCCGTGAACG<br>ACCACGAGATCGTCGGCTGGGCCGTGGACCAGGACGTGTCCGGATCGGTC<br>GATCCGTTCGACGCGCCAGCACTGGGCCCCTGGCTGTCTGAGCACCGGAA<br>ACACGAGTGGGACATCCTCGTGGCGTGGAAGCTCGACCGCCTGTCGCGGC<br>GAGCGATCCCGATGAACAAGCTGTTCGGTTGGATGATCGACAACGAAAAG<br>ACTCTGGTCTGCGTATCGGAGAATCTGGACCTCGGGACGTGGGTCGGTCG<br>AATGATCGCCAACGTCATCGCCGGGGTCGCAGAGGGTGAGCTGGAGGCC<br>ATCCGGGAGCGGACGACCGCCTCGCATAAGAAGCTCAGGGAGCTGGGAA<br>GGTGGGCCGGGGGCCCGACGTACTACGGGTACGTGCCGAAGCCCCGCGA<br>CGGCGCGGGGTGGGAGCTGGACATCGACCCGCACGCTGCTGGCGTGCTG<br>ACGGAGATCATCGAAAAGACCATCGCCGGTCAGTCGACGGAGTCCATCGT<br>GGTCGAGCTGAACGAGCGCGGGGAGCTGGCTCCGTCCGACTACCACCGG<br>AAGCGGAACGGCAAGCCGATCCGGGGGACGAAGTGGAGCACGTCGTGGC<br>TGCGGTCGCAGCTCAAGTCCAAGACCCTGCTCGGCCACATGACCCACAACG<br>GTGAAACCGTCTACGACGACGCCGGCCTCCCTGTCCAGAAGGGCCCTGCCT<br>TGGTCGACCGGGACACATACAAGCAACTGCAGGACGCGCTGGAGAGTCGT<br>GGGATCAACCGGACCCGGCGCCGAACCGGAGCCTCACCGCTGCTCGGTGT<br>CGCCGTGTGCGATGTCTGCGAGGGGCCGCTGTACTACCGGCAGACCAAGA<br>ACGCCAAGGGCACGGCCATGCTGCGGCAGTACATCTGCAAGCACGGCCGC<br>TACGGCAACACTCAGGCCAACGGCGGGGAGCCGTACAACATCATCCAGGC<br>CGACCTCTTGGAGGCCACCGTCGAAGAGCTGTTCCTGTCGAAGATGGGTG<br>ACCTGCCCCGCGTCGAGCGGGTGTTCATCCCCGGCGAAGGACATCAGCAC<br>GAGCTGGAAACGGCTGAGCGAGCCGTGGAGGACTTGACATCGCTTCTGG<br>GCACGATCACCCAGGAGAGTGCGAGAAAGCGTCTCCTGGCTCAACTCGCC<br>GCCGCCCACGAGCGGCTGGCTCATCTCGAAGAGCTCCCGAGCTCCGAGCC<br>CCGCTGGGAAACCCGAGAGACAGGGGAGACGTACCGCGAAGCGTGGGA<br>GGGCGCGACGGTCGAGGAGCGTCGGCAGATTCTGCTCAAAGCCGGTGTG<br>ACATTGAAGGTCCAGATGAAGGACCGAGTGCCGAGAGTGCATCCCGGTGT<br>CATCGTCGCGAACTGGATCGAGCCACACGACATCGAGAAGCGCCTGGCCT<br>CTTGA |
| 45 Museum | MRALVVIRLSRVTDATTSPERQLESCQQLCAQRGWDVVGVAEDLDVSGAVD<br>PFDRKRRPNLARWLSFEEQPFDVIVAYRVDRLTRSIRHLQQLVHWAEDHKKLI<br>VSATEAHFDTTTPFAAVVIALMGTVAQMELEAIKERNRSAAHFNIRAGKYRGS<br>LPPWGYMPARVDGEWRLLVDPVQRERILEVYHRVVDNHEPLHLVAHDLNQR<br>GILSPKDYFAKLQGREPKGREWSATALKRSLISEAMLGYATLNGKTVRDDDGA<br>PLVRAEPILTREQLEALRAELVKTDRTKPAVSTPSLLLRVLFCAVCGEPAYKFTG<br>GGRKNARYRCRSWGWAQRCGNGTVAMAEWDAFCEEQVLDLLGDAERLEK<br>VWVAGSDSAVELAEVNAELVDLTSLIGSPAYRVGSPQREALDARIAALAARQE<br>ELEGLEARPSGWEWRETGQRFGDWWREQDTAAKNTWLRSMNVRLTFDVR<br>GGLTRTIDFGDLQEYEQHLRLGSALDLVNAEKPPTGR |
| 46 Museum | ATGCGCGCTTTGGTAGTGATCCGCTTGTCCCGTGTGACCGATGCTACGACT<br>TCACCCGAGCGTCAGCTGGAGTCTTGCCAGCAGCTCTGCGCGCCAGCGCGG<br>CTGGGACGTCGTCGGGGTGGCGAGGATCTGGACGTGTCCGGAGCGGTC<br>GATCCGTTCGACCGGAAGCGCCGCCCGAACCTGGCCCGGTGGCTGTCGTT<br>CGAGGAGCAACCGTTCGATGTGATCGTGGCGTACCGGGTGGATCGGTTGA<br>CCCGCTCGATCCGGCATCTTCAGCAGCTGGTCCACTGGGCCGAGGACCACA<br>AGAAGCTGATCGTCTCCGCGACCGAAGCGCACTTCGATACGACGACGCCG<br>TCGCGGCGGTCGTGATCGCGCTTATGGGAACGGTGGCGCAGATGGAATT<br>AGAAGCGATCAAAGAGCGGAACCGTTCGGCTGCGCATTTCAACATCCGCG<br>CGGGGAAATACCGCGGCTCCCTGCCGCCGTGGGGTTACATGCCCGCCCGC<br>GTGGACGGGGAGTGGAGGCTGCTCGTCGACCCCGTGCAGCGCGAACGCA |

TABLE 1-continued

Amino-acid and Nucleotide Sequences

| SEQ ID NO: Species | Sequence |
|---|---|
| | TCCTCGAGGTCTATCACCGCGTCGTCGACAACCACGAGCCTCTGCATCTGG<br>TCGCCCACGACCTGAACCAGCGTGGCATCCTGTCGCCGAAGGACTACTTCG<br>CGAAGCTGCAGGGCCGAGAGCCCAAGGGCCGGGAGTGGTCGGCTACCGC<br>GCTGAAGCGCTCGCTGATCTCCGAGGCGATGCTCGGGTACGCGACTCTGA<br>ACGGTAAGACCGTCCGAGACGACGACGGAGCCCCGCTGGTGCGGGCTGA<br>GCCGATCCTGACCCGTGAGCAGCTGGAGGCGCTGCGCGCCGAGCTCGTCA<br>AGACCGACCGGACCAAGCCCGCAGTGTCTACCCCGTCGCTGCTGCTGCGG<br>GTGTTGTTCTGCGCAGTGTGCGGTGAGCCCGCATACAAGTTCACCGGTGG<br>CGGTAGGAAGAACGCTCGCTACCGCTGCCGGTCGTGGGGTTGGGCACAGC<br>GGTGCGGTAACGGCACGTGGCAATGGCGGAGTGGGACGCGTTCTGCGA<br>GGAGCAGGTGCTGGATCTGCTCGGGGACGCAGAGCGTCTGGAGAAAGTC<br>TGGGTAGCAGGTTCGGACTCGGCAGTCGAACTCGCGGAGGTGAACGCGG<br>AGCTGGTGGACCTGACGTCGCTGATCGGCTCTCCGGCGTACCGGGTCGGT<br>TCTCCGCAGCGCGAAGCACTGGATGCTCGTATTGCGGCGCTGGCCGCGCG<br>GCAAGAGGAGTTGGAAGGGCTAGAGGCTCGTCCGTCTGGCTGGGAGTGG<br>CGCGAAACCGGGCAGCGGTTCGGGGACTGGTGGCGGGAGCAGGACACCG<br>CGGCAAAGAACACCTGGCTTCGGTCGATGAACGTTCGGCTGACGTTCGAC<br>GTCCGCGGCGGGCTGACTCGGACGATCGACTTCGGGGATCTGCAGGAGTA<br>TGAGCAGCATCTGAGGCTGGGCTCGGCTCTAGACCTCGTAAACGCAGAAA<br>AGCCCCCTACGGGCCGCTAG |
| 47 PattyP | MRALVVIRLSRVTDATTSPERQLESCQQLCAQRGWDVVGVAEDLDVSGAVD<br>PFDRKRRPNLARWLAFEEQPFDVIVAYRVDRLTRSIRHLQQLVHWAEDHKKL<br>VVSATEAHFDTTTPFAAVVIALMGTVAQMELEAIKERNRSAAHFNIRAGKYRG<br>SLPPWGYLPTRVDGEWRLVPDPVQRERILEVYHRVVDNHEPLHLVAHDLNRR<br>GVLSPKDYFAKLQGREPRGREWSATALKRSLISEAMLGYTTLNGKTVRDDDG<br>APLVRAEPILTREQLESLRAELVKTDRTKPAVSTPSLLLRVLFCAVCGEPAYKFAG<br>GQRKNPRYRCRSMGFPKHCGNGTVAMAEWDAFCEEQVLDLLGDAERLEKV<br>WVAGSDSAVELAEVNAELVDLTSLIGSPAYRVGSPQREALDARIAALAARQEE<br>LEGLEARPSGWEWRETGQRFGDWWREQDASGKNTWLRSMNVRLTFDVRG<br>GLTRTIDFGDLQEYEQHLRLGSVVERLHTGMS |
| 48 PattyP | ATGAGAGCACTGGTGGTCATCCGACTGTCCCGCGTCACCGATGCTACGACT<br>TCACCCGAGCGTCAGCTGGAGTCTTGCCAGCAGCTCTGCGCACAGCGCGG<br>TTGGGACGTCGTCGGTGTAGCGGAGGATCTGGACGTCTCCGGAGCAGTCG<br>ATCCGTTCGACCGGAAGCGCCGCCCGAACCTGGCACGATGGCTAGCATTC<br>GAGGAGCAACCGTTCGACGTCATCGTGGCGTACCGGGTGGACCGGTTGAC<br>CCGCTCGATCCGGCATCTGCAGCAGCTGGTGCACTGGGCCGAGGACCATA<br>AGAAGCTGGTCGTCTCCGCGACCGAAGCCCACTTCGACACGACGACGCCG<br>TCGCGGCGGTCGTCATCGCGCTTATGGGAACGGTGGCGCAGATGGAATT<br>AGAAGCGATCAAAGAGCGGAACCGTTCGGCAGCACATTTCAATATCCGCG<br>CCGGTAAATACCGCGGTTCCCTGCCGCCGTGGGGTTACCTGCCTACGCGCG<br>TGGACGGTGAGTGGCGGCTGGTGCCGGACCCGGTGCAGCGAGAGCGCAT<br>CCTCGAGGTGTATCACCGCGTCGTCGACAACCACGAGCCGCTGCACCTGGT<br>GGCCCACGACCTGAACCGGCGTGGTGTCCTGTCGCCGAAGGACTACTTCG<br>CGAAGCTGCAAGGCCGCGAGCCGCGGGGCCGGGAGTGGTCGGCTACCGC<br>GCTGAAGCGCTCGCTGATCTCGGAGGCGATGCTCGGGTATACGACGCTGA<br>ACGGCAAGACCGTCCGAGACGACGACGGGGCTCCGCTGGTGCGGGCCGA<br>GCCGATCCTGACGCGCGAGCAGCTGGAATCGCTGCGGGCGGAACTGGTCA<br>AGACCGACCGGACCAAGCCCGCAGTGTCCACCCCGTCGCTGCTGCTGCGG<br>GTGTTGTTCTGCGCAGTGTGCGGGGAGCCCGCGTACAAGTTCGCCGGTGG<br>TCAGCGCAAGAACCCGCGCTACCGCTGCCGCTCGATGGGGTTCCCGAAGC<br>ACTGCGGTAACGGTACGGTGGCGATGGCCGAGTGGGACGCGTTCTGCGA<br>GGAGCAGGTGCTGGATCTGCTCGGGGACGCGGAGCGTCTGGAGAAAGTC<br>TGGGTAGCCGGTTCGGACTCGGCAGTCGAACTCGCAGAGGTGAACGCGG<br>AGCTGGTGGACCTGACGTCGCTGATCGGCTCTCCGGCATACCGGGTTGGT<br>TCTCCGCAGCGCGAGGCGCTCGACGCTCGTATCGCAGCACTGGCCGCACG<br>GCAAGAGGAGTTGGAAGGGCTAGAGGCTCGTCCGTCGGGCTGGGAGTGG<br>CGAGAAACCGGGCAGAGGTTCGGGGACTGGTGGCGGGAGCAGGACGCCT<br>CGGGTAAGAACACCTGGCTTCGGTCGATGAACGTTCGGCTGACGTTCGAC<br>GTCCGCGGCGGGCTGACTCGCACGATCGACTTCGGGGATCTGCAGGAGTA<br>CGAGCAGCATCTCAGGCTCGGCAGCGTGGTCGAACGGCTACACACCGGGA<br>TGTCGTAG |
| 49 Rebeuca | MRVLGRLRLSRSTEESTSIERQREIVTAWAESNGHTLVGWAEDVDVSGAIDPF<br>DTPSLGPWLDERRGEWDILCAWKLDRLGRDAIRLNKLFGWCQEHGKTVASC<br>SEGIDLSTPVGRLIANVIAFLAEGEREAIRERVTSSKQKLREVGRWGGGKPPFG<br>YMGIPNPDGQGHILVVDPVAKPVVRRIVDDILDGKPLTRLCTELTEERYLTPAE<br>YYATLKAGAPRQKAEPDETPAKWRPTALRNLLRSKALRGYAHHKGQTVRDLK<br>GQPVRLAEPLVDADEWELLQETLDRVQANWSGRRVEGVSPLSGVVVCITCDR<br>PLHHDRYLVKRPYGDYPRYYRCRDRHGKNLPAEMVETLMEESFLARVGDYP<br>VRERVWVQGDTNWADLKEAVAAYDELVQAAGRAKSATAKERLQRQLDALD<br>ERIAELESAPATEAHWEYRPTGGTYRDAWETADTDERREILRRSGIVLAVGVD<br>GVDGRRSKHNPGALHFDFRVPEELTQRLGVS |

TABLE 1-continued

Amino-acid and Nucleotide Sequences

| SEQ ID NO: | Species | Sequence |
|---|---|---|
| 50 | Rebeuca | ATGCGAGTGCTCGGAAGATTGCGTTTGTCCAGGTCAACGGAGGAATCTAC<br>CTCCATCGAGCGGCAGCGGGAGATTGTCACCGCTTGGGCAGAGTCTAACG<br>GTCACACCCTCGTGGGTTGGGCCGAGGACGTTGACGTGTCTGGTGCAATC<br>GACCCGTTCGACACCCCGTCGCTCGGTCCGTGGCTGGACGAGCGGCGAGG<br>CGAGTGGGACATCCTCTGCGCGTGGAAGCTCGACCGGCTGGGCCGTGATG<br>CCATCCGGCTCAACAAGCTCTTCGGTTGGTGCCAGGAGCACGGCAAGACC<br>GTGGCCTCGTGCAGCGAGGGCATCGACCTCAGCACGCCGGTCGGTCGGCT<br>CATCGCCAACGTCATCGCCTTCCTGGCCGAGGGTGAGCGGGAAGCGATCC<br>GCGAGCGCGTCACGTCCTCGAAGCAGAAGCTGCGCGAGGTAGGCCGGTG<br>GGGTGGTGGTAAGCCGCCGTTCGGTTACATGGGCATCCCCAACCCGGACG<br>GTCAGGGACACATCCTCGTGGTCGATCCGGTGGCCAAGCCGGTGGTGCGC<br>CGGATCGTGGACGACATCCTCGACGGCAAGCCGCTCACGCGGCTCTGCAC<br>GGAGCTGACCGAGGAGCGATACCTCACGCCGGCAGAGTACTACGCAACCC<br>TCAAGGCAGGGGCACCGAGGCAGAAGGCCGAGCCCGACGAAACCCCTGC<br>AAAGTGGCGGCCGACCGCTCTCCGCAACCTTCTCCGGAGCAAGGCCCTGC<br>GGGGTTACGCCCATCACAAGGGGCAGACCGTCAGGGACCTCAAGGGGCA<br>GCCTGTGCGCCTCGCTGAGCCACTGGTGGACGCCGACGAATGGGAACTAC<br>TGCAGGAGACTCTCGACCGCGTACAGGCAAACTGGTCGGGTCGACGGGTC<br>GAGGGTGTCAGCCCGCTGTCCGGTGTCGTGGTCTGCATCACCTGTGACCGT<br>CCGCTGCACCACGACCGGTATCTGGTGAAGCGGCCATACGGTGACTACCC<br>CTACCGGTACTACCGGTGCCGTGACCGCCACGGCAAGAACCTCCCGGCAG<br>AGATGGTCGAAACCCTCATGGAAGAGTCCTTCCTGGCACGCGTGGGTGAC<br>TATCCGGTGCGGGAGAGGGTCTGGGTCCAGGGTGACACGAATTGGGCAG<br>ATCTGAAGGAGGCTGTGGCAGCCTACGACGAACTGGTGCAGGCAGCCGG<br>CCGCGCCAAGAGCGCAACGGCGAAGGAGAGACTGCAGAGGCAGCTCGAT<br>GCACTAGACGAGCGGATCGCGGAGCTTGAGTCCGCACCCGCCACCGAGGC<br>CCACTGGGAGTACCGGCCGACCGGAGGTACCTACCGGGACGCCTGGGAG<br>ACAGCAGACACCGACGAGCGCCGCGAGATCCTGCGGCGGTCGGGGATCG<br>TCCTGGCGGTCGGAGTCGACGGCGTGGATGGCCGTCGCTCCAAGCACAAC<br>CCAGGAGCCCTGCACTTCGACTTCCGGGTCCCCGAGGAACTGACCCAGCG<br>GCTCGGAGTCTCCTGA |
| 51 | Rey | MTATLERHLDTPQQEALRVGVYLRMSTDKELGIDRQREDCLALAERLGWVPV<br>EYIDNDRSATKENVKREGFDALSEDIRDGRIDSIITWRSDRLYRKMKDLLPLIDLI<br>QGVNKTGKRIPIETCQTGLIDLTTDAGRMTAKILAAVSENEGEVRTARQMRAY<br>EQIADSGRRLGAPAFGWTHDPRDPQIVPEEAAAIRQAYADVLAGCTLYSIAKK<br>WNEDGLRTTRGNQFVGSVVGKILRSPRNAGLLTFRDEIVGEGTWEPIVDRET<br>WEAACAVLDQKNTGKKGPRVRSTLLSGIVRCGACGNKMAAGKNSNGEPIYK<br>CKRYEVCKHGVTRVRKKVDKYVEMSMVAKLEQRKWIVGTQVDAEQAKGLH<br>AEAEAEALRARKASFGEALADGTLTPAQVKDATDRVNAKLEEIDAKLARLTRSRVF<br>DGLLGHDDLEKVWLGLDLERKRAIIESLCDKIVIQHVGQTGRSAAKLPLGHAIKI<br>HWHDPSND |
| 52 | Rey | ATGACAGCGACCCTCGAGCGACACCTCGACACCCCGCAGCAGGAGGCCCT<br>GCGGGTGGGTGTCTACCTGCGCATGTCCACCGACAAGGAGCTGGGCATCG<br>ATCGCCAGCGCGAGGACTGCCTGGCGCTGGCTGAGCGTCTGGGCTGGGTT<br>CCCGTCGAGTACATCGACAACGACCGCAGCGCCACCAAGGAGAACGTCAA<br>GCGCGAAGGCTTCGATGCGCTGAGCGAGGACATCCGCGATGGCCGGATC<br>GACAGCATCATCACGTGGCGCAGCGACCGGCTGTACCGAAAGATGAAGG<br>ATCTACTCCCCCTGATCGATCTGATCCAGGGTGTTAATAAGACAGGCAAGC<br>GGATCCCCATCGAAACCTGCCAGACTGGCCTGATCGATCTCACCACCGACG<br>CCGGTCGGATGACAGCGAAGATCCTTGCCGCTGTCTCGGAGAACGAGGGC<br>GAGGTAAGGACGGCGCGACAGATGCGAGCCTACGAGCAGATCGCCGACA<br>GTGGCCGTCGCCTGGGCGCTCCCGCGTTCGGCTGGACCCATGACCCCAGG<br>GACCCGCAGATCGTGCCCGAGGAGGCCGCTGCGATCCGGCAGGCGTACG<br>CCGACGTGCTCGCTGGCTGCACCCTCTACTCCATCGCGAAGAAGTGGAACG<br>AGGACGGTCTGCGCACCACGCGTGGCAACCAGTTCGTCGGGTCGGTCGTC<br>GGGAAGATCCTGCGAAGCCCCCGCAATGCGGGCCTGCTGACCTTCAGGGA<br>CGAGATCGTGGGCGAAGGCACCTGGGAGCCCATCGTTGATCGGGAAACCT<br>GGGAGGCAGCCTGTGCGGTGCTCGACCAGAAGAACACCGGCAAGAAGGG<br>TCCACGTGTACGGTCGACCCTCCTGTCGGGGATCGTGCGCTGCGGTGCCTG<br>CGGCAACAAGATGGCTGCCGGGAAGAACTCCAACGGTGAGCCCATCTACA<br>AGTGCAAGCGCTACGAGGTCTGCAAGCACGGTGTTACCCGTGTGCGTAAG<br>AAGGTCGACAAGTATGTCGAGATGTCCATGGTGGCGAAGCTGGAGCAGC<br>GCAAGTGGATTGTCGGCACCCAGGTCGACGCGGAGCAGGCCAAGGGGCT<br>TCACGCTGAGGCTGAAGCTCTACGCGCTCGCAAGGCATCGTTCGGTGAGG<br>CCCTGGCCGACGGCACCCTCACACCGGCTCAGGTGAAGGACGCCACCGAC<br>CGGGTGAACGCCAAGCTGGAAGAGATCGATGCCAAGCTAGCCCGCCTTAC<br>ACGATCTCGCGTGTTCGACGGGCTGCTCGGTCATGACGATCTTGAAAAGGT<br>TGGCTGGGACTGGATCTCGAGCGTAAGCGTGCGATCATCGAGTCGCTAT<br>GCGACAAGATCGTGATCCAGCATGTCGGGCAGACGGGTCGCTCTGCGGCC<br>AAACTGCCCCTCGGTCACGCCATCAAGATCCACTGGCATGATCCCAGCAAC<br>GACTGA |

TABLE 1-continued

Amino-acid and Nucleotide Sequences

| SEQ ID NO: | Species | Sequence |
|---|---|---|
| 53 | Sarfire | MRALVVIRLSRVTDATTSPERQLESCQQLCAQRGWDVVGVAEDLDVSGAVD<br>PFDRKRRPNLARWLAFEEQPFDVIVAYRVDRLTRSIRHLQQLVHWAEDHKKL<br>VVSATEAHFDTTTPFAAVVIALMGTVAQMELEAIKERNRSAAHFNIRAGKYRG<br>SLPPWGYLPTRVDGEWRLVPDPVQRERILEVYHRVVDNHEPLHLVAHDLNRR<br>GVLSPKDYFAKLQGREPQGREWSATALKRSLISEAMLGYATLNGKTVRDDDG<br>APLVRAEPILTREQLEALRAELVKTSRAKPAVATPSLLLRVLFCAVCGEPAYKFD<br>AGRKIPRYRCRSFGFAVRCGNGTVPIAEWDAFCEEQVLDLLGDSERLEKVWV<br>AGSDSAVELAEVNAELVDLTSLIGSPAYRAGSPQREALDARIAALAARQEELEG<br>LEARPSGWEWRETGQRFGDWWRDQDTAGKNTWLRSMNVRLTFDVRGGL<br>TRTIDFGDLQEYEQHLRLGSALDLVNAEKPPTGR |
| 54 | Sarfire | ATGAGAGCACTGGTAGTCATCCGCCTGTCCCGCGTCACCGATGCTACGACT<br>TCACCGGAGCGCCAGCTGGAGTCTTGCCAGCAGCTCTGCGCCCAGCGCGG<br>TTGGGACGTCGTCGGTGTAGCAGAGGATCTGGACGTCTCCGGAGCAGTCG<br>ATCCGTTCGACCGGAAGCGCCGCCCGAACCTGGCCCGGTGGCTAGCGTTC<br>GAGGAGCAGCCGTTCGATGTGATCGTGGCGTACCGGGTGGACCGGTTGAC<br>CCGATCGATCCGGCATCTGCAGCAGCTGGTCCACTGGGCCGAGGACCACA<br>AGAAGCTGGTCGTCTCCGCAACCGAAGCACTTCGACACGACGACGCCG<br>TCGCAGCAGTCGTCATCGCGCTTATGGGAACGGTGGCACAGATGGAATT<br>AGAAGCGATCAAAGAGCGGAACCGTTCGGCTGCGCATTTCAATATCCGCG<br>CCGGGAAATACCGCGGCTCCCTGCCGCCGTGGGGTTACCTGCCTACGCGC<br>GTGGACGGGGAGTGGCGGCTGGTGCCGGACCCTGTGCAGCGAGAGCGCA<br>TCCTCGAGGTGTATCACCGCGTCGTCGACAACCACGAGCCGCTGCACCTGG<br>TGGCCCACGACCTGAACCGGCGAGGCGTCCTGTCGCCTAAGGACTACTTC<br>GCGAAGCTGCAGGGCCGCGAGCCGCAGGGCCGGGAGTGGTCGGCTACCG<br>CGCTGAAGCGCTCGCTGATCTCTGAGGCGATGCTCGGGTACGCGACGCTG<br>AACGGTAAGACCGTCCGAGACGACGACGGAGCCCCGCTGGTGCGGGCTG<br>AGCCGATCCTGACCCGTGAGCAGCTGGAGGCGCTGCGCGCCGAGCTCGTC<br>AAGACCTCCCGGGCAAAGCCCGCAGTGGCTACTCCGTCGCTGCTGCTGCG<br>GGTGTTGTTCTGCGCGGTGTGCGGGGAGCCCGCGTACAAGTTCGACGCCG<br>GTCGGAAGATCCCCCGCTACCGCTGCCGGTCGTTCGGGTTCGCGGTTCGCT<br>GCGGGAACGGCACGGTGCCGATCGCGGAGTGGGACGCGTTCTGCGAGGA<br>GCAGGTGCTCGATCTGCTCGGGGATTCGGAGCGGCTGGAGAAAGTCTGG<br>GTAGCCGGCTCGGACTCCGCGGTAGAACTCGCGGAGGTGAACGCGGAGC<br>TGGTGGATCTGACGTCGCTGATCGGCTCCCCGGCATACCGGGCCGGTTCTC<br>CGCAGCGGGAGGCACTGGACGCTCGTATCGCAGCGCTGGCCGCACGGCA<br>GGAGGAGCTGGAAGGGCTAGAGGCTCGCCCGTCGGGTTGGGAGTGGCGC<br>GAAACCGGTCAGAGGTTCGGGGACTGGTGGCGGGATCAGGACACCGCAG<br>GTAAGAACACCTGGCTGGTCGATGAACGTTCGGCTGACGTTCGACGTC<br>CGCGGTGGTCTGACTCGCACGATCGACTTCGGTGATCTGCAGGAGTACGA<br>GCAGCATCTGAGGCTGGGCTCGGCTCTAGACCTCGTAAACGCAGAAAAGC<br>CCCCTACGGGTCGCTAG |
| 55 | Scowl | MRALVVIRLSRVTDATTSPERQLESCQQLCAQRGWDVVGVAEDLDVSGAVD<br>PFDRKRRPNLARWLSFEDQPFDVIVAYRVDRLTRSIRHLQQLVHWAEDHKKL<br>VVSATEAHFDTTTPFAAVVIALMGTVAQMELEAIKERNRSAAHFNIRAGKYRG<br>SLPPWGYLPTRVDGEWRLVPDPVQRERILEVYHRVVDNHEPLHLVAHDLNRR<br>GVLSPKDYFAQLQGREPQGRAWSATALKRSLISEAMLGYTTLNGKTVRDDDG<br>APLVRAEPILTREQLEALRAELVKTDRTKPAVSAPSLLLRVLFCAVCGEPAYKFD<br>AGRKIPRYRCRSFGFAQRCGNGTIPIAEWDAFCEEQVLDLLGDSERLEKVWVA<br>GSDSAVELAEVNAELVDLTSLIGSPAYRVGSPQREALDSRIAALAARQEELEGLE<br>ARPSGWEWRETGQRFGDWWREQDIAAKNTWLRSMNVRLTFDVRGGLTRT<br>IDFGDLQEYEQHLRLGSVVERLHTGMS |
| 56 | Scowl | ATGAGAGCACTGGTAGTCATCCGACTGTCCCGCGTCACCGATGCTACGACC<br>TCACCGGAGCGTCAGCTGGAGTCTTGCCAGCAGCTCTGCGCCCAGCGCGG<br>TTGGGACGTCGTCGGTGTAGCAGAGGATCTGGACGTCTCGGGAGCAGTCG<br>ATCCGTTCGACCGGAAGCGTCGCCCGAACCTGGCCCGGTGGCTGTCGTTC<br>GAGGATCAACCGTTCGATGTGATCGTGGCGTACCGGGTAGACCGGTTGAC<br>CCGCTCGATCCGGCATCTTCAGCAGCTGGTCCACTGGGCCGAGGACCACA<br>AGAAGCTGGTCGTCTCCGCGACCGAAGCGCACTTCGATACGACGACGCCG<br>TCGCAGCAGTCGTCATCGCGCTTATGGGAACGGTGGCGCAGATGGAATT<br>AGAAGCGATCAAAGAGCGGAACCGTTCGGCGGCGCATTTCAATATCCGCG<br>CCGGGAAATACCGAGGCTCCCTGCCGCCGTGGGGATACCTGCCTACGCGC<br>GTGGACGGGGAGTGGCGGCTGGTGCCAGACCCGGTGCAGCGAGAGCGCA<br>TCCTCGAGGTGTATCACCGCGTCGTCGACAACCACGAGCCGCTGCACCTGG<br>TGGCCCACGACCTGAACCGGCGTGGTGTCCTGTCGCCGAAGGACTACTTC<br>GCGCAGCTGCAGGGCAGGGAGCCGCAGGGCCGGGCGTGGTCGGCTACCG<br>CGCTGAAGCGCTCGCTGATCTCTGAGGCGATGCTCGGGTATACGACGCTG<br>AACGGCAAGACCGTCCGAGACGACGACGGGGCTCCGCTGGTGCGGGCTG<br>AGCCGATCCTGACCCGCGAGCAGCTGGAGGCGCTGCGCGCCGAGCTCGTC<br>AAGACCGACCGGACCAAGCCCGCAGTGTCCGCACCGTCGCTGCTGCTGCG<br>GGTGTTGTTCTGCGCGGTGTGCGGGGAGCCTGCCTACAAGTTCGACGCCG |

TABLE 1-continued

Amino-acid and Nucleotide Sequences

| SEQ ID NO: Species | Sequence |
|---|---|
| | GCCGGAAGATCCCCCGCTACCGCTGCAGGTCGTTCGGGTTCGCACAGCGC<br>TGCGGGAACGGCACCATACCGATCGCAGAGTGGGACGCATTCTGCGAGG<br>AGCAGGTGCTGGATCTGCTCGGGGACTCGGAGCGTCTGGAGAAAGTCTG<br>GGTAGCAGGCTCGGACTCGGCAGTCGAACTCGCAGAGGTGAACGCAGAG<br>CTGGTGGACCTGACGTCGCTGATCGGCTCTCCGGCATACCGGGTCGGTTCT<br>CCGCAGCGCGAGGCACTCGACTCCCGGATCGCAGCACTGGCCGCACGGCA<br>GGAGGAGTTGGAAGGGCTGGAGGCACGTCCGTCGGGTTGGGAGTGGCGC<br>GAAACCGGGCAGCGGTTCGGGGACTGGTGGCGGGAGCAGGACATCGCAG<br>CAAAGAACACCTGGCTTCGGTCGATGAACGTTCGGTTGACGTTCGACGTCC<br>GCGGCGGGCTGACTCGCACGATCGACTTCGGGGATCTGCAGGAGTACGA<br>GCAGCATCTCAGGCTCGGCAGCGTGGTCGAACGGCTACACACCGGGATGT<br>CGTAG |
| 57 Severus | MPSKRALLVIRLSRVTDATTSPERQLADCQALCAQRGYEVAGVAEDLDVSGSI<br>DPFDRKKRPNLAHWLHDRHNEFDVVVAYRVDRLTRSVRYLQKLVNWAEDH<br>DKLVVSATEPHFDTTSPFAAVLIALLGTVAQMELEAIAERNRSAARHNIRAGKY<br>RGSKPPWGYMPQRDDEGVWRLVQDPDQVKIIHEVVQRVLEGEPTQRIANDL<br>TLRGIPTPKDAFAISQGRKPEGLAWNMTTLKRSLKSEAMLGRVTNAAGKSIRK<br>EDGAPVIRSTPILTREVFDRVQVELETRARSGGPTTRSTALLLRVIYCAICGMPA<br>YQYSGGTSGKASRYRCSSSPRSNTDPNIKKCGNRTFAVAEADAVVVKTLLGLL<br>GDSERKEKIWESGCDHSAELADLDATLADLTDQLGTGVFARGTPQRARLDARI<br>AELAARQAALSAEAVRPAGWTWHGTGERFSDWWERQDVTAKNVWLRSM<br>NIQLTFDRERFYLDLGDIVQLTEQFDPQGPVAQWQGLLAAMQAEGIAGVEIR<br>GGEAQATPRDDDMRGALGMTGAPLVD |
| 58 Severus | ATGCCATCGAAGAGAGCATTGCTGGTCATCCGGCTCAGCCGGGTGACGGA<br>TGCAACGACCTCCCCCGAGCGTCAGCTCGCGGACTGCCAGGCGCTGTGTG<br>CTCAGCGCGGATACGAGGTGGCAGGCGTGGCCGAGGACCTCGACGTGTC<br>CGGGTCCATCGACCCGTTCGACCGGAAGAAGCGGCCCAACCTGGCCCACT<br>GGCTCCACGACCGTCACAACGAGTTCGACGTGGTGGTTGCCTACAGGGTA<br>GATCGCCTCACCCGATCCGTGCGTTACCTGCAGAAGCTGGTCAACTGGGCA<br>GAGGACCACGACAAGCTCGTCGTCTCCGCAACCGAGCCGCACTTCGACAC<br>CACGAGCCCGTTCGCCGCCGTGCTGATCGCACTGCTGGGCACCGTGGCCC<br>AGATGGAGCTGGAGGCCATCGCAGAGCGCAACCGCTCTGCTGCCCGACAC<br>AACATCAGGGCAGGGAAGTACCGAGGGTCCAAGCCCCCATGGGGCTACAT<br>GCCCCAGAGAGACGATGAGGGGGTCTGGCGGCTGGTGCAGGACCCTGAT<br>CAGGTCAAGATCATTCACGAGGTCGTGCAGCGGGTGTTGGAGGGTGAGCC<br>GACGCAGCGGATCGCCAATGACCTGACCCTGCGCGGGATTCCGACGCCGA<br>AGGATGCGTTCGCGATCTCCCAGGGCCGCAAGCCCGAGGGGCTGGCGTG<br>GAACATGACGACGCTCAAGCGGTCGTTGAAGTCGGAGGCAATGCTCGGCC<br>GCGTGACGAACGCGGCGGGGAAGTCCATCCGGAAGGAGGACGGGGCCCC<br>GGTGATCCGGTCCACCCCGATCCTGACGAGAGAGGTGTTCGACCGGGTGC<br>AGGTCGAGCTTGAGACTCGGGCTCGGAGCGGAGGTCCGACGACGCGATC<br>TACCGCACTGCTGCTGCGGGTGATCTACTGCGCAATCTGCGGTATGCCCGC<br>ATACCAGTACAGCGGTGGTACCAGCGGCAAGGCATCTCGGTACCGGTGCA<br>GCTCGTCTCCCCGGAGCAACACAGACCCGAACATCAAGAAGTGCGGTAAC<br>CGAACATTCGCGGTGGCCGAGGCCGACGCAGTGGTGGTCAAGACCCTGCT<br>GGGTCTGCTCGGTGACTCCGAGCGCAAGGAGAAGATCTGGGAATCCGGCT<br>GTGACCACTCGGCAGAGCTGGCCGACCTCGACGCCACGCTGGCCGATCTG<br>ACCGACCAGCTTGGTACCGGAGTGTTCGCCAGGGGGACGCCACAGCGGG<br>CCCGTCTGGACGCCAGGATCGCAGAGCTGGCCGCGAGGCAGGCTGCCCTA<br>TCGGCAGAGGCCGTTCGGCCCGCAGGATGGACGTGGCACGGCACTGGTG<br>AGCGTTTCAGTGATTGGTGGGAGCGGCAGGACGTTACCGCGAAGAATGTC<br>TGGCTGCGTCGATGAACATCCAACTCACGTTCGACCGTGAGCGGTTCTAT<br>CTCGACCTCGGAGACATCGTCCAACTGACCGAGCAGTTTGACCCGCAGGG<br>CCCGGTGGCCCAGTGGCAGGGTCTGCTCGCAGCCGATGCAAGCCGAAGGC<br>ATTGCCGGCGTGGAGATTCGAGGGGGTGAAGCACAGGCGACACCGAGGG<br>ATGACGACATGAGAGGGCCCTCGGAATGACAGGAGCCCCCCTGGTCGAT<br>TAG |
| 59 Sheen | MRVLGRLRLSRSTEESTSIERQREIVTAWADSNGHTVVGWAEDVDVSGAVDP<br>FDTPSLGPWLDERRGEWDILCAWKLDRLGRDAIRLNKLFLWCQENGKTVAST<br>SEGIDLGTPVGRLIANVIAFLAEGEREAIRERVTSSKQKLREVGRWGGGKPPFG<br>YMGIPNPDGQGYILVVDPIAKPVVRRIVDDVVDGKPLTRLCAELTEERYLTPAE<br>YYATLKAGAPRQQADPGEVIAKWRPTAVRNLLRSKALRGHAHHRGQTVRDD<br>QGRPVRLAEPLVDSDEWELLQETLDGIQADFSGRRVEGASPLSGVAVCMTCG<br>RPLHFSRHMVKRPYGDYPYQYYRCQDRHGKNVPADVLDELVEENFLLKVGDY<br>PVRERVWVQGDTNWADMKEAVAAYDELVQAAGRAKSATAKERLQRQLDA<br>LDTRIAELESAPATEAHWEYRETGSTYRDAWENSDTDQRRELLKKSGITVAVGI<br>DGVEGRRSKHNPGALRFDIRVPAELTQRLGAS |
| 60 Sheen | ATGCGTGTACTAGGTAGACTGCGTCTGTCCAGGTCAACGGAGGAATCTAC<br>CTCCATCGAGAGGCAACGAGAGATCGTCACCGCATGGGCCGATTCTAACG<br>GCCACACGGTCGTCGGTTGGGCAGAGGACGTTGACGTCTCGGGTGCAGTG |

TABLE 1-continued

Amino-acid and Nucleotide Sequences

| SEQ ID NO: | Species | Sequence |
|---|---|---|
| | | GACCCGTTCGACACACCGTCGCTGGGGCCGTGGCTGGATGAGCGCCGGG<br>GCGAGTGGGACATCCTCTGCGCCTGGAAACTGGACCGCCTGGGTCGTGAT<br>GCCATCCGGCTCAACAAGCTGTTCCTGTGGTGCCAGGAGAACGGCAAGAC<br>GGTGGCGTCCACGAGTGAGGGTATCGACCTCGGTACGCCGGTTGGTCGGC<br>TCATCGCAAACGTGATCGCGTTCCTTGCCGAGGGTGAGCGTGAGGCCATC<br>CGGGAGAGGGTCACGTCCTCGAAGCAGAAGCTGCGGGAGGTAGGTCGGT<br>GGGGTGGCGGTAAGCCGCCCTTCGGTTACATGGGCATCCCCAACCCCGAC<br>GGACAGGGCTACATCCTCGTGGTCGATCCCATCGCCAAGCCGGTGGTGCG<br>CCCGGATCGTGGACGACGTTGTCGACGGCAAGCCGCTGACGCGGCTGTGCG<br>CCGAGCTGACCGAGGAGCGGTACCTGACGCCTGCGGAGTACTACGCCACC<br>CTCAAGGCCGGTGCCCCGAGGCAGCAGGCCGACCCCGGTGAGGTGATCG<br>CCAAGTGGCGTCCGACCGCCGTCCGACAACCTGCTCCGCAGCAAAGCCCTCC<br>GGGGGCACGCCCACCACAGGGGACAGACCGTCAGAGACGACCAGGGACG<br>CCCTGTGCGGCTCGCTGAGCCGCTTGTGGACTCCGATGAATGGGAGTTGC<br>TGCAGGAGACTCTGGACGGCATCCAGGCAGACTTCTCCGGTCGTCGGGTC<br>GAGGGGGCAAGCCCGCTCTCCGGTGTCGCCGTCTGCATGACGTGCGGACG<br>CCCCCTGCACTTCTCCCGGCACATGGTGAAGCGCCCCTACGGCGACTACCC<br>GTACCAGTACTACCGCTGCCAGGACCGGCACGGGAAGAACGTGCCCGCCG<br>ACGTACTCGATGAATTGGTCGAGGAGAACTTCCTCCTGAAGGTGGGCGAC<br>TACCCGGTGCGTGAGCGGGTGTGGGTCCAGGGTGACACCAACTGGGCCG<br>ACATGAAGGAGGCAGTAGCCGCATACGACGAACTGGTGCAGGCCGCTGG<br>CCGTGCTAAGTCGGCAACCGCCAAGGAACGCCTGCAGCGCCAACTGGACG<br>CCCTCGATACCCGCATCGCAGAGCTGGAGTCGGCCCCGGCAACCGAGGCC<br>CACTGGGAGTACCGGGAAACCGGTAGCACCTACCGGGACGCCTGGGAGA<br>ACTCCGACACCGATCAGCGCCGGGAGCTGTTGAAGAAGTCTGGCATCACC<br>GTGGCCGTCGGCATCGACGGCGTGGAAGGCCGTCGCTCCAAACACAATCC<br>CGGTGCCCTGCGCTTCGACATCCGAGTGCCGGCAGAACTGACCCAGCGCC<br>TGGGAGCGTCCTGA |
| 61 | SkiPole | MRALVVIRLSRVTDATTSPERQLESCRQLCAQRGWDVVGVAEDLDVSGAVD<br>PFDRKRRPNLARWLAFEEQPFDVIVAYRVDRLTRSIRHLQQLVHWAEDHKKL<br>VVSATEAHFDTTTPFAAVVIALMGTVAQMELEAIKERNRSAAHFNIRAGKYRG<br>SLPPWGYLPTRVDGEWRLVPDPVQRERILEVYHRVVDNHEPLHLVAHDLNRR<br>GVLSPKDYFAKLQGREPQGREWSATALKRSLISEAMLGYATLNGKTVRDDDG<br>APLVRAAPILTREQLEALRAELVKTDRTKPAVSTPSLLLRVLFCAVCGEPAYKFA<br>GGGRKHPRYRCRSMGFPKHCGNGTVAMAEWDAFCEEQVLDLLGDAERLEK<br>VWVAGSDSAVELAEVNAELVDLTSLIGSPAYRAGSPQREALDARIAALAARQE<br>ELEGLEARPSGWEWRETGQRFGDWWRDQDTAGKNTWLRSMNVRLTFDVR<br>GGLTRTIDFGDLQEYEQHLRLGAALDLVNAEKPPTGR |
| 62 | SkiPole | ATGAGAGCTCTCGTCGTGATCCGCTTGTCCCGCGTCACCGATGCTACGACC<br>TCACCGGAGCGTCAGCTGGAGTCTTGCCGGCAGCTCTGCGCCCAGCGCGG<br>TTGGGACGTCGTCGGTGTAGCGGAGGATCTGGACGTCTCCGGAGCAGTCG<br>ATCCGTTCGACCGGAAGCGCAGACCGAACCTGGCACGGTGGCTAGCATTC<br>GAGGAGCAACCGTTCGACGTCATCGTGGCGTACCGGGTGGACCGGTTGAC<br>CCGCTCGATCCGGCATCTTCAGCAGCTGGTCCACTGGGCGGAGGACCACA<br>AGAAGCTGGTCGTCTCCGCGACCGAAGCCCACTTCGACACGACGACGCCG<br>TTCGCGGCGGTCGTCATCGCGCTTATGGGAACGGTGGCGCAGATGGAATT<br>AGAAGCGATCAAAGAGCGGAACCGTTCGGCTGCACATTTCAATATTCGCG<br>CCGGGAAATACCGCGGTTCCCTGCCGCCGTGGGGTTACCTGCCTACGCGC<br>GTGGACGGGGAGTGGCGGCTGGTGCCGGACCCGGTGCAGCGCGAGCGCA<br>TCCTCGAGGTGTATCACCGCGTCGTCGACAACCACGAGCCGCTGCACCTGG<br>TGGCACACGACCTGAACCGGCGTGGTGTCCTGTCGCCGAAGGACTACTTC<br>GCAAAGCTGCAAGGTCGCGAGCCGCAGGGGCGGGAGTGGTCGGCTACCG<br>CACTGAAGCGCTCGCTGATCTCCGAGGCGATGCTCGGGTACGCGACTCTG<br>AACGGTAAGACCGTCCGAGACGACGACGGAGCCCCGCTGGTGCGGGCTG<br>CGCCGATCCTGACCCGTGAGCAGCTGGAGGCGCTGCGCGCCGAGCTCGTC<br>AAGACCGACCGGACCAAGCCCGCAGTGTCTACCCCGTCGCTGCTGCTGCG<br>GGTGCTGTTCTGCGCAGTGTGCGGTGAGCCCGCATACAAGTTCGCAGGTG<br>GAGGACGCAAGCACCCGCGCTACCGCTGCCGCTCGATGGGTTTCCCGAAG<br>CACTGCGGTAACGGTACGGTCGCAATGGCCGAGTGGGACGCATTCGTCGA<br>GGAGCAGGTGCTGGATCTGCTCGGGGACGCAGAGCGTCTGGAGAAAGTC<br>TGGGTAGCTGGCTCGGACTCAGCAGTAGAACTCGCAGAGGTGAACGCAG<br>AGCTGGTGGACCTGACGTCGCTGATCGGTTCCCGGCGTACCGGGCCGGT<br>TCTCCGCAGCGCGAGGCGCTGGATGCTCGTATCGCGGCGCTGGCCGCGCG<br>GCAGGAGGAGTTGGAAGGGCTAGAGGCTCGCCCGTCGGGCTGGGAGTGG<br>CGCGAAACCGGGCAGAGGTTCGGGGACTGGTGGCGGGATCAGGACACCG<br>CGGGTAAGAACACCTGGCTCCGGTCGATGAACGTTCGGCTGACGTTCGAC<br>GTCCGAGGCGGCCTGACTCGTACGATCGACTTCGGGGATCTGCAGGAGTA<br>TGAGCAGCATCTGAGGCTGGGCGCGGCTCTAGACCTCGTAAACGCAGAAA<br>AGCCCCCTACGGGCCGCTAG |
| 63 | Switzer | MRALVVIRLSRVTDATTSPERQLESCQQLCAQRGWDVVGVAEDLDVSGAVD<br>PFDRKRRPNLARWLAFEEQPFDVIVAYRVDRLTRSIRHLQQLVHWAEDHKKL |

TABLE 1-continued

Amino-acid and Nucleotide Sequences

| SEQ ID NO: | Species | Sequence |
|---|---|---|
| | | VVSATEAHFDTTTPFAAVVIALMGTVAQMELEAIKERNRSAAHFNIRAGKYRG<br>SLPPWGYLPTRVDGEWRLVPDPVQRERILEVYHRVVDNHEPLHLVAHDLNRR<br>GVLSPKDYFAKLQGREPQGREWSATALKRSLISEAMLGYATLNGKTVRDDDG<br>APLVRSEPILTREQLEALRAELVKTDRTKPAVSTPSLLLRVLFCAVCGEPAYKFTG<br>GGRKNARYRCRSWGWAQRCGNGTVAMAEWDAFCEEQVLDLLGDAERLEK<br>VWVAGSDSAVELAEVNAELVDLTSLIGSPAYRAGSPQREALDARIAALAARQE<br>ELEGLEARPSGWEWRETGQRFGDWWRDQDTAAKNTWLRSMNVRLTFDVR<br>GGLTRTIDFGDLQEYEQHLRLGSVVERLHTGMS |
| 64 | Switzer | ATGAGAGCACTGGTAGTCATCCGCCTGTCCCGCGTCACCGATGCTACGACT<br>TCACCGGAGCGTCAGCTGGAGTCTTGCCAGCAGCTCTGCGCCCAGCGCGG<br>TTGGGACGTCGTCGGTGTAGCGGAAGATCTGGACGTCTCCGGAGCAGTCG<br>ATCCGTTCGACCGGAAGCGCCGCCCGAACCTGGCACGGTGGCTAGCATTC<br>GAGGAGCAACCGTTCGATGTCATCGTGGCGTACCGGGTAGACCGGCTGAC<br>CCGATCGATCCGGCATCTGCAGCAGCTGGTCCACTGGGCCGAGGACCACA<br>AGAAGCTGGTCGTCTCCGCGACCGAAGCCCACTTCGACACGACGACGCCG<br>TTCGCGGCGGTCGTCATCGCGCTTATGGGAACGGTGGCGCAGATGGAATT<br>AGAAGCGATCAAAGAGCGGAACCGTTCGGCTGCACATTTCAATATCCGCG<br>CCGGGAAATACCGAGGTTCCCTGCCGCGTGGGGATACCTGCCTACGCGC<br>GTGGACGGGGAGTGGCGGCTGGTGCCGGACCCGGTGCAGCGAGAGCGC<br>ATCCTCGAGGTGTATCACCGCGTCGTCGACAACCACGAGCCGCTGCACCTG<br>GTGGCCCACGACCTGAACCGGCGTGGTGTCCTGTCGCCTAAGGACTACTTC<br>GCGAAGCTGCAAGGCCGAGAGCCGCAGGGCCGGGAGTGGTCGGCTACCG<br>CGCTGAAGCGCTCGCTGATCTCCGAGGCGATGCTCGGGTACGCGACTCTG<br>AACGGTAAGACCGTACGAGACGACGACGGGGCTCCGCTGGTGCGGTCTG<br>AGCCGATCCTGACCCGCGAGCAACTAGAGGCGCTGCGCGCCGAGCTCGTC<br>AAGACCGACCGGACCAAGCCCGCAGTGTCTACTCCGTCGCTGCTGCTGCG<br>GGTGCTGTTCTGCGCAGTGTGCGGGGAGCCCGCATACAAGTTCACCGGTG<br>GCGGTAGGAAGAACGCACGCTACCGCTGCCGGTCGTGGGGCTGGGCGCA<br>GCGGTGCGGGAACGGAACGGTCGCGATGGCTGAGTGGGACGCGTTCTGC<br>GAGGAGCAGGTGCTGGATCTGCTCGGTGACGCAGAGCGTCTGGAGAAAG<br>TCTGGGTAGCCGGTTCGGACTCGGCGGTCGAACTCGCAGAGGTGAACGCG<br>GAGCTGGTGGACCTGACGTCGCTGATCGGTTCTCCGGCCTACCGGGCAGG<br>TTCTCCGCAGCGCGAGGCGCTGGATGCTCGTATCGCGGCGCTGGCCGCGC<br>GGCAGGAGGAGTTGGAAGGGCTAGAGGCTCGCCCGTCGGGCTGGGAGTG<br>GCGCGAAACCGGTCAGAGGTTCGGTGACTGGTGGCGGGATCAGGACACC<br>GCGGCAAAGAACACCTGGCTCCGGTCGATGAACGTTCGGCTGACGTTCGA<br>CGTCCGCGGCGGGCTGACTCGCACGATCGACTTCGGGGATCTGCAGGAGT<br>ACGAGCAGCATCTCAGGCTCGGTAGCGTGGTCGAACGGCTACACACCGGT<br>ATGTCGTAG |
| 65 | Theia | MRVLGRIRLSRMMEESTSVERQREFIETWARQNDHEIVGWAEDLDVSGSVD<br>PFDTQGLGPWLKEPKLREWDILCAWKLDRLARRAVPLHKLFGMCQDEQKVL<br>VCVSDNIDLSTWVGRLVASVIAGVAEGELEAIRERTLSSQRKLRELGRWAGGK<br>PAYGFKAQEREDSAGYELVHDEHAANVMLGVIEKVLAGQSTESVARELNEAG<br>ELAPSDYIRARAGRKTRGTKWSNAQIRQLLKSKTLLGHVTHNGATVRDDDGIP<br>IRKGPALISEEKFDQLQAALDARSFKVTNRSAKASPLLGVAICGLCGRPMHIRQ<br>HRRNGNLYRYYRCDSGSHSGGGGAAPEHPSNIIKADDLEALVEEHFLDEVGRF<br>NVQEKVYVPASDHRAELDEAVRAVEELTQLLGTMTSATMKSRLMGQLTALD<br>ERIARLENLPSEEARWDYRATDQTYAEAWEEADTEGRRQLLIRSGITAEVKVT<br>GGDRGVRGVLEFHLKVPEDVRERLSA |
| 66 | Theia | ATGCGGGTTCTTGGGAGAATACGACTCTCCAGAATGATGGAGGAGTCTAC<br>CAGTGTGGAACGCCAACGTGAGTTCATCGAGACGTGGGCGCGGCAGAAC<br>GATCACGAAATCGTCGGATGGGCTGAGGACCTGGACGTGTCCGGCTCGGT<br>CGATCCGTTCGACACGCAGGGGCTAGGTCCGTGGCTCAAGGAGCCGAAGC<br>TCAGGGAGTGGGACATCCTCTGCGCCTGGAAGCTGGACCGACTTGCTCGA<br>CGCGCCGTACCGCTGCACAAACTGTTCGGGATGTGCCAGGACGAGCAAAA<br>GGTCCTCGTGTGCGTCAGCGACAACATCGACCTGTCGACGTGGGTCGGAC<br>GCCTCGTGGCGTCGGTCATCGCAGGTGTTGCCGAGGGAGAGCTGGAGGC<br>GATCAGGGAGCGGACTCTGTCATCCCAGCGGAAGCTTCGGGAGCTTGGCC<br>GGTGGGCCGGTGGTAAACCTGCCTACGGCTTCAAGGCACAGGAGCGGGA<br>GGACTCAGCCGGGTACGAGCTGGTCATGACGAGCACGCGGCCAACGTG<br>ATGCTCGGTGTCATCGAGAAGGTGCTGGCCGGTCAGTCGACGGAGTCTGT<br>CGCCAGGGAGCTCAACGAGGCAGGGGAGCTGGCACCGTCCGACTACATC<br>AGGGCCAGGGCCGGTCGCAAGACCAGGGGCACGAAGTGGAGCAACGCTC<br>AGATCCGGCAGCTCCTCAAGTCCAAGACTCTGCTCGGGCACGTCACCCACA<br>ACGGGGCCACCGTGCGGGACGACGACGGCATACCGATCCGGAAGGGTCC<br>TGCGCTCATCTCAGAGGAGAAGTTCGATCAGCTCCAGGCCGCGCTCGATG<br>CGCGGTCGTTCAAGGTCACCAACCGATCAGCCAAGGCGTCCCCTCTGCTCG<br>GGTGGCGATCTGTGGCCTGTGCGGTCGTCCGATGCACATACGTCAGCAT<br>CGTCGCAACGGCAACCTCTATCGGTACTACCGCTGCGATAGCGGCAGCCAC<br>TCCGGAGGCGGCGGTGCCGCCCCTGAACACCCGTCGAACATCATCAAGGC<br>CGACGACCTGGAGGCCCTGGTCGAGGAACACTTCCTAGACGAAGTCGGCA |

TABLE 1-continued

Amino-acid and Nucleotide Sequences

| SEQ ID NO: Species | Sequence |
|---|---|
| | GGTTCAACGTGCAGGAGAAGGTGTACGTCCCAGCGTCCGATCACCGGGCA<br>GAGCTGGACGAGGCTGTACGGGCCGTAGAGGAACTGACGCAGCTTCTCG<br>GGACGATGACATCGGCCACGATGAAATCTCGCCTAATGGGCCAACTCACG<br>GCGCTAGACGAGCGCATCGCGAGACTGGAGAACCTCCCGAGTGAGGAAG<br>CCCGATGGGACTACCGTGCAACCGACCAGACGTACGCCGAAGCGTGGGA<br>GGAAGCCGACACCGAAGGCAGACGGCAGCTCCTCATCAGATCCGGAATCA<br>CCCGCTGAGGTCAAGGTGACTGGCCGGTGACCGAGGAGTCAGGGGTGTGCT<br>GGAGTTTCACCTGAAGGTCCCCGAGGACGTGAGAGAACGCCTCTCCGCTT<br>AA |
| 67 Trouble | MRALVVIRLSRVTDATTSPERQLESCRQLCAQRGWDVVGVAEDLDVSGAVD<br>PFDRKRRPNLARWLAFEEQPFDVIVAYRVDRLTRSIRHLQQLVHWAEDHKKL<br>VVSATEAHFDTTTPFAAVVIALMGTVAQMELEAIKERNRSTAHFNIRAGKYRG<br>SLPPWGYLPTRVDGEWRLVSDPVQRERILEVYHRVVDNHEPLHQIAHDLNQR<br>GLPSPKDYFAKLQGREPKGREWSATALKRSLISEAMLGYATLNGKTVRDDDG<br>APLVRAEPILTREQLEALRAELVKTDRTKPAVATPSLLLRVLFCAVCGEPAYKFT<br>GGGRKNARYRCRSWGWAQRCGNGTVAMAEWDAFCEEQVLDLLGGSERLE<br>KVWVAGSDSAVELAEVNAELVDLTSLIGSPAYRVGSPQREALDARIAALAARQ<br>EELEGLEARPSGWEWRETGQRFGDWWREQGTAAKNTWLRSMNVRLTFDV<br>RGGLTRTIDFGDLQEYEQHLRLGSVVERLHAGMS |
| 68 Trouble | ATGAGAGCACTGGTAGTCATCCGACTGTCCCGCGTCACCGATGCTACGACC<br>TCACCGGAGCGCCAGCTGGAGTCTTGCCGACAGCTCTGCGCCCAGCGCGG<br>TTGGGACGTCGTCGGTGTAGCGGAGGATCTGGACGTCTCCGGAGCAGTCG<br>ATCCGTTCGACCGGAAGCGCCGCCCGAACCTGGCACGGTGGCTAGCATTC<br>GAGGAGCAACCGTTCGATGTGATCGTGGCGTACCGGGTAGACCGGTTGAC<br>CCGATCGATCCGGCATCTGCAGCAGCTGGTCCACTGGGCTGAGGACCACA<br>AGAAGCTGGTCGTCTCCGCGACCGAAGCGCACTTCGATACGACGACGCCG<br>TCGCGGCGGTCGTGATCGCGCTTATGGGAACGGTGGCGCAGATGGAATT<br>AGAAGCGATCAAAGAGCGGAACCGCTCGACTGCACATTTCAATATCCGCG<br>CCGGGAAATACCGAGGTTCCCTGCCGCCGTGGGGTTACCTGCCTACGCGC<br>GTGGACGGGGAGTGGCGGCTGGTGTCGGACCCGGTGCAGCGCGAACGCA<br>TCCTCGAGGTCTATCACCGCGTCGTCGACAACCACGAGCCTCTGCACCAGA<br>TCGCCCACGACCTGAACCAGCGCGGCCTACCGTCGCCGAAGGACTACTTCG<br>CGAAGCTGCAGGGCGAGAGCCCAAGGGTCGGGAGTGGTCGGCTACCGC<br>GCTGAAGCGGTCGCTGATCTCGGAGGCGATGCTCGGGTACGCGACGCTGA<br>ACGGTAAGACCGTCCGAGACGACGACGGCGCCCCGCTGGTGCGGGCCGA<br>GCCGATCCTGACGCGTGAGCAGCTGGAGGCGCTGCGCGCCGAGCTCGTCA<br>AGACCGACCGGACCAAGCCCGCAGTGGCTACTCCGTCGCTGCTGCTGCGG<br>GTGTTGTTCTGCGCAGTGTGCGGTGAGCCCGCGTACAAGTTCACCGGTGG<br>CGGTAGGAAGAACGCTCGCTACCGCTGCCGGTCGTGGGGATGGGCGCAG<br>CGGTGCGGCAACGGAACGGTCGCGATGGCGGAGTGGGATGCGTTCTGCG<br>AGGAGCAGGTGCTGGATCTGCTCGGTGGCTCGGAGCGTCTGGAGAAAGT<br>CTGGGTAGCAGGCTCGGACTCGGCAGTCGAACTCGCAGAGGTGAACGCA<br>GAGCTGGTGGACCTGACGTCGCTGATCGGTTCCCCCGCATACCGGGTCGG<br>TTCTCCGCAGCGCGAGGCACTGGATGCTCGTATCGCGGCACTGGCCGCAC<br>GGCAGGAGGAGTTGGAAGGGCTGGAGGCTCGCCCGTCGGGTTGGGAGTG<br>GCGCGAGACTGGGCAGAGGTTCGGTGACTGGTGGCGGGAGCAGGGTACC<br>GCGGCAAAGAACACCTGGCTCCGGTCGATGAACGTTCGGCTGACGTTCGA<br>CGTCCGCGGTGGGCTGACTCGCACGATCGACTTCGGGGATCTGCAGGAGT<br>ACGAGCAGCATCTCAGGCTCGGTAGCGTGGTCGAACGGCTACACGCAGGG<br>ATGTCGTAG |
| 69 Veracruz | MYPTFVRVLGRLRLSRSTEESTSIERQREIVTAWADSNGHTVVGWAEDVDVS<br>GAIDPFDTPSLGVWLDERRGEWDILCAWKLDRLGRDAIRLNKLFLWCQEHGK<br>TVTSCSEGIDLGTPVGRLIANVIAFLAEGEREAIRERVASSKQKLREIGRWGGGK<br>PPFGYMGVRNPDGQGHILVVDPVAKPVVRRIVEDILEGKPLTRLCTELTEERYL<br>TPAEYYATLKAGAPRQQAEEGEVTAKWRPTAVRNLLRSKALRGHANHKGQT<br>VRDDQGRAIQLAEPLVDADEWELLQETLDGIAADFSGRRVEGASPLSGVAVC<br>MTCDKPLHHDRYLVKRPYGDYPYRYYRCRDRHGKNVPAETLEELVEDAFLQR<br>VGDFPVRERVWVQGDTNWADLKEAVAAYDELVQAAGRAKSATARERLQRQ<br>LDILDERIAELESAPNTEAHWEYQPTGGTYRDAWENSDADERRELLRRSGIVV<br>AVHIDGVEGRRSKHNPGALHFDIRVPHELTQRLIAP |
| 70 Veracruz | ATGTATCCTACCTTCGTGCGTGTGTTGGGTAGACTGCGTCTGTCGAGGTCA<br>ACGGAGGAATCCACCTCGATTGAGAGGCAAAGGGAGATCGTCACCGCCTG<br>GGCCGATTCTAACGGTCACACCGTCGTCGGATGGGCAGAGGACGTAGACG<br>TATCGGGTGCCATCGACCCCTTCGACACCCCGTCTCTGGGGGTGTGGTTGG<br>ACGAGCGCCGGGCGAGTGGGACATCCTGTGCGCCTGGAAACTGGACCG<br>CCTGGGCCGTGATGCCATCCGGCTGAACAAGCTCTTCCTGTGGTGCCAGGA<br>GCACGGCAAGACGGTGACATCGTGCAGTGAGGGAATCGACCTCGGCACG<br>CCGGTCGGCCGGCTCATCGCCAACGTGATCGCATTCCTGGCCGAGGGGGA<br>GCGGGAGGCCATCCGCGAGCGGGTCGCATCCTCGAAGCAGAAGCTGCGC<br>GAGATCGGTCGGTGGGGTGGCGGTAAGCCGCCCTTCGGATACATGGGGTG |

TABLE 1-continued

Amino-acid and Nucleotide Sequences

| SEQ ID NO: | Species | Sequence |
|---|---|---|
| | | TCCGCAACCCAGACGGACAGGGACACATCCTTGTGGTCGATCCCGTCGCA<br>AAGCCAGTCGTGCGCCGGATCGTGGAGGACATCCTGGAGGGCAAGCCGC<br>TCACGCGGCTCTGCACCGAGCTGACCGAGGAGCGGTACCTGACCCCTGCG<br>GAGTACTACGCCACCCTCAAGGCCGGTGCCCCGAGGCAGCAGGCCGAGG<br>AGGGGGAGGTGACCGCCAAGTGGCGTCCGACCGCCGTCAGGAACCTGCT<br>CCGCAGCAAAGCCCTCCGGGGCCACGCCCATCACAAGGGCCAGACCGTCA<br>GAGACGACCAGGGGAGGGCTATCCAGCTCGCTGAGCCCTTGTCGACGCC<br>GACGAGTGGGAGTTGCTGCAGGAAACCCTGGACGGTATCGCCGCCGACTT<br>CTCCGGTCGGCGCGTCGAGGGTGCCAGCCCGCTCTCCGGTGTCGCAGTCT<br>GCATGACGTGTGACAAGCCCCTGCACCATGACCGGTATCTGGTGAAGAGG<br>CCCTACGGTGACTACCCCTACCGGTACTACCGGTGCCGTGATCGGCACGGC<br>AAGAACGTCCCAGCCGAAACCCTGGAGGAGTTGGTCGAGGACGCATTCCT<br>GCAGCGCGTAGGTGACTTCCCGGTGCGCGAGCGGGTGTGGGTCCAGGGT<br>GACACCAACTGGGCAGACCTGAAGGAGGCAGTGGCAGCGTATGACGAAC<br>TGGTGCAGGCCGCTGGCCGTGCCAAGTCGGCCACGGCGCGAGAGCGCCTC<br>CAGAGGCAACTGGACATCCTGGACGAGCGGATCGCGGAGCTGGAGTCCG<br>CACCGAACACCGAGGCCCACTGGGAGTACCAGCCGACCGGAGGGACCTAC<br>CGGGACGCCTGGGAGAACTCCGACGCCGACGAGCGCCGCGAGCTACTGC<br>GGCGGTCCGGGATCGTCGTGGCGGTCCACATCGACGGCGTGGAAGGCCG<br>ACGCTCCAAGCACAACCCCGGAGCCCTCCACTTCGACATCCGGGTCCCGCA<br>CGAACTGACACAGAGACTCATCGCCCCATGA |
| 71 | Lockley | MRALVVIRLSRVTDATTSPERQLESCQQLCAQRGWDVVGVAEDLDVSGAVD<br>PFDRKRRPNLARWLAFEEQPFDVIVAYRVDRLTRSIRHLQQLVHWAEDHKKLI<br>VSATEAHFDTTTPFAAVVIALMGTVAQMELEAIKERNRSAAHFNIRAGKYRGS<br>LPPWGYLPTRVDGEWRLVPDPVQRERILEVYHRVVDNHEPLHLVAHDLNRR<br>GVLSPKDYFAKLQGRDPQGREWSATALKRSLISEAMLGYATLNGKTVRDDDG<br>APLVRAEPILTREQLEALRAELVKTDRTKPAVSTPSLLLRVLFCAVCGEPAYKFTG<br>GGRRNARYRCRSWGWAQRCGNGTVAMAEWDAFCEEQVLDLLGDAERLEK<br>VWVAGSDSAVELAEVNAELVDLTSLIGSPAYRVGSPQREALDARIAALAARQE<br>ELEGLEARPSGWEWRETGQRFGDWWREQDTSGKNTWLRSMNVRLTFDVR<br>GGLTRTIDFGDLQEYEQHLRLGSVVERLHTGMS |
| 72 | Lockley | ATGAGAGCTCTCGTCGTGATCCGCTTGTCCCGCGTCACCGATGCTACGACC<br>TCACCGGAGCGTCAGCTGGAGTCTTGCCGGCAGCTCTGCGCCCAGCGCGG<br>TTGGGACGTCGTCGGTGTAGCGGAGGATCTGGACGTCTCCGGAGCAGTCG<br>ATCCGTTCGACCGGAAGCGCAGACCGAACCTGGCACGGTGGCTAGCATTC<br>GAGGAGCAACCGTTCGACGTCATCGTGGCGTACCGGGTGGACCGGTTGAC<br>CCGCTCGATCCGGCATCTTCAGCAGCTGGTCCACTGGGCGGAGGACCACA<br>AGAAGCTGGTCGTCTCCGCGACCGAAGCCCACTTCGACACGACGACGCCG<br>TCGCGGCGGTCGTCATCGCGCTTATGGGAACGGTGGCCAGATGGAATT<br>AGAAGCGATCAAAGAGCGGAACCGTTCGGCTGCACATTTCAATATTCGCG<br>CCGGGAAATACCGCGGTTCCCTGCCGCCGTGGGGTTACCTGCCTACGCGC<br>GTGGACGGGGAGTGGCGGCTGGTGCCGGACCCGGTGCAGCGCGAGCGCA<br>TCCTCGAGGTGTATCACCGCGTCGTCGACAACCACGAGCCGCTGCACCTGG<br>TGGCACACGACCTGAACCGGCGTGGTGTCCTGTCGCCGAAGGACTACTTC<br>GCAAAGCTGCAAGGTCGCGAGCCGCAGGGGCGGGAGTGGTCGGCTACCG<br>CACTGAAGCGCTCGCTGATCTCCGAGGCGATGCTCGGGTACGCGACTCTG<br>AACGGTAAGACCGTCCGAGACGACGACGGAGCCCCGCTGGTCGGGCTG<br>CGCCGATCCTGACCCGTGAGCAGCTGGAGGCGCTGCGCGCCGAGCTCGTC<br>AAGACCGACCGGACCAAGCCCGCAGTGTCTACCCCGTCGCTGCTGCTGCG<br>GGTGCTGTTCTGCGCAGTGTGCGGTGAGCCCGCATACAAGTTCGCAGGTG<br>GAGGACGCAAGCACCCGCGCTACCGCTGCCGCTCGATGGGTTTCCCGAAG<br>CACTGCGGGTAACGGTACGGTCGCAATGGCCGAGTGGGACGCATTCTGCGA<br>GGAGCAGGTGCTGGATCTGCTCGGGGACGCAGAGCGTCTGGAGAAAGTC<br>TGGGTAGCTGGCTCGGACTCAGCAGTAGAACTCGCAGAGGTGAACGCAG<br>AGCTGGTGGACCTGACGTCGCTGATCGGTTCCCCGGCGTACCGGGCCGGT<br>TCTCCGCAGCGCGAGGCGCTGGATGCTCGTATCGCGGCGCTGGCCGCGCG<br>GCAGGAGGAGTTGGAAGGGCTAGAGGCTCGCCCGTCGGGCTGGGAGTGG<br>CGCGAAACCGGGCAGAGGTTCGGGGACTGGTGGCGGGATCAGGACACCG<br>CGGGTAAGAACACCTGGCTCCGGTCGATGAACGTTCGGCTGACGTTCGAC<br>GTCCGAGGCGGCCTGACTCGTACGATCGACTTCGGGGATCTGCAGGAGTA<br>TGAGCAGCATCTGAGGCTGGGCGCGGCTCTAGACCTCGTAAACGCAGAAA<br>AGCCCCCTACGGGCCGCTAG |
| 73 | BxB1 | MRALVVIRLSRVTDATTSPERQLESCQQLCAQRGWDVVGVAEDLDVSGAVD<br>PFDRKRRPNLARWLAFEEQPFDVIVAYRVDRLTRSIRHLQQLVHWAEDHKKL<br>VVSATEAHFDTTTPFAAVVIALMGTVAQMELEAIKERNRSAAHFNIRAGKYRG<br>SLPPWGYLPTRVDGEWRLVPDPVQRERILEVYHRVVDNHEPLHLVAHDLNRR<br>GVLSPKDYFAQLQGREPQGREWSATALKRSMISEAMLGYATLNGKTVRDDD<br>GAPLVRAEPILTREQLEALRAELVKTSRAKPAVSTPSLLLRVLFCAVCGEPAYKF<br>AGGGRKHPRYRCRSMGFPKHCGNGTVAMAEWDAFCEEQVLDLLGDAERLE |

TABLE 1-continued

Amino-acid and Nucleotide Sequences

| SEQ ID NO: | Species | Sequence |
|---|---|---|
| | | KVWVAGSDSAVELAEVNAELVDLTSLIGSPAYRAGSPQREALDARIAALAARQ<br>EELEGLEARPSGWEWRETGQRFGDWWREQDTAAKNTWLRSMNVRLTFDV<br>RGGLTRTIDFGDLQEYEQHLRLGSVVERLHTGMS |
| 74 | BxB1 | ATGAGAGCACTGGTGGTCATCCGACTGAGTAGGGTCACAGACGCAACAAC<br>AAGCCCCGAGAGGCAGCTGGAATCATGTCAGCAGCTGTGCGCACAGCGA<br>GGATGGGACGTGGTCGGAGTGGCAGAGGATCTGGACGTGAGCGGCGCTG<br>TCGATCCATTCGACAGAAAGCGGAGGCCCAACCTGGCAAGGTGGCTGGCT<br>TTCGAGGAACAGCCCTTTGATGTGATCGTCGCCTACAGAGTGGACAGGCT<br>GACACGCTCTATTCGACATCTGCAGCAGCTGGTGCATTGGGCCGAGGACC<br>ACAAGAAACTGGTGGTCAGTGCAACTGAAGCCCACTTCGATACCACAACTC<br>CTTTTGCCGCTGTGGTCATCGCACTGATGGGCACCGTGGCCCAGATGGAG<br>CTGGAAGCTATCAAGGAGCGAAACCGGAGTGCAGCCCATTTCAATATTCG<br>GGCCGGGAAATACAGAGGATCACTGCCCCCTTGGGGCTATCTGCCTACCC<br>GGGTGGATGGGGAGTGGAGACTGGTGCCAGACCCCGTCCAGAGAGAGAG<br>GATTCTGGAAGTGTACCACAGGGTGGTCGATAACCACGAACCACTGCATCT<br>GGTCGCCCACGACCTGAATAGGCGCGGCGTGCTGAGCCCAAAAGATTATT<br>TTGCTCAGCTGCAGGGAAGGGAGCCACAGGGACGAGAATGGTCCGCTAC<br>CGCCCTGAAGCGGAGCATGATCAGTGAGGCTATGCTGGGCTACGCAACTC<br>TGAATGGGAAAACCGTCCGGGACGATGACGGAGCACCACTGGTGAGGGC<br>TGAGCCTATTCTGACACGCGAGCAGCTGGAAGCTCTGCGGGCAGAACTGG<br>TGAAAACCTCCAGAGCCAAACCTGCCGTGAGCACCCCAAGCCTGCTGCTGA<br>GGGTGCTGTTCTGCGCCGTCTGTGGGGAGCCAGCATACAAGTTTGCCGGC<br>GGGGGAAGAAAACATCCCCGCTATCGATGCCGGTCTATGGGATTCCCTAA<br>GCACTGTGGAAACGGCACTGTGGCTATGGCCGAGTGGGACGCCTTTTGTG<br>AGGAACAGGTGCTGGATCTGCTGGGAGACGCCGAGAGGCTGGAAAAAGT<br>GTGGGTCGCTGGCAGCGACTCCGCTGTGAGCTGGCAGAAGTCAATGCCG<br>AGCTGGTGGATCTGACCTCCCTGATCGGATCTCCTGCATATAGGGCAGGCT<br>CACCCACAGCGAGAAGCTCTGGACGCACGAATTGCTGCACTGGCAGCTCGA<br>CAGGAGGAACTGGAGGGGCTGGAAGCACGACCTAGCGGATGGGAGTGG<br>CGAGAAACAGGCCAGCGGTTTGGGGATTGGTGGAGAGAGCAGGACACAG<br>CAGCCAAGAACACTTGGCTGAGAAGTATGAATGTCAGGCTGACTTTCGAT<br>GTGCGCGGCGGGCTGACCCGAACAATCGATTTTGGCGACCTGCAGGAGTA<br>TGAACAGCACCTGAGACTGGGGAGCGTGGTCGAAAGACTGCACACTGGG<br>ATGTCATAG |
| 75 | Peaches | METMPQPLRALVGARVSVVQGPQKVSQQAQLETARKWAEAQGHEIVGTFE<br>DLGVSASVRPDERPDLGKWLTDEGASKWDVIVWSKMDRAFRSTKHCVDFA<br>QWAEEERQKVVMFAEDNLRLDYRPGAAKGIDAMMAELFVYLGSFFAQLELNR<br>FKSRAQDSHRVLRQTDRWASGLPPLGYKTVPHPSGKGFGLDTDEDTKAVLYD<br>MAGKLLDGWSLIGIAKDLNDRGVLGSRSRARLAKGKPIDQAPWNVSTVKDAL<br>TNLKTQGIKMTGKGKHAKPVLDDKGEQIVLAPPTFDWDTWKQIQDAVALRE<br>QAPRSRVHTKNPMLGIGICGKCGATLAQQHSRKKSDKSVVYRYYRCSRTPVN<br>CDGVFIVADEADTLLEEAFLYEWADQPVTRRVFVPGEDHTYELEQINETIARLR<br>RESDAGLIVSDEDERIYLERMRSLITRRTKLEAMPRRSAGWVEETTGQTYGEA<br>WETEDHQQLLKDAKVKFILYSNKPRNIEVVVPQDRVAVDLAI |
| 76 | Peaches | ATGGAGACAATGCCTCAGCCACTGAGGGCTCTGGTGGGAGCTAGAGTGA<br>GTGTGGTGCAGGGGCCTCAGAAAGTGTCACAGCAGGCCCAGCTGGAGAC<br>AGCTAGAAAGTGGGCCGAGGCTCAGGGCCACGAAATCGTGGGGACTTTT<br>GAAGATCTGGGCGTGAGCGCTTCCGTGAGGCCAGATGAGCGCCCCGACCT<br>GGGGAAGTGGCTGACAGATGAAGGAGCCAGCAAATGGGACGTGATTGTG<br>TGGTCCAAGATGGATCGCGCCTTCCGGTCTACCAAACATTGCGTGGACTTT<br>GCCCAGTGGGCTGAGGAAAGACAGAAGGTGGTCATGTTCGCCGAGGATA<br>ACCTGCGGCTGGACTACAGACCTGGAGCCGCTAAAGGCATCGACGCCATG<br>ATGGCTGAGCTGTTTGTGTATCTGGGGAGTTTCTTTGCCCAGCTGGAACTG<br>AATAGGTTCAAGTCCCGCGCTCAGGATTCTCACAGAGTGCTGAGGCAGAC<br>TGACAGATGGGCTAGCGGACTGCCCCCTCTGGGCTACAAAACCGTGCCCC<br>ATCCTTCCGGCAAGGGGTTTGGACTGGACACAGATGAGGACACTAAAGCC<br>GTGCTGTATGATATGGCTGGGAAGCTGCTGGACGGATGGTCCCTGATCGG<br>CATTGCCAAAGATCTGAACGACCGCGGGGTGCTGGGATCTCGGAGTAGAG<br>CCAGGCTGGCTAAAGGCAAGCCTATCGATCAGGCCCCATGGAACGTGTCT<br>ACCGTGAAGGACGCTCTGACCAATCTGAAAACACAGGGAATTAAGATGAC<br>AGGCAAAGGGAAGCACGCCAAACCAGTGCTGGACGATAAGGGAGAGCAG<br>ATCGTGCTGGCTCCACCAACTTTCGATTGGGACACCTGGAAACAGATTCAG<br>GATGCTGTGGCTCTGAGGGAACAGGCTCCTCGCAGCCGGGTGCACACTAA<br>AAACCCAATGCTGGGAATCGGCATTTGCGGCAAGTGTGGAGCTACCCTGG<br>CTCAGCAGCATTCACGCAAAAAGTCAGATAAGAGCGTGGTGTACCGCTAC<br>TATCGGTGCAGCAGAACACCCGTGAATTGTGACGGTGTTCATCGTGGC<br>CGATGAGGCTGACACTCTGCTGGAGGAAGCCTTTCTGTACGAATGGGCTG<br>ATCAGCCCGTGACCCGGAGAGTGTTCGTGCCTGGGGAGGACCACACCTAT<br>GAGCTGGAACAGATCAATGAGACAATTGCCCGGCTGAGGCGCGAAAGTG<br>ACGCTGGACTGATCGTGTCAGATGAGGACGAAAGAATCTACCTGGAGAGA<br>ATGCGGAGCCTGATCACTCGGAGAACCAAGCTGGAAGCTATGCCAAGGAG |

US 10,731,153 B2

TABLE 1-continued

Amino-acid and Nucleotide Sequences

| SEQ ID NO: | Species | | Sequence |
|---|---|---|---|
| | | | GAGTGCTGGATGGGTGGAGGAAACCACAGGGCAGACATACGGAGAGGCC<br>TGGGAGACTGAAGATCATCAGCAGCTGCTGAAAGACGCTAAAGTGAAGTT<br>TATCCTGTATTCCAACAAGCCAAGGAATATTGAAGTGGTGGTGCCACAGG<br>ATAGGGTGGCTGTGGACCTGGCTATTTGA |
| 77 | BxZ2 | | MAQPLRALVGARVSVVQGPQKVSHIAQQETGAKWVAEQGHTVVGSFKDLD<br>VSATVSPFERPDLGPWLSPELEGEWDILVFSKIDRMFRSTRDCVKFAEWAEAH<br>GKILVFAEDNMTLNYRDKDRSGSLESMMSELFIYIGSFFAQLELNRFKSRARDS<br>HRVLRGMDRWASGVPPLGFRIVDHPSGKGKGLDTDPEGKAILEDMAAKLLD<br>GWSFIRIAQDLNQRKVLTNMDKAKIAKGKPPHPNPWTVNTVIESLTSPRTQGI<br>KMTKHGTRGGSKIGTTVLDAEGNPIRLAPPTFDPATWKQIQEAAARRQGNRR<br>SKTYTANPMLGVGHCGACGASLAQQFTHRKLADGTEVTYRTYRCGRTPLNCN<br>GISMRGDEADGLLEQLFLEQYGSQPVTEKVFVPGEDHSEELEQVRATIDRLRR<br>ESDAGLIATAEDERIYFERMKSLIDRRTRLEAQPRRASGWVTQETDKTNADEW<br>TKASTPDERRRLLMKQGIRFELVRGKPDPEVRLFTPGEIPEGEPLPEPSPR |
| 78 | BxZ2 | | ATGGCACAGCCACTGAGGGCACTGGTCGGAGCACGGGTCAGCGTCGTCCA<br>GGGGCCACAGAAAGTCTCCCACATCGCACAGCAGGAGACTGGAGCAAAG<br>TGGGTGGCAGAGCAGGGACACACGTGGTCGGAAGCTTCAAAGACCTGG<br>ACGTGAGCGCCACCGTCTCTCCTTTTGAACGCCCAGATCTGGGACCCTGGC<br>TGTCCCCTGAGCTGGAAGGGGAGTGGGACATCCTGGTGTTCAGCAAGATT<br>GATAGGATGTTTAGATCCACTCGGGACTGCGTGAAGTTCGCAGAATGGGC<br>AGAGGCCCATGGAAAAATCCTGGTCTTTGCCGAGGACAACATGACCCTGA<br>ATTACCGCGACAAGGATCGAAGCGGATCCCTGGAATCTATGATGAGTGAG<br>CTGTTCATCTATATTGGGTCTTTCTTTGCTCAGCTGGAGCTGAACAGGTTCA<br>AGAGTCGCGCACGAGATTCACACCGCGTGCTGCGAGGCATGGACAGATG<br>GGCATCTGGAGTGCCACCTCTGGGCTTCCGGATCGTCGACCATCCCAGTGG<br>GAAGGGCAAAGGACTGGACACAGATCCTGAAGGCAAGGCTATTCTGGAG<br>GACATGGCCGCTAAACTGCTGGATGGATGGAGCTTTATCCGCATTGCACA<br>GGATCTGAACCAGAGGAAGGTGCTGACTAATATGGACAAGGCCAAATCG<br>CTAAGGGCAAACCACCCCACCCCAACCCTTGGACAGTGAATACTGTCATCG<br>AGTCACTGACCAGCCCCCGCACACAGGGAATTAAGATGACTAAACATGGG<br>ACCAGGGGCGGATCCAAGATCGGCACCACAGTGCTGGATGCCGAGGGAA<br>ATCCTATTCGGCTGGCACCTCCAACCTTCGACCCAGCCACATGGAAGCAGA<br>TCCAGGAAGCAGCAGCTAGGAGACAGGGAAACCGGCGCAGTAAAACTTA<br>CACCGCCAATCCTATGCTGGGAGTGGGACACTGCGGAGCATGTGGAGCCT<br>CACTGGCTCAGCAGTTTACCCATAGAAAGCTGGCTGATGGCACCGAGGTC<br>ACATACAGGACTTATAGATGCGGACGGACACCACTGAACTGTAATGGAAT<br>TTCTATGCGGGGGGACGAAGCTGATGGCCTGCTGGAACAGCTGTTCCTGG<br>AGCAGTACGGGTCACAGCCAGTGACCGAAAAGGTGTTTGTCCCCGGCGAG<br>GACCACAGCGAGGAACTGGAACAGGTCAGGGCCACAATCGACAGACTGC<br>GAAGGGAGAGTGATGCTGGGCTGATCGCTACTGCAGAAGATGAGCGGAT<br>CTACTTCGAGCGCATGAAATCCCTGATTGACAGACGGACAAGGCTGGAAG<br>CTCAGCCACGCCGAGCATCTGGCTGGGTGACCCAGGAGACAGACAAGACT<br>AACGCCGATGAATGGACAAAAGCTAGCACTCCCGATGAGAGGAGACGGC<br>TGCTGATGAAGCAGGGGATCCGATTCGAGCTGGTGCGGGGCAAACCAGA<br>CCCCGAAGTCAGACTGTTCACCCCCGGCGAAATCCCCGAAGGCGAGCCCCT<br>GCCCGAGCCCTCCCCAGATGATAA |
| 79 | Peaches | attB/attP | GCGGTCTCCATCGGGATCTGCACATCGAGCAGCATGCCGACCAG |
| 80 | Peaches | attB/attP | GCGGTCTCCATCGGGATCTGCAGATCGAGCAGCATGCCGACCAG |
| 81 | Peaches | attB/attP | GCGGTCTCCATCGGGATCTGCCCATCGAGCAGCATGCCGACCAG |
| 82 | Peaches | attB/attP | GCGGTCTCCATCGGGATCTGCTCATCGAGCAGCATGCCGACCAG |
| 83 | Peaches | attB/attP | GCGGTCTCCATCGGGATCTGCTGATCGAGCAGCATGCCGACCAG |
| 84 | Peaches | attB/attP | GCGGTCTCCATCGGGATCTGCTTATCGAGCAGCATGCCGACCAG |
| 85 | BxB1 | attB | GGCTTGTCGACGACGGCacCCTCCGTCGTCAGGATCAT |
| 86 | BxB1 | attB | GGCTTGTCGACGACGGCagCCTCCGTCGTCAGGATCAT |
| 87 | BxB1 | attB | GGCTTGTCGACGACGGCccCCTCCGTCGTCAGGATCAT |
| 88 | BxB1 | attB | GGCTTGTCGACGACGGCtcCCTCCGTCGTCAGGATCAT |
| 89 | BxB1 | attB | GGCTTGTCGACGACGGCtgCCTCCGTCGTCAGGATCAT |
| 90 | BxB1 | attB | GGCTTGTCGACGACGGCttCCTCCGTCGTCAGGATCAT |

TABLE 1-continued

Amino-acid and Nucleotide Sequences

| SEQ ID NO: | Species | | Sequence |
|---|---|---|---|
| 91 | BxB1 | attP | GTGGTTTGTCTGGTCAACCACCGCacGCTCAGTGGTGTACGGTACAAACCCA |
| 92 | BxB1 | attP | GTGGTTTGTCTGGTCAACCACCGCagGCTCAGTGGTGTACGGTACAAACCCA |
| 93 | BxB1 | attP | GTGGTTTGTCTGGTCAACCACCGCccGCTCAGTGGTGTACGGTACAAACCCA |
| 94 | BxB1 | attP | GTGGTTTGTCTGGTCAACCACCGCtcGCTCAGTGGTGTACGGTACAAACCCA |
| 95 | BxB1 | attP | GTGGTTTGTCTGGTCAACCACCGCtgGCTCAGTGGTGTACGGTACAAACCCA |
| 96 | BxB1 | attB | GTGGTTTGTCTGGTCAACCACCGCttGCTCAGTGGTGTACGGTACAAACCCA |
| 97 | Rebeuca | attB | CGGTATTCGGCGCGATCCGCGGCacGAAGAACATCACCCTGAACATCG |
| 98 | Rebeuca | attB | CGGTATTCGGCGCGATCCGCGGCagGAAGAACATCACCCTGAACATCG |
| 99 | Rebeuca | attB | CGGTATTCGGCGCGATCCGCGGCccGAAGAACATCACCCTGAACATCG |
| 100 | Rebeuca | attB | CGGTATTCGGCGCGATCCGCGGCtcGAAGAACATCACCCTGAACATCG |
| 101 | Rebeuca | attB | CGGTATTCGGCGCGATCCGCGGCtgGAAGAACATCACCCTGAACATCG |
| 102 | Rebeuca | attB | CGGTATTCGGCGCGATCCGCGGCttGAAGAACATCACCCTGAACATCG |
| 103 | Rebeuca | attP | AGAGCATCGGAGCCTTTCGGGGATGTGATETTCGAGacGAAGAACAT |
| 104 | Rebeuca | attP | AGAGCATCGGAGCCTTTCGGGGATGTGATGTTCGAGagGAAGAACAT |
| 105 | Rebeuca | attP | AGAGCATCGGAGCCTTTCGGGGATGTGATGTTCGAGccGAAGAACAT |
| 106 | Rebeuca | attP | AGAGCATCGGAGCCTTTCGGGGATGTGATGTTCGAGtcGAAGAACAT |
| 107 | Rebeuca | attP | AGAGCATCGGAGCCTTTCGGGGATGTGATGTTCGAGtgGAAGAACAT |
| 108 | Rebeuca | attP | AGAGCATCGGAGCCTTTCGGGGATGTGATGTTCGAGttGAAGAACAT |
| 109 | Veracruz | attB | CGGTATTCGGCGCGATCCGCGGCacGAAGAACATCACCCTGAACATCG |
| 110 | Veracruz | attB | CGGTATTCGGCGCGATCCGCGGCagGAAGAACATCACCCTGAACATCG |
| 111 | Veracruz | attB | CGGTATTCGGCGCGATCCGCGGCccGAAGAACATCACCCTGAACATCG |
| 112 | Veracruz | attB | CGGTATTCGGCGCGATCCGCGGCtcGAAGAACATCACCCTGAACATCG |
| 113 | Veracruz | attB | CGGTATTCGGCGCGATCCGCGGCtgGAAGAACATCACCCTGAACATCG |
| 114 | Veracruz | attB | CGGTATTCGGCGCGATCCGCGGCttGAAGAACATCACCCTGAACATCG |
| 115 | Veracruz | attP | GTATTGGGGGAACGCGATATTCGAGacGTAGAACATCACCTTCACCAAATTC |
| 116 | Veracruz | attP | GTATTGGGGGAACGCGATATTCGAGagGTAGAACATCACCTTCACCAAATTC |
| 117 | Veracruz | attP | GTATTGGGGGAACGCGATATTCGAGccGTAGAACATCACCTTCACCAAATTC |
| 118 | Veracruz | attP | GTATTGGGGGAACGCGATATTCGAGtcGTAGAACATCACCTTCACCAAATTC |
| 119 | Veracruz | attP | GTATTGGGGGAACGCGATATTCGAGtgGTAGAACATCACCTTCACCAAATTC |
| 120 | Veracruz | attB | GTATTGGGGGAACGCGATATTCGAGttGTAGAACATCACCTTCACCAAATTC |
| 121 | Theia | attB | TGGGTGAACGCAAAGATGGGGacCTCGATGCCGAGCTCGTCGCA |

TABLE 1-continued

Amino-acid and Nucleotide Sequences

| SEQ ID NO: | Species | | Sequence |
|---|---|---|---|
| 122 | Theia | attB | TGGGTGAACGCAAAGATGGGGagCTCGATGCCGAGCTCGTCGCA |
| 123 | Theia | attB | TGGGTGAACGCAAAGATGGGGccCTCGATGCCGAGCTCGTCGCA |
| 124 | Theia | attB | TGGGTGAACGCAAAGATGGGGtcCTCGATGCCGAGCTCGTCGCA |
| 125 | Theia | attB | TGGGTGAACGCAAAGATGGGGtgCTCGATGCCGAGCTCGTCGCA |
| 126 | Theia | attB | TGGGTGAACGCAAAGATGGGGttCTCGATGCCGAGCTCGTCGCA |
| 127 | Theia | attP | TTGTCAAAGTCTAAAGATGGGGacCTCAATATTCATGCTTTGCGAA |
| 128 | Theia | attP | TTGTCAAAGTCTAAAGATGGGGagCTCAATATTCATGCTTTGCGAA |
| 129 | Theia | attP | TTGTCAAAGTCTAAAGATGGGGccCTCAATATTCATGCTTTGCGAA |
| 130 | Theia | attP | TTGTCAAAGTCTAAAGATGGGGtcCTCAATATTCATGCTTTGCGAA |
| 131 | Theia | attP | TTGTCAAAGTCTAAAGATGGGGtgCTCAATATTCATGCTTTGCGAA |
| 132 | Theia | attB | TTGTCAAAGTCTAAAGATGGGGttCTCAATATTCATGCTTTGCGAA |
| 133 | Benedict | attB | TGGGTGAACGCAAAGATGGGGacCTCGATGCCGAGCTCGTCGCA |
| 134 | Benedict | attB | TGGGTGAACGCAAAGATGGGGagCTCGATGCCGAGCTCGTCGCA |
| 135 | Benedict | attB | TGGGTGAACGCAAAGATGGGGccCTCGATGCCGAGCTCGTCGCA |
| 136 | Benedict | attB | TGGGTGAACGCAAAGATGGGGtcCTCGATGCCGAGCTCGTCGCA |
| 137 | Benedict | attB | TGGGTGAACGCAAAGATGGGGtgCTCGATGCCGAGCTCGTCGCA |
| 138 | Benedict | attB | TGGGTGAACGCAAAGATGGGGttCTCGATGCCGAGCTCGTCGCA |
| 139 | Benedict | attP | TTCGCAAAGCCTCAAAATCGGGacCTCGATATTCATGCTTTGTGAA |
| 140 | Benedict | attP | TTCGCAAAGCCTCAAAATCGGGagCTCGATATTCATGCTTTGTGAA |
| 141 | Benedict | attP | TTCGCAAAGCCTCAAAATCGGGccCTCGATATTCATGCTTTGTGAA |
| 142 | Benedict | attP | TTCGCAAAGCCTCAAAATCGGGtcCTCGATATTCATGCTTTGTGAA |
| 143 | Benedict | attP | TTCGCAAAGCCTCAAAATCGGGtgCTCGATATTCATGCTTTGTGAA |
| 144 | PhiC31 | attB | GTGCGGGTGCCAGGGCGTGCCCacGGGCTCCCCGGGCGCGTACTCC |
| 145 | PhiC31 | attB | GTGCGGGTGCCAGGGCGTGCCCagGGGCTCCCCGGGCGCGTACTCC |
| 146 | PhiC31 | attB | GTGCGGGTGCCAGGGCGTGCCCccGGGCTCCCCGGGCGCGTACTCC |
| 147 | PhiC31 | attB | GTGCGGGTGCCAGGGCGTGCCCtcGGGCTCCCCGGGCGCGTACTCC |
| 148 | PhiC31 | attB | GTGCGGGTGCCAGGGCGTGCCCtgGGGCTCCCCGGGCGCGTACTCC |
| 149 | PhiC31 | attB | GTGCGGGTGCCAGGGCGTGCCCttGGGCTCCCCGGGCGCGTACTCC |
| 150 | PhiC31 | attP | GTGCCCCAACTGGGGTAACCTacGAGTTCTCTCAGTTGGGGG |
| 151 | PhiC31 | attP | GTGCCCCAACTGGGGTAACCTagGAGTTCTCTCAGTTGGGGG |
| 152 | PhiC31 | attP | GTGCCCCAACTGGGGTAACCTccGAGTTCTCTCAGTTGGGGG |
| 153 | PhiC31 | attP | GTGCCCCAACTGGGGTAACCTtcGAGTTCTCTCAGTIGGGGG |
| 154 | PhiC31 | attP | GTGCCCCAACTGGGGTAACCTtgGAGTTCTCTCAGTTGGGGG |
| 155 | PhiC31 | attB | GTGCCCCAACTGGGGTAACCTttGAGTTCTCTCAGTTGGGGG |
| 160 | PhiC31 | | MDTYAGAYDRQSRERENSSAASPATQRSANEDKAADLQREVERDGGRERFS<br>AFGTAERPEFERILNECRAGRLNMIIVYDVSRFSRLKVMDAIPIVSELLALGVTIV<br>STQEGVFRQGNVMDLIHLIMRLDASHKESSLKSAKILDTKNLQRELGGYVGGK<br>APYGFELVSETKEITRNGRMVNVVINKLAHSTTPLTGPFEEEPDVIRWWWREI<br>KTHKHLPFKPGSQAAIHPGSITGLCKRMDADAVPTRGETIGKKTASSAWDPAT<br>VMRILRDPRIAGFAAEVIYKKKPDGTPTTKIEGYRIQRDPITLRPVELDCGPIIEP |

TABLE 1-continued

Amino-acid and Nucleotide Sequences

| SEQ ID NO: | Species | Sequence |
|---|---|---|
| | | AEWYELQAWLDGRGRGKGLSRGQAILSAMDKLYCECGAVMTSKRGEESIKD<br>SYRCRRRKVVDPSAPGQHEGTCNVSMAALDKFVAERIFNKIRHAEGDEETLAL<br>LWEAARRFGKLTEAPEKSGERANLVAERADALNALEELYEDRAAGAYDGPVG<br>RKHFRKQQAALTLRQQGAEERLAELEAAEAPKLPLDQWFPEDADADPTGPKS<br>WWGRASVDDKRVFVGLFVDKIVVTKSTTGRGQGTPIEKRASITWAKPPTDDD<br>EDDAQDGTEDVAA |
| 161 | PhiC31 | GTGGACACGTACGCGGGTGCTTACGACCGTCAGTCGCGCGAGCGCGAGA<br>ATTCGAGCGCAGCAAGCCCAGCGACACAGCGTAGCGCCAACGAAGACAA<br>GGCGGCCGACCTTCAGCGCGAAGTCGAGCGCGACGGGGGCCGGTTCAGG<br>TTCGTCGGGCATTTCAGCGAAGCGCCGGGCACGTCGGCGTTCGGGACGGC<br>GGAGCGCCCGGAGTTCGAACGCATCCTGAACGAATGCCGCGCCGGGCGG<br>CTCAACATGATCATTGTCTATGACGTGTCGCGCTTCTCGCGCCTGAAGGTC<br>ATGGACGCGATTCCGATTGTCTCGGAATTGCTCGCCCTGGGCGTGACGATT<br>GTTTCCACTCAGGAAGGCGTCTTCCGGCAGGGAAACGTCATGGACCTGATT<br>CACCTGATTATGCGGCTCGACGCGTCGCACAAAGAATCTTCGCTGAAGTCG<br>GCGAAGATTCTCGACACGAAGAACCTTCAGCGCGAATTGGGCGGGTACGT<br>CGGCGGGAAGGCGCCTTACGGCTTCGAGCTTGTTTCGGAGACGAAGGAG<br>ATCACGCGCAACGGCCGAATGGTCAATGTCGTCATCAACAAGCTTGCGCAC<br>TCGACCACTCCCCTTACCGGACCCTTCGAGTTCGAGCCCGACGTAATCCGG<br>TGGTGGTGGCGTGAGATCAAGCACGCACAAACACCTTCCCTTCAAGCCGGG<br>CAGTCAAGCCGCCATTCACCCGGGCAGCATCACGGGGCTTTGTAAGCGCA<br>TGGACGCTGACGCCGTGCCGACCCGGGGCGAGACGATTGGGAAGAAGAC<br>CGCTTCAAGCGCCTGGGACCCGGCAACCGTTATGCGAATCCTTCGGGACCC<br>GCGTATTGCGGGCTTCGCCGCTGAGGTGATCTACAAGAAGAAGCCGGACG<br>GCACGCCGACCACGAAGATTGAGGGTTACCGCATTCAGCGCGACCCGATC<br>ACGCTCCGGCCGGTCGAGCTTGATTGCGGACCGATCATCGAGCCCGCTGA<br>GTGGTATGAGCTTCAGGCGTGGTTGGACGGCAGGGGGCGCGGCAAGGGG<br>CTTTCCCGGGGGCAAGCCATTCTGTCCGCCATGGACAAGCTGTACTGCGAG<br>TGTGGCGCCGTCATGACTTCGAAGCGCGGGGAAGAATCGATCAAGGACTC<br>TTACCGCTGCCGTCGCCGGAAGGTGGTCGACCCGTCCGCACCTGGGCAGC<br>ACGAAGGCACGTGCAACGTCAGCATGGCGGCACTCGACAAGTTCGTTGCG<br>GAACGCATCTTCAACAAGATCAGGCACGCCGAAGGCGACGAAGAGACGTT<br>GGCGCTTCTGTGGGAAGCCGCCCGACGCTTCGGCAAGCTCACTGAGGCGC<br>CTGAGAAGAGCGGCAACGGGCGAACCTTGTTGCGGAGCGCGCCGACGC<br>CCTGAACGCCCTTGAAGAGCTGTACGAAGACCGCGCGGCAGGCGCGTACG<br>ACGGACCCGTTGGCAGGAAGCACTTCCGGAAGCAACAGGCAGCGCTGAC<br>GCTCCGGCAGCAAGGGGCGGAAGAGCGGCTTGCCGAACTTGAAGCCGCC<br>GAAGCCCCGAAGCTTCCCCTTGACCAATGGTTCCCCGAAGACGCCGACGCT<br>GACCCGACCGGCCCTAAGTCGTGGTGGGGGCGCGCGTCAGTAGACGACA<br>AGCGCGTGTTCGTCGGGCTCTTCGTAGACAAGATCGTTGTCACGAAGTCGA<br>CTACGGGCAGGGGGCAGGGAACGCCCATCGAGAAGCGCGCTTCGATCAC<br>GTGGGCGAAGCCGCCGACCGACGACGACGAAGACGACGCCCAGGACGGC<br>ACGGAAGACGTAGCGGCGTAG |

REFERENCES

1. Malchin, N., Goltsman, J., Dabool, L., Gorovits, R., Bao, Q., Dröge, P., Yagil, E. and Kolot, M., Optimization of coliphage HK022 Integrase activity in human cells. (2009) Gene, 437, 9-13.
2. Krishnakumar, R., Grose, C., Haft, D. H., Zaveri, J., Alperovich, N., Gibson, D. G., Merryman, C., and Glass, J. I., Simultaneous non-contiguous deletions using large synthetic DNA and site-specific recombinases. (2014) Nucl. Acids Res., 42, 1-8.
3. Park J T, Leach S D. TAILOR: transgene activation and inactivation using lox and rox in zebrafish. (2013) PLoS One. 8(12):e85218.
4. Long D, Zhao A, Xu L, Lu W, Guo Q, Zhang Y, Xiang Z. In vivo site-specific integration of transgene in silkworm via PhiC31 integrase-mediated cassette exchange. (2013) Insect Biochem Mol Biol. 43(11):997-1008.
5. Turan S, Qiao J, Madden S, Benham C, Kotz M, Schambach A, Bode J. Expanding Flp-RMCE options: the potential of Recombinase Mediated Twin-Site Targeting (RMTT). Gene. (2014) 546(2):135-44.
6. Osterwalder, M., Galli, A., Rosen, B., Skarnes, W. C., Zeller, R. and Lopez-Rios, J. Dual RMCE for efficient re-engineering of mouse mutant alleles. (2010) Nat Meth, 7, 893-895.
7. Jaina, P., Hsua, T., Araia, M., Biermanna, K., Thalera, D. S., Nguyena, A., Gonzáleza, P. A., Tufarielloa, J. M., Kriakova, J., Chena, B., Larsena, M. H., and Jacobs Jr., W. R., Specialized transduction designed for precise high-throughput unmarked deletions in *Mycobacterium* tuberculosis. (2014) mBio. 5, e01245-14.
8. Wang, Y., Krushel, L. A. and Edelman, G. M. Targeted DNA recombination in vivo using an adenovirus carrying the cre recombinase gene. (1996) Proc. Natl. Acad. Sci. U.S.A., 93, 3932-3936.
9. Grindley N D, Whiteson K L, Rice P A. Mechanisms of site-specific recombination. Annu Rev Biochem. (2006) 75:567-605.
10. G Pan, K. L. P. D. S. Mechanism of cleavage and ligation by FLP recombinase: classification of mutations in FLP protein by in vitro complementation analysis. Molecular and Cellular Biology, 13, 3167.

11. Esposito, D. and Scocca, J. J. (1997) The integrase family of tyrosine recombinases: evolution of a conserved active site domain. Nucleic Acids Res., 25, 3605-3614.
12. Mumm, J. P., Landy, A., and Gelles, J. Viewing single lambda site-specific recombination events from start to finish. (2006). 25, 4586-4595.
13. Anastassiadis K, Fu J, Patsch C, Hu S, Weidlich S, Duerschke K, Buchholz F, Edenhofer F, Stewart A F. Dre recombinase, like Cre, is a highly efficient site-specific recombinase in *E. coli*, mammalian cells and mice. Dis Model Mech. (2009) 2 (9-10):508-15.
14. Zuwen Zhang, B. L. Cre recombinase-mediated inversion using lox66 and lox71: method to introduce conditional point mutations into the CREB-binding protein. (2002) Nucleic Acids Res., 30, e90.
15. Gaj, T., Gaj, T., Mercer, A. C., Mercer, A. C., Gersbach, C. A., Gersbach, C. A., Gordley, R. M., Gordley, R. M., Barbas, C. F. and Barbas, C. F. Structure-guided reprogramming of serine recombinase DNA sequence specificity. (2011) Proc. Natl. Acad. Sci. U.S.A., 108, 498-503.
16. Hubbard E J. FLP/FRT and Cre/lox recombination technology in *C. elegans*. (2014) Methods. 68(3):417-24.
17. Turan S, Zehe C, Kuehle J, Qiao J, Bode J. Recombinase-mediated cassette exchange (RMCE)—a rapidly-expanding toolbox for targeted genomic modifications. Gene. 2013 Feb. 15; 515(1):1-27.
18. Smith, M. C. M. and Thorpe, H. M. Diversity in the serine recombinases. (2002) Mol Microbiol, 44, 299-307.
19. Xu, Z., Thomas, L., Davies, B., Chalmers, R., Smith, M. and Brown, W. Accuracy and efficiency define Bxb1 integrase as the best of fifteen candidate serine recombinases for the integration of DNA into the human genome. (2013) BMC Biotechnol, 13, 87.
20. Thyagarajan, B., Ausländer, S., Thyagarajan, B., Olivares, E. C., Ausländer, D., Olivares, E. C., Hollis, R. P., Müller, M., Hollis, R. P., Ginsburg, D. S., et al. Site-specific genomic integration in mammalian cells mediated by phage phiC31 integrase. (2001) Molecular and Cellular Biology, 21, 3926-3934.
21. Kim, A. I., Ghosh, P., Aaron, M. A., Bibb, L. A., Jain, S. and Hatfull, G. F. Mycobacteriophage Bxb1 integrates into the *Mycobacterium smegmatis* groEL1 gene. (2003) Mol Microbiol, 50, 463-473.
22. Singh, S., Rockenbach, K., Dedrick, R. M., VanDemark, A. P. and Hatfull, G. F. Cross-talk between Diverse Serine Integrases. (2014) Journal of Molecular Biology, 426, 318-331.
23. Hatfull, G. F., the Science Education Alliance Phage Hunters Advancing Genomics and Evolutionary Science Program, the Kwazulu-Natal Research Institute for Tuberculosis and HIV Mycobacterial Genetics Course Students the Phage Hunters Integrating Research and Education Program Complete Genome Sequences of 138 Mycobacteriophages. (2012) Journal of Virology, 86, 2382-2384.
24. Park, A., Jeong, H., Lee, J., Lee, C. The inhibitory effect of phloretin on the formation of *Escherichia coli* O157: H7 biofilm in a microfluidic system. (2012) BioChip J. 6, 299-305.
25. Barreca D, Bellocco E, Laganà G, Ginestra G, Bisignano C. Biochemical and antimicrobial activity of phloretin and its glycosilated derivatives present in apple and kumquat. (2014) Food Chem. 160:292-7.
26. Terán, W., Felipe, A., Segura, A., Rojas, A., Ramos, J., and Gallegos, M. Antibiotic-Dependent Induction of *Pseudomonas putida* DOT-T1E TtgABC Efflux Pump Is Mediated by the Drug Binding Repressor TtgR (2003) Antimicrob Agents Chemother. 47, 3067-3072.
27. Rutherford K, Yuan P, Perry K, Sharp R, Van Duyne G D. Attachment site recognition and regulation of directionality by the serine integrases. (2013) Nucleic Acids Res. 41(17):8341-56.
28. Singh, S., Ghosh, P., Hatfull, G. F. Attachment site selection and identity in Bxb1 serine integrase-mediated site-specific recombination. (2013) PLOS Genetics. 9, e1003490.
29. Hasty, J., McMillen, D. & Collins, J. J. Engineered gene circuits. (2002) Nature 420, 224-230.
30. Shimada T, Yamazaki Y, Tanaka K, Ishihama A. The whole set of constitutive promoters recognized by RNA polymerase RpoD holoenzyme of *Escherichia coli*. (2014) PLoS One. 9(3):e90447.
31. Johansen, T. E., Scholler, M. S., Tolstoy, S., Schwartz, T. Biosynthesis of peptide precursors and protease inhibitors using new constitutive and inducible eukaryotic expression vectors. (1990) FEBS. 267(2), 289-94.
32. Hayashi, K., Nakazawa, M., Ishizaki, Y., Hiraoka, N., Regulation of inter- and intramolecular ligation with T4 DNA ligase in the presence of polyethylene glycol. (1986) Nucl. Acids Res. 14(19):7617-31.
33. Gardner, T. S., Cantor, C. R. and Collins, J. J. Construction of a genetic toggle switch in *Escherichia coli*. (2000) Nature, 403, 339-342.
34. Danino, T., Mondragón-Palomino, O., Tsimring, L. and Hasty, J. A synchronized quorum of genetic clocks. (2010) Nature, 463, 326-330.
35. Moon, T. S., Lou, C., Tamsir, A., Stanton, B. C. and Voigt, C. A. Genetic programs constructed from layered logic gates in single cells. (2012) Nature, 491, 249-253.
36. Purnick, P. E. M. and Weiss, R. The second wave of synthetic biology: from modules to systems. (2009) Nature Reviews Molecular Cell Biology, 10, 410-422.
37. Wang, B., Kitney, R. I., Joly, N. and Buck, M. Engineering modular and orthogonal genetic logic gates for robust digital-like synthetic biology. (2011) Nat Commun, 2, 508.
38. Friedland, A. E., Lu, T. K., Wang, X., Shi, D., Church, G., Collins, J. J., Synthetic Gene Networks That Count (2009) Synthetic Gene Networks That Count. 324, 1199-1202.
39. Elowitz, M. B. and Leibler, S. A synthetic oscillatory network of transcriptional regulators. (2000) Nature, 403, 335-338.
40. Siuti, P., Yazbek, J. and Lu, T. K. Synthetic circuits integrating logic and memory in living cells. (2013) Nature Biotechnology, 31, 448-452.
41. Bleris, L., Xie, Z., Glass, D., Adadey, A., Sontag, E. and Benenson, Y. Synthetic incoherent feedforward circuits show adaptation to the amount of their genetic template. (2011) Mol Syst Biol, 7, 519.
42. Mukherji, S., Ebert, M. S., Zheng, G. X. Y., Tsang, J. S., Sharp, P. A. and van Oudenaarden, A. MicroRNAs can generate thresholds in target gene expression. (2011) Nat Genet, 43, 854-859.
43. Tigges, M., Marquez-Lago, T. T., Stelling, J. and Fussenegger, M. A tunable synthetic mammalian oscillator. (2009) Nature, 457, 309-312.
44. Siciliano, V., Menolascina, F., Marucci, L., Fracassi, C., Garzilli, I., Moretti, M. N. and di Bernardo, D. Construction and modelling of an inducible positive feedback loop stably integrated in a mammalian cell-line. (2011) PLoS Comp Biol, 7, e1002074.
45. Lanitis, E., Poussin, M., Klattenhoff, A. W., Song, D., Sandaltzopoulos, R., June, C. H. and Powell, D. J. Chimeric antigen receptor T Cells with dissociated signaling domains exhibit focused antitumor activity with reduced potential for toxicity in vivo. (2013) Cancer Immunol Res, 1, 43-53. 46. Grushkin, D. The new drug circuit. (2012) Nat Med, 18, 1452-1454.
47. Ye, H., Baba, M. D. E., Peng, R. W. and Fussenegger, M. A Synthetic Optogenetic Transcription Device Enhances Blood-Glucose Homeostasis in Mice. (2011) Science, 332, 1565-1568.
48. Ishihara, K., Oshimura, M. and Nakao, M. CTCF-dependent chromatin insulator is linked to epigenetic remodeling. (2006) Mol. Cell, 23, 733-742.

All publications, patents and sequence database entries mentioned herein, including those items listed below, are hereby incorporated by reference for the teachings referenced herein as if each individual publication or patent was specifically and individually indicated to be incorporated by reference. In case of conflict, the present application, including any definitions herein, will control.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

Articles such as "a," "an," and "the," as used herein, may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim or another portion of the description. For example, any claim that is dependent on another claim can be modified to include one or more limitations found in any other claim that is dependent on the same base claim.

Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. An isolated cell comprising a plurality of landing pads integrated into the genomic DNA of the isolated cell, wherein each landing pad comprises
   a constitutive promoter operably linked to a nucleotide sequence encoding a detectable marker, followed by a nucleotide sequence encoding a first selectable marker, and
   an attB site of a large serine recombinase, wherein the attB site is between the promoter and the nucleotide sequence encoding the detectable marker, and
   wherein the attB sites of the large serine recombinase in the plurality of landing pads each comprises a different central dinucleotide
   and wherein the large serine recombinase is selected from the group consisting of: BxB1, BxZ2, PhiC31, Peaches, Veracruz, Rebeuca, Theia, Benedict, PattyP, Trouble, KSSJEB, Lockley, Scowl, Switzer, Bob3, Abrogate, Doom, ConceptII, Anglerfish, SkiPole, Museum, and Severus.

2. The isolated cell of claim 1, wherein:
   if the large serine recombinase is Peaches, then the attB sites are selected from SEQ ID NOs: 79-84;
   if the large serine recombinase is BxB1, then the attB sites are selected from SEQ ID NOs: 85-90;
   if the large serine recombinase is Rebeuca, then the attB sites are selected from SEQ ID NOs: 97-102;
   if the large serine recombinase is Veracruz, then the attB sites are selected from SEQ ID NOs: 109-114;
   if the large serine recombinase is Theia, then the attB sites are selected from SEQ ID NOs: 121-126;
   if the large serine recombinase is Benedict, then the attB sites are selected from SEQ ID NOs: 133-138; or
   if the large serine recombinase is PhiC31, then the attB sites are selected from SEQ ID NOs: 144-149.

3. The isolated cell of claim 1, wherein the large serine recombinase is selected from the group consisting of: BxB1, and PhiC31.

4. A method of integrating a plurality of genetic sequences or circuits into an isolated cell, comprising:
   delivering into the isolated cell of claim 1 a plurality of integrative vectors, each comprising an attP site, one or more genetic sequences or gene cassettes that express components of the genetic circuit, and a promoterless second selectable marker,
   wherein the isolated cell expresses the large serine recombinase, and
   wherein each attP site is selected to allow site-specific recombination between the attB site in one of the landing pads and the attP site in the integrative vector, which results in the insertion of the coding sequence of the second selectable marker in frame with the constitutive promoter in the landing pad;
   screening for cells with the integration of the genetic sequence or circuit in media comprising a drug to which the second selectable marker confers resistance.

5. The method of claim 4, wherein the one or more gene cassettes that express components of the genetic circuit comprise a promoter operably linked to a sequence encoding a polypeptide that is part of the genetic circuit.

6. The method of claim 4, wherein the large serine recombinase is selected from the group consisting of: BxB1, and PhiC31.

7. The isolated cell of claim 1, wherein the number of landing pads is 2, 3, 4, 5, 6, 7, 8, 9, 10, 11, or 12.

8. The isolated cell of claim 1, wherein each landing pad is capable of being integrated into the genomic DNA of the isolated cell using a zinc-finger nuclease, TALEN or CRISPR-Cas system.

9. The isolated cell of claim 1, wherein the detectable marker is a fluorescent protein.

10. The isolated cell of claim 9, wherein the fluorescent protein is selected from the group consisting of EYFP, eGFP, eYFP, eCFP, mKate2, mCherry, mPlum, mGrape2, mRaspberry, mGrape1, mStrawberry, mTangerine, mBanana, and mHoneydew.

11. The isolated cell of claim 1, wherein the first selectable marker hydrolyzes a first drug.

12. The isolated cell of claim 11, wherein the first drug is selected from a group consisting of: puromycin, hygromycin, G418, neomycin, and bleomycin.

13. The isolated cell of claim 1, wherein the large serine recombinase is selected from the group consisting of: SEQ ID NO: 73 (BxB1), SEQ ID NO: 77 (BxZ2), SEQ ID NO: 160 (PhiC31), SEQ ID NO: 75 (Peaches), SEQ ID NO: 69 (Veracruz), SEQ ID NO: 49 (Rebeuca), SEQ ID NO: 65 (Theia), SEQ ID NO: 27 (Benedict), SEQ ID NO: 47 (PattyP), SEQ ID NO: 67 (Trouble), SEQ ID NO: 39 (KSSJEB), SEQ ID NO: 71 (Lockley), SEQ ID NO: 55 (Scowl), SEQ ID NO: 63 (Switzer), SEQ ID NO: 29 (Bob3), SEQ ID NO: 21 (Abrogate), SEQ ID NO: 41 (Doom), SEQ ID NO: 33 (ConceptII), SEQ ID NO: 25 (Anglerfish), SEQ ID NO: 61 (SkiPole), SEQ ID NO: 45 (Museum), and SEQ ID NO: 57 (Severus).

14. The method of claim 4, wherein the large serine recombinase is selected from the group consisting of: SEQ ID NO: 73 (BxB1), SEQ ID NO: 77 (BxZ2), SEQ ID NO: 160 (PhiC31), SEQ ID NO: 75 (Peaches), SEQ ID NO: 69 (Veracruz), SEQ ID NO: 49 (Rebeuca), SEQ ID NO: 65 (Theia), SEQ ID NO: 27 (Benedict), SEQ ID NO: 47 (PattyP), SEQ ID NO: 67 (Trouble), SEQ ID NO: 39 (KSSJEB), SEQ ID NO: 71 (Lockley), SEQ ID NO: 55 (Scowl), SEQ ID NO: 63 (Switzer), SEQ ID NO: 29 (Bob3), SEQ ID NO: 21 (Abrogate), SEQ ID NO: 41 (Doom), SEQ ID NO: 33 (ConceptII), SEQ ID NO: 25 (Anglerfish), SEQ ID NO: 61 (SkiPole), SEQ ID NO: 45 (Museum), and SEQ ID NO: 57 (Severus).

* * * * *

UNITED STATES PATENT AND TRADEMARK OFFICE
CERTIFICATE OF CORRECTION

PATENT NO. : 10,731,153 B2  
APPLICATION NO. : 15/410875  
DATED : August 4, 2020  
INVENTOR(S) : Ron Weiss et al.

Page 1 of 1

It is certified that error appears in the above-identified patent and that said Letters Patent is hereby corrected as shown below:

On the Title Page

The title should read:  
(54) NOVEL RECOMBINASES AND TARGET SEQUENCES

Signed and Sealed this  
Twenty-ninth Day of September, 2020

Andrei Iancu  
*Director of the United States Patent and Trademark Office*

SEQUENCE LISTING

```
<160> NUMBER OF SEQ ID NOS: 161

<210> SEQ ID NO 1
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 1
cggtgcgggt gccagggcgt gcccttgggc tccccgggcg cgtactccac         50
```

<210> SEQ ID NO 2
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 2
gtggagtacg cgcccgggga gcccaagggc acgccctggc acccgcaccg        50

<210> SEQ ID NO 3
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 3
gtgccccaac tggggtaacc tttgagttct ctcagttggg gg              42

<210> SEQ ID NO 4
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 4
cccccaactg agagaactca aaggttaccc cagttggggc ac              42

<210> SEQ ID NO 5
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 5
ggcttgtcga cgacggcggt ctccgtcgtc aggatcat                   38

<210> SEQ ID NO 6
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 6
atgatcctga cgacggagac cgccgtcgtc gacaagcc                   38

<210> SEQ ID NO 7
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 7
gtggtttgtc tggtcaacca ccgcggtctc agtggtgtac ggtacaaacc ca   52

<210> SEQ ID NO 8
<211> LENGTH: 52
<212> TYPE: DNA
<213> ORGANISM: Artificial Sequence
<220> FEATURE:
<223> OTHER INFORMATION: Synthetic Polynucleotide

```
<400> SEQUENCE: 8
tgggtttgta ccgtacacca ctgagaccgc ggtggttgac cagacaaacc ac        52

<210> SEQ ID NO 9
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 9
gtattggggg aacgcgatat tcgaggagta gaacatcacc ttcaccaaat tc        52

<210> SEQ ID NO 10
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 10
gaatttggtg aaggtgatgt tctactcctc gaatatcgcg ttcccccaat ac        52

<210> SEQ ID NO 11
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 11
cctttcgggg gatgtgatgt tcgaggagaa gaacatcacc ctgaacatcg cg        52

<210> SEQ ID NO 12
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 12
cgcgatgttc agggtgatgt tcttctcctc gaacatcaca tcccccgaaa gg        52

<210> SEQ ID NO 13
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 13
cggtattcgg cgcgatccgc ggcgagaaga acatcaccct gaacatcg            48

<210> SEQ ID NO 14
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 14
cgatgttcag ggtgatgttc ttctcgccgc ggatcgcgcc gaataccg             48

<210> SEQ ID NO 15
```

<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 15
ttcgcaaagc ctcaaaatcg ggaactcgat attcatgctt tgtgaa        46

<210> SEQ ID NO 16
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 16
ttcacaaagc atgaatatcg agttcccgat tttgaggctt tgcgaa        46

<210> SEQ ID NO 17
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 17
ttgtcaaagt ctaaagatgg ggaactcaat attcatgctt tgcgaa        46

<210> SEQ ID NO 18
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 18
ttcgcaaagc atgaatattg agttccccat ctttagactt tgacaa        46

<210> SEQ ID NO 19
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 19
cagtgggtga acgcaaagat ggggaactcg atgccgagct cgtcgcagag        50

<210> SEQ ID NO 20
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 20
ctctgcgacg agctcggcat cgagttcccc atctttgcgt tcacccactg        50

<210> SEQ ID NO 21
<211> LENGTH: 500
<212> TYPE: PRT
<213> ORGANISM: Artificial Sequence
<220> FEATURE:
<223> OTHER INFORMATION: Synthetic Polypeptide

<400> SEQUENCE: 21

```
Met Arg Ala Leu Val Val Ile Arg Leu Ser Arg Val Thr Asp Ala Thr
1               5                   10                  15

Thr Ser Pro Glu Arg Gln Leu Glu Ser Cys Gln Gln Leu Cys Ala Gln
            20                  25                  30

Arg Gly Trp Asp Val Val Gly Val Ala Glu Asp Leu Asp Val Ser Gly
            35                  40                  45

Ala Val Asp Pro Phe Asp Arg Arg Arg Pro Asn Leu Ala Arg Trp
50                  55                  60

Leu Ala Phe Glu Glu Gln Pro Phe Asp Val Ile Val Ala Tyr Arg Val
65                  70                  75                  80

Asp Arg Leu Thr Arg Ser Ile Arg His Leu Gln Gln Leu Val His Trp
                85                  90                  95

Ala Glu Asp His Lys Lys Leu Val Val Ser Ala Thr Glu Ala His Phe
            100                 105                 110

Asp Thr Thr Thr Pro Phe Ala Ala Val Val Ile Ala Leu Met Gly Thr
            115                 120                 125

Val Ala Gln Met Glu Leu Glu Ala Ile Lys Glu Arg Asn Arg Ser Ala
        130                 135                 140

Ala His Phe Asn Ile Arg Ala Gly Lys Tyr Arg Gly Ser Leu Pro Pro
145                 150                 155                 160

Trp Gly Tyr Leu Pro Thr Arg Val Asp Gly Glu Trp Arg Leu Val Pro
                165                 170                 175

Asp Pro Val Gln Arg Glu Arg Ile Leu Glu Val Tyr His Arg Val Val
            180                 185                 190

Asp Asn His Glu Pro Leu His Leu Val Ala His Asp Leu Asn Arg Arg
        195                 200                 205

Gly Val Leu Ser Pro Lys Asp Tyr Phe Ala Lys Leu Gln Gly Arg Glu
210                 215                 220

Pro Arg Gly Arg Glu Trp Ser Ala Thr Ala Leu Lys Arg Ser Leu Ile
225                 230                 235                 240

Ser Glu Ala Met Leu Gly Tyr Ala Thr Leu Asn Gly Lys Thr Val Arg
                245                 250                 255

Asp Asp Asp Gly Ala Pro Leu Val Arg Ala Glu Pro Ile Leu Thr Arg
            260                 265                 270

Glu Gln Leu Glu Ala Leu Arg Ala Glu Leu Val Lys Thr Asp Arg Ala
        275                 280                 285

Lys Pro Ser Val Ser Thr Pro Ser Met Leu Leu Arg Val Leu Phe Cys
        290                 295                 300

Ala Val Cys Gly Glu Pro Ala Tyr Lys Phe Thr Gly Gly Gly Arg Lys
305                 310                 315                 320

Asn Ala Arg Tyr Arg Cys Arg Ser Trp Gly Trp Ala Gln Arg Cys Gly
                325                 330                 335

Asn Gly Thr Val Ala Met Ala Glu Trp Asp Ser Phe Cys Glu Glu Gln
            340                 345                 350

Val Leu Asp Leu Leu Gly Asp Ser Glu Arg Leu Glu Lys Val Trp Val
        355                 360                 365

Ala Gly Ser Asp Ser Ala Val Glu Leu Ala Glu Val Asn Ala Glu Leu
        370                 375                 380

Val Asp Leu Thr Ser Leu Ile Gly Ser Pro Ala Tyr Arg Ala Gly Ser
385                 390                 395                 400

Pro Gln Arg Glu Ala Leu Asp Ala Arg Ile Ala Ala Leu Ala Ala Arg
                405                 410                 415
```

Gln Glu Glu Leu Glu Gly Leu Glu Ala Arg Pro Ser Gly Trp Glu Trp
                420                 425                 430

Arg Glu Thr Gly Gln Arg Phe Gly Asp Trp Trp Arg Glu Gln Asp Thr
            435                 440                 445

Ala Gly Lys Asn Thr Trp Leu Arg Ser Met Asn Val Arg Leu Thr Phe
        450                 455                 460

Asp Val Arg Gly Gly Leu Thr Arg Thr Ile Asp Phe Gly Asp Leu Gln
465                 470                 475                 480

Glu Tyr Glu Gln His Leu Arg Leu Gly Ser Val Val Glu Arg Leu His
                485                 490                 495

Ala Gly Met Ser
            500

<210> SEQ ID NO 22
<211> LENGTH: 1503
<212> TYPE: DNA
<213> ORGANISM: Artificial Sequence
<220> FEATURE:
<223> OTHER INFORMATION: Synthetic Polynucleotide

<400> SEQUENCE: 22
atgagagcac tggtagtgat ccgactgtcc cgcgtcaccg atgctacgac ttcaccggag     60
cgccagctgg agtcttgcca gcagctctgc gcccagcgcg ggtgggacgt cgtcggggta    120
gcagaggatc tggacgtctc cggagcagtc gatccgttcg accggaggcg cagaccgaac    180
ctggcccggt ggctagcgtt cgaggagcaa ccgttcgacg tgatcgtggc gtaccgggta    240
gaccggctga cccgatcaat ccggcatctg cagcagctgg tccactgggc cgaggaccac    300
aagaagctgg tcgtctccgc gaccgaagcg cacttcgaca cgacaacgcc gttcgcggcg    360
gtcgtcatcg cgcttatggg aacggtggcc agatgcgaat tagaagcgat caaagagcgg    420
aaccgatcgg cggcgcattt caatatccgc gccggtaaat accgaggttc cctgccgccg    480
tggggttacc tgcctacgcg cgtggacggg gagtggcggc tggtgccgga cccggtgcag    540
cgagagcgca tcctcgaggt gtatcaccgc gtcgtcgaca accacgagcc gctgcacctg    600
gtggcacacg acctgaaccg gcgtggtgtc ctgtcgccta aggactactt cgcaaagctg    660
caaggtcggg agccgcgggg ccgggagtgg tcggctaccg cgctgaagcg ctcgctgatc    720
tccgaggcga tgctcgggta cgcgactctg aacggtaaga ccgtccgaga cgacgacgga    780
gctccgctgg tgcgggctga ccgatcctg acccgtgagc agctggaggc gctgcgcgcc    840
gagctcgtca agaccgaccg ggcaaagcca tcggtgtcga ctccgtcgat gttgctgcgg    900
gtgttgttct gcgcagtgtg cggggagccc gcatacaagt tcaccggggg cggtaggaag    960
aacgcacgat accgctgccg gtcgtggggc tgggcacagc ggtgcggcaa cggcacggtc   1020
gcaatggcag agtgggactc gttctgcgag gagcaggtgc tggatctgct cggggactcg   1080
gagcgcctgg agaaagtctg ggtagcaggc tcggactccg cagtcgaact cgcggaggtg   1140
aacgcggagc tggtggacct gacgtcgctg atcggctccc cggcctaccg ggccggttct   1200
ccgcagcgcg aagcgctgga tgctcgtatt gcggcgctgg cagcacggca ggaggagctg   1260
gagggtctag aggcacgccc gtcggttgg gagtggcgcg agactgggca gcggttcggg   1320
gactggtggc gggagcagga caccgcgggt aagaacacct ggcttcggtc gatgaacgtt   1380
cggctgacgt tcgacgtccg cggcgggctg actcgcacga tcgacttcgg ggatctgcag   1440
gagtacgagc agcacctcag gctcggcagc gtggtcgaac gactacacgc cgggatgtcg   1500
tag                                                                1503

<210> SEQ ID NO 23
<211> LENGTH: 493
<212> TYPE: PRT
<213> ORGANISM: Artificial Sequence
<220> FEATURE:
<223> OTHER INFORMATION: Synthetic Polypeptide

<400> SEQUENCE: 23

```
Met Arg Val Leu Gly Arg Ile Arg Leu Ser Arg Val Met Glu Glu Ser
1               5                   10                  15

Thr Ser Val Glu Arg Gln Arg Glu Ile Ile Glu Thr Trp Ala Arg Gln
            20                  25                  30

Asn Asp His Glu Ile Ile Gly Trp Ala Glu Asp Leu Asp Val Ser Gly
        35                  40                  45

Ser Val Asp Pro Phe Glu Thr Pro Ala Leu Gly Pro Trp Leu Thr Asp
    50                  55                  60

His Arg Lys His Glu Trp Asp Ile Leu Val Ala Trp Lys Leu Asp Arg
65                  70                  75                  80

Leu Ser Arg Arg Ala Ile Pro Met Asn Lys Leu Phe Gly Trp Val Met
                85                  90                  95

Glu Asn Asp Lys Thr Leu Val Cys Val Ser Glu Asn Leu Asp Leu Ser
            100                 105                 110

Thr Trp Ile Gly Arg Met Ile Ala Asn Val Ile Ala Gly Val Ala Glu
        115                 120                 125

Gly Glu Leu Glu Ala Ile Arg Glu Arg Thr Lys Gly Ser Gln Lys Lys
    130                 135                 140

Leu Arg Glu Leu Gly Arg Trp Gly Gly Gly Lys Pro Tyr Tyr Gly Tyr
145                 150                 155                 160

Arg Ala Gln Glu Arg Glu Asp Ala Ala Gly Trp Glu Leu Val Pro Asp
                165                 170                 175

Glu His Ala Ser Lys Val Leu Leu Ser Ile Ile Glu Lys Val Leu Glu
            180                 185                 190

Gly Gln Ser Thr Glu Ser Ile Ala Arg Glu Leu Asn Glu Arg Gly Glu
        195                 200                 205

Leu Ser Pro Ser Asp Tyr Leu Arg His Arg Ala Gly Lys Pro Thr Arg
    210                 215                 220

Gly Gly Lys Trp Ser Asn Ala His Ile Arg Gln Gln Leu Arg Ser Lys
225                 230                 235                 240

Thr Leu Leu Gly Tyr Ser Thr His Asn Gly Glu Thr Ile Arg Asp Glu
                245                 250                 255

Arg Gly Ile Ala Val Arg Lys Gly Pro Ala Leu Val Ser Gln Asp Val
            260                 265                 270

Phe Asp Arg Leu Gln Ala Ala Leu Asp Ser Arg Ser Phe Lys Val Thr
        275                 280                 285

Asn Arg Ser Ala Lys Ala Ser Pro Leu Leu Gly Val Leu Val Cys Arg
    290                 295                 300

Val Cys Glu Arg Pro Met His Leu Arg Gln His His Asn Lys Lys Arg
305                 310                 315                 320

Gly Lys Thr Tyr Arg Tyr Tyr Gln Cys Val Gly Gly Val Glu Lys Thr
                325                 330                 335

His Pro Ala Asn Leu Thr Asn Ala Asp Gln Met Glu Gln Leu Val Glu
            340                 345                 350

Glu Ser Phe Leu Ala Glu Leu Gly Asp Arg Lys Ile Gln Glu Arg Val
        355                 360                 365
```

```
Tyr Ile Pro Ala Glu Ser His Arg Ala Glu Leu Asp Glu Ala Val Arg
        370                 375                 380

Ala Val Glu Glu Ile Thr Pro Leu Leu Gly Thr Val Thr Ser Asp Thr
385                 390                 395                 400

Met Arg Lys Arg Leu Leu Asp Gln Leu Ser Ala Leu Asp Ala Arg Ile
                405                 410                 415

Ser Glu Leu Glu Lys Leu Pro Glu Ser Glu Ala Arg Trp Glu Tyr Arg
            420                 425                 430

Glu Gly Asp Glu Thr Tyr Ala Glu Ala Trp Asn Arg Gly Asp Ala Glu
        435                 440                 445

Ala Arg Arg Gln Leu Leu Leu Lys Ser Gly Ile Thr Ala Ala Ala Glu
    450                 455                 460

Met Lys Gly Arg Glu Ala Arg Val Asn Pro Gly Val Leu His Phe Asp
465                 470                 475                 480

Leu Arg Ile Pro Glu Asp Ile Leu Glu Arg Met Ser Ala
            485                 490
```

<210> SEQ ID NO 24
<211> LENGTH: 1482
<212> TYPE: DNA
<213> ORGANISM: Artificial Sequence
<220> FEATURE:
<223> OTHER INFORMATION: Synthetic Polynucleotide

<400> SEQUENCE: 24

```
atgcgagttc ttggaagaat acgactctcg cgggtcatgg aggaatcgac atcggtcgag      60
aggcagcgag agatcatcga cgtgggcg cgtcagaacg accacgagat catcggctgg       120
gctgaggacc tcgacgtgtc tggatcggtc gatccgttcg agacgccagc cttgggtccg      180
tggcttaccg accaccggaa gcacgagtgg gacatcctcg tggcatggaa gctcgaccgg     240
ctgtccaggc gagctatccc gatgaacaaa ctcttcggct gggtcatgga gaacgacaag     300
accctcgtct gcgtgtcgga gaatctggac ctgtcgacgt ggatcggtcg gatgatcgcc     360
aacgtcatcg ctggcgtggc agaaggtgag ttggaggcga tacgagagag gaccaagggc     420
tctcagaaga agctacgtga gcttggccgc tggggaggag gcaagcccta ttacggctac     480
cgcgcgcaag agcgtgagga cgctgctggg tgggagctgg tgcctgacga gcacgcctcg     540
aaggtcctgc tctcgatcat cgagaaggtc ctcgaagggc agtcgacgga gtcgatagct     600
cgtgagctga cgagagagg agagctgtcc ccgtctgact accttcggca cagggctggt      660
aagccgacca gaggcggtaa gtggagcaac gcgcacatcc gtcagcagct ccgctccaag     720
actctcctgg ttactccac gcataacggc gaaaccatcc gagacgagcg ggggatcgcg       780
gtacgcaaag ggccggcgct ggtttcccag gacgtgttcg accgcctcca ggcggcgctt     840
gattctcgat ccttcaaggt gacgaacagg tcagcgaaag cgtcgccgtt gctcggcgtc     900
ctcgtctgcc gggtgtgcga acgaccgatg cacctgcgtc agcaccacaa caagaagcgc    960
ggcaagacct accgctacta ccagtgcgtg ggcggtgttg aaaagaccca ccctgccaat   1020
ctcaccaacg ccgatcagat ggagcagttg gtcgaagagt ccttccttgc tgaactcggt   1080
gaccggaaga tccaagagag ggtttacatc cctgcggagt cacatcgagc cgagttggac  1140
gaggctgtac gggccgttga ggagataacc cctctgctgg caccgtcac gtcggacacc    1200
atgcgaaagc gtctcctgga tcagctgagc gcgttagatg ctcgtatctc cgagctggag   1260
aagctgcccg agtccgaagc tcggtgggag taccgagaag gcgacgaaac ctacgccgag   1320
```

```
gcgtggaacc ggggtgacgc ggaagcccgt cgacagctcc tgctcaagtc ggggatcacg    1380
gcggctgctg agatgaaggg cagagaggcc cgagtcaacc cggggggtctt acacttcgac    1440 ctacgaatac cggaggacat cttagaaagg atgagcgcgt ga                       1482
```

<210> SEQ ID NO 25
<211> LENGTH: 503
<212> TYPE: PRT
<213> ORGANISM: Artificial Sequence
<220> FEATURE:
<223> OTHER INFORMATION: Synthetic Polypeptide

<400> SEQUENCE: 25

```
Met Arg Ala Leu Val Val Ile Arg Leu Ser Arg Val Thr Asp Ala Thr
1               5                   10                  15

Thr Ser Pro Glu Arg Gln Leu Glu Ser Cys Arg Gln Leu Cys Ala Gln
            20                  25                  30

Arg Gly Trp Glu Val Val Gly Val Ala Glu Asp Leu Asp Val Ser Gly
        35                  40                  45

Ala Val Asp Pro Phe Asp Arg Lys Arg Arg Pro Asn Leu Ala Arg Trp
    50                  55                  60

Leu Ala Phe Glu Glu Gln Pro Phe Asp Val Ile Val Ala Tyr Arg Val
65                  70                  75                  80

Asp Arg Leu Thr Arg Ser Ile Arg His Leu Gln Gln Leu Val His Trp
                85                  90                  95

Ala Glu Asp His Lys Lys Leu Val Val Ser Ala Thr Glu Ala His Phe
            100                 105                 110

Asp Thr Thr Thr Pro Phe Ala Ala Val Val Ile Ala Leu Met Gly Thr
        115                 120                 125

Val Ala Gln Met Glu Leu Glu Ser Ile Lys Glu Arg Asn Arg Ser Ala
    130                 135                 140

Ala His Phe Asn Ile Arg Ala Gly Lys Tyr Arg Gly Ser Leu Pro Pro
145                 150                 155                 160

Trp Gly Tyr Leu Pro Thr Arg Val Asp Gly Glu Trp Arg Leu Val Pro
                165                 170                 175

Asp Pro Val Gln Arg Glu Arg Ile Leu Glu Val Tyr His Arg Val Val
            180                 185                 190

Asp Asn His Glu Pro Leu His Leu Val Ala His Asp Leu Asn Arg Arg
        195                 200                 205

Gly Val Leu Ser Pro Lys Asp Tyr Phe Ala Lys Leu Gln Gly Arg Glu
    210                 215                 220

Pro Gln Gly Arg Ala Trp Ser Ala Thr Ala Leu Lys Arg Ser Leu Ile
225                 230                 235                 240

Ser Glu Ala Met Leu Gly Tyr Thr Thr Leu Asn Gly Lys Thr Val Arg
                245                 250                 255

Asp Asp Asp Gly Ala Pro Leu Val Arg Ala Glu Pro Ile Leu Thr Arg
            260                 265                 270

Glu Gln Leu Glu Ala Leu Arg Ala Glu Leu Val Lys Thr Asp Arg Thr
        275                 280                 285

Lys Pro Ala Val Ser Thr Pro Ser Leu Leu Arg Val Leu Phe Cys
    290                 295                 300

Ala Val Cys Gly Glu Pro Ala Tyr Lys Phe Asp Ala Gly Arg Lys Ile
305                 310                 315                 320

Pro Arg Tyr Arg Cys Arg Ser Phe Gly Phe Ala Gln Arg Cys Gly Asn
                325                 330                 335
```

Gly Thr Ile Pro Ile Ala Glu Trp Asp Ala Phe Cys Glu Glu Val
                340                 345                 350

Leu Asp Leu Leu Gly Asp Ser Glu Arg Leu Glu Lys Val Trp Val Ala
            355                 360                 365

Gly Ser Asp Ser Ala Val Glu Leu Ala Glu Val Asn Ala Glu Leu Val
        370                 375                 380

Asp Leu Thr Ser Leu Ile Gly Ser Pro Ala Tyr Arg Val Gly Ser Pro
385                 390                 395                 400

Gln Arg Glu Ala Leu Asp Ala Arg Ile Ala Leu Ala Ala Arg Gln
                405                 410                 415

Glu Glu Leu Glu Gly Leu Glu Ala Arg Pro Ser Gly Trp Glu Trp Arg
                420                 425                 430

Glu Thr Gly Gln Arg Phe Gly Asp Trp Trp Arg Asp Gln Asp Thr Ala
            435                 440                 445

Gly Lys Asn Thr Trp Leu Arg Ser Met Asn Val Arg Leu Thr Phe Asp
        450                 455                 460

Val Arg Gly Gly Leu Thr Arg Thr Ile Asp Phe Gly Asp Leu Gln Glu
465                 470                 475                 480

Tyr Glu Gln His Leu Arg Leu Gly Ser Ala Leu Asp Leu Val Asn Ala
                485                 490                 495

Glu Lys Pro Pro Thr Gly Arg
            500

<210> SEQ ID NO 26
<211> LENGTH: 1512
<212> TYPE: DNA
<213> ORGANISM: Artificial Sequence
<220> FEATURE:
<223> OTHER INFORMATION: Synthetic Polynucleotide

<400> SEQUENCE: 26
atgagagcac tggtagtgat ccgactgtcc cgcgtcaccg atgctacgac ctccccggag      60
cgtcagctgg agtcttgccg gcagctctgc gcccagcgcg gctggaggt ggtcggggta     120 gcagaggatc tggacgtctc cggagcagtc gatccgttcg accggaagcg cagaccgaac    180
ctggcccggt ggctagcgtt cgaggagcaa ccgttcgacg tgatcgtggc gtaccgggta    240
gaccgactga cccgatcgat ccgtcatctg cagcagctgg tccactgggc gaggaccac     300 aagaagctgg tcgtttccgc gaccgaagcc cacttcgata cgacgacgcc gttcgcggcg    360
gtcgtcatcg cgcttatggg aactgtggcg cagatggaat tagaatcgat caaagagcgg    420
aaccgatcgg cggcgcattt caatatccgc gccggtaaat accgcggttc cctgccgccg    480
tggggctacc tgcccacgcg cgtggacggg gagtggaggc tggtgcctga cccggtgcag    540
cgcgagcgca tcctcgaggt gtatcaccgc gtcgtcgaca ccacgagcc gctgcacctg     600 gtggcacacg acctgaaccg gcgtggtgtc ctgtcgccga aggactactt cgcaaagctg    660
cagggtcggg agccgcaggg gcgggcgtgg tcagccaccg cgctgaagcg ctcgctgatc    720
tctgaggcga tgctcgggta tacgacgctg aacggcaaga ccgtccgaga cgacgacggg    780
gctccgctgg tgcgggctga gccgatcctg accgcgagc agctggaggc gctgcgcgcc    840
gagctcgtca agaccgaccg gacgaagccc gcggtgtcga cgccgtcgct gctgctgcgg    900
gtgttgttct gcgcggtgtg cggggagcct gcctacaagt cgacgcagg ccggaagatc     960 ccccgctacc gctgcaggtc gttcgggttc gcacagcgct gcgggaacgg caccataccg    1020
atcgcagagt gggacgcatt ctgcgaggag caggtgctgg atctgctcgg ggactcggag    1080

```
cgtctggaga aagtctgggt agcaggctcg gactcggcgg tcgaactcgc ggaggtgaac   1140
gcggagctgg tggacctgac gtcgttgatc ggctctccgg cctaccgggt cggttctccg   1200
cagcgcgaag cactggatgc tcgtattgcg gcgctggccg cgcggcagga ggagctggaa   1260
gggctagagg ctcgcccgtc gggttgggag tggcgcgaaa ccggtcagag gttcggtgac   1320
tggtggcggg atcaggacac cgcgggtaag aacacctggc tccggtcgat gaacgttcgg   1380
ctgacgttcg acgtccgcgg cgggctgact cgcacgatcg acttcgggga tctgcaggag   1440
tatgagcagc atctgaggct gggctcggct ctggacctcg taaacgcaga aaagccccct   1500
acgggccgct ag                                                       1512
```

<210> SEQ ID NO 27
<211> LENGTH: 493
<212> TYPE: PRT
<213> ORGANISM: Artificial Sequence
<220> FEATURE:
<223> OTHER INFORMATION: Synthetic Polypeptide

<400> SEQUENCE: 27

```
Met Arg Val Leu Gly Arg Ile Arg Leu Ser Arg Val Met Glu Glu Ser
1               5                   10                  15

Thr Ser Val Glu Arg Gln Arg Glu Ile Ile Glu Thr Trp Ala Arg Gln
            20                  25                  30

Asn Asp His Glu Ile Ile Gly Trp Ala Glu Asp Leu Asp Val Ser Gly
        35                  40                  45

Ser Val Asp Pro Phe Glu Thr Pro Ala Leu Gly Pro Trp Leu Thr Asp
    50                  55                  60

His Arg Lys His Glu Trp Asp Ile Leu Val Ala Trp Lys Leu Asp Arg
65                  70                  75                  80

Leu Ser Arg Arg Ala Ile Pro Met Asn Lys Leu Phe Gly Trp Val Met
                85                  90                  95

Glu Asn Asp Lys Thr Leu Val Cys Val Ser Glu Asn Leu Asp Leu Ser
            100                 105                 110

Thr Trp Ile Gly Arg Met Ile Ala Asn Val Ile Ala Gly Val Ala Glu
        115                 120                 125

Gly Glu Leu Glu Ala Ile Arg Glu Arg Thr Lys Gly Ser Gln Lys Lys
    130                 135                 140

Leu Arg Glu Leu Gly Arg Trp Gly Gly Lys Pro Tyr Tyr Gly Tyr
145                 150                 155                 160

Arg Ala Gln Glu Arg Glu Asp Ala Ala Gly Trp Glu Leu Val Pro Asp
                165                 170                 175

Glu His Ala Ser Ala Val Leu Leu Ser Ile Ile Glu Lys Val Leu Glu
            180                 185                 190

Gly Gln Ser Thr Glu Ser Ile Ala Arg Glu Leu Asn Glu Arg Gly Glu
        195                 200                 205

Leu Ser Pro Ser Asp Tyr Leu Arg His Arg Ala Gly Lys Pro Thr Arg
    210                 215                 220

Gly Gly Lys Trp Ser Asn Ala His Ile Arg Gln Gln Leu Arg Ser Lys
225                 230                 235                 240

Thr Leu Leu Gly Tyr Ser Thr His Asn Gly Glu Thr Ile Arg Asp Glu
                245                 250                 255

Arg Gly Ile Ala Val Arg Lys Gly Pro Ala Leu Val Ser Gln Asp Val
            260                 265                 270

Phe Asp Arg Leu Gln Ala Ala Leu Asp Ser Arg Ser Phe Lys Val Thr
        275                 280                 285
```

Asn Arg Ser Ala Lys Ala Ser Pro Leu Leu Gly Val Leu Ile Cys Arg
        290                 295                 300

Val Cys Glu Arg Pro Met His Leu Arg Gln His His Asn Lys Lys Arg
305                 310                 315                 320

Gly Lys Thr Tyr Arg Tyr Tyr Gln Cys Val Gly Gly Val Glu Lys Thr
                325                 330                 335

His Pro Ala Asn Leu Thr Asn Ala Asp Gln Met Glu Gln Leu Val Glu
            340                 345                 350

Glu Ser Phe Leu Ala Glu Leu Gly Asp Arg Lys Ile Gln Glu Arg Val
        355                 360                 365

Tyr Ile Pro Ala Glu Ser His Arg Ala Glu Leu Asp Glu Ala Val Arg
    370                 375                 380

Ala Val Glu Glu Ile Thr Pro Leu Leu Gly Thr Val Thr Ser Asp Thr
385                 390                 395                 400

Met Arg Lys Arg Leu Leu Asp Gln Leu Ser Ala Leu Asp Ala Arg Ile
                405                 410                 415

Ser Glu Leu Glu Lys Leu Pro Glu Ser Glu Ala Arg Trp Glu Tyr Arg
            420                 425                 430

Glu Gly Asp Glu Thr Tyr Ala Glu Ala Trp Asn Arg Gly Asp Ala Glu
        435                 440                 445

Ala Arg Arg Gln Leu Leu Lys Ser Gly Ile Thr Ala Ala Ala Glu
    450                 455                 460

Met Lys Gly Arg Glu Ala Arg Val Asn Pro Gly Val Leu His Phe Asp
465                 470                 475                 480

Leu Arg Ile Pro Glu Asp Ile Leu Glu Arg Met Ser Ala
                485                 490

<210> SEQ ID NO 28
<211> LENGTH: 1482
<212> TYPE: DNA
<213> ORGANISM: Artificial Sequence
<220> FEATURE:
<223> OTHER INFORMATION: Synthetic Polynucleotide

<400> SEQUENCE: 28
atgcgagttc ttggaagaat acgactctcg cgggtcatgg aagaatcgac atcggtcgag    60
aggcagcgag agatcatcga aacctgggcg cgtcagaacg accacgagat catcggctgg   120
gctgaagacc tagacgtgtc tggatcggtc gatccgttcg agacgccagc cttgggtccg   180
tggcttaccg accaccggaa gcacgagtgg gacatcctcg tggcgtggaa gctcgaccgg   240
ctgtccaggc gagctatccc gatgaacaaa ctcttcggct gggtcatgga gaacgacaag   300
accctcgtct cgcgtgtcgga gaatctggac ctgtcgacat ggatcggtcg gatgatcgcc   360
aacgtcatcg ctggcgtggc agaggggggag ttggaggcga tacgagagag gaccaagggc   420
tctcagaaga agctacgtga gcttggccgc tggggaggag gcaagcccta ctacggctac   480
cgcgcgcaag agcgtgagga cgctgctggg tgggagctgg tgcccgacga gcacgcctcg   540
gcggtcctgc tctccatcat cgagaaggtc ctcgaagggc agtcgacgga gtcgatagct   600
cgtgagctga cgagagagg agagctgtcc ccttctgact accttcggca cagggccggt   660
aagccgacca ggggcggtaa gtggagcaac gcgcacatcc gtcagcagct ccgctccaag   720
actctcctgg gttactccac gcataacggc gaaaccatcc gagacgagcg ggggatcgcg   780
gtacgcaaag gccggcggct ggtttcccag gacgtgttcg accgcctcca ggcggcgctt   840
gattctcgat ccttcaaggt gacgaacagg tcagcgaaag cgtcgccgtt gctcggcgtc   900

```
ctcatctgcc gggtgtgcga acgaccgatg cacctgcgtc agcaccacaa caagaagcgc    960
ggcaagacct accgctacta ccagtgcgtg ggcggtgttg aaaagaccca ccctgccaat   1020
ctcaccaacg ccgatcagat ggagcagttg gtcgaagagt ccttccttgc tgaactcggt   1080
gaccggaaga tccaagagag ggtgtacatc cctgcggagt cacatcgggc cgagttggac   1140
gaggctgtac gggccgttga ggagataacc ccactgctgg gcaccgtcac atcggacacc   1200
atgcgaaagc gtctcctgga tcagctgagc gcgttagatg ctcgtatctc cgagctggag   1260
aagctgcccg agtccgaagc tcggtgggag tatcgagaag cgacgaaac  ctacgccgag   1320
gcgtggaacc ggggtgacgc ggaagcgcgt cgacagctcc tgctcaagtc ggggatcacg   1380
gcggctgctg agatgaaggg cagagaggcc cgagtcaacc cgggggtctt acacttcgac   1440
ctacgaatac cggaggacat cttagaaagg atgagcgcgt ga                     1482
```

<210> SEQ ID NO 29
<211> LENGTH: 500
<212> TYPE: PRT
<213> ORGANISM: Artificial Sequence
<220> FEATURE:
<223> OTHER INFORMATION: Synthetic Polypeptide

<400> SEQUENCE: 29

```
Met Arg Ala Leu Val Val Ile Arg Leu Ser Arg Val Thr Asp Ala Thr
1               5                   10                  15

Thr Ser Pro Glu Arg Gln Leu Glu Ser Cys Gln Gln Leu Cys Ala Gln
            20                  25                  30

Arg Gly Trp Asp Val Val Gly Val Ala Glu Asp Leu Asp Val Ser Gly
        35                  40                  45

Ala Val Asp Pro Phe Asp Arg Lys Arg Pro Asn Leu Ala Arg Trp
50                  55                  60

Leu Ala Phe Glu Glu Gln Pro Phe Asp Val Ile Val Ala Tyr Arg Val
65                  70                  75                  80

Asp Arg Leu Thr Arg Ser Ile Arg His Leu Gln Gln Leu Val His Trp
                85                  90                  95

Ala Glu Asp His Lys Lys Leu Ile Val Ser Ala Thr Glu Ala His Phe
            100                 105                 110

Asp Thr Thr Thr Pro Phe Ala Ala Val Val Ile Ala Leu Met Gly Thr
        115                 120                 125

Val Ala Gln Met Glu Leu Glu Ala Ile Lys Glu Arg Asn Arg Ser Ala
130                 135                 140

Ala His Phe Asn Ile Arg Ala Gly Lys Tyr Arg Gly Ser Leu Pro Pro
145                 150                 155                 160

Trp Gly Tyr Met Pro Ala Arg Val Asp Gly Glu Trp Arg Leu Leu Val
                165                 170                 175

Asp Pro Val Gln Arg Glu Arg Ile Leu Glu Val Tyr His Arg Val Val
            180                 185                 190

Asp Asn His Glu Pro Leu His Leu Val Ala His Asp Leu Asn Gln Arg
        195                 200                 205

Gly Ile Leu Ser Pro Lys Asp Tyr Phe Ala Lys Leu Gln Gly Arg Glu
    210                 215                 220

Pro Lys Gly Arg Glu Trp Ser Ala Thr Ala Leu Lys Arg Ser Leu Ile
225                 230                 235                 240

Ser Glu Ala Met Leu Gly Tyr Thr Thr Leu Asn Gly Lys Thr Val Arg
                245                 250                 255
```

Asp Asp Asp Gly Ala Pro Leu Val Arg Ala Glu Pro Ile Leu Thr Arg
            260                 265                 270

Glu Gln Leu Glu Ser Leu Arg Ala Glu Leu Val Lys Thr Asp Arg Thr
        275                 280                 285

Lys Pro Ala Val Ser Thr Pro Ser Leu Leu Leu Arg Val Leu Phe Cys
    290                 295                 300

Ala Val Cys Gly Glu Pro Ala Tyr Lys Phe Thr Gly Gly Arg Lys
305                 310                 315                 320

Asn Ala Arg Tyr Arg Cys Arg Ser Trp Gly Trp Ala Gln Arg Cys Gly
                325                 330                 335

Asn Gly Thr Val Ala Met Ala Glu Trp Asp Ala Phe Cys Glu Glu Gln
            340                 345                 350

Val Leu Asp Leu Leu Gly Asp Ala Glu Arg Leu Glu Lys Val Trp Val
        355                 360                 365

Ala Gly Ser Asp Ala Ala Val Glu Leu Thr Glu Leu Asn Ala Glu Leu
    370                 375                 380

Val Asp Leu Thr Ser Leu Ile Gly Ser Pro Ala Tyr Arg Ala Gly Ser
385                 390                 395                 400

Pro Gln Arg Glu Ala Leu Asp Ala Arg Ile Ala Ala Leu Ala Ala Arg
                405                 410                 415

Gln Glu Glu Leu Glu Gly Leu Glu Ala Arg Pro Ser Gly Trp Glu Trp
            420                 425                 430

Arg Glu Thr Gly Gln Arg Phe Gly Asp Trp Trp Arg Asp Gln Asp Thr
        435                 440                 445

Ala Gly Lys Asn Thr Trp Leu Arg Ser Met Asn Val Arg Leu Thr Phe
    450                 455                 460

Asp Val Arg Gly Gly Leu Thr Arg Thr Ile Asp Phe Gly Asp Leu Gln
465                 470                 475                 480

Glu Tyr Glu Gln His Leu Arg Leu Gly Ser Val Val Glu Gln Leu His
                485                 490                 495

Thr Gly Met Ser
            500

<210> SEQ ID NO 30
<211> LENGTH: 1503
<212> TYPE: DNA
<213> ORGANISM: Artificial Sequence
<220> FEATURE:
<223> OTHER INFORMATION: Synthetic Polynucleotide

<400> SEQUENCE: 30
atgagagcac tggtagtcat ccgactgtcc cgcgtcaccg atgctacgac ctcaccggag     60
cgtcagctgg agtcttgcca gcagctctgc gcccagcgcg gctggacgt cgtcggggta    120 gcagaggatc tggacgtctc cggagcagtc gatccgttcg accggaagcg ccgcccgaac    180
ctggcccgat ggctagcgtt cgaggagcaa ccgttcgacg tcatcgtggc gtaccgggtg    240
gaccggttga cccgctcgat ccggcatctg cagcagctgg tgcactgggc cgaggaccac    300
aagaagctga tcgtctccgc gaccgaagcg cacttcgata cgacgacgcc gttcgcggcg    360
gtcgtgatcg cgcttatggg aacggtggcg cagatggaat tagaagcgat caaagagcgg    420
aaccgttcgg ctgcgcattt caacatccgc gcgggtaaat accgcggttc cctgccgccg    480
tggggttaca tgcccgcacg cgtggacggg gagtggaggc tgctcgtcga ccccgtgcag    540
cgcgaacgca tcctcgaggt ctataccgc gtcgtcgaca ccacgagcc tctgcatctg    600 gtcgcacacg acctgaacca gcgtggtatc ctgtcgccga aggactactt cgcaaagctg    660

```
cagggtcgag agcccaaggg ccgggagtgg tcggctaccg cgctgaagcg ctcgctgatc    720
tcggaggcga tgctcgggta tacgacgctg aacggcaaga ccgtccgaga cgacgacggg    780
gctccgctgg tgcgggccga gccgatcctg acgcgcgagc agctggaatc gctgcgggcg    840
gaactggtca agaccgaccg gaccaagccc gcagtgtcca ccccgtcgct gctgctgcgg    900
gtgctgttct gcgcagtgtg cggggagccc gcatacaagt tcaccggggg cggcaggaag    960
aacgctcgct accgctgccg gtcgtggggc tgggcgcagc ggtgcggcaa cggcacggtg   1020
gcaatggccg agtgggacgc attctgcgag gagcaggtgt tggatctgct cggggacgca   1080
gagcgtctgg agaaagtctg ggtagcaggc tcggacgctg ctgtggagct gacggagctc   1140
aacgcagagc tggtggatct gacgtcgctg atcggctccc cggcataccg ggcaggttct   1200
ccgcagcgcg aggcactgga tgctcgtatc gcagcactgg cagcgcggca ggaggagttg   1260
gaagggctag aggcacgccc gtcgggctgg gagtggcgcg aaaccgggca gaggttcggg   1320
gactggtggc gggatcagga caccgcaggt aagaacacct ggctccggtc gatgaacgtt   1380
cggctgacgt tcgacgtccg cggcgggctg actcgcacga tcgacttcgg ggatctgcag   1440
gagtacgagc agcatctcag gctcggcagc gtggtcgaac agctacacac cgggatgtcg   1500
tag                                                                 1503

<210> SEQ ID NO 31
<211> LENGTH: 486
<212> TYPE: PRT
<213> ORGANISM: Artificial Sequence
<220> FEATURE:
<223> OTHER INFORMATION: Synthetic Polypeptide

<400> SEQUENCE: 31

Met Thr Ala Thr Leu Glu Thr Pro Pro Gln Val Val Ala Pro Pro Arg
1               5                   10                  15

Leu Arg Ala Ala Val Tyr Leu Arg Met Ser Thr Asp Lys Glu Leu Gly
            20                  25                  30

Ile Asp Arg Gln Arg Glu Asp Cys Val Ala Leu Cys Glu Arg Leu Gly
        35                  40                  45

Trp Asp Pro Val Leu Tyr Val Asp Asn Asp Arg Ser Ala Val Lys Glu
    50                  55                  60

Asn Val Arg Arg Glu Ala Tyr Glu Gln Met Cys Glu Asp Ile Arg Asp
65                  70                  75                  80

Gly Arg Ile Asp Ala Ile Ile Thr Trp Arg Ser Asp Arg Leu Tyr Arg
                85                  90                  95

Lys Met Lys Ser Leu Leu Pro Leu Ile Asp Leu Ile Gln Gly Val Asn
            100                 105                 110

Lys Asn Gly Lys Arg Ile Pro Ile Glu Thr Cys Gln Thr Gly Leu Ile
        115                 120                 125

Asp Leu Thr Thr Asp Ala Gly Arg Met Thr Ala Lys Ile Leu Ala Ala
    130                 135                 140

Val Ala Glu Asn Glu Gly Glu Val Arg Thr Ala Arg Gln Met Arg Ala
145                 150                 155                 160

Tyr Glu Gln Ile Ala Glu Ser Gly Arg Ser Leu Gly Ala Pro Ala Phe
                165                 170                 175

Gly Tyr Thr Asn Asp Pro Lys Ala Arg Val Arg Glu Ile Val Pro Glu
            180                 185                 190

Glu Ala Ala Ala Ile Arg Glu Gly Tyr Asp Asp Val Leu Ala Gly Cys
        195                 200                 205
```

```
Thr Leu Tyr Ser Ile Ala Lys Lys Trp Asn Asp Arg Gly Leu Lys Thr
    210                 215                 220
Pro Arg Gly Asn Ala Phe Val Ala Thr Val Val Gly Arg Ile Leu Arg
225                 230                 235                 240
Asn Pro Arg Tyr Ala Gly Leu Tyr Arg Phe Arg Gly Glu Ile Ile Gly
                245                 250                 255
Glu Gly Asp Trp Glu Pro Ile Val Asp Val Glu Thr Trp Ala Met Ala
            260                 265                 270
Thr Ala Val Leu Asp Gly Lys Asn Thr Gly Pro Lys Gly Pro Arg Val
            275                 280                 285
Arg Thr Thr Leu Leu Ser Gly Ile Val Arg Cys Gly His Cys Gly Asn
    290                 295                 300
Arg Met Ser Ala Ser Lys Asn Ser Asn Gly Glu Pro Ile Tyr Lys Cys
305                 310                 315                 320
Lys Arg Tyr Glu Val Cys Asn His Gly Val Thr Arg Val Arg Lys Lys
                325                 330                 335
Val Asp Lys Tyr Val Glu Ala Arg Ile Val Ala Lys Leu Glu Glu Arg
            340                 345                 350
Lys Trp Val Val Gly Thr Lys Ser Asp Ala Asp Gln Ala Lys Ala Leu
            355                 360                 365
His Thr Glu Ala Glu Thr Leu Arg Ala Arg Lys Ala Ser Phe Thr Asp
    370                 375                 380
Ala Leu Val Asp Gly Thr Leu Thr Pro Ala Gln Val Lys Glu Ala Ser
385                 390                 395                 400
Asp Lys Val Asp Ala Lys Leu Glu Glu Ile Glu Arg Gln Leu Ala Arg
                405                 410                 415
Leu Thr Lys Ser Arg Val Tyr Asp Gly Leu Leu Gly His Asp Asp Leu
            420                 425                 430
Glu Ala Val Trp Val Gly Leu Pro Leu Asp Arg Lys Arg Ala Ile Ile
            435                 440                 445
Glu Gln Leu Cys Asp Lys Ile Val Ile Arg His Val Glu Ile Thr Gly
    450                 455                 460
Arg Ala Ala Ala Lys Leu Pro Leu Gly His Asn Ile Asp Ile Tyr Trp
465                 470                 475                 480
His Lys Pro Ser Asp Asp
                485

<210> SEQ ID NO 32
<211> LENGTH: 1461
<212> TYPE: DNA
<213> ORGANISM: Artificial Sequence
<220> FEATURE:
<223> OTHER INFORMATION: Synthetic Polynucleotide

<400> SEQUENCE: 32
atgacagcaa cccttgaaac cccaccacag gtcgtcgcgc cgccccggct gagggctgcg    60
gtctacctcc gcatgtccac cgacaaagag ctgggcatcg accgccaacg cgaggactgc   120
gtcgccctgt gcgagcgcct cggctgggat cccgtgctct acgtcgacaa cgaccgcagc   180
gccgtcaaag agaacgtgcg ccgcgaagcg tacgagcaga tgtgcgagga catccgcgac   240
ggccgcatcg acgccatcat cacgtggcgc tccgaccggc tctaccgcaa gatgaagtcc   300
ctgctgccgc tcatcgacct gatccagggc gtcaacaaga acggcaagcg gatccccatc   360
gagacgtgcc agacagggct catcgatctc accaccgacg caggccgcat gacggctaag   420
```

| | |
|---|---|
| atcctggcag ccgtagcgga gaacgagggc gaggtcagga cagccaggca gatgcgcgca | 480 |
| tacgagcaga tcgcagagag cggccggtca ctggggggccc cagcgttcgg ctacaccaac | 540 |
| gaccccaagg cccgcgtgcg tgagatcgtg cccgaagaag ccgccgcaat ccgcgagggc | 600 |
| tacgacgatg tgctcgccgg atgcacgttg tactcgattg cgaagaagtg gaacgaccgt | 660 |
| ggactcaaga caccccgcgg caacgcgttc gtcgccaccg tcgtcggccg catcctcagg | 720 |
| aaccccgct atgcgggcct gtaccgcttc aggggcgaga tcatcggtga gggcgactgg | 780 |
| gagcccatcg tggacgttga cgtgggcg atggccacag cggtcctcga cggcaagaac | 840 |
| accggcccaa agggcccag ggtgcgcaca acgctgctct cgggcatcgt gcggtgcgga | 900 |
| cactgcggca accggatgtc ggccagcaag aacagcaacg gcgagccgat ctacaagtgc | 960 |
| aagcgctacg aggtctgcaa ccacggtgtt acgcgagtac gcaagaaggt cgacaagtac | 1020 |
| gtcgaggcgc ggatcgtggc caagctcgaa gagcgcaagt gggttgtcgg caccaagtcc | 1080 |
| gacgcggacc aagccaaggc cctgcacaca gaggccgaga cgctgcgggc ccgcaaggct | 1140 |
| tcgttcaccg acgccctggt cgatggcacc ctgacaccg cacaggtgaa ggaggccagc | 1200 |
| gacaaggtcg acgcgaagct ggaggagatt gaacgccagc tagcccgcct caccaagtct | 1260 |
| cgggtgtatg acgggctgct gggtcacgac gacctggagg ccgtctgggt ggggctgccg | 1320 |
| ctggaccgca gcgggccat catcgagcag ctatgcgaca agatcgtgat acggcatgtc | 1380 |
| gagatcaccg ccgtgctgc cgccaagctg ccgcttggcc acaacatcga catctactgg | 1440 |
| cataagccca gcgatgactg a | 1461 |

<210> SEQ ID NO 33
<211> LENGTH: 504
<212> TYPE: PRT
<213> ORGANISM: Artificial Sequence
<220> FEATURE:
<223> OTHER INFORMATION: Synthetic Polypeptide

<400> SEQUENCE: 33

```
Met Arg Ala Leu Val Val Ile Arg Leu Ser Arg Val Thr Asp Ala Thr
1               5                   10                  15

Thr Ser Pro Glu Arg Gln Leu Glu Ser Cys Gln Gln Leu Cys Ala Gln
            20                  25                  30

Arg Gly Trp Asp Val Val Gly Val Ala Glu Asp Leu Asp Val Ser Gly
        35                  40                  45

Ala Val Asp Pro Phe Asp Arg Lys Arg Pro Asn Leu Ala Arg Trp
    50                  55                  60

Leu Ala Phe Glu Glu Gln Pro Phe Asp Val Ile Val Ala Tyr Arg Val
65                  70                  75                  80

Asp Arg Leu Thr Arg Ser Ile Arg His Leu Gln Gln Leu Val His Trp
                85                  90                  95

Ala Glu Asp His Lys Lys Leu Val Val Ser Ala Thr Glu Ala His Phe
            100                 105                 110

Asp Thr Thr Thr Pro Phe Ala Ala Val Val Ile Ala Leu Met Gly Thr
        115                 120                 125

Val Ala Gln Met Glu Leu Glu Ala Ile Lys Glu Arg Asn Arg Ser Ala
    130                 135                 140

Ala His Phe Asn Ile Arg Ala Gly Lys Tyr Arg Gly Ser Leu Pro Pro
145                 150                 155                 160

Trp Gly Tyr Leu Pro Thr Arg Val Asp Gly Glu Trp Arg Leu Val Pro
                165                 170                 175
```

Asp Pro Val Gln Arg Glu Arg Ile Leu Glu Val Tyr His Arg Val Val
                180                 185                 190

Asp Asn His Glu Pro Leu His Leu Val Ala His Asp Leu Asn Gln Arg
            195                 200                 205

Gly Val Leu Ser Pro Lys Asp Tyr Phe Ala Lys Leu Gln Gly Arg Glu
        210                 215                 220

Pro Gln Gly Arg Glu Trp Ser Ala Thr Ala Leu Lys Arg Ser Leu Ile
225                 230                 235                 240

Ser Glu Ala Met Leu Gly Tyr Ala Thr Leu Asn Gly Lys Thr Val Arg
                245                 250                 255

Asp Asp Asp Gly Ala Pro Leu Val Arg Ala Glu Pro Ile Leu Thr Arg
            260                 265                 270

Glu Gln Leu Glu Ala Leu Arg Ala Glu Leu Val Lys Ala Asp Arg Thr
        275                 280                 285

Lys Pro Ala Val Ser Thr Pro Ser Leu Leu Leu Arg Val Leu Phe Cys
290                 295                 300

Ala Val Cys Gly Glu Pro Ala Tyr Lys Phe Thr Gly Gly Gly Arg Lys
305                 310                 315                 320

Asn Ala Arg Tyr Arg Cys Arg Ser Trp Gly Trp Ala Gln Arg Cys Gly
                325                 330                 335

Asn Gly Thr Val Ala Met Ala Glu Trp Asp Ala Phe Cys Glu Glu Gln
            340                 345                 350

Val Leu Asp Leu Leu Gly Asp Ser Glu Arg Leu Glu Lys Val Trp Val
        355                 360                 365

Ala Gly Ser Asp Ser Ala Val Glu Leu Ala Glu Val Asn Ala Glu Leu
    370                 375                 380

Val Asp Leu Thr Ser Leu Ile Gly Ser Pro Ala Tyr Arg Ala Gly Ser
385                 390                 395                 400

Pro Gln Arg Glu Ala Leu Asp Ala Arg Ile Ala Ala Leu Ala Ala Arg
                405                 410                 415

Gln Glu Glu Leu Glu Gly Leu Glu Ala Arg Pro Ser Gly Trp Glu Trp
            420                 425                 430

Arg Glu Thr Gly Gln Arg Phe Gly Asp Trp Trp Arg Asp Gln Asp Thr
        435                 440                 445

Ala Gly Lys Asn Ala Trp Leu Arg Ser Met Asn Val Arg Leu Thr Phe
    450                 455                 460

Asp Val Arg Gly Gly Leu Thr Arg Thr Ile Asp Phe Gly Asp Leu Gln
465                 470                 475                 480

Glu Tyr Glu Gln His Leu Arg Leu Gly Ser Ala Leu Asp Leu Val Asn
                485                 490                 495

Ala Glu Lys Pro Pro Thr Gly Arg
            500

<210> SEQ ID NO 34
<211> LENGTH: 1515
<212> TYPE: DNA
<213> ORGANISM: Artificial Sequence
<220> FEATURE:
<223> OTHER INFORMATION: Synthetic Polynucleotide

<400> SEQUENCE: 34
atgagagcac tggtagtcat ccgcctgtcc cgcgtcaccg atgctacgac ttcgccggag     60
cgtcagctgg agtcttgcca gcagctctgc gcccagcgcg ttgggacgt cgtcggtgta    120 gcagaggatc tggacgtctc cggagcggtc gatccgttcg accggaagcg cagaccgaac    180

```
ctggcccggt ggctagcatt cgaggagcaa ccgttcgatg tcatcgtggc ataccgggta    240
gaccggctga cccgatcgat ccggcatctg cagcagctgg tccactgggc tgaggaccat    300
aagaagctgg tcgtctccgc aaccgaagcc cacttcgaca cgacgacgcc gttcgcagcg    360
gtcgtcatcg cgcttatggg aacggtggcg cagatggaat tagaagcgat caaagagcgg    420
aaccgttcgg cggcgcattt caatatccgc gccggtaaat accgtggaag cctgccgccg    480
tggggttacc tgcctacgcg cgtggacggt gagtggcggc tggtgccgga cccggtgcag    540
cgagagcgca tcctcgaggt gtatcaccgc gtcgtcgaca ccacgagcc gctgcacctg    600 gtggcccacg acctgaacca gcgcggcgtc ctgtcgccga aggactactt cgcgaagctg    660
caaggccgcg agccgcaggg ccgggagtgg tcggctaccg cgctgaagcg ctcgctgatc    720
tccgaggcga tgctcgggta cgcgactctg aacggtaaga ccgtccgaga cgacgacgga    780
gccccgctgg tgcgggctga ccgatcctg acccgtgagc agctggaggc gctgcgcgcc    840
gagctcgtga aggccgaccg gaccaagccc gcagtgtcta ccccgtcgct gctgctgcgg    900
gtgctgttct gcgcagtgtg cggtgagccc gcatacaagt tcaccggtgg cggtaggaag    960
aacgctcgct accgctgccg gtcgtggggt tgggcacagc ggtgcggtaa cggcacggtg   1020
gcgatggcag agtgggacgc attctgcgag agcaggtgt tggatctgct cggggactcg   1080
gagcgtctgg agaaagtctg ggtagcaggt tcggactccg cagtagaact cgcggaggtg   1140
aacgcggagc tggtggacct gacgtcgctg atcggctccc cggcgtaccg ggccggttct   1200
ccgcagcgcg aggcgctgga tgctcgtatc gcggcgctgg ccgcgcggca ggaggagttg   1260
gaagggctag aggctcgccc gtcgggttgg gagtggcgcg aaaccgggca gaggttcggg   1320
gactggtggc gggatcagga caccgcgggt aagaacgcgt ggctccggtc gatgaacgtt   1380
cggctgacgt tcgacgtccg cggcgggctg actcgcacga tcgacttcgg ggatctgcag   1440
gagtatgagc agcatctgag gctgggctcg gctctggacc tcgtaaacgc agaaaagccc   1500
cctacgggcc gctag                                                     1515
```

```
<210> SEQ ID NO 35
<211> LENGTH: 487
<212> TYPE: PRT
<213> ORGANISM: Artificial Sequence
<220> FEATURE:
<223> OTHER INFORMATION: Synthetic Polypeptide

<400> SEQUENCE: 35
```

Met Arg Val Leu Gly Arg Ile Arg Leu Ser Arg Leu Ser Asp Glu Ser
1               5                   10                  15

Thr Ser Pro Glu Arg Gln Arg Glu Ile Ile Glu Gly Trp Ala Lys Ser
            20                  25                  30

Asn Asp His Thr Ile Val Gly Trp Ala Glu Asp Leu Asp Val Ser Gly
        35                  40                  45

Ser Val Asp Pro Phe Asp Thr Pro Ala Leu Gly Pro Trp Leu Ser Glu
    50                  55                  60

Pro Lys Leu His Glu Trp Asp Ile Leu Cys Ala Trp Lys Leu Asp Arg
65                  70                  75                  80

Leu Ser Arg Arg Ala Ile Pro Met Asn Lys Leu Phe Gly Trp Val Met
                85                  90                  95

Asp His Asp Lys Thr Leu Val Cys Val Asn Asp Asn Ile Asp Leu Ser
            100                 105                 110

Thr Trp Ile Gly Arg Met Val Ala Asn Val Ile Ala Gly Val Ala Glu
        115                 120                 125

Gly Glu Leu Glu Ala Ile Arg Glu Arg Thr Ala Ser His Arg Lys
130                 135                 140

Leu Arg Glu Leu Gly Arg Trp Pro Gly Gly Arg Pro Ser Tyr Gly Tyr
145                 150                 155                 160

Arg Ala Val Glu Arg Glu Asp Ala Ala Gly Trp Val Leu Glu Pro Asp
                165                 170                 175

Pro Val Ser Ser Val Val Leu Arg Ser Ile Ile Asp Trp Val Leu Gln
            180                 185                 190

Gly Gln Ser Val Glu Ser Ile Ala Lys Asp Leu Thr Ala Met Gly Glu
        195                 200                 205

Val Ser Pro Ser Asp Tyr Val Arg Gln Arg Ala Gly Glu Ala Pro Arg
210                 215                 220

Gly His Pro Trp His Gly Arg Thr Ile Val Lys Leu Leu Arg Ser Lys
225                 230                 235                 240

Thr Leu Leu Gly Tyr Val Thr His Asn Gly Thr Thr Val Arg Asp Glu
                245                 250                 255

Asn Gly Val Pro Val Gln Lys Gly Pro Pro Leu Val Asp Gln Asp Thr
            260                 265                 270

Phe Asn Arg Leu Gln Ala Ala Leu Asp Asp Gly Ser Arg Pro Lys Thr
        275                 280                 285

Val Asn Arg Thr Ser Lys Ala Ser Pro Leu Leu Gly Val Ala Leu Cys
290                 295                 300

Trp Asp Cys Glu Lys Pro Leu Tyr Ser Arg Arg Gln Thr Thr Ala Gly
305                 310                 315                 320

Lys Val Tyr Arg Tyr Tyr His Cys Arg Asp Gly His Thr Gln Ser Ile
                325                 330                 335

Pro Ala Asp Asp Leu Gln Gln Leu Val Glu Glu Arg Phe Leu Asn Ala
            340                 345                 350

Leu Gly Asp Gln Glu Val His Glu Met Val Tyr Leu Pro Ala Glu Ser
        355                 360                 365

His Gln Ala Glu Leu Glu Glu Ala Gln Ile Ala Val Gln Glu Leu Thr
370                 375                 380

Ser Ala Leu Gly Arg Met Lys Ser Asn Tyr Ala Gln Gln Arg Ile His
385                 390                 395                 400

Thr Gln Leu Glu Ala Leu Asp Lys Arg Ile Gln Glu Leu Glu Gly Leu
                405                 410                 415

Pro Thr Ser Glu Ala Arg Ser Glu Met Arg Pro Thr Gly Gly Leu Tyr
            420                 425                 430

Lys Asp Ala Trp Glu Glu Ala Asp Glu Gln Gly Arg Arg Glu Leu Leu
        435                 440                 445

Ile Lys Ser Gly Ile Thr Ala Lys Ala Lys Leu Glu Gly Arg Val Pro
450                 455                 460

Asn Gln Ser Gly Gly Ala Leu Ser Phe Asp Leu Val Val Pro Glu Asp
465                 470                 475                 480

Leu Leu Ala Arg Met Ser Val
                485

<210> SEQ ID NO 36
<211> LENGTH: 1464
<212> TYPE: DNA
<213> ORGANISM: Artificial Sequence
<220> FEATURE:
<223> OTHER INFORMATION: Synthetic Polynucleotide

<400> SEQUENCE: 36

```
atgcgtgttc ttgggagaat caggctgtcc aggctcagcg acgaatctac cagtcccgag      60
cggcagcgag agatcatcga gggttgggca aagtccaacg accacaccat cgtcggttgg     120
gcagaggatc tggacgtgtc cggttccgtc gacccgttcg acaccccggc cttgggtccg     180
tggctgtcgg agccgaaact gcacgagtgg gacatcctct cgcatggaa gctcgaccgc     240
ctctcgcggc gagcgatccc gatgaacaaa ctcttcggtt gggtgatgga tcacgacaag     300
acactcgtat cgtcaacga caacatcgac ctctcgacgt ggatcggtcg catggtcgca     360
aacgtcatcg ctggtgtggc cgaggggag ttggaggcga tccgggagag gacgacggcc     420
tctcaccgga agctccggga gttgggccgg tggccgggag cagaccgtc ctacggctac      480
cgcgccgtcg agcgcgagga cgcagcaggg tgggtgttgg agcctgaccc ggtgtcgtcg     540
gtggtcctcc ggtcgatcat cgactgggtc ctgcaggggc agtccgtcga gtcgatagcc     600
aaggatctga ccgcgatggg agaggtgtcc ccgtccgact acgtccgtca gcgggccggt     660
gaggccccac ggggacaccc gtggcatggc cgcaccatcg tcaagctgtt gcggtccaag     720
accctcctgg ggtacgtcac gcacaacggg acgaccgtcc gggacgagaa cggtgtgccg     780
gtccagaaag gccaccgct ggtcgaccag gacaccttca accggctgca ggccgctctc     840
gatgacggct ccagacccaa gaccgtcaac cggacctcga aggcgtcccc gctactcggg     900
gtcgccctgt gttgggactg cgagaagccg ctgtactccc ccgcagac gacggcgggg      960
aaggtgtacc ggtactacca ctgccgcgac ggccacaccc agtccatccc cgccgacgac    1020
ctacaacaac tcgtggagga gcggttcctg aacgcactcg ggaccagga ggtccacgag    1080
atggtttacc tcccagcgga atcgcaccag gccgagctag aggaggctca gatcgccgta    1140
caggagttga cgagcgccct cgggaggatg aagtccaact acgcgcagca gcgcatccac    1200
acgcaactgg aggctctgga caaacgcata caggagcttg agggactacc gacctccgag    1260
gcccggtcgg agatgcgccc gacaggtggg ctgtacaagg acgcctggga ggaggccgac    1320
gagcaaggtc gccgggagct tctgatcaag tcagggatca cggccaaggc caagctggag    1380
ggccgggtgc ccaaccagtc cggaggggca ttgtcgttcg atctcgttgt gccagaggat    1440
cttctggcac gaatgtccgt gtaa                                            1464
```

<210> SEQ ID NO 37
<211> LENGTH: 498
<212> TYPE: PRT
<213> ORGANISM: Artificial Sequence
<220> FEATURE:
<223> OTHER INFORMATION: Synthetic Polypeptide

<400> SEQUENCE: 37

Met Arg Val Leu Gly Arg Leu Arg Ile Ser Arg Ala Thr Glu Glu Ser
1               5                   10                  15

Thr Ser Ile Glu Arg Gln Arg Glu Leu Val Glu Gln Trp Ala Ala Ala
            20                  25                  30

His Glu His Glu Ile Val Gly Trp Ala Val Asp Gln Asp Val Ser Gly
        35                  40                  45

Ser Val Asp Pro Phe Asp Ala Pro Ala Leu Gly Pro Trp Leu Ser Asp
    50                  55                  60

His Arg Lys His Glu Trp Asp Ile Leu Cys Ala Trp Lys Leu Asp Arg
65                  70                  75                  80

Leu Ser Arg Arg Ala Ile Pro Met Asn Lys Leu Phe Gly Trp Met Ile
                85                  90                  95

```
Asp Asn Asp Lys Thr Leu Val Cys Val Ser Glu Asn Leu Asp Leu Gly
            100                 105                 110

Thr Trp Val Gly Arg Met Ile Ala Asn Val Ile Ala Gly Val Ala Glu
        115                 120                 125

Gly Glu Leu Glu Ala Ile Arg Glu Arg Thr Thr Ala Ser His Lys Lys
    130                 135                 140

Leu Arg Glu Leu Gly Arg Trp Ala Gly Gly Pro Thr Tyr Tyr Gly Tyr
145                 150                 155                 160

Val Pro Lys Pro Arg Asp Gly Ala Gly Trp Glu Leu Asp Ile Asp Leu
                165                 170                 175

His Ala Ala Gly Val Leu Arg Glu Ile Ile Glu Lys Thr Ile Ala Gly
            180                 185                 190

Gln Ser Thr Glu Ser Ile Val Val Glu Leu Asn Glu Arg Gly Glu Leu
        195                 200                 205

Ser Pro Ser Asp Tyr His Arg Lys Ser Gly Lys Pro Ile Arg Gly
210                 215                 220

Thr Lys Trp Asn Thr Ser Trp Leu Arg Thr Gln Leu Lys Ser Lys Thr
225                 230                 235                 240

Leu Leu Gly His Met Thr His Asn Gly Glu Thr Val Tyr Asp Asp Ala
            245                 250                 255

Gly Leu Pro Val Gln Lys Gly Pro Ala Leu Ile Asp Arg Asp Thr Tyr
        260                 265                 270

Lys Gln Leu Gln Asp Ala Leu Gln Ser Arg Gly Ile Asn Arg Thr Lys
    275                 280                 285

Arg Arg Thr Gly Ala Ser Pro Leu Leu Gly Val Ala Val Cys Asp Val
290                 295                 300

Cys Asp Gly Pro Leu Tyr Tyr Arg Gln Thr Lys Asn Gln Lys Gly Thr
305                 310                 315                 320

Ala Met Leu Arg Gln Tyr Ile Cys Lys His Gly Arg Tyr Gly Asn Thr
            325                 330                 335

Lys Ala Asn Gly Gly Glu Pro Tyr Asn Ile Ile Gln Ala Asp Leu Leu
        340                 345                 350

Glu Ala Thr Val Glu Glu Leu Phe Leu Ser Lys Met Gly Asp Leu Pro
    355                 360                 365

Arg Val Glu Arg Val Phe Ile Pro Gly Glu Gly His Gln His Glu Leu
370                 375                 380

Glu Thr Ala Glu Arg Ala Val Glu Asp Leu Thr Ser Leu Leu Gly Thr
385                 390                 395                 400

Ile Thr Gln Glu Gly Ala Arg Lys Arg Leu Leu Ala Gln Leu Ser Ala
            405                 410                 415

Ala His Glu Arg Leu Ala His Leu Glu Glu Leu Pro Ser Ser Glu Pro
        420                 425                 430

Arg Trp Glu Thr Arg Glu Thr Gly Glu Thr Tyr Arg Glu Ala Trp Glu
    435                 440                 445

Ser Ala Thr Thr Glu Glu Arg Arg Gln Ile Leu Leu Lys Ala Gly Val
450                 455                 460

Thr Leu Lys Val Gln Met Lys Gly Arg Val Pro Arg Val His Pro Gly
465                 470                 475                 480

Val Ile Val Ala Asn Trp Ile Glu Pro His Asp Ile Glu Lys Arg Leu
            485                 490                 495

Ala Ser

<210> SEQ ID NO 38
```

<211> LENGTH: 1497
<212> TYPE: DNA
<213> ORGANISM: Artificial Sequence
<220> FEATURE:
<223> OTHER INFORMATION: Synthetic Polynucleotide

<400> SEQUENCE: 38

```
atgcgagttc ttggaagatt gcgaatctca cgagccactg aagaatctac cagcatcgag    60
cggcagcgcg agttggtcga gcagtgggcg gcggctcacg agcacgagat cgtcggctgg   120
gccgtggatc aggacgtgtc cggatcggtc gatccgttcg acgcgccagc acttgggccc   180
tggctgtctg accatcggaa acacgaatgg gacatcctgt gcgcctggaa gctggaccgc   240
ctgtcgcggc gagcgatccc gatgaacaag ctgttcggtt ggatgatcga caacgacaag   300
acgctcgtct gcgtgtcgga gaatctggac ctcgggacgt gggtcggtcg catgatcgcc   360
aacgtcatcg ccggggtcgc agagggtgaa ttggaggcga tccgggagcg gacgactgcc   420
tcgcacaaga agctcaggga gctgggaagg tgggccggtg gcccacgta ctacggctac   480
gtgccgaagc cccgcgacgg cgcggggtgg gagctggaca tcgacctgca cgctgcgggc   540
gtgctgaggg agatcatcga aaagaccatc gccggtcagt cgaccgagtc catcgtggtc   600
gagctcaacg agcgaggga gctgtccccg tccgactacc accggaagcg gagcgggaag   660
ccgatccggg gcacgaagtg gaacacgtcg tggctgcgga cgcagctcaa gtccaagacc   720
ctgcttggtc acatgaccca caacggcgaa accgtctacg acgacgccgg cctccccgtc   780
cagaagggcc ctgcgctgat cgaccgggac acctacaagc aactgcagga cgcactgcag   840
agtcgcggga tcaaccggac caagcgcagg accgggccct cgccgctgct cggtgtcgcc   900
gtctgcgatg tctgcgacgg gccgctgtac taccgccaga ccaagaacca gaagggcacg   960
gccatgctgc ggcagtacat ctgcaagcac ggccgctacg caacaccaa ggccaacggc  1020
ggggagccgt acaacatcat tcaggccgat ctattggagg ccacagtcga gagctgttc  1080
ctctccaaga tgggcgatct gccccgcgtc gagcgggtgt tcatcccagg cgaaggacac  1140
cagcatgagc tggaaacggc tgagcgagcc gtggaggact tgacatcgct tctgggcacg  1200
atcacccagg agggtgcgag aaagcgtctc ctggcgcaac tctcagccgc ccacgaacgg  1260
ctggcccacc tcgaggagct cccgagctcc gagccccgct gggaaacccg agagacaggg  1320
gagacgtacc gcgaagcgtg ggagagcgcg acgaccgagg agcgtcggca gattctgctc  1380
aaagccggtg tgacactcaa ggtccagatg aagggccggg tgccgagagt gcatcccggc  1440
gtcatcgtcg cgaactggat cgagccgcac gacatcgaga agcgcctggc ttcctga     1497
```

<210> SEQ ID NO 39
<211> LENGTH: 500
<212> TYPE: PRT
<213> ORGANISM: Artificial Sequence
<220> FEATURE:
<223> OTHER INFORMATION: Synthetic Polypeptide

<400> SEQUENCE: 39

```
Met Arg Ala Leu Val Val Ile Arg Leu Ser Arg Val Thr Asp Ala Thr
 1               5                  10                  15

Thr Ser Pro Glu Arg Gln Leu Glu Ser Cys Gln Gln Leu Cys Ala Gln
            20                  25                  30

Arg Gly Trp Asp Val Val Gly Val Ala Glu Asp Leu Asp Val Ser Gly
        35                  40                  45

Ala Val Asp Pro Phe Asp Arg Lys Arg Arg Pro Asn Leu Ala Arg Trp
    50                  55                  60
```

```
Leu Ala Phe Glu Glu Gln Pro Phe Asp Val Ile Val Ala Tyr Arg Val
 65                  70                  75                  80

Asp Arg Leu Thr Arg Ser Ile Arg His Leu Gln Gln Leu Val His Trp
                 85                  90                  95

Ala Glu Asp His Lys Lys Leu Val Val Ser Ala Thr Glu Ala His Phe
                100                 105                 110

Asp Thr Thr Thr Pro Phe Ala Ala Val Val Ile Ala Leu Met Gly Thr
            115                 120                 125

Val Ala Gln Met Glu Leu Glu Ala Ile Lys Glu Arg Asn Arg Ser Ala
130                 135                 140

Ala His Phe Asn Ile Arg Ala Gly Lys Tyr Arg Gly Ser Leu Pro Pro
145                 150                 155                 160

Trp Gly Tyr Leu Pro Thr Arg Val Asp Gly Glu Trp Arg Leu Leu Val
                165                 170                 175

Asp Pro Val Gln Arg Glu Arg Ile Leu Glu Val Tyr His Arg Val Val
            180                 185                 190

Asp Asn His Glu Pro Leu His Leu Val Ala His Asp Leu Asn Gln Arg
        195                 200                 205

Gly Ile Leu Ser Pro Lys Asp Tyr Phe Ala Gln Leu Gln Gly Arg Glu
210                 215                 220

Pro Gln Gly Arg Ala Trp Ser Ala Thr Ala Leu Lys Arg Ser Leu Ile
225                 230                 235                 240

Ser Glu Ala Met Leu Gly Tyr Ala Thr Leu Asn Gly Lys Thr Val Arg
                245                 250                 255

Asp Asp Asp Gly Ala Pro Leu Val Arg Ala Glu Pro Ile Leu Thr Arg
            260                 265                 270

Glu Gln Leu Glu Ala Leu Arg Ala Glu Leu Val Lys Thr Asp Arg Thr
        275                 280                 285

Lys Pro Ala Val Ser Thr Pro Ser Leu Leu Leu Arg Val Leu Phe Cys
290                 295                 300

Ala Val Cys Gly Glu Pro Ala Tyr Lys Phe Ala Gly Gly Gly Arg Lys
305                 310                 315                 320

His Pro Arg Tyr Arg Cys Arg Ser Met Gly Phe Pro Lys His Cys Gly
                325                 330                 335

Asn Gly Thr Val Ala Met Ala Glu Trp Asp Ala Phe Cys Glu Glu Gln
            340                 345                 350

Val Leu Asp Leu Leu Gly Asp Ala Glu Arg Leu Glu Lys Val Trp Val
        355                 360                 365

Ala Gly Ser Asp Ala Ala Val Glu Leu Ala Glu Leu Asn Ala Glu Leu
        370                 375                 380

Val Asp Leu Thr Ser Leu Ile Gly Ser Pro Ala Tyr Arg Ala Gly Ser
385                 390                 395                 400

Pro Gln Arg Glu Ala Leu Asp Ala Arg Ile Glu Ala Leu Ala Ala Arg
                405                 410                 415

Gln Glu Glu Leu Glu Gly Leu Glu Ala Arg Pro Ser Gly Trp Glu Trp
            420                 425                 430

Arg Glu Thr Gly Gln Arg Phe Gly Asp Trp Arg Glu Gln Asp Thr
        435                 440                 445

Ala Ala Lys Asn Thr Trp Leu Arg Ser Met Asn Val Arg Leu Thr Phe
        450                 455                 460

Asp Val Arg Gly Gly Leu Thr Arg Thr Ile Asp Phe Gly Asp Leu Gln
465                 470                 475                 480
```

Glu Tyr Glu Gln His Leu Arg Leu Gly Ser Val Val Glu Arg Leu His
            485                 490                 495

Thr Gly Met Ser
        500

<210> SEQ ID NO 40
<211> LENGTH: 1503
<212> TYPE: DNA
<213> ORGANISM: Artificial Sequence
<220> FEATURE:
<223> OTHER INFORMATION: Synthetic Polynucleotide

<400> SEQUENCE: 40

```
atgagagcac tggtagtcat ccgcctgtcc cgcgtcaccg atgctacgac ttcaccggag      60
cgtcagctgg agtcttgcca gcagctctgc gcacagcgcg gttgggacgt cgtcggtgtg     120
gcggaggatc tggacgtctc cggagcagtc gatccgttcg accggaagcg cagaccgaac     180
ctggcacggt ggctggcatt cgaggagcaa ccgttcgatg tgatcgtggc gtaccgggta     240
gaccggttga cccgatcgat ccggcatctg cagcagctgg tccactgggc ggaggaccac     300
aagaagctgg tcgtctccgc gaccgaagcg cacttcgaca cgacgacgcc gttcgcggcg     360
gtcgtgatcg cgcttatggg tacgtggcg cagatggaat tagaagcgat caaagagcgg      420
aaccgttcgg ctgcacattt caatatccgc gccggtaaat accgaggttc cctgccgccg     480
tggggttacc tgcctacgcg cgtggacggg gagtggaggc tgctcgtcga ccccgtgcaa     540
cgagagcgca tcctcgaggt ctatcaccgc gtcgtcgaca accacgagcc gctgcatctg     600
gtcgcccacg acctgaacca gcgcggcatc ctgtcgccca aggactactt cgcgcagctg     660
cagggccggg agccgcaggg gcgggcgtgg tcggctaccg cgttgaagcg ctcgctgatc     720
tccgaggcga tgctcgggta cgcgactctg aacggtaaga ccgtccgaga cgacgacgga     780
gctccgctgg tgcgggccga ccgatcctg acgcgagagc agctggaggc gctgcgcgcc      840
gagctcgtca agaccgaccg gaccaagccc gcagtgtcta ccccgtcgct gctgctgcgg     900
gtgctgttct gcgcagtgtg cggggagccc gcatacaagt tcgcagggg aggacgtaag      960
cacccgcgct accgctgccg ctcgatgggg ttcccgaagc actgcgggaa cggcacggtc    1020
gcaatggcag agtgggacgc attctgcgag gagcaggtgc tggatctgct cggggacgca    1080
gagcggctgg agaaggtatg ggtcgcaggc tcggacgctg ctgtggagct ggcagagctc    1140
aacgcagagc tggtggacct gacgtcgctg atcggctccc cggcataccg cgcaggttcc    1200
ccgcagcggg aggcattgga cgcacgtatc gaggctctgg ctgcacggca agaggagttg    1260
gaagggctgg aggctcgccc gtcgggttgg gagtggcgcg aaaccgggca gcggttcggt    1320
gactggtggc gagagcagga caccgcagca aagaacacct ggctccggtc gatgaacgtc    1380
cggctgacgt tcgacgtccg cggcgggctg actcgcacga tcgacttcgg ggatctgcag    1440
gagtacgagc agcatctcag gctcggcagc gtggtcgaac ggctacacac cgggatgtcg    1500
tag                                                                 1503
```

<210> SEQ ID NO 41
<211> LENGTH: 499
<212> TYPE: PRT
<213> ORGANISM: Artificial Sequence
<220> FEATURE:
<223> OTHER INFORMATION: Synthetic Polypeptide

<400> SEQUENCE: 41

Met Arg Ala Leu Val Val Ile Arg Leu Ser Arg Val Thr Asp Ala Thr

-continued

```
 1               5                   10                  15
Thr Ser Pro Glu Arg Gln Leu Glu Ser Cys Gln Gln Leu Cys Ala Gln
                20                  25                  30

Arg Gly Trp Glu Val Val Gly Val Ala Glu Asp Leu Asp Val Ser Gly
            35                  40                  45

Ala Val Asp Pro Phe Asp Arg Lys Arg Arg Pro Asn Leu Ala Arg Trp
        50                  55                  60

Leu Ala Phe Glu Glu Gln Pro Phe Asp Val Ile Val Ala Tyr Arg Val
65                  70                  75                  80

Asp Arg Leu Thr Arg Ser Ile Arg His Leu Gln Gln Leu Val His Trp
                85                  90                  95

Ala Glu Asp His Lys Lys Leu Val Val Ser Ala Thr Glu Ala His Phe
            100                 105                 110

Asp Thr Thr Thr Pro Phe Ala Ala Val Val Ile Ala Leu Met Gly Thr
        115                 120                 125

Val Ala Gln Met Glu Leu Glu Ala Ile Lys Glu Arg Asn Arg Ser Ala
            130                 135                 140

Ala His Phe Asn Ile Arg Ala Gly Lys Tyr Arg Gly Ser Leu Pro Pro
145                 150                 155                 160

Trp Gly Tyr Leu Pro Thr Arg Val Asp Gly Glu Trp Arg Leu Val Pro
                165                 170                 175

Asp Pro Val Gln Arg Glu Arg Ile Leu Glu Val Tyr His Arg Val Val
            180                 185                 190

Asp Asn His Glu Pro Leu His Leu Val Ala His Asp Leu Asn Arg Arg
        195                 200                 205

Gly Val Leu Ser Pro Lys Asp Tyr Phe Ala Lys Leu Gln Gly Arg Glu
    210                 215                 220

Pro Gln Gly Arg Glu Trp Ser Ala Thr Ala Leu Lys Arg Ser Leu Ile
225                 230                 235                 240

Ser Glu Ala Met Leu Gly Tyr Ala Thr Leu Asn Gly Lys Thr Val Arg
                245                 250                 255

Asp Asp Asp Gly Ala Pro Leu Val Arg Ala Glu Pro Ile Leu Thr Arg
            260                 265                 270

Glu Gln Leu Glu Ala Leu Arg Ala Glu Leu Val Lys Thr Asp Arg Ala
        275                 280                 285

Lys Pro Ala Val Ser Thr Pro Ser Leu Leu Arg Val Leu Phe Cys
290                 295                 300

Ala Val Cys Gly Glu Pro Ala Tyr Lys Phe Asp Ala Gly Arg Lys Ile
305                 310                 315                 320

Pro Arg Tyr Arg Cys Arg Ser Phe Gly Phe Ala Gln Arg Cys Gly Asn
                325                 330                 335

Gly Thr Val Pro Ile Ala Glu Trp Asp Ala Phe Cys Glu Glu Gln Val
            340                 345                 350

Leu Asp Leu Leu Gly Asp Ser Glu Arg Leu Lys Val Trp Val Ala
        355                 360                 365

Gly Ser Asp Ser Ala Val Glu Leu Ala Glu Val Asn Ala Glu Leu Val
    370                 375                 380

Asp Leu Thr Ser Leu Ile Gly Ser Pro Ala Tyr Arg Val Gly Ser Pro
385                 390                 395                 400

Gln Arg Glu Ala Leu Asp Ala Arg Ile Ala Ala Leu Ala Ala Arg Gln
                405                 410                 415

Glu Glu Leu Glu Gly Leu Glu Ala Arg Pro Ser Gly Trp Glu Trp Arg
            420                 425                 430
```

Glu Thr Gly Gln Arg Phe Gly Asp Trp Trp Arg Glu Gln Asp Thr Ser
            435                 440                 445

Ala Lys Asn Thr Trp Leu Arg Ser Met Asn Val Arg Leu Thr Phe Asp
    450                 455                 460

Val Arg Gly Gly Leu Thr Arg Thr Ile Asp Phe Gly Asp Leu Gln Glu
465                 470                 475                 480

Tyr Glu Gln His Leu Arg Leu Gly Ser Val Val Glu Gln Leu His Ala
                485                 490                 495

Gly Met Ser

<210> SEQ ID NO 42
<211> LENGTH: 1500
<212> TYPE: DNA
<213> ORGANISM: Artificial Sequence
<220> FEATURE:
<223> OTHER INFORMATION: Synthetic Polynucleotide

<400> SEQUENCE: 42

```
atgagagcac tggtagtcat ccgcctgtcc cgtgtcaccg atgctacgac ttcacctgag        60
cgtcagctgg agtcttgcca gcagctctgc gcacagcgcg gttgggacgt cgtcggtgta       120
gcggaggatc tggacgtctc cggagcagtc gatccgttcg accggaagcg ccgcccgaac       180
ctggcacggt ggctgtcatt cgaggagcaa ccgttcgatg tgatcgtggc gtaccgggta       240
gaccggttga cccgctcgat ccggcatctg cagcagctgg tccactgggc cgaggaccac       300
aagaagctga tcgtctccgc gactgaatcg cacttcgaca cgacgtcgcc gtttgcggcg       360
gtcgtgatcg cgcttatggg aacggtggcg cagatggagt tggaggcgat caaggagcgg       420
aaccgctcgg cagcacactt caacatccgc gccggtaagt accgtggttc cctgccgccg       480
tggggttaca tgcccgcacg cgtggacggg gagtggcggc tggtgccgga cccggtgcag       540
cgcgagcgca tcctcgaggt gtatcaccgc gtcgtcgaca ccacgagcc gctgcacctg       600 gtggcacacg acctgaaccg cgtggtgtc ctgtcgccga aggactactt cgcaaagctg       660
caaggtcgcg agccgcgggg tcgggagtgg tcggctaccg cgctgaagcg ctcgctgatc       720
tccgaggcga tgctcgggta cgcgactctg aacggtaaga ccgtccgaga cgacgacgga       780
gccccgctgg tgcgggctga gccgatcctg acccgtgagc agctggaggc gctgcgcgcc       840
gagctcgtca agaccgaccg gatgaagccc gcagtgtcca ccccgtcgct gctgctgcgg       900
gtgctgttct gtgcagtgtg tggggagccc gcatacaagt cgacgccgg ccggaagatc       960 cccgctacc gctgtaggtc gttcgggttc gcacagcgct gtgggaacgg caccataccg      1020
atcgcagagt gggacgcatt ctgtgaggag caggtgctgg atctgctcgg ggacgcagag      1080
cggctggaga aggtgtgggt cgcaggctcg gacgcagcag tggagctggc agagctcaac      1140
gcggagctgg tggatctgac gtcgctgatc ggctccccgg cataccgggc aggctctccg      1200
cagcgcgagg cactggacgc tcgtatcgcg gcgctggccg cgcggcagga ggagctggaa      1260
gggctagagg ctcgcccgtc gggctgggag tggcgcgaaa ccgggcagag gttcggggac      1320
tggtggcgag agcaggacac cgcggcaaag aacacctggc ttcggtcgat gaacgttcgg      1380
ctgacgttcg acgtccgcgg cgggctgact cgcacgatcg acttcgggga tctgcaggag      1440
tacgagcagc atctcaggct cggcagcgtg gtcgaacagc tacacaccgg gatgtcgtag      1500
```

<210> SEQ ID NO 43
<211> LENGTH: 498
<212> TYPE: PRT

<213> ORGANISM: Artificial Sequence
<220> FEATURE:
<223> OTHER INFORMATION: Synthetic Polypeptide

<400> SEQUENCE: 43

Met Arg Val Leu Gly Arg Leu Arg Ile Ser Arg Ala Thr Glu Glu Ser
1               5                   10                  15

Thr Ser Ile Glu Arg Gln Arg Glu Ile Val Glu Gln Trp Ala Ser Val
            20                  25                  30

Asn Asp His Glu Ile Val Gly Trp Ala Val Asp Gln Val Ser Gly
        35                  40                  45

Ser Val Asp Pro Phe Asp Ala Pro Ala Leu Gly Pro Trp Leu Ser Glu
    50                  55                  60

His Arg Lys His Glu Trp Asp Ile Leu Val Ala Trp Lys Leu Asp Arg
65                  70                  75                  80

Leu Ser Arg Arg Ala Ile Pro Met Asn Lys Leu Phe Gly Trp Met Ile
                85                  90                  95

Asp Asn Glu Lys Thr Leu Val Cys Val Ser Glu Asn Leu Asp Leu Gly
            100                 105                 110

Thr Trp Val Gly Arg Met Ile Ala Asn Val Ile Ala Gly Val Ala Glu
        115                 120                 125

Gly Glu Leu Glu Ala Ile Arg Glu Arg Thr Thr Ala Ser His Lys Lys
130                 135                 140

Leu Arg Glu Leu Gly Arg Trp Ala Gly Gly Pro Thr Tyr Tyr Gly Tyr
145                 150                 155                 160

Val Pro Lys Pro Arg Asp Gly Ala Gly Trp Glu Leu Asp Ile Asp Pro
                165                 170                 175

His Ala Ala Gly Val Leu Thr Glu Ile Ile Glu Lys Thr Ile Ala Gly
            180                 185                 190

Gln Ser Thr Glu Ser Ile Val Val Glu Leu Asn Glu Arg Gly Glu Leu
        195                 200                 205

Ala Pro Ser Asp Tyr His Arg Lys Arg Asn Gly Lys Pro Ile Arg Gly
210                 215                 220

Thr Lys Trp Ser Thr Ser Trp Leu Arg Ser Gln Leu Lys Ser Lys Thr
225                 230                 235                 240

Leu Leu Gly His Met Thr His Asn Gly Glu Thr Val Tyr Asp Asp Ala
                245                 250                 255

Gly Leu Pro Val Gln Lys Gly Pro Ala Leu Val Asp Arg Asp Thr Tyr
            260                 265                 270

Lys Gln Leu Gln Asp Ala Leu Glu Ser Arg Gly Ile Asn Arg Thr Arg
        275                 280                 285

Arg Arg Thr Gly Ala Ser Pro Leu Leu Gly Val Ala Val Cys Asp Val
290                 295                 300

Cys Glu Gly Pro Leu Tyr Tyr Arg Gln Thr Lys Asn Ala Lys Gly Thr
305                 310                 315                 320

Ala Met Leu Arg Gln Tyr Ile Cys Lys His Gly Arg Tyr Gly Asn Thr
                325                 330                 335

Gln Ala Asn Gly Gly Glu Pro Tyr Asn Ile Ile Gln Ala Asp Leu Leu
            340                 345                 350

Glu Ala Thr Val Glu Glu Leu Phe Leu Ser Lys Met Gly Asp Leu Pro
        355                 360                 365

Arg Val Glu Arg Val Phe Ile Pro Gly Glu Gly His Gln His Glu Leu
370                 375                 380

Glu Thr Ala Glu Arg Ala Val Glu Asp Leu Thr Ser Leu Leu Gly Thr

```
                385               390               395                400
        Ile Thr Gln Glu Ser Ala Arg Lys Arg Leu Leu Ala Gln Leu Ala Ala
                        405                 410                 415

Ala His Glu Arg Leu Ala His Leu Glu Glu Leu Pro Ser Ser Glu Pro
                        420                 425                 430

Arg Trp Glu Thr Arg Glu Thr Gly Glu Thr Tyr Arg Glu Ala Trp Glu
                        435                 440                 445

Gly Ala Thr Val Glu Glu Arg Arg Gln Ile Leu Leu Lys Ala Gly Val
                450                 455                 460

Thr Leu Lys Val Gln Met Lys Asp Arg Val Pro Arg Val His Pro Gly
        465                 470                 475                 480

Val Ile Val Ala Asn Trp Ile Glu Pro His Asp Ile Glu Lys Arg Leu
                        485                 490                 495

Ala Ser

<210> SEQ ID NO 44
<211> LENGTH: 1497
<212> TYPE: DNA
<213> ORGANISM: Artificial Sequence
<220> FEATURE:
<223> OTHER INFORMATION: Synthetic Polynucleotide

<400> SEQUENCE: 44
atgcgagttc ttggaagatt gcgaatttcc cgagccactg aggaatctac cagcatcgag      60
cggcagcgcg agatcgtgga gcagtgggcg tccgtgaacg accacgagat cgtcggctgg     120
gccgtggacc aggacgtgtc cggatcggtc gatccgttcg acgcgccagc actgggcccc     180
tggctgtctg agcaccggaa acacgagtgg gacatcctcg tggcgtggaa gctcgaccgc     240
ctgtcgcggc gagcgatccc gatgaacaag ctgttcggtt ggatgatcga caacgaaaag     300
actctggtct gcgtatcgga gaatctggac ctcgggacgt gggtcggtcg aatgatcgcc     360
aacgtcatcg ccggggtcgc agagggtgag ctggaggcca tccggagcg acgaccgcc      420 tcgcataaga agctcaggga gctgggaagg tgggccgggg gcccgacgta ctacgggtac     480
gtgccgaagc cccgcgacgg cgcggggtgg gagctggaca tcgacccgca cgctgctggc     540
gtgctgacgg agatcatcga aaagaccatc gccggtcagt cgacggagtc catcgtggtc     600
gagctgaacg agcgcgggga gctggctccg tccgactacc accggaagcg gaacggcaag     660
ccgatccggg ggacgaagtg gagcacgtcg tggctgcggt cgcagctcaa gtccaagacc     720
ctgctcggcc acatgaccca caacggtgaa accgtctacg acgacgccgg cctccctgtc     780
cagaagggcc ctgccttggt cgaccgggac acatacaagc aactgcagga cgcgctggag     840
agtcgtggga tcaaccggac ccggcgccga accgagcct caccgctgct cggtgtcgcc     900
gtgtgcgatg tctgcgaggg gccgctgtac taccggcaga ccaagaacgc caagggcacg     960
gccatgctgc ggcagtacat ctgcaagcac ggccgctacg caacactca ggccaacggc     1020 ggggagccgt acaacatcat ccaggccgac ctcttggagg ccaccgtcga agagctgttc     1080
ctgtcgaaga tgggtgacct gccccgcgtc gagcgggtgt tcatccccgg cgaaggacat     1140
cagcacgagc tggaaacggc tgagcgagcc gtggaggact tgacatcgct tctgggcacg     1200
atcacccagg agagtgcgag aaagcgtctc ctggctcaac tcgccgccgc ccacgagcgg     1260
ctggctcatc tcgaagagct cccgagctcc gagccccgct gggaaacccg agagacaggg     1320
gagacgtacc gcgaagcgtg ggagggcgcg acgtcgagg agcgtcggca gattctgctc     1380
aaagccggtg tgacattgaa ggtccagatg aaggaccgag tgccgagagt gcatcccggt     1440
```
gtcatcgtcg cgaactggat cgagccacac gacatcgaga agcgcctggc ctcttga      1497

<210> SEQ ID NO 45
<211> LENGTH: 504
<212> TYPE: PRT
<213> ORGANISM: Artificial Sequence
<220> FEATURE:
<223> OTHER INFORMATION: Synthetic Polypeptide

<400> SEQUENCE: 45

```
Met Arg Ala Leu Val Val Ile Arg Leu Ser Arg Val Thr Asp Ala Thr
1               5                   10                  15

Thr Ser Pro Glu Arg Gln Leu Glu Ser Cys Gln Gln Leu Cys Ala Gln
            20                  25                  30

Arg Gly Trp Asp Val Val Gly Val Ala Glu Asp Leu Asp Val Ser Gly
        35                  40                  45

Ala Val Asp Pro Phe Asp Arg Lys Arg Pro Asn Leu Ala Arg Trp
    50                  55                  60

Leu Ser Phe Glu Glu Gln Pro Phe Asp Val Ile Val Ala Tyr Arg Val
65                  70                  75                  80

Asp Arg Leu Thr Arg Ser Ile Arg His Leu Gln Gln Leu Val His Trp
                85                  90                  95

Ala Glu Asp His Lys Lys Leu Ile Val Ser Ala Thr Glu Ala His Phe
            100                 105                 110

Asp Thr Thr Thr Pro Phe Ala Ala Val Val Ile Ala Leu Met Gly Thr
        115                 120                 125

Val Ala Gln Met Glu Leu Glu Ala Ile Lys Glu Arg Asn Arg Ser Ala
130                 135                 140

Ala His Phe Asn Ile Arg Ala Gly Lys Tyr Arg Gly Ser Leu Pro Pro
145                 150                 155                 160

Trp Gly Tyr Met Pro Ala Arg Val Asp Gly Glu Trp Arg Leu Leu Val
                165                 170                 175

Asp Pro Val Gln Arg Glu Arg Ile Leu Glu Val Tyr His Arg Val Val
            180                 185                 190

Asp Asn His Glu Pro Leu His Leu Val Ala His Asp Leu Asn Gln Arg
        195                 200                 205

Gly Ile Leu Ser Pro Lys Asp Tyr Phe Ala Lys Leu Gln Gly Arg Glu
    210                 215                 220

Pro Lys Gly Arg Glu Trp Ser Ala Thr Ala Leu Lys Arg Ser Leu Ile
225                 230                 235                 240

Ser Glu Ala Met Leu Gly Tyr Ala Thr Leu Asn Gly Lys Thr Val Arg
                245                 250                 255

Asp Asp Asp Gly Ala Pro Leu Val Arg Ala Glu Pro Ile Leu Thr Arg
            260                 265                 270

Glu Gln Leu Glu Ala Leu Arg Ala Glu Leu Val Lys Thr Asp Arg Thr
        275                 280                 285

Lys Pro Ala Val Ser Thr Pro Ser Leu Leu Leu Arg Val Leu Phe Cys
    290                 295                 300

Ala Val Cys Gly Glu Pro Ala Tyr Lys Phe Thr Gly Gly Gly Arg Lys
305                 310                 315                 320

Asn Ala Arg Tyr Arg Cys Arg Ser Trp Gly Trp Ala Gln Arg Cys Gly
                325                 330                 335

Asn Gly Thr Val Ala Met Ala Glu Trp Asp Ala Phe Cys Glu Glu Gln
            340                 345                 350
```

```
Val Leu Asp Leu Leu Gly Asp Ala Glu Arg Leu Glu Lys Val Trp Val
            355                 360                 365
Ala Gly Ser Asp Ser Ala Val Glu Leu Ala Glu Val Asn Ala Glu Leu
        370                 375                 380
Val Asp Leu Thr Ser Leu Ile Gly Ser Pro Ala Tyr Arg Val Gly Ser
385                 390                 395                 400
Pro Gln Arg Glu Ala Leu Asp Ala Arg Ile Ala Leu Ala Ala Arg
                405                 410                 415
Gln Glu Glu Leu Glu Gly Leu Glu Ala Arg Pro Ser Gly Trp Glu Trp
            420                 425                 430
Arg Glu Thr Gly Gln Arg Phe Gly Asp Trp Trp Arg Glu Gln Asp Thr
        435                 440                 445
Ala Ala Lys Asn Thr Trp Leu Arg Ser Met Asn Val Arg Leu Thr Phe
    450                 455                 460
Asp Val Arg Gly Gly Leu Thr Arg Thr Ile Asp Phe Gly Asp Leu Gln
465                 470                 475                 480
Glu Tyr Glu Gln His Leu Arg Leu Gly Ser Ala Leu Asp Leu Val Asn
                485                 490                 495
Ala Glu Lys Pro Pro Thr Gly Arg
            500

<210> SEQ ID NO 46
<211> LENGTH: 1515
<212> TYPE: DNA
<213> ORGANISM: Artificial Sequence
<220> FEATURE:
<223> OTHER INFORMATION: Synthetic Polynucleotide

<400> SEQUENCE: 46
atgcgcgctt tggtagtgat ccgcttgtcc cgtgtgaccg atgctacgac ttcacccgag      60
cgtcagctgg agtcttgcca gcagctctgc gcccagcgcg gctgggacgt cgtcggggtg     120
gcggaggatc tggacgtgtc cggagcggtc gatccgttcg accggaagcg ccgcccgaac     180
ctggcccggt ggctgtcgtt cgaggagcaa ccgttcgatg tgatcgtggc gtaccgggtg     240
gatcggttga cccgctcgat ccggcatctt cagcagctgg tccactgggc cgaggaccac     300
aagaagctga tcgtctccgc gaccgaagcg cacttcgata cgacgacgcc gttcgcggcg     360
gtcgtgatcg cgcttatggg aacggtggcg cagatggaat tagaagcgat caaagagcgg     420
aaccgttcgg ctgcgcattt caacatccgc gcggggaaat accgcggctc cctgccgccg     480
tggggttaca tgcccgcccg cgtggacggg gagtggaggc tgctcgtcga ccccgtgcag     540
cgcgaacgca tcctcgaggt ctatcaccgc gtcgtcgaca accacgagcc tctgcatctg     600
gtcgcccacg acctgaacca gcgtggcatc ctgtcgccga aggactactt cgcgaagctg     660
cagggccgag agcccaaggg ccgggagtgg tcggctaccg cgctgaagcg ctcgctgatc     720
tccgaggcga tgctcgggta cgcgactctg aacggtaaga ccgtccgaga cgacgacgga     780
gccccgctgg tgcgggctga gccgatcctg acccgtgagc agctggaggc gctgcgcgcc     840
gagctcgtca agaccgaccg gaccaagccc gcagtgtcta cccgtcgct gctgctgcgg     900 gtgttgttct gcgcagtgtg cggtgagccc gcatacaagt tcaccggtgg cggtaggaag     960
aacgctcgct accgctgccg gtcgtggggt tgggcacagc ggtgcggtaa cggcacggtg    1020
gcaatggcgg agtgggacgc gttctgcgag gagcaggtgc tggatctgct cggggacgca    1080
gagcgtctgg agaaagtctg ggtagcaggt tcggactcgg cagtcgaact cgcggaggtg    1140
aacgcggagc tggtggacct gacgtcgctg atcggctctc cggcgtaccg ggtcggttct    1200
```

-continued

```
ccgcagcgcg aagcactgga tgctcgtatt gcggcgctgg ccgcgcggca agaggagttg    1260
gaagggctag aggctcgtcc gtctggctgg gagtggcgcg aaaccgggca gcggttcggg    1320
gactggtggc gggagcagga caccgcggca agaacacct ggcttcggtc gatgaacgtt     1380
cggctgacgt tcgacgtccg cggcgggctg actcggacga tcgacttcgg ggatctgcag    1440
gagtatgagc agcatctgag gctgggctcg gctctagacc tcgtaaacgc agaaaagccc    1500
cctacgggcc gctag                                                     1515
```

<210> SEQ ID NO 47
<211> LENGTH: 500
<212> TYPE: PRT
<213> ORGANISM: Artificial Sequence
<220> FEATURE:
<223> OTHER INFORMATION: Synthetic Polypeptide

<400> SEQUENCE: 47

```
Met Arg Ala Leu Val Val Ile Arg Leu Ser Arg Val Thr Asp Ala Thr
1               5                   10                  15

Thr Ser Pro Glu Arg Gln Leu Glu Ser Cys Gln Gln Leu Cys Ala Gln
            20                  25                  30

Arg Gly Trp Asp Val Val Gly Val Ala Glu Asp Leu Asp Val Ser Gly
        35                  40                  45

Ala Val Asp Pro Phe Asp Arg Lys Arg Pro Asn Leu Ala Arg Trp
    50                  55                  60

Leu Ala Phe Glu Glu Gln Pro Phe Asp Val Ile Val Ala Tyr Arg Val
65                  70                  75                  80

Asp Arg Leu Thr Arg Ser Ile Arg His Leu Gln Gln Leu Val His Trp
                85                  90                  95

Ala Glu Asp His Lys Lys Leu Val Val Ser Ala Thr Glu Ala His Phe
            100                 105                 110

Asp Thr Thr Thr Pro Phe Ala Ala Val Val Ile Ala Leu Met Gly Thr
        115                 120                 125

Val Ala Gln Met Glu Leu Glu Ala Ile Lys Glu Arg Asn Arg Ser Ala
    130                 135                 140

Ala His Phe Asn Ile Arg Ala Gly Lys Tyr Arg Gly Ser Leu Pro Pro
145                 150                 155                 160

Trp Gly Tyr Leu Pro Thr Arg Val Asp Gly Glu Trp Arg Leu Val Pro
                165                 170                 175

Asp Pro Val Gln Arg Glu Arg Ile Leu Glu Val Tyr His Arg Val Val
            180                 185                 190

Asp Asn His Glu Pro Leu His Leu Val Ala His Asp Leu Asn Arg Arg
        195                 200                 205

Gly Val Leu Ser Pro Lys Asp Tyr Phe Ala Lys Leu Gln Gly Arg Glu
    210                 215                 220

Pro Arg Gly Arg Glu Trp Ser Ala Thr Ala Leu Lys Arg Ser Leu Ile
225                 230                 235                 240

Ser Glu Ala Met Leu Gly Tyr Thr Thr Leu Asn Gly Lys Thr Val Arg
                245                 250                 255

Asp Asp Asp Gly Ala Pro Leu Val Arg Ala Glu Pro Ile Leu Thr Arg
            260                 265                 270

Glu Gln Leu Glu Ser Leu Arg Ala Glu Leu Val Lys Thr Asp Arg Thr
        275                 280                 285

Lys Pro Ala Val Ser Thr Pro Ser Leu Leu Leu Arg Val Leu Phe Cys
    290                 295                 300
```

```
Ala Val Cys Gly Glu Pro Ala Tyr Lys Phe Ala Gly Gly Gln Arg Lys
305                 310                 315                 320

Asn Pro Arg Tyr Arg Cys Arg Ser Met Gly Phe Pro Lys His Cys Gly
            325                 330                 335

Asn Gly Thr Val Ala Met Ala Glu Trp Asp Ala Phe Cys Glu Glu Gln
        340                 345                 350

Val Leu Asp Leu Leu Gly Asp Ala Glu Arg Leu Glu Lys Val Trp Val
    355                 360                 365

Ala Gly Ser Asp Ser Ala Val Glu Leu Ala Glu Val Asn Ala Glu Leu
370                 375                 380

Val Asp Leu Thr Ser Leu Ile Gly Ser Pro Ala Tyr Arg Val Gly Ser
385                 390                 395                 400

Pro Gln Arg Glu Ala Leu Asp Ala Arg Ile Ala Ala Leu Ala Ala Arg
            405                 410                 415

Gln Glu Glu Leu Glu Gly Leu Glu Ala Arg Pro Ser Gly Trp Glu Trp
        420                 425                 430

Arg Glu Thr Gly Gln Arg Phe Gly Asp Trp Trp Arg Glu Gln Asp Ala
    435                 440                 445

Ser Gly Lys Asn Thr Trp Leu Arg Ser Met Asn Val Arg Leu Thr Phe
450                 455                 460

Asp Val Arg Gly Gly Leu Thr Arg Thr Ile Asp Phe Gly Asp Leu Gln
465                 470                 475                 480

Glu Tyr Glu Gln His Leu Arg Leu Gly Ser Val Val Glu Arg Leu His
            485                 490                 495

Thr Gly Met Ser
            500

<210> SEQ ID NO 48
<211> LENGTH: 1503
<212> TYPE: DNA
<213> ORGANISM: Artificial Sequence
<220> FEATURE:
<223> OTHER INFORMATION: Synthetic Polynucleotide

<400> SEQUENCE: 48
atgagagcac tggtggtcat ccgactgtcc cgcgtcaccg atgctacgac ttcacccgag      60
cgtcagctgg agtcttgcca gcagctctgc gcacagcgcg gttgggacgt cgtcggtgta     120
gcggaggatc tggacgtctc cggagcagtc gatccgttcg accggaagcg ccgcccgaac     180
ctggcacgat ggctagcatt cgaggagcaa ccgttcgacg tcatcgtggc gtaccgggtg     240
gaccggttga cccgctcgat ccggcatctg cagcagctgg tgcactgggc cgaggaccat     300
aagaagctgg tcgtctccgc gaccgaagcc cacttcgaca cgacgacgcc gttcgcggcg     360
gtcgtcatcg cgcttatggg aacggtggcg cagatggaat agaagcgat caaagagcgg     420 aaccgttcgg cagcacattt caatatccgc gccggtaaat accgcggttc cctgccgccg     480
tggggttacc tgcctacgcg cgtggacggt gagtggcggc tggtgccgga cccggtgcag     540
cgagagcgca tcctcgaggt gtatcaccgc gtcgtcgaca ccacgagcc gctgcacctg     600 gtggcccacg acctgaaccg gcgtggtgtc ctgtcgccga aggactactt cgcgaagctg     660
caaggccgcg agccgcgggg ccgggagtgg tcggctaccg cgctgaagcg ctcgctgatc     720
tcggaggcga tgctcgggta tacgacgctg aacggcaaga ccgtccgaga cgacgacggg     780
gctccgctgg tgcgggccga ccgatcctg acgcgcgagc agctggaatc gctgcgggcg     840
gaactggtca agaccgaccg gaccaagccc gcagtgtcca ccccgtcgct gctgctgcgg     900
```

```
gtgttgttct gcgcagtgtg cggggagccc gcgtacaagt tcgccggtgg tcagcgcaag    960
aacccgcgct accgctgccg ctcgatgggg ttcccgaagc actgcggtaa cggtacggtg   1020
gcgatggccg agtgggacgc gttctgcgag gagcaggtgc tggatctgct cggggacgcg   1080
gagcgtctgg agaaagtctg ggtagccggt tcggactcgg cagtcgaact cgcagaggtg   1140
aacgcggagc tggtggacct gacgtcgctg atcggctctc cggcataccg ggttggttct   1200
ccgcagcgcg aggcgctcga cgctcgtatc gcagcactgg ccgcacggca agaggagttg   1260
gaagggctag aggctcgtcc gtcgggctgg gagtggcgag aaaccgggca gaggttcggg   1320
gactggtggc gggagcagga cgcctcgggt aagaacacct ggcttcggtc gatgaacgtt   1380
cggctgacgt tcgacgtccg cggcgggctg actcgcacga tcgacttcgg ggatctgcag   1440
gagtacgagc agcatctcag gctcggcagc gtggtcgaac ggctacacac cgggatgtcg   1500
tag                                                                 1503
```

<210> SEQ ID NO 49
<211> LENGTH: 502
<212> TYPE: PRT
<213> ORGANISM: Artificial Sequence
<220> FEATURE:
<223> OTHER INFORMATION: Synthetic Polypeptide

<400> SEQUENCE: 49

```
Met Arg Val Leu Gly Arg Leu Arg Leu Ser Arg Ser Thr Glu Glu Ser
1               5                   10                  15

Thr Ser Ile Glu Arg Gln Arg Glu Ile Val Thr Ala Trp Ala Glu Ser
            20                  25                  30

Asn Gly His Thr Leu Val Gly Trp Ala Glu Asp Val Asp Val Ser Gly
        35                  40                  45

Ala Ile Asp Pro Phe Asp Thr Pro Ser Leu Gly Pro Trp Leu Asp Glu
    50                  55                  60

Arg Arg Gly Glu Trp Asp Ile Leu Cys Ala Trp Lys Leu Asp Arg Leu
65                  70                  75                  80

Gly Arg Asp Ala Ile Arg Leu Asn Lys Leu Phe Gly Trp Cys Gln Glu
                85                  90                  95

His Gly Lys Thr Val Ala Ser Cys Ser Glu Gly Ile Asp Leu Ser Thr
            100                 105                 110

Pro Val Gly Arg Leu Ile Ala Asn Val Ile Ala Phe Leu Ala Glu Gly
        115                 120                 125

Glu Arg Glu Ala Ile Arg Glu Arg Val Thr Ser Ser Lys Gln Lys Leu
    130                 135                 140

Arg Glu Val Gly Arg Trp Gly Gly Lys Pro Pro Phe Gly Tyr Met
145                 150                 155                 160

Gly Ile Pro Asn Pro Asp Gly Gln Gly His Ile Leu Val Val Asp Pro
                165                 170                 175

Val Ala Lys Pro Val Val Arg Arg Ile Val Asp Asp Ile Leu Asp Gly
            180                 185                 190

Lys Pro Leu Thr Arg Leu Cys Thr Glu Leu Thr Glu Glu Arg Tyr Leu
        195                 200                 205

Thr Pro Ala Glu Tyr Tyr Ala Thr Leu Lys Ala Gly Ala Pro Arg Gln
    210                 215                 220

Lys Ala Glu Pro Asp Glu Thr Pro Ala Lys Trp Arg Pro Thr Ala Leu
225                 230                 235                 240

Arg Asn Leu Leu Arg Ser Lys Ala Leu Arg Gly Tyr Ala His His Lys
```

245                 250                 255
Gly Gln Thr Val Arg Asp Leu Lys Gly Gln Pro Val Arg Leu Ala Glu
            260                 265                 270

Pro Leu Val Asp Ala Asp Glu Trp Glu Leu Leu Gln Glu Thr Leu Asp
        275                 280                 285

Arg Val Gln Ala Asn Trp Ser Gly Arg Val Glu Gly Val Ser Pro
    290                 295                 300

Leu Ser Gly Val Val Cys Ile Thr Cys Asp Arg Pro Leu His His
305                 310                 315                 320

Asp Arg Tyr Leu Val Lys Arg Pro Tyr Gly Asp Tyr Pro Tyr Arg Tyr
                325                 330                 335

Tyr Arg Cys Arg Asp Arg His Gly Lys Asn Leu Pro Ala Glu Met Val
            340                 345                 350

Glu Thr Leu Met Glu Glu Ser Phe Leu Ala Arg Val Gly Asp Tyr Pro
        355                 360                 365

Val Arg Glu Arg Val Trp Val Gln Gly Asp Thr Asn Trp Ala Asp Leu
    370                 375                 380

Lys Glu Ala Val Ala Ala Tyr Asp Glu Leu Val Gln Ala Ala Gly Arg
385                 390                 395                 400

Ala Lys Ser Ala Thr Ala Lys Glu Arg Leu Gln Arg Gln Leu Asp Ala
                405                 410                 415

Leu Asp Glu Arg Ile Ala Glu Leu Glu Ser Ala Pro Ala Thr Glu Ala
            420                 425                 430

His Trp Glu Tyr Arg Pro Thr Gly Gly Thr Tyr Arg Asp Ala Trp Glu
        435                 440                 445

Thr Ala Asp Thr Asp Glu Arg Arg Glu Ile Leu Arg Arg Ser Gly Ile
    450                 455                 460

Val Leu Ala Val Gly Val Asp Gly Val Asp Gly Arg Arg Ser Lys His
465                 470                 475                 480

Asn Pro Gly Ala Leu His Phe Asp Phe Arg Val Pro Glu Glu Leu Thr
                485                 490                 495

Gln Arg Leu Gly Val Ser
            500

<210> SEQ ID NO 50
<211> LENGTH: 1509
<212> TYPE: DNA
<213> ORGANISM: Artificial Sequence
<220> FEATURE:
<223> OTHER INFORMATION: Synthetic Polynucleotide

<400> SEQUENCE: 50
atgcgagtgc tcggaagatt gcgtttgtcc aggtcaacgg aggaatctac ctccatcgag     60
cggcagcggg agattgtcac cgcttgggca gagtctaacg gtcacaccct cgtgggttgg    120
gccgaggacg ttgacgtgtc tggtgcaatc gacccgttcg acaccccgtc gctcggtccg    180
tggctggacg agcggcgagg cgagtgggac atcctctgcg cgtggaagct cgaccggctg    240
ggccgtgatg ccatccggct caacaagctc ttcggttggt gccaggagca cggcaagacc    300
gtggcctcgt gcagcgaggg catcgacctc agcacgccgg tcgtcggct catcgccaac    360 gtcatcgcct tcctggccga gggtgagcgg gaagcgatcc gcgagcgcgt cacgtcctcg    420
aagcagaagc tgcgcgaggt aggccggtgg ggtggtggta agccgccgtt cggttacatg    480
ggcatcccca acccggacgg tcagggacac atcctcgtgg tcgatccggt ggccaagccg    540
gtggtgcgcc ggatcgtgga cgacatcctc gacggcaagc cgctcacgcg gctctgcacg    600

```
gagctgaccg aggagcgata cctcacgccg gcagagtact acgcaaccct caaggcaggg      660
gcaccgaggc agaaggccga gcccgacgaa acccctgcaa agtggcggcc gaccgctctc      720
cgcaaccttc tccggagcaa ggccctgcgg ggttacgccc atcacaaggg gcagaccgtc      780
agggacctca aggggcagcc tgtgcgcctc gctgagccac tggtggacgc cgacgaatgg      840
gaactactgc aggagactct cgaccgcgta caggcaaact ggtcgggtcg acgggtcgag      900
ggtgtcagcc cgctgtccgg tgtcgtggtc tgcatcacct gtgaccgtcc gctgcaccac      960
gaccggtatc tggtgaagcg gccatacggt gactacccct accggtacta ccggtgccgt     1020
gaccgccacg gcaagaacct cccggcagag atggtcgaaa ccctcatgga agagtccttc     1080
ctggcacgcg tgggtgacta tccggtgcgg gagagggtct gggtccaggg tgacacgaat     1140
tgggcagatc tgaaggaggc tgtggcagcc tacgacgaac tggtgcaggc agccggccgc     1200
gccaagagcg caacggcgaa ggagagactg cagaggcagc tcgatgcact agacgagcgg     1260
atcgcggagc ttgagtccgc acccgccacc gaggcccact gggagtaccg gccgaccgga     1320
ggtacctacc gggacgcctg ggagacagca gacaccgacg agcgccgcga gatcctgcgg     1380
cggtcgggga tcgtcctggc ggtcggagtc gacggcgtgg atggccgtcg ctccaagcac     1440
aacccaggag ccctgcactt cgacttccgg gtccccgagg aactgaccca gcggctcgga     1500
gtctcctga                                                             1509
```

<210> SEQ ID NO 51
<211> LENGTH: 484
<212> TYPE: PRT
<213> ORGANISM: Artificial Sequence
<220> FEATURE:
<223> OTHER INFORMATION: Synthetic Polypeptide

<400> SEQUENCE: 51

```
Met Thr Ala Thr Leu Glu Arg His Leu Asp Thr Pro Gln Gln Glu Ala
1               5                   10                  15

Leu Arg Val Gly Val Tyr Leu Arg Met Ser Thr Asp Lys Glu Leu Gly
            20                  25                  30

Ile Asp Arg Gln Arg Glu Asp Cys Leu Ala Leu Ala Glu Arg Leu Gly
        35                  40                  45

Trp Val Pro Val Glu Tyr Ile Asp Asn Asp Arg Ser Ala Thr Lys Glu
    50                  55                  60

Asn Val Lys Arg Glu Gly Phe Asp Ala Leu Ser Glu Asp Ile Arg Asp
65                  70                  75                  80

Gly Arg Ile Asp Ser Ile Ile Thr Trp Arg Ser Asp Arg Leu Tyr Arg
                85                  90                  95

Lys Met Lys Asp Leu Leu Pro Leu Ile Asp Leu Ile Gln Gly Val Asn
            100                 105                 110

Lys Thr Gly Lys Arg Ile Pro Ile Glu Thr Cys Gln Thr Gly Leu Ile
        115                 120                 125

Asp Leu Thr Thr Asp Ala Gly Arg Met Thr Ala Lys Ile Leu Ala Ala
    130                 135                 140

Val Ser Glu Asn Glu Gly Glu Val Arg Thr Ala Arg Gln Met Arg Ala
145                 150                 155                 160

Tyr Glu Gln Ile Ala Asp Ser Gly Arg Arg Leu Gly Ala Pro Ala Phe
                165                 170                 175

Gly Trp Thr His Asp Pro Arg Asp Pro Gln Ile Val Pro Glu Glu Ala
            180                 185                 190
```

Ala Ala Ile Arg Gln Ala Tyr Ala Asp Val Leu Ala Gly Cys Thr Leu
            195                 200                 205

Tyr Ser Ile Ala Lys Lys Trp Asn Glu Asp Gly Leu Arg Thr Thr Arg
210                 215                 220

Gly Asn Gln Phe Val Gly Ser Val Val Gly Lys Ile Leu Arg Ser Pro
225                 230                 235                 240

Arg Asn Ala Gly Leu Leu Thr Phe Arg Asp Glu Ile Val Gly Glu Gly
                245                 250                 255

Thr Trp Glu Pro Ile Val Asp Arg Glu Thr Trp Glu Ala Ala Cys Ala
                260                 265                 270

Val Leu Asp Gln Lys Asn Thr Gly Lys Lys Gly Pro Arg Val Arg Ser
            275                 280                 285

Thr Leu Leu Ser Gly Ile Val Arg Cys Gly Ala Cys Gly Asn Lys Met
290                 295                 300

Ala Ala Gly Lys Asn Ser Asn Gly Glu Pro Ile Tyr Lys Cys Lys Arg
305                 310                 315                 320

Tyr Glu Val Cys Lys His Gly Val Thr Arg Val Arg Lys Lys Val Asp
                325                 330                 335

Lys Tyr Val Glu Met Ser Met Val Ala Lys Leu Glu Gln Arg Lys Trp
                340                 345                 350

Ile Val Gly Thr Gln Val Asp Ala Glu Gln Ala Lys Gly Leu His Ala
            355                 360                 365

Glu Ala Glu Ala Leu Arg Ala Arg Lys Ala Ser Phe Gly Glu Ala Leu
370                 375                 380

Ala Asp Gly Thr Leu Thr Pro Ala Gln Val Lys Asp Ala Thr Asp Arg
385                 390                 395                 400

Val Asn Ala Lys Leu Glu Glu Ile Asp Ala Lys Leu Ala Arg Leu Thr
                405                 410                 415

Arg Ser Arg Val Phe Asp Gly Leu Leu Gly His Asp Leu Glu Lys
                420                 425                 430

Val Trp Leu Gly Leu Asp Leu Glu Arg Lys Arg Ala Ile Ile Glu Ser
            435                 440                 445

Leu Cys Asp Lys Ile Val Ile Gln His Val Gly Gln Thr Gly Arg Ser
450                 455                 460

Ala Ala Lys Leu Pro Leu Gly His Ala Ile Lys Ile His Trp His Asp
465                 470                 475                 480

Pro Ser Asn Asp

<210> SEQ ID NO 52
<211> LENGTH: 1455
<212> TYPE: DNA
<213> ORGANISM: Artificial Sequence
<220> FEATURE:
<223> OTHER INFORMATION: Synthetic Polynucleotide

<400> SEQUENCE: 52
atgacagcga cccctcgagcg acacctcgac accccgcagc aggaggccct gcgggtgggt        60
gtctacctgc gcatgtccac cgacaaggag ctgggcatcg atcgccagcg cgaggactgc       120
ctggcgctgg ctgagcgtct gggctgggtt cccgtcgagt acatcgacaa cgaccgcagc       180
gccaccaagg agaacgtcaa gcgcgaaggc ttcgatgcgc tgagcgagga catccgcgat       240
ggccggatcg acagcatcat cacgtggcgc agcgaccggc tgtaccgaaa gatgaaggat       300
ctactccccc tgatcgatct gatccagggt gttaataaga caggcaagcg gatccccatc       360
gaaacctgcc agactggcct gatcgatctc accaccgacg ccggtcggat gacagcgaag       420

```
atccttgccg ctgtctcgga gaacgagggc gaggtaagga cggcgcgaca gatgcgagcc    480
tacgagcaga tcgccgacag tggccgtcgc ctgggcgctc ccgcgttcgg ctggacccat    540
gaccccaggg acccgcagat cgtgcccgag gaggccgctg cgatccggca ggcgtacgcc    600
gacgtgctcg ctggctgcac cctctactcc atcgcgaaga agtggaacga ggacggtctg    660
cgcaccacgc gtggcaacca gttcgtcggg tcggtcgtcg ggaagatcct gcgaagcccc    720
cgcaatgcgg gcctgctgac cttcaggggac gagatcgtgg gcgaaggcac ctgggagccc    780
atcgttgatc gggaaacctg ggaggcagcc tgtgcggtgc tcgaccagaa gaacaccggc    840
aagaagggtc cacgtgtacg gtcgaccctc ctgtcgggga tcgtgcgctg cggtgcctgc    900
ggcaacaaga tggctgccgg gaagaactcc aacggtgagc ccatctacaa gtgcaagcgc    960
tacgaggtct gcaagcacgg tgttacccgt gtgcgtaaga aggtcgacaa gtatgtcgag   1020
atgtccatgg tggcgaagct ggagcagcgc aagtggattg tcggcaccca ggtcgacgcg   1080
gagcaggcca aggggcttca cgctgaggct gaagctctac gcgctcgcaa ggcatcgttc   1140
ggtgaggccc tggccgacgg caccctcaca ccggctcagg tgaaggacgc caccgaccgg   1200
gtgaacgcca agctggaaga gatcgatgcc aagctagccc gccttacacg atctcgcgtg   1260
ttcgacgggc tgctcggtca tgacgatctt gaaaaggttt ggctgggact ggatctcgag   1320
cgtaagcgtg cgatcatcga gtcgctatgc gacaagatcg tgatccagca tgtcgggcag   1380
acgggtcgct ctgcggccaa actgcccctc ggtcacgcca tcaagatcca ctggcatgat   1440
cccagcaacg actga                                                    1455
```

<210> SEQ ID NO 53
<211> LENGTH: 503
<212> TYPE: PRT
<213> ORGANISM: Artificial Sequence
<220> FEATURE:
<223> OTHER INFORMATION: Synthetic Polypeptide

<400> SEQUENCE: 53

```
Met Arg Ala Leu Val Val Ile Arg Leu Ser Arg Val Thr Asp Ala Thr
1               5                  10                  15

Thr Ser Pro Glu Arg Gln Leu Glu Ser Cys Gln Gln Leu Cys Ala Gln
            20                  25                  30

Arg Gly Trp Asp Val Val Gly Val Ala Glu Asp Leu Asp Val Ser Gly
        35                  40                  45

Ala Val Asp Pro Phe Asp Arg Lys Arg Pro Asn Leu Ala Arg Trp
    50                  55                  60

Leu Ala Phe Glu Glu Gln Pro Phe Asp Val Ile Val Ala Tyr Arg Val
65                  70                  75                  80

Asp Arg Leu Thr Arg Ser Ile Arg His Leu Gln Gln Leu Val His Trp
                85                  90                  95

Ala Glu Asp His Lys Lys Leu Val Val Ser Ala Thr Glu Ala His Phe
            100                 105                 110

Asp Thr Thr Thr Pro Phe Ala Ala Val Val Ile Ala Leu Met Gly Thr
        115                 120                 125

Val Ala Gln Met Glu Leu Glu Ala Ile Lys Glu Arg Asn Arg Ser Ala
    130                 135                 140

Ala His Phe Asn Ile Arg Ala Gly Lys Tyr Arg Gly Ser Leu Pro Pro
145                 150                 155                 160

Trp Gly Tyr Leu Pro Thr Arg Val Asp Gly Glu Trp Arg Leu Val Pro
                165                 170                 175
```

Asp Pro Val Gln Arg Glu Arg Ile Leu Glu Val Tyr His Arg Val Val
        180                 185                 190

Asp Asn His Glu Pro Leu His Leu Val Ala His Asp Leu Asn Arg Arg
        195                 200                 205

Gly Val Leu Ser Pro Lys Asp Tyr Phe Ala Lys Leu Gln Gly Arg Glu
        210                 215                 220

Pro Gln Gly Arg Glu Trp Ser Ala Thr Ala Leu Lys Arg Ser Leu Ile
225                 230                 235                 240

Ser Glu Ala Met Leu Gly Tyr Ala Thr Leu Asn Gly Lys Thr Val Arg
                245                 250                 255

Asp Asp Asp Gly Ala Pro Leu Val Arg Ala Glu Pro Ile Leu Thr Arg
                260                 265                 270

Glu Gln Leu Glu Ala Leu Arg Ala Glu Leu Val Lys Thr Ser Arg Ala
            275                 280                 285

Lys Pro Ala Val Ala Thr Pro Ser Leu Leu Leu Arg Val Leu Phe Cys
        290                 295                 300

Ala Val Cys Gly Glu Pro Ala Tyr Lys Phe Asp Ala Gly Arg Lys Ile
305                 310                 315                 320

Pro Arg Tyr Arg Cys Arg Ser Phe Gly Phe Ala Val Arg Cys Gly Asn
                325                 330                 335

Gly Thr Val Pro Ile Ala Glu Trp Asp Ala Phe Cys Glu Glu Gln Val
                340                 345                 350

Leu Asp Leu Leu Gly Asp Ser Glu Arg Leu Glu Lys Val Trp Val Ala
            355                 360                 365

Gly Ser Asp Ser Ala Val Glu Leu Ala Glu Val Asn Ala Glu Leu Val
        370                 375                 380

Asp Leu Thr Ser Leu Ile Gly Ser Pro Ala Tyr Arg Ala Gly Ser Pro
385                 390                 395                 400

Gln Arg Glu Ala Leu Asp Ala Arg Ile Ala Ala Leu Ala Ala Arg Gln
                405                 410                 415

Glu Glu Leu Glu Gly Leu Glu Ala Arg Pro Ser Gly Trp Glu Trp Arg
                420                 425                 430

Glu Thr Gly Gln Arg Phe Gly Asp Trp Trp Arg Asp Gln Asp Thr Ala
            435                 440                 445

Gly Lys Asn Thr Trp Leu Arg Ser Met Asn Val Arg Leu Thr Phe Asp
        450                 455                 460

Val Arg Gly Gly Leu Thr Arg Thr Ile Asp Phe Gly Asp Leu Gln Glu
465                 470                 475                 480

Tyr Glu Gln His Leu Arg Leu Gly Ser Ala Leu Asp Leu Val Asn Ala
                485                 490                 495

Glu Lys Pro Pro Thr Gly Arg
            500

<210> SEQ ID NO 54
<211> LENGTH: 1512
<212> TYPE: PRT
<213> ORGANISM: Artificial Sequence
<220> FEATURE:
<223> OTHER INFORMATION: Synthetic Polypeptide

<400> SEQUENCE: 54

Ala Thr Gly Ala Gly Ala Gly Cys Ala Cys Thr Gly Gly Thr Ala Gly
1               5                   10                  15

Thr Cys Ala Thr Cys Cys Gly Cys Cys Thr Gly Thr Cys Cys Cys Gly
            20                  25                  30

-continued

```
Cys Gly Thr Cys Ala Cys Cys Gly Ala Thr Gly Cys Thr Ala Cys Gly
        35                  40                  45

Ala Cys Thr Thr Cys Ala Cys Cys Gly Gly Ala Gly Cys Gly Cys Cys
    50                  55                  60

Ala Gly Cys Thr Gly Gly Ala Gly Thr Cys Thr Thr Gly Cys Cys Ala
65                  70                  75                  80

Gly Cys Ala Gly Cys Thr Cys Thr Gly Cys Gly Cys Cys Cys Ala Gly
                85                  90                  95

Cys Gly Cys Gly Gly Thr Thr Gly Gly Gly Ala Cys Gly Thr Cys Gly
            100                 105                 110

Thr Cys Gly Gly Thr Gly Thr Ala Gly Cys Ala Gly Ala Gly Gly Ala
        115                 120                 125

Thr Cys Thr Gly Gly Ala Cys Gly Thr Cys Thr Cys Cys Gly Gly Ala
    130                 135                 140

Gly Cys Ala Gly Thr Cys Gly Ala Thr Cys Cys Gly Thr Thr Cys Gly
145                 150                 155                 160

Ala Cys Cys Gly Gly Ala Ala Gly Cys Gly Cys Cys Gly Cys Cys Cys
                165                 170                 175

Gly Ala Ala Cys Cys Thr Gly Gly Cys Cys Cys Gly Gly Thr Gly Gly
            180                 185                 190

Cys Thr Ala Gly Cys Gly Thr Thr Cys Gly Ala Gly Gly Ala Gly Cys
        195                 200                 205

Ala Gly Cys Cys Gly Thr Thr Cys Gly Ala Thr Gly Thr Gly Ala Thr
    210                 215                 220

Cys Gly Thr Gly Gly Cys Gly Thr Ala Cys Cys Gly Gly Gly Thr Gly
225                 230                 235                 240

Gly Ala Cys Cys Gly Gly Thr Thr Gly Ala Cys Cys Cys Gly Ala Thr
                245                 250                 255

Cys Gly Ala Thr Cys Cys Gly Gly Cys Ala Thr Cys Thr Gly Cys Ala
            260                 265                 270

Gly Cys Ala Gly Cys Thr Gly Gly Thr Cys Cys Ala Cys Thr Gly Gly
        275                 280                 285

Gly Cys Cys Gly Ala Gly Gly Ala Cys Cys Ala Cys Ala Ala Gly Ala
    290                 295                 300

Ala Gly Cys Thr Gly Gly Thr Cys Gly Thr Cys Thr Cys Cys Gly Cys
305                 310                 315                 320

Ala Ala Cys Cys Gly Ala Ala Gly Cys Ala Cys Ala Cys Thr Thr Cys
                325                 330                 335

Gly Ala Cys Ala Cys Gly Ala Cys Gly Ala Cys Gly Cys Cys Gly Thr
            340                 345                 350

Thr Cys Gly Cys Ala Gly Cys Ala Gly Thr Cys Gly Thr Cys Ala Thr
        355                 360                 365

Cys Gly Cys Gly Cys Thr Thr Ala Thr Gly Gly Gly Ala Ala Cys Gly
    370                 375                 380

Gly Thr Gly Gly Cys Ala Cys Ala Gly Ala Thr Gly Gly Ala Ala Thr
385                 390                 395                 400

Thr Ala Gly Ala Ala Gly Cys Gly Ala Thr Cys Ala Ala Ala Gly Ala
                405                 410                 415

Gly Cys Gly Gly Ala Ala Cys Cys Gly Thr Thr Cys Gly Gly Cys Thr
            420                 425                 430

Gly Cys Gly Cys Ala Thr Thr Thr Cys Ala Ala Thr Ala Thr Cys Cys
        435                 440                 445
```

-continued

```
Gly Cys Gly Cys Cys Gly Gly Ala Ala Thr Ala Cys Cys Gly
450                 455                 460
Cys Gly Gly Cys Thr Cys Cys Thr Gly Cys Cys Gly Cys Cys Gly
465                 470                 475                 480
Thr Gly Gly Gly Thr Thr Ala Cys Thr Gly Cys Cys Thr Ala
            485                 490                 495
Cys Gly Cys Gly Cys Gly Thr Gly Ala Cys Gly Gly Gly Ala
            500                 505                 510
Gly Thr Gly Gly Cys Gly Gly Cys Thr Gly Gly Thr Gly Cys Cys Gly
        515                 520                 525
Gly Ala Cys Cys Thr Gly Thr Gly Cys Ala Gly Cys Gly Ala Gly
530                 535                 540
Ala Gly Cys Gly Cys Ala Thr Cys Cys Thr Cys Gly Ala Gly Thr
545                 550                 555                 560
Gly Thr Ala Thr Cys Ala Cys Cys Gly Cys Gly Thr Cys Gly Thr Cys
            565                 570                 575
Gly Ala Cys Ala Ala Cys Cys Ala Cys Gly Ala Gly Cys Cys Gly Cys
            580                 585                 590
Thr Gly Cys Ala Cys Cys Thr Gly Gly Thr Gly Gly Cys Cys Cys Ala
595                 600                 605
Cys Gly Ala Cys Cys Thr Gly Ala Ala Cys Cys Gly Gly Cys Gly Ala
            610                 615                 620
Gly Gly Cys Gly Thr Cys Thr Gly Thr Gly Gly Cys Cys Thr Ala
625                 630                 635                 640
Ala Gly Gly Ala Cys Thr Ala Cys Thr Thr Cys Gly Cys Gly Ala Ala
            645                 650                 655
Gly Cys Thr Gly Cys Ala Gly Gly Cys Cys Gly Cys Gly Ala Gly
        660                 665                 670
Cys Cys Gly Cys Ala Gly Gly Gly Cys Cys Gly Gly Ala Gly Thr
        675                 680                 685
Gly Gly Thr Cys Gly Gly Cys Thr Ala Cys Cys Gly Cys Gly Cys Thr
        690                 695                 700
Gly Ala Ala Gly Cys Gly Cys Thr Cys Gly Cys Thr Gly Ala Thr Cys
705                 710                 715                 720
Thr Cys Thr Gly Ala Gly Gly Cys Gly Ala Thr Gly Cys Thr Cys Gly
            725                 730                 735
Gly Gly Thr Ala Cys Gly Cys Gly Ala Cys Gly Cys Thr Gly Ala Ala
            740                 745                 750
Cys Gly Gly Thr Ala Ala Gly Ala Cys Cys Gly Thr Cys Cys Gly Ala
        755                 760                 765
Gly Ala Cys Gly Ala Cys Gly Ala Cys Gly Ala Gly Cys Cys Cys
770                 775                 780
Cys Gly Cys Thr Gly Gly Thr Gly Cys Gly Gly Cys Thr Gly Ala
785                 790                 795                 800
Gly Cys Cys Gly Ala Thr Cys Cys Thr Gly Ala Cys Cys Gly Thr
            805                 810                 815
Gly Ala Gly Cys Ala Gly Cys Thr Gly Gly Ala Gly Cys Gly Cys
            820                 825                 830
Thr Gly Cys Gly Cys Gly Cys Gly Ala Gly Cys Thr Cys Gly Thr
            835                 840                 845
Cys Ala Ala Gly Ala Cys Cys Thr Cys Cys Gly Gly Gly Cys Ala
850                 855                 860
Ala Ala Gly Cys Cys Cys Gly Cys Ala Gly Thr Gly Gly Cys Thr Ala
```

-continued

```
865                 870                 875                 880

Cys Thr Cys Cys Gly Thr Cys Gly Cys Thr Gly Cys Thr Gly Cys Thr
                885                 890                 895

Gly Cys Gly Gly Gly Thr Gly Thr Thr Gly Thr Thr Cys Thr Gly Cys
            900                 905                 910

Gly Cys Gly Gly Thr Gly Thr Gly Cys Gly Gly Gly Gly Ala Gly Cys
        915                 920                 925

Cys Cys Gly Cys Gly Thr Ala Cys Ala Ala Gly Thr Thr Cys Gly Ala
    930                 935                 940

Cys Gly Cys Cys Gly Gly Thr Cys Gly Gly Ala Ala Gly Ala Thr Cys
945                 950                 955                 960

Cys Cys Cys Cys Gly Cys Thr Ala Cys Cys Gly Cys Thr Gly Cys Cys
                965                 970                 975

Gly Gly Thr Cys Gly Thr Thr Cys Gly Gly Gly Thr Thr Cys Gly Cys
            980                 985                 990

Gly Gly Thr Thr Cys Gly Cys Thr  Gly Cys Gly Gly Gly  Ala Ala Cys
        995                 1000                1005

Gly Gly  Cys Ala Cys Gly Gly  Thr Gly Cys Cys Gly  Ala Thr Cys
    1010                 1015                 1020

Gly Cys  Gly Gly Ala Gly Thr  Gly Gly Gly Ala Cys  Gly Cys Gly
    1025                 1030                 1035

Thr Thr  Cys Thr Gly Cys Gly  Ala Gly Gly Ala Gly  Cys Ala Gly
    1040                 1045                 1050

Gly Thr  Gly Cys Thr Cys Gly  Ala Thr Cys Thr Gly  Cys Thr Cys
    1055                 1060                 1065

Gly Gly  Gly Gly Ala Thr Thr  Cys Gly Gly Ala Gly  Cys Gly Gly
    1070                 1075                 1080

Cys Thr  Gly Gly Ala Gly Ala  Ala Ala Gly Thr Cys  Thr Gly Gly
    1085                 1090                 1095

Gly Thr  Ala Gly Cys Cys Gly  Gly Cys Thr Cys Gly  Gly Ala Cys
    1100                 1105                 1110

Thr Cys  Cys Gly Cys Gly Gly  Thr Ala Gly Ala Ala  Cys Thr Cys
    1115                 1120                 1125

Gly Cys  Gly Gly Ala Gly Gly  Thr Gly Ala Ala Cys  Gly Cys Gly
    1130                 1135                 1140

Gly Ala  Gly Cys Thr Gly Gly  Thr Gly Gly Ala Thr  Cys Thr Gly
    1145                 1150                 1155

Ala Cys  Gly Thr Cys Gly Cys  Thr Gly Ala Thr Cys  Gly Gly Cys
    1160                 1165                 1170

Thr Cys  Cys Cys Cys Gly Gly  Cys Ala Thr Ala Cys  Cys Gly Gly
    1175                 1180                 1185

Gly Cys  Cys Gly Gly Thr Thr  Cys Thr Cys Cys Gly  Cys Ala Gly
    1190                 1195                 1200

Cys Gly  Gly Gly Ala Gly Gly  Cys Ala Cys Thr Gly  Gly Ala Cys
    1205                 1210                 1215

Gly Cys  Thr Cys Gly Thr Ala  Thr Cys Gly Cys Ala  Gly Cys Gly
    1220                 1225                 1230

Cys Thr  Gly Gly Cys Cys Gly  Cys Ala Cys Gly Gly  Cys Ala Gly
    1235                 1240                 1245

Gly Ala  Gly Gly Ala Gly Cys  Thr Gly Gly Ala Ala  Gly Gly Gly
    1250                 1255                 1260

Cys Thr  Ala Gly Ala Gly Gly  Cys Thr Cys Gly Cys  Cys Cys Gly
    1265                 1270                 1275
```

```
Thr Cys Gly Gly Gly Thr Gly Gly Gly Ala Gly Thr Gly Gly
    1280                1285                1290

Cys Gly Cys Gly Ala Ala Ala Cys Cys Gly Gly Thr Cys Ala Gly
    1295                1300                1305

Ala Gly Gly Thr Thr Cys Gly Gly Gly Ala Cys Thr Gly Gly
    1310                1315                1320

Thr Gly Gly Cys Gly Gly Ala Thr Cys Ala Gly Gly Ala Cys
    1325                1330                1335

Ala Cys Cys Gly Cys Ala Gly Gly Thr Ala Ala Gly Ala Ala Cys
    1340                1345                1350

Ala Cys Cys Thr Gly Gly Cys Thr Ala Cys Gly Gly Thr Cys Gly
    1355                1360                1365

Ala Thr Gly Ala Ala Cys Gly Thr Thr Cys Gly Gly Cys Thr Gly
    1370                1375                1380

Ala Cys Gly Thr Thr Cys Gly Ala Cys Gly Thr Cys Cys Gly Cys
    1385                1390                1395

Gly Gly Thr Gly Gly Thr Cys Thr Gly Ala Cys Thr Cys Gly Cys
    1400                1405                1410

Ala Cys Gly Ala Thr Cys Gly Ala Cys Thr Thr Cys Gly Gly Thr
    1415                1420                1425

Gly Ala Thr Cys Thr Gly Cys Ala Gly Gly Ala Gly Thr Ala Cys
    1430                1435                1440

Gly Ala Gly Cys Ala Gly Cys Ala Thr Cys Thr Gly Ala Gly Gly
    1445                1450                1455

Cys Thr Gly Gly Gly Cys Thr Cys Gly Gly Cys Thr Cys Thr Ala
    1460                1465                1470

Gly Ala Cys Cys Thr Cys Gly Thr Ala Ala Ala Cys Gly Cys Ala
    1475                1480                1485

Gly Ala Ala Ala Ala Gly Cys Cys Cys Cys Thr Ala Cys Gly
    1490                1495                1500

Gly Gly Thr Cys Gly Cys Thr Ala Gly
    1505                1510

<210> SEQ ID NO 55
<211> LENGTH: 499
<212> TYPE: PRT
<213> ORGANISM: Artificial Sequence
<220> FEATURE:
<223> OTHER INFORMATION: Synthetic Polypeptide

<400> SEQUENCE: 55

Met Arg Ala Leu Val Val Ile Arg Leu Ser Arg Val Thr Asp Ala Thr
1               5                   10                  15

Thr Ser Pro Glu Arg Gln Leu Glu Ser Cys Gln Gln Leu Cys Ala Gln
            20                  25                  30

Arg Gly Trp Asp Val Val Gly Val Ala Glu Asp Leu Asp Val Ser Gly
        35                  40                  45

Ala Val Asp Pro Phe Asp Arg Lys Arg Arg Pro Asn Leu Ala Arg Trp
    50                  55                  60

Leu Ser Phe Glu Asp Gln Pro Phe Asp Val Ile Val Ala Tyr Arg Val
65                  70                  75                  80

Asp Arg Leu Thr Arg Ser Ile Arg His Leu Gln Gln Leu Val His Trp
                85                  90                  95

Ala Glu Asp His Lys Lys Leu Val Val Ser Ala Thr Glu Ala His Phe
            100                 105                 110
```

Asp Thr Thr Thr Pro Phe Ala Ala Val Val Ile Ala Leu Met Gly Thr
            115                 120                 125

Val Ala Gln Met Glu Leu Glu Ala Ile Lys Glu Arg Asn Arg Ser Ala
130                 135                 140

Ala His Phe Asn Ile Arg Ala Gly Lys Tyr Arg Gly Ser Leu Pro Pro
145                 150                 155                 160

Trp Gly Tyr Leu Pro Thr Arg Val Asp Gly Glu Trp Arg Leu Val Pro
                165                 170                 175

Asp Pro Val Gln Arg Glu Arg Ile Leu Glu Val Tyr His Arg Val Val
            180                 185                 190

Asp Asn His Glu Pro Leu His Leu Val Ala His Asp Leu Asn Arg Arg
        195                 200                 205

Gly Val Leu Ser Pro Lys Asp Tyr Phe Ala Gln Leu Gln Gly Arg Glu
    210                 215                 220

Pro Gln Gly Arg Ala Trp Ser Ala Thr Ala Leu Lys Arg Ser Leu Ile
225                 230                 235                 240

Ser Glu Ala Met Leu Gly Tyr Thr Thr Leu Asn Gly Lys Thr Val Arg
                245                 250                 255

Asp Asp Asp Gly Ala Pro Leu Val Arg Ala Glu Pro Ile Leu Thr Arg
            260                 265                 270

Glu Gln Leu Glu Ala Leu Arg Ala Glu Leu Val Lys Thr Asp Arg Thr
        275                 280                 285

Lys Pro Ala Val Ser Ala Pro Ser Leu Leu Leu Arg Val Leu Phe Cys
    290                 295                 300

Ala Val Cys Gly Glu Pro Ala Tyr Lys Phe Asp Ala Gly Arg Lys Ile
305                 310                 315                 320

Pro Arg Tyr Arg Cys Arg Ser Phe Gly Phe Ala Gln Arg Cys Gly Asn
                325                 330                 335

Gly Thr Ile Pro Ile Ala Glu Trp Asp Ala Phe Cys Glu Glu Gln Val
            340                 345                 350

Leu Asp Leu Leu Gly Asp Ser Glu Arg Leu Glu Lys Val Trp Val Ala
        355                 360                 365

Gly Ser Asp Ser Ala Val Glu Leu Ala Glu Val Asn Ala Glu Leu Val
    370                 375                 380

Asp Leu Thr Ser Leu Ile Gly Ser Pro Ala Tyr Arg Val Gly Ser Pro
385                 390                 395                 400

Gln Arg Glu Ala Leu Asp Ser Arg Ile Ala Ala Leu Ala Ala Arg Gln
                405                 410                 415

Glu Glu Leu Glu Gly Leu Glu Ala Arg Pro Ser Gly Trp Glu Trp Arg
            420                 425                 430

Glu Thr Gly Gln Arg Phe Gly Asp Trp Trp Arg Glu Gln Asp Ile Ala
        435                 440                 445

Ala Lys Asn Thr Trp Leu Arg Ser Met Asn Val Arg Leu Thr Phe Asp
    450                 455                 460

Val Arg Gly Gly Leu Thr Arg Thr Ile Asp Phe Gly Asp Leu Gln Glu
465                 470                 475                 480

Tyr Glu Gln His Leu Arg Leu Gly Ser Val Val Glu Arg Leu His Thr
                485                 490                 495

Gly Met Ser

<210> SEQ ID NO 56
<211> LENGTH: 1500
<212> TYPE: DNA

<213> ORGANISM: Artificial Sequence
<220> FEATURE:
<223> OTHER INFORMATION: Synthetic Polynucleotide

<400> SEQUENCE: 56

```
atgagagcac tggtagtcat ccgactgtcc cgcgtcaccg atgctacgac ctcaccggag      60
cgtcagctgg agtcttgcca gcagctctgc gcccagcgcg gttgggacgt cgtcggtgta     120
gcagaggatc tggacgtctc gggagcagtc gatccgttcg accggaagcg tcgcccgaac     180
ctggcccggt ggctgtcgtt cgaggatcaa ccgttcgatg tgatcgtggc gtaccgggta     240
gaccggttga cccgctcgat ccggcatctt cagcagctgg tccactgggc cgaggaccac     300
aagaagctgg tcgtctccgc gaccgaagcg cacttcgata cgacgacgcc gttcgcagca     360
gtcgtcatcg cgcttatggg aacggtggcg cagatggaat agaagcgat caaagagcgg      420
aaccgttcgg cggcgcattt caatatccgc gccgggaaat accgaggctc cctgccgccg     480
tggggatacc tgcctacgcg cgtggacggg gagtggcggc tggtgccaga cccggtgcag     540
cgagagcgca tcctcgaggt gtatcaccgc gtcgtcgaca ccacgagcc gctgcacctg      600
gtggcccacg acctgaaccg gcgtggtgtc ctgtcgccga aggactactt cgcgcagctg     660
cagggcaggg agccgcaggg ccgggcgtgg tcggctaccg cgctgaagcg ctcgctgatc     720
tctgaggcga tgctcgggta tacgacgctg aacggcaaga ccgtccgaga cgacgacggg     780
gctccgctgg tgcgggctga gccgatcctg acccgcgagc agctggaggc gctgcgcgcc     840
gagctcgtca agaccgaccg gaccaagccc gcagtgtccg caccgtcgct gctgctgcgg     900
gtgttgttct gcgcggtgtg cggggagcct gcctacaagt cgacgccgg ccggaagatc      960
ccccgctacc gctgcaggtc gttcgggttc gcacagcgct gcgggaacgg caccatacccg    1020
atcgcagagt gggacgcatt ctgcgaggag caggtgctgg atctgctcgg ggactcggag    1080
cgtctggaga aagtctgggt agcaggctcg gactcggcag tcgaactcgc agaggtgaac    1140
gcagagctgg tggacctgac gtcgctgatc ggctctccgg cataccgggt cggttctccg    1200
cagcgcgagg cactcgactc ccggatcgca gcactggccg cacggcagga ggagttggaa    1260
gggctggagg cacgtccgtc gggttgggag tggcgcgaaa ccgggcagcg gttcggggac    1320
tggtggcggg agcaggacat cgcagcaaag aacacctggc ttcggtcgat gaacgttcgg    1380
ttgacgttcg acgtccgcgg cgggctgact cgcacgatcg acttcgggga tctgcaggag    1440
tacgagcagc atctcaggct cggcagcgtg gtcgaacggc tacacaccgg gatgtcgtag    1500
```

<210> SEQ ID NO 57
<211> LENGTH: 548
<212> TYPE: PRT
<213> ORGANISM: Artificial Sequence
<220> FEATURE:
<223> OTHER INFORMATION: Synthetic Polypeptide

<400> SEQUENCE: 57

Met Pro Ser Lys Arg Ala Leu Leu Val Ile Arg Leu Ser Arg Val Thr
1               5                   10                  15

Asp Ala Thr Thr Ser Pro Glu Arg Gln Leu Ala Asp Cys Gln Ala Leu
            20                  25                  30

Cys Ala Gln Arg Gly Tyr Glu Val Ala Gly Val Ala Glu Asp Leu Asp
        35                  40                  45

Val Ser Gly Ser Ile Asp Pro Phe Asp Arg Lys Lys Arg Pro Asn Leu
    50                  55                  60

Ala His Trp Leu His Asp Arg His Asn Glu Phe Asp Val Val Val Ala

```
                65                  70                  75                  80
            Tyr Arg Val Asp Arg Leu Thr Arg Ser Val Arg Tyr Leu Gln Lys Leu
                                85                  90                  95

Val Asn Trp Ala Glu Asp His Asp Lys Leu Val Ser Ala Thr Glu
                        100                 105                 110

Pro His Phe Asp Thr Thr Ser Pro Phe Ala Ala Val Leu Ile Ala Leu
                        115                 120                 125

Leu Gly Thr Val Ala Gln Met Glu Leu Glu Ala Ile Ala Glu Arg Asn
                    130                 135                 140

Arg Ser Ala Ala Arg His Asn Ile Arg Ala Gly Lys Tyr Arg Gly Ser
            145                 150                 155                 160

Lys Pro Pro Trp Gly Tyr Met Pro Gln Arg Asp Asp Glu Gly Val Trp
                            165                 170                 175

Arg Leu Val Gln Asp Pro Asp Gln Val Lys Ile Ile His Glu Val Val
                        180                 185                 190

Gln Arg Val Leu Glu Gly Glu Pro Thr Gln Arg Ile Ala Asn Asp Leu
                    195                 200                 205

Thr Leu Arg Gly Ile Pro Thr Pro Lys Asp Ala Phe Ala Ile Ser Gln
                210                 215                 220

Gly Arg Lys Pro Glu Gly Leu Ala Trp Asn Met Thr Thr Leu Lys Arg
            225                 230                 235                 240

Ser Leu Lys Ser Glu Ala Met Leu Gly Arg Val Thr Asn Ala Ala Gly
                            245                 250                 255

Lys Ser Ile Arg Lys Glu Asp Gly Ala Pro Val Ile Arg Ser Thr Pro
                        260                 265                 270

Ile Leu Thr Arg Glu Val Phe Asp Arg Val Gln Val Glu Leu Glu Thr
                    275                 280                 285

Arg Ala Arg Ser Gly Gly Pro Thr Thr Arg Ser Thr Ala Leu Leu Leu
                290                 295                 300

Arg Val Ile Tyr Cys Ala Ile Cys Gly Met Pro Ala Tyr Gln Tyr Ser
            305                 310                 315                 320

Gly Gly Thr Ser Gly Lys Ala Ser Arg Tyr Arg Cys Ser Ser Ser Pro
                            325                 330                 335

Arg Ser Asn Thr Asp Pro Asn Ile Lys Lys Cys Gly Asn Arg Thr Phe
                        340                 345                 350

Ala Val Ala Glu Ala Asp Ala Val Val Val Lys Thr Leu Leu Gly Leu
                    355                 360                 365

Leu Gly Asp Ser Glu Arg Lys Glu Lys Ile Trp Glu Ser Gly Cys Asp
                370                 375                 380

His Ser Ala Glu Leu Ala Asp Leu Asp Ala Thr Leu Ala Asp Leu Thr
            385                 390                 395                 400

Asp Gln Leu Gly Thr Gly Val Phe Ala Arg Gly Thr Pro Gln Arg Ala
                            405                 410                 415

Arg Leu Asp Ala Arg Ile Ala Glu Leu Ala Ala Arg Gln Ala Ala Leu
                        420                 425                 430

Ser Ala Glu Ala Val Arg Pro Ala Gly Trp Thr Trp His Gly Thr Gly
                    435                 440                 445

Glu Arg Phe Ser Asp Trp Trp Glu Arg Gln Asp Val Thr Ala Lys Asn
                450                 455                 460

Val Trp Leu Arg Ser Met Asn Ile Gln Leu Thr Phe Asp Arg Glu Arg
            465                 470                 475                 480

Phe Tyr Leu Asp Leu Gly Asp Ile Val Gln Leu Thr Glu Gln Phe Asp
                            485                 490                 495
```

```
Pro Gln Gly Pro Val Ala Gln Trp Gln Gly Leu Leu Ala Ala Met Gln
                500                 505                 510

Ala Glu Gly Ile Ala Gly Val Glu Ile Arg Gly Gly Glu Ala Gln Ala
            515                 520                 525

Thr Pro Arg Asp Asp Asp Met Arg Gly Ala Leu Gly Met Thr Gly Ala
        530                 535                 540

Pro Leu Val Asp
545

<210> SEQ ID NO 58
<211> LENGTH: 1647
<212> TYPE: DNA
<213> ORGANISM: Artificial Sequence
<220> FEATURE:
<223> OTHER INFORMATION: Synthetic Polynucleotide

<400> SEQUENCE: 58
```

| | | |
|---|---|---|
| atgccatcga agagagcatt gctggtcatc cggctcagcc gggtgacgga tgcaacgacc | 60 |
| tcccccgagc gtcagctcgc ggactgccag gcgctgtgtg ctcagcgcgg atacgaggtg | 120 |
| gcaggcgtgg ccgaggacct cgacgtgtcc gggtccatcg acccgttcga ccggaagaag | 180 |
| cggcccaacc tggcccactg gctccacgac cgtcacaacg agttcgacgt ggtggttgcc | 240 |
| tacagggtag atcgcctcac ccgatccgtg cgttacctgc agaagctggt caactgggca | 300 |
| gaggaccacg acaagctcgt cgtctccgca accgagccgc acttcgacac cacgagcccg | 360 |
| ttcgccgccg tgctgatcgc actgctgggc accgtggccc agatggagct ggaggccatc | 420 |
| gcagagcgca accgctctgc tgcccgacac aacatcaggg cagggaagta ccgagggtcc | 480 |
| aagcccccat ggggctacat gccccagaga gacgatgagg gggtctggcg gctggtgcag | 540 |
| gaccctgatc aggtcaagat cattcacgag gtcgtgcagc gggtgttgga gggtgagccg | 600 |
| acgcagcgga tcgccaatga cctgacccta cgcgggattc cgacgccgaa ggatgcgttc | 660 |
| gcgatctccc agggccgcaa gcccgagggg ctggcgtgga acatgacgac gctcaagcgg | 720 |
| tcgttgaagt cggaggcaat gctcggccgc gtgacgaacg cggcggggaa gtccatccgg | 780 |
| aaggaggacg gggcccccggt gatccggtcc accccgatcc tgacgagaga ggtgttcgac | 840 |
| cgggtgcagg tcgagcttga gactcgggct cggagcggag gtccgacgac gcgatctacc | 900 |
| gcactgctgc tgcgggtgat ctactgcgca atctgcggta tgcccgcata ccagtacagc | 960 |
| ggtggtacca gcggcaaggc atctcggtac cggtgcagct cgtctccccg gagcaacaca | 1020 |
| gacccgaaca tcaagaagtg cggtaaccga acattcgcgg tggccgaggc cgacgcagtg | 1080 |
| gtggtcaaga ccctgctggg tctgctcggt gactccgagc gcaaggagaa gatctgggaa | 1140 |
| tccggctgtg accactcggc agagctggcc gacctcgacg ccacgctggc cgatctgacc | 1200 |
| gaccagcttg gtaccggagt gttcgccagg gggacgccac agcgggcccg tctggacgcc | 1260 |
| aggatcgcag agctggccgc gaggcaggct gccctatcgg cagaggccgt tcggcccgca | 1320 |
| ggatggacgt ggcacggcac tggtgagcgt ttcagtgatt ggtgggagcg gcaggacgtt | 1380 |
| accgcgaaga atgtctggct gcggtcgatg aacatccaac tcacgttcga ccgtgagcgg | 1440 |
| ttctatctcg acctcggaga catcgtccaa ctgaccgagc agtttgaccc gcagggcccg | 1500 |
| gtggcccagt ggcagggtct gctcgcagcg atgcaagccg aaggcattgc cggcgtggag | 1560 |
| attcgagggg gtgaagcaca ggcgacaccg agggatgacg acatgagagg ggccctcgga | 1620 |
| atgacaggag ccccccctggt cgattag | 1647 |

<210> SEQ ID NO 59
<211> LENGTH: 502
<212> TYPE: PRT
<213> ORGANISM: Artificial Sequence
<220> FEATURE:
<223> OTHER INFORMATION: Synthetic Polypeptide

<400> SEQUENCE: 59

```
Met Arg Val Leu Gly Arg Leu Arg Leu Ser Arg Ser Thr Glu Glu Ser
1               5                   10                  15

Thr Ser Ile Glu Arg Gln Arg Glu Ile Val Thr Ala Trp Ala Asp Ser
            20                  25                  30

Asn Gly His Thr Val Val Gly Trp Ala Glu Asp Val Asp Val Ser Gly
        35                  40                  45

Ala Val Asp Pro Phe Asp Thr Pro Ser Leu Gly Pro Trp Leu Asp Glu
    50                  55                  60

Arg Arg Gly Glu Trp Asp Ile Leu Cys Ala Trp Lys Leu Asp Arg Leu
65                  70                  75                  80

Gly Arg Asp Ala Ile Arg Leu Asn Lys Leu Phe Leu Trp Cys Gln Glu
                85                  90                  95

Asn Gly Lys Thr Val Ala Ser Thr Ser Glu Gly Ile Asp Leu Gly Thr
            100                 105                 110

Pro Val Gly Arg Leu Ile Ala Asn Val Ile Ala Phe Leu Ala Glu Gly
        115                 120                 125

Glu Arg Glu Ala Ile Arg Glu Arg Val Thr Ser Ser Lys Gln Lys Leu
    130                 135                 140

Arg Glu Val Gly Arg Trp Gly Gly Lys Pro Pro Phe Gly Tyr Met
145                 150                 155                 160

Gly Ile Pro Asn Pro Asp Gly Gln Gly Tyr Ile Leu Val Val Asp Pro
                165                 170                 175

Ile Ala Lys Pro Val Val Arg Arg Ile Val Asp Asp Val Val Asp Gly
            180                 185                 190

Lys Pro Leu Thr Arg Leu Cys Ala Glu Leu Thr Glu Glu Arg Tyr Leu
        195                 200                 205

Thr Pro Ala Glu Tyr Tyr Ala Thr Leu Lys Ala Gly Ala Pro Arg Gln
    210                 215                 220

Gln Ala Asp Pro Gly Glu Val Ile Ala Lys Trp Arg Pro Thr Ala Val
225                 230                 235                 240

Arg Asn Leu Leu Arg Ser Lys Ala Leu Arg Gly His Ala His His Arg
                245                 250                 255

Gly Gln Thr Val Arg Asp Asp Gln Gly Arg Pro Val Arg Leu Ala Glu
            260                 265                 270

Pro Leu Val Asp Ser Asp Glu Trp Glu Leu Leu Gln Glu Thr Leu Asp
        275                 280                 285

Gly Ile Gln Ala Asp Phe Ser Gly Arg Arg Val Glu Gly Ala Ser Pro
    290                 295                 300

Leu Ser Gly Val Ala Val Cys Met Thr Cys Gly Arg Pro Leu His Phe
305                 310                 315                 320

Ser Arg His Met Val Lys Arg Pro Tyr Gly Asp Tyr Pro Tyr Gln Tyr
                325                 330                 335

Tyr Arg Cys Gln Asp Arg His Gly Lys Asn Val Pro Ala Asp Val Leu
            340                 345                 350

Asp Glu Leu Val Glu Glu Asn Phe Leu Leu Lys Val Gly Asp Tyr Pro
        355                 360                 365
```

```
Val Arg Glu Arg Val Trp Val Gln Gly Asp Thr Asn Trp Ala Asp Met
    370                 375                 380

Lys Glu Ala Val Ala Ala Tyr Asp Glu Leu Val Gln Ala Ala Gly Arg
385                 390                 395                 400

Ala Lys Ser Ala Thr Ala Lys Glu Arg Leu Gln Arg Gln Leu Asp Ala
                405                 410                 415

Leu Asp Thr Arg Ile Ala Glu Leu Glu Ser Ala Pro Ala Thr Glu Ala
            420                 425                 430

His Trp Glu Tyr Arg Glu Thr Gly Ser Thr Tyr Arg Asp Ala Trp Glu
            435                 440                 445

Asn Ser Asp Thr Asp Gln Arg Arg Glu Leu Leu Lys Lys Ser Gly Ile
    450                 455                 460

Thr Val Ala Val Gly Ile Asp Gly Val Glu Gly Arg Arg Ser Lys His
465                 470                 475                 480

Asn Pro Gly Ala Leu Arg Phe Asp Ile Arg Val Pro Ala Glu Leu Thr
                485                 490                 495

Gln Arg Leu Gly Ala Ser
            500

<210> SEQ ID NO 60
<211> LENGTH: 1509
<212> TYPE: DNA
<213> ORGANISM: Artificial Sequence
<220> FEATURE:
<223> OTHER INFORMATION: Synthetic Polynucleotide

<400> SEQUENCE: 60
atgcgtgtac taggtagact gcgtctgtcc aggtcaacgg aggaatctac ctccatcgag      60
aggcaacgag agatcgtcac cgcatgggcc gattctaacg gccacacggt cgtcggttgg     120
gcagaggacg ttgacgtctc gggtgcagtg acccgttcg acacaccgtc gctggggccg     180
tggctggatg agcgccgggg cgagtgggac atcctctgcg cctggaaact ggaccgcctg     240
ggtcgtgatg ccatccggct caacaagctg ttcctgtggt gccaggagaa cggcaagacg     300
gtggcgtcca cgagtgaggg tatcgacctc ggtacgccgg ttggtcggct catcgcaaac     360
gtgatcgcgt tccttgccga gggtgagcgt gaggccatcc gggagagggt cacgtcctcg     420
aagcagaagc tgcgggaggt aggtcggtgg ggtggcggta agccgccctt cggttacatg     480
ggcatcccca accccgacgg acagggctac atcctcgtgg tcgatcccat cgccaagccg     540
gtggtgcgcc ggatcgtgga cgacgttgtc gacggcaagc cgctgacgcg gctgtgcgcc     600
gagctgaccg aggagcggta cctgacgcct gcggagtact acgccaccct caaggccggt     660
gccccgaggc agcaggccga ccccggtgag gtgatcgcca gtggcgtcc gaccgccgtc     720 cgcaacctgc tccgcagcaa agccctccgg ggcacgccc accacagggg acagaccgtc     780
agagacgacc agggacgccc tgtgcggctc gctgagccgc ttgtggactc gatgaatgg      840 gagttgctgc aggagactct ggacggcatc caggcagact tctccggtcg tcgggtcgag     900
ggggcaagcc cgctctccgg tgtcgccgtc tgcatgacgt gcggacgccc cctgcacttc     960
tcccggcaca tggtgaagcg cccctacggc gactacccgt accagtacta ccgctgccag    1020
gaccggcacg ggaagaacgt gcccgccgac gtactcgatg aattggtcga ggagaacttc    1080
ctcctgaagg tgggcgacta cccggtgcgt gagcgggtgt gggtccaggg tgacaccaac    1140
tgggccgaca tgaaggaggc agtagccgca tacgacgaac tggtgcaggc cgctggccgt    1200
gctaagtcgg caaccgccaa ggaacgcctg cagcgccaac tggacgccct cgatacccgc    1260
```

```
atcgcagagc tggagtcggc cccggcaacc gaggcccact gggagtaccg ggaaaccggt    1320
agcacctacc gggacgcctg ggagaactcc gacaccgatc agcgccggga gctgttgaag    1380
aagtctggca tcaccgtggc cgtcggcatc gacggcgtgg aaggccgtcg ctccaaacac    1440
aatcccggtg ccctgcgctt cgacatccga gtgccggcag aactgaccca gcgcctggga    1500
gcgtcctga                                                           1509
```

<210> SEQ ID NO 61
<211> LENGTH: 504
<212> TYPE: PRT
<213> ORGANISM: Artificial Sequence
<220> FEATURE:
<223> OTHER INFORMATION: Synthetic Polypeptide

<400> SEQUENCE: 61

```
Met Arg Ala Leu Val Val Ile Arg Leu Ser Arg Val Thr Asp Ala Thr
1               5                   10                  15

Thr Ser Pro Glu Arg Gln Leu Glu Ser Cys Arg Gln Leu Cys Ala Gln
            20                  25                  30

Arg Gly Trp Asp Val Val Gly Val Ala Glu Asp Leu Asp Val Ser Gly
        35                  40                  45

Ala Val Asp Pro Phe Asp Arg Lys Arg Arg Pro Asn Leu Ala Arg Trp
    50                  55                  60

Leu Ala Phe Glu Glu Gln Pro Phe Asp Val Ile Val Ala Tyr Arg Val
65                  70                  75                  80

Asp Arg Leu Thr Arg Ser Ile Arg His Leu Gln Gln Leu Val His Trp
                85                  90                  95

Ala Glu Asp His Lys Lys Leu Val Val Ser Ala Thr Glu Ala His Phe
            100                 105                 110

Asp Thr Thr Thr Pro Phe Ala Ala Val Val Ile Ala Leu Met Gly Thr
        115                 120                 125

Val Ala Gln Met Glu Leu Glu Ala Ile Lys Glu Arg Asn Arg Ser Ala
    130                 135                 140

Ala His Phe Asn Ile Arg Ala Gly Lys Tyr Arg Gly Ser Leu Pro Pro
145                 150                 155                 160

Trp Gly Tyr Leu Pro Thr Arg Val Asp Gly Glu Trp Arg Leu Val Pro
                165                 170                 175

Asp Pro Val Gln Arg Glu Arg Ile Leu Glu Val Tyr His Arg Val Val
            180                 185                 190

Asp Asn His Glu Pro Leu His Leu Val Ala His Asp Leu Asn Arg Arg
        195                 200                 205

Gly Val Leu Ser Pro Lys Asp Tyr Phe Ala Lys Leu Gln Gly Arg Glu
    210                 215                 220

Pro Gln Gly Arg Glu Trp Ser Ala Thr Ala Leu Lys Arg Ser Leu Ile
225                 230                 235                 240

Ser Glu Ala Met Leu Gly Tyr Ala Thr Leu Asn Gly Lys Thr Val Arg
                245                 250                 255

Asp Asp Asp Gly Ala Pro Leu Val Arg Ala Ala Pro Ile Leu Thr Arg
            260                 265                 270

Glu Gln Leu Glu Ala Leu Arg Ala Glu Leu Val Lys Thr Asp Arg Thr
        275                 280                 285

Lys Pro Ala Val Ser Thr Pro Ser Leu Leu Leu Arg Val Leu Phe Cys
    290                 295                 300

Ala Val Cys Gly Glu Pro Ala Tyr Lys Phe Ala Gly Gly Gly Arg Lys
305                 310                 315                 320
```

```
His Pro Arg Tyr Arg Cys Arg Ser Met Gly Phe Pro Lys His Cys Gly
            325                 330                 335

Asn Gly Thr Val Ala Met Ala Glu Trp Asp Ala Phe Cys Glu Gln
            340                 345                 350

Val Leu Asp Leu Leu Gly Asp Ala Glu Arg Leu Glu Lys Val Trp Val
            355                 360                 365

Ala Gly Ser Asp Ser Ala Val Glu Leu Ala Glu Val Asn Ala Glu Leu
        370                 375                 380

Val Asp Leu Thr Ser Leu Ile Gly Ser Pro Ala Tyr Arg Ala Gly Ser
385                 390                 395                 400

Pro Gln Arg Glu Ala Leu Asp Ala Arg Ile Ala Ala Leu Ala Ala Arg
                405                 410                 415

Gln Glu Glu Leu Glu Gly Leu Glu Ala Arg Pro Ser Gly Trp Glu Trp
            420                 425                 430

Arg Glu Thr Gly Gln Arg Phe Gly Asp Trp Trp Arg Asp Gln Asp Thr
        435                 440                 445

Ala Gly Lys Asn Thr Trp Leu Arg Ser Met Asn Val Arg Leu Thr Phe
    450                 455                 460

Asp Val Arg Gly Gly Leu Thr Arg Thr Ile Asp Phe Gly Asp Leu Gln
465                 470                 475                 480

Glu Tyr Glu Gln His Leu Arg Leu Gly Ala Ala Leu Asp Leu Val Asn
                485                 490                 495

Ala Glu Lys Pro Pro Thr Gly Arg
            500

<210> SEQ ID NO 62
<211> LENGTH: 1515
<212> TYPE: DNA
<213> ORGANISM: Artificial Sequence
<220> FEATURE:
<223> OTHER INFORMATION: Synthetic Polynucleotide

<400> SEQUENCE: 62
atgagagctc tcgtcgtgat ccgcttgtcc cgcgtcaccg atgctacgac ctcaccggag    60
cgtcagctgg agtcttgccg gcagctctgc gcccagcgcg gttgggacgt cgtcggtgta   120
gcggaggatc tggacgtctc cggagcagtc gatccgttcg accggaagcg cagaccgaac   180
ctggcacggt ggctagcatt cgaggagcaa ccgttcgacg tcatcgtggc gtaccgggtg   240
gaccggttga cccgctcgat ccggcatctt cagcagctgg tccactgggc ggaggaccac   300
aagaagctgg tcgtctccgc gaccgaagcc cacttcgaca cgacgacgcc gttcgcggcg   360
gtcgtcatcg cgcttatggg aacggtggcg cagatggaat tagaagcgat caaagagcgg   420
aaccgttcgg ctgcacattt caatattcgc gccgggaaat accgcggttc cctgccgccg   480
tggggttacc tgcctacgcg cgtggacggg gagtggcggc tggtgccgga cccggtgcag   540
cgcgagcgca tcctcgaggt gtatcaccgc gtcgtcgaca ccacgagcc gctgcacctg   600 gtggcacacg acctgaaccg gcgtggtgtc ctgtcgccga aggactactt cgcaaagctg   660
caaggtcgcg agccgcaggg gcgggagtgg tcggctaccg cactgaagcg ctcgctgatc   720
tccgaggcga tgctcgggta cgcgactctg aacggtaaga ccgtccgaga cgacgacgga   780
gccccgctgg tgcgggctgc gccgatcctg accgtgagc agctggaggc gctgcgcgcc   840
gagctcgtca agaccgaccg gaccaagccc gcagtgtcta ccccgtcgct gctgctgcgg   900
gtgctgttct gcgcagtgtg cggtgagccc gcatacaagt tcgcaggtgg aggacgcaag   960
```

```
cacccgcgct accgctgccg ctcgatgggt ttcccgaagc actgcggtaa cggtacggtc    1020
gcaatggccg agtgggacgc attctgcgag gagcaggtgc tggatctgct cggggacgca    1080
gagcgtctgg agaaagtctg ggtagctggc tcggactcag cagtagaact cgcagaggtg    1140
aacgcagagc tggtggacct gacgtcgctg atcggttccc cggcgtaccg ggccggttct    1200
ccgcagcgcg aggcgctgga tgctcgtatc gcggcgctgg ccgcgcggca ggaggagttg    1260
gaagggctag aggctcgccc gtcgggctgg gagtggcgcg aaaccgggca gaggttcggg    1320
gactggtggc gggatcagga caccgcgggt aagaacacct ggctccggtc gatgaacgtt    1380
cggctgacgt tcgacgtccg aggcggcctg actcgtacga tcgacttcgg ggatctgcag    1440
gagtatgagc agcatctgag gctgggcgcg gctctagacc tcgtaaacgc agaaaagccc    1500
cctacgggcc gctag                                                     1515
```

<210> SEQ ID NO 63
<211> LENGTH: 500
<212> TYPE: PRT
<213> ORGANISM: Artificial Sequence
<220> FEATURE:
<223> OTHER INFORMATION: Synthetic Polypeptide

<400> SEQUENCE: 63

```
Met Arg Ala Leu Val Val Ile Arg Leu Ser Arg Val Thr Asp Ala Thr
1               5                   10                  15

Thr Ser Pro Glu Arg Gln Leu Glu Ser Cys Gln Gln Leu Cys Ala Gln
            20                  25                  30

Arg Gly Trp Asp Val Val Gly Val Ala Glu Asp Leu Asp Val Ser Gly
        35                  40                  45

Ala Val Asp Pro Phe Asp Arg Lys Arg Pro Asn Leu Ala Arg Trp
    50                  55                  60

Leu Ala Phe Glu Glu Gln Pro Phe Asp Val Ile Val Ala Tyr Arg Val
65                  70                  75                  80

Asp Arg Leu Thr Arg Ser Ile Arg His Leu Gln Gln Leu Val His Trp
                85                  90                  95

Ala Glu Asp His Lys Lys Leu Val Val Ser Ala Thr Glu Ala His Phe
            100                 105                 110

Asp Thr Thr Thr Pro Phe Ala Ala Val Val Ile Ala Leu Met Gly Thr
        115                 120                 125

Val Ala Gln Met Glu Leu Glu Ala Ile Lys Glu Arg Asn Arg Ser Ala
    130                 135                 140

Ala His Phe Asn Ile Arg Ala Gly Lys Tyr Arg Gly Ser Leu Pro Pro
145                 150                 155                 160

Trp Gly Tyr Leu Pro Thr Arg Val Asp Gly Glu Trp Arg Leu Val Pro
                165                 170                 175

Asp Pro Val Gln Arg Glu Arg Ile Leu Glu Val Tyr His Arg Val Val
            180                 185                 190

Asp Asn His Glu Pro Leu His Leu Val Ala His Asp Leu Asn Arg Arg
        195                 200                 205

Gly Val Leu Ser Pro Lys Asp Tyr Phe Ala Lys Leu Gln Gly Arg Glu
    210                 215                 220

Pro Gln Gly Arg Glu Trp Ser Ala Thr Ala Leu Lys Arg Ser Leu Ile
225                 230                 235                 240

Ser Glu Ala Met Leu Gly Tyr Ala Thr Leu Asn Gly Lys Thr Val Arg
                245                 250                 255

Asp Asp Asp Gly Ala Pro Leu Val Arg Ser Glu Pro Ile Leu Thr Arg
```

```
            260                 265                 270
Glu Gln Leu Glu Ala Leu Arg Ala Glu Leu Val Lys Thr Asp Arg Thr
            275                 280                 285

Lys Pro Ala Val Ser Thr Pro Ser Leu Leu Leu Arg Val Leu Phe Cys
        290                 295                 300

Ala Val Cys Gly Glu Pro Ala Tyr Lys Phe Thr Gly Gly Gly Arg Lys
305                 310                 315                 320

Asn Ala Arg Tyr Arg Cys Arg Ser Trp Gly Trp Ala Gln Arg Cys Gly
                325                 330                 335

Asn Gly Thr Val Ala Met Ala Glu Trp Asp Ala Phe Cys Glu Glu Gln
            340                 345                 350

Val Leu Asp Leu Leu Gly Asp Ala Glu Arg Leu Glu Lys Val Trp Val
        355                 360                 365

Ala Gly Ser Asp Ser Ala Val Glu Leu Ala Glu Val Asn Ala Glu Leu
    370                 375                 380

Val Asp Leu Thr Ser Leu Ile Gly Ser Pro Ala Tyr Arg Ala Gly Ser
385                 390                 395                 400

Pro Gln Arg Glu Ala Leu Asp Ala Arg Ile Ala Ala Leu Ala Ala Arg
                405                 410                 415

Gln Glu Glu Leu Glu Gly Leu Glu Ala Arg Pro Ser Gly Trp Glu Trp
            420                 425                 430

Arg Glu Thr Gly Gln Arg Phe Gly Asp Trp Trp Arg Asp Gln Asp Thr
        435                 440                 445

Ala Ala Lys Asn Thr Trp Leu Arg Ser Met Asn Val Arg Leu Thr Phe
    450                 455                 460

Asp Val Arg Gly Gly Leu Thr Arg Thr Ile Asp Phe Gly Asp Leu Gln
465                 470                 475                 480

Glu Tyr Glu Gln His Leu Arg Leu Gly Ser Val Val Glu Arg Leu His
                485                 490                 495

Thr Gly Met Ser
            500

<210> SEQ ID NO 64
<211> LENGTH: 1503
<212> TYPE: DNA
<213> ORGANISM: Artificial Sequence
<220> FEATURE:
<223> OTHER INFORMATION: Synthetic Polynucleotide

<400> SEQUENCE: 64
atgagagcac tggtagtcat ccgcctgtcc cgcgtcaccg atgctacgac ttcaccggag      60
cgtcagctgg agtcttgcca gcagctctgc gcccagcgcg gttggacgt cgtcggtgta     120 gcggaagatc tggacgtctc cggagcagtc gatccgttcg accggaagcg ccgcccgaac     180
ctggcacggt ggctagcatt cgaggagcaa ccgttcgatg tcatcgtggc gtaccgggta     240
gaccggctga cccgatcgat ccggcatctg cagcagctgg tccactgggc cgaggaccac     300
aagaagctgg tcgtctccgc gaccgaagcc cacttcgaca cgacgacgcc gttcgcggcg     360
gtcgtcatcg cgcttatggg aacggtggcg cagatggaat tagaagcgat caaagagcgg     420
aaccgttcgg ctgcacattt caatatccgc gccgggaaat accgaggttc cctgccgccg     480
tggggatacc tgcctacgcg cgtggacggg gagtggcggc tggtgccgga cccggtgcag     540
cgagagcgca tcctcgaggt gtatcaccgc gtcgtcgaca ccacgagcc gctgcacctg     600 gtggcccacg acctgaaccg gcgtggtgtc ctgtcgccta aggactactt cgcgaagctg     660
```

```
caaggccgag agccgcaggg ccgggagtgg tcggctaccg cgctgaagcg ctcgctgatc    720
tccgaggcga tgctcgggta cgcgactctg aacggtaaga ccgtacgaga cgacgacggg    780
gctccgctgg tgcggtctga gccgatcctg acccgcgagc aactagaggc gctgcgcgcc    840
gagctcgtca agaccgaccg gaccaagccc gcagtgtcta ctccgtcgct gctgctgcgg    900
gtgctgttct gcgcagtgtg cggggagccc gcatacaagt tcaccggtgg cggtaggaag    960
aacgcacgct accgctgccg gtcgtggggc tgggcgcagc ggtgcgggaa cggaacggtc   1020
gcgatggctg agtgggacgc gttctgcgag gagcaggtgc tggatctgct cggtgacgca   1080
gagcgtctgg agaaagtctg ggtagccggt tcggactcgg cggtcgaact cgcagaggtg   1140
aacgcggagc tggtggacct gacgtcgctg atcggttctc cggcctaccg ggcaggttct   1200
ccgcagcgcg aggcgctgga tgctcgtatc gcggcgctgg ccgcgcggca ggaggagttg   1260
gaagggctag aggctcgccc gtcgggctgg gagtggcgcg aaaccggtca gaggttcggt   1320
gactggtggc gggatcagga caccgcggca agaacacct ggctccggtc gatgaacgtt    1380
cggctgacgt tcgacgtccg cggcgggctg actcgcacga tcgacttcgg ggatctgcag   1440
gagtacgagc agcatctcag gctcggtagc gtggtcgaac ggctacacac cggtatgtcg   1500
tag                                                                 1503
```

<210> SEQ ID NO 65
<211> LENGTH: 497
<212> TYPE: PRT
<213> ORGANISM: Artificial Sequence
<220> FEATURE:
<223> OTHER INFORMATION: Synthetic Polypeptide

<400> SEQUENCE: 65

```
Met Arg Val Leu Gly Arg Ile Arg Leu Ser Arg Met Met Glu Glu Ser
1               5                   10                  15

Thr Ser Val Glu Arg Gln Arg Glu Phe Ile Glu Thr Trp Ala Arg Gln
            20                  25                  30

Asn Asp His Glu Ile Val Gly Trp Ala Glu Asp Leu Asp Val Ser Gly
        35                  40                  45

Ser Val Asp Pro Phe Asp Thr Gln Gly Leu Gly Pro Trp Leu Lys Glu
    50                  55                  60

Pro Lys Leu Arg Glu Trp Asp Ile Leu Cys Ala Trp Lys Leu Asp Arg
65                  70                  75                  80

Leu Ala Arg Arg Ala Val Pro Leu His Lys Leu Phe Gly Met Cys Gln
                85                  90                  95

Asp Glu Gln Lys Val Leu Val Cys Val Ser Asp Asn Ile Asp Leu Ser
            100                 105                 110

Thr Trp Val Gly Arg Leu Val Ala Ser Val Ile Ala Gly Val Ala Glu
        115                 120                 125

Gly Glu Leu Glu Ala Ile Arg Glu Arg Thr Leu Ser Ser Gln Arg Lys
    130                 135                 140

Leu Arg Glu Leu Gly Arg Trp Ala Gly Gly Lys Pro Ala Tyr Gly Phe
145                 150                 155                 160

Lys Ala Gln Glu Arg Glu Asp Ser Ala Gly Tyr Glu Leu Val His Asp
                165                 170                 175

Glu His Ala Ala Asn Val Met Leu Gly Val Ile Glu Lys Val Leu Ala
            180                 185                 190

Gly Gln Ser Thr Glu Ser Val Ala Arg Glu Leu Asn Glu Ala Gly Glu
        195                 200                 205
```

```
Leu Ala Pro Ser Asp Tyr Ile Arg Ala Arg Ala Gly Arg Lys Thr Arg
    210                 215                 220
Gly Thr Lys Trp Ser Asn Ala Gln Ile Arg Gln Leu Leu Lys Ser Lys
225                 230                 235                 240
Thr Leu Leu Gly His Val Thr His Asn Gly Ala Thr Val Arg Asp Asp
                245                 250                 255
Asp Gly Ile Pro Ile Arg Lys Gly Pro Ala Leu Ile Ser Glu Glu Lys
            260                 265                 270
Phe Asp Gln Leu Gln Ala Ala Leu Asp Ala Arg Ser Phe Lys Val Thr
        275                 280                 285
Asn Arg Ser Ala Lys Ala Ser Pro Leu Leu Gly Val Ala Ile Cys Gly
    290                 295                 300
Leu Cys Gly Arg Pro Met His Ile Arg Gln His Arg Arg Asn Gly Asn
305                 310                 315                 320
Leu Tyr Arg Tyr Tyr Arg Cys Asp Ser Gly Ser His Ser Gly Gly Gly
                325                 330                 335
Gly Ala Ala Pro Glu His Pro Ser Asn Ile Ile Lys Ala Asp Asp Leu
            340                 345                 350
Glu Ala Leu Val Glu Glu His Phe Leu Asp Glu Val Gly Arg Phe Asn
        355                 360                 365
Val Gln Glu Lys Val Tyr Val Pro Ala Ser Asp His Arg Ala Glu Leu
    370                 375                 380
Asp Glu Ala Val Arg Ala Val Glu Glu Leu Thr Gln Leu Leu Gly Thr
385                 390                 395                 400
Met Thr Ser Ala Thr Met Lys Ser Arg Leu Met Gly Gln Leu Thr Ala
                405                 410                 415
Leu Asp Glu Arg Ile Ala Arg Leu Glu Asn Leu Pro Ser Glu Glu Ala
            420                 425                 430
Arg Trp Asp Tyr Arg Ala Thr Asp Gln Thr Tyr Ala Glu Ala Trp Glu
        435                 440                 445
Glu Ala Asp Thr Glu Gly Arg Arg Gln Leu Leu Ile Arg Ser Gly Ile
    450                 455                 460
Thr Ala Glu Val Lys Val Thr Gly Gly Asp Arg Gly Val Arg Gly Val
465                 470                 475                 480
Leu Glu Phe His Leu Lys Val Pro Glu Asp Val Arg Glu Arg Leu Ser
                485                 490                 495
Ala

<210> SEQ ID NO 66
<211> LENGTH: 1494
<212> TYPE: DNA
<213> ORGANISM: Artificial Sequence
<220> FEATURE:
<223> OTHER INFORMATION: Synthetic Polynucleotide

<400> SEQUENCE: 66
atgcgggttc ttgggagaat acgactctcc agaatgatgg aggagtctac cagtgtggaa      60
cgccaacgtg agttcatcga cgtgggcg cggcagaacg atcacgaaat cgtcggatgg      120
gctgaggacc tggacgtgtc cggctcggtc gatccgttcg acacgcaggg gctaggtccg      180
tggctcaagg agccgaagct cagggagtgg acatcctct gcgcctggaa gctggaccga      240
cttgctcgac gcgccgtacc gctgcacaaa ctgttcggga tgtgccagga cgagcaaaag      300
gtcctcgtgt gcgtcagcga caacatcgac ctgtcgacgt gggtcggacg cctcgtggcg      360
tcggtcatcg caggtgttgc cgagggagag ctggaggcga tcagggagcg gactctgtca      420
```

```
tcccagcgga agcttcggga gcttggccgg tgggccggtg gtaaacctgc ctacggcttc    480
aaggcacagg agcgggagga ctcagccggg tacgagctgg tgcatgacga gcacgcggcc    540
aacgtgatgc tcggtgtcat cgagaaggtg ctggccggtc agtcgacgga gtctgtcgcc    600
agggagctca acgaggcagg ggagctggca ccgtccgact acatcagggc cagggccggt    660
cgcaagacca ggggcacgaa gtggagcaac gctcagatcc ggcagctcct caagtccaag    720
actctgctcg gcacgtcac ccacaacggg gccaccgtgc gggacgacga cggcataccg    780
atccggaagg gtcctgcgct catctcagag gagaagttcg atcagctcca ggccgcgctc    840
gatgcgcggt cgttcaaggt caccaaccga tcagccaagg cgtcccctct gctcggggtg    900
gcgatctgtg gcctgtgcgg tcgtccgatg cacatacgtc agcatcgtcg caacggcaac    960
ctctatcggt actaccgctg cgatagcggc agccactccg gaggcggcgg tgccgccccct   1020
gaacacccgt cgaacatcat caaggccgac gacctggagg ccctggtcga ggaacacttc   1080
ctagacgaag tcggcaggtt caacgtgcag gagaaggtgt acgtcccagc gtccgatcac   1140
cgggcagagc tggacgaggc tgtacgggcc gtagaggaac tgacgcagct tctcgggacg   1200
atgacatcgg ccacgatgaa atctcgccta atgggccaac tcacggcgct agacgagcgc   1260
atcgcgagac tggagaacct cccgagtgag gaagcccgat gggactaccg tgcaaccgac   1320
cagacgtacg ccgaagcgtg ggaggaagcc gacaccgaag cagacggca gctcctcatc     1380
agatccggaa tcaccgctga ggtcaaggtg actggcggtg accgaggagt cagggtgtg    1440
ctggagtttc acctgaaggt ccccgaggac gtgagagaac gcctctccgc ttaa          1494
```

<210> SEQ ID NO 67
<211> LENGTH: 500
<212> TYPE: PRT
<213> ORGANISM: Artificial Sequence
<220> FEATURE:
<223> OTHER INFORMATION: Synthetic Polypeptide

<400> SEQUENCE: 67

```
Met Arg Ala Leu Val Val Ile Arg Leu Ser Arg Val Thr Asp Ala Thr
1               5                   10                  15

Thr Ser Pro Glu Arg Gln Leu Glu Ser Cys Arg Gln Leu Cys Ala Gln
            20                  25                  30

Arg Gly Trp Asp Val Val Gly Val Ala Glu Asp Leu Asp Val Ser Gly
        35                  40                  45

Ala Val Asp Pro Phe Asp Arg Lys Arg Pro Asn Leu Ala Arg Trp
    50                  55                  60

Leu Ala Phe Glu Glu Gln Pro Phe Asp Val Ile Val Ala Tyr Arg Val
65                  70                  75                  80

Asp Arg Leu Thr Arg Ser Ile Arg His Leu Gln Gln Leu Val His Trp
                85                  90                  95

Ala Glu Asp His Lys Lys Leu Val Val Ser Ala Thr Glu Ala His Phe
            100                 105                 110

Asp Thr Thr Thr Pro Phe Ala Ala Val Val Ile Ala Leu Met Gly Thr
        115                 120                 125

Val Ala Gln Met Glu Leu Glu Ala Ile Lys Glu Arg Asn Arg Ser Thr
    130                 135                 140

Ala His Phe Asn Ile Arg Ala Gly Lys Tyr Arg Gly Ser Leu Pro Pro
145                 150                 155                 160

Trp Gly Tyr Leu Pro Thr Arg Val Asp Gly Glu Trp Arg Leu Val Ser
                165                 170                 175
```

Asp Pro Val Gln Arg Glu Arg Ile Leu Glu Val Tyr His Arg Val Val
            180                 185                 190

Asp Asn His Glu Pro Leu His Gln Ile Ala His Asp Leu Asn Gln Arg
        195                 200                 205

Gly Leu Pro Ser Pro Lys Asp Tyr Phe Ala Lys Leu Gln Gly Arg Glu
    210                 215                 220

Pro Lys Gly Arg Glu Trp Ser Ala Thr Ala Leu Lys Arg Ser Leu Ile
225                 230                 235                 240

Ser Glu Ala Met Leu Gly Tyr Ala Thr Leu Asn Gly Lys Thr Val Arg
                245                 250                 255

Asp Asp Asp Gly Ala Pro Leu Val Arg Ala Glu Pro Ile Leu Thr Arg
            260                 265                 270

Glu Gln Leu Glu Ala Leu Arg Ala Glu Leu Val Lys Thr Asp Arg Thr
        275                 280                 285

Lys Pro Ala Val Ala Thr Pro Ser Leu Leu Leu Arg Val Leu Phe Cys
    290                 295                 300

Ala Val Cys Gly Glu Pro Ala Tyr Lys Phe Thr Gly Gly Gly Arg Lys
305                 310                 315                 320

Asn Ala Arg Tyr Arg Cys Arg Ser Trp Gly Trp Ala Gln Arg Cys Gly
                325                 330                 335

Asn Gly Thr Val Ala Met Ala Glu Trp Asp Ala Phe Cys Glu Glu Gln
            340                 345                 350

Val Leu Asp Leu Leu Gly Gly Ser Glu Arg Leu Glu Lys Val Trp Val
        355                 360                 365

Ala Gly Ser Asp Ser Ala Val Glu Leu Ala Glu Val Asn Ala Glu Leu
    370                 375                 380

Val Asp Leu Thr Ser Leu Ile Gly Ser Pro Ala Tyr Arg Val Gly Ser
385                 390                 395                 400

Pro Gln Arg Glu Ala Leu Asp Ala Arg Ile Ala Ala Leu Ala Ala Arg
                405                 410                 415

Gln Glu Glu Leu Glu Gly Leu Glu Ala Arg Pro Ser Gly Trp Glu Trp
            420                 425                 430

Arg Glu Thr Gly Gln Arg Phe Gly Asp Trp Arg Glu Gln Gly Thr
        435                 440                 445

Ala Ala Lys Asn Thr Trp Leu Arg Ser Met Asn Val Arg Leu Thr Phe
    450                 455                 460

Asp Val Arg Gly Gly Leu Thr Arg Thr Ile Asp Phe Gly Asp Leu Gln
465                 470                 475                 480

Glu Tyr Glu Gln His Leu Arg Leu Gly Ser Val Val Glu Arg Leu His
                485                 490                 495

Ala Gly Met Ser
            500

<210> SEQ ID NO 68
<211> LENGTH: 1503
<212> TYPE: DNA
<213> ORGANISM: Artificial Sequence
<220> FEATURE:
<223> OTHER INFORMATION: Synthetic Polynucleotide

<400> SEQUENCE: 68
atgagagcac tggtagtcat ccgactgtcc cgcgtcaccg atgctacgac ctcaccggag      60
cgccagctgg agtcttgccg acagctctgc gcccagcgcg gttgggacgt cgtcggtgta     120
gcggaggatc tggacgtctc cggagcagtc gatccgttcg accggaagcg ccgcccgaac     180

```
ctggcacggt ggctagcatt cgaggagcaa ccgttcgatg tgatcgtggc gtaccgggta      240
gaccggttga cccgatcgat ccggcatctg cagcagctgg tccactgggc tgaggaccac      300
aagaagctgg tcgtctccgc gaccgaagcg cacttcgata cgacgacgcc gttcgcggcg      360
gtcgtgatcg cgcttatggg aacggtggcg cagatggaat tagaagcgat caaagagcgg      420
aaccgctcga ctgcacattt caatatccgc gccgggaaat accgaggttc cctgccgccg      480
tggggttacc tgcctacgcg cgtggacggg gagtggcggc tggtgtcgga cccggtgcag      540
cgcgaacgca tcctcgaggt ctatcaccgc gtcgtcgaca accacgagcc tctgcaccag      600
atcgcccacg acctgaacca gcgcggccta ccgtcgccga aggactactt cgcgaagctg      660
cagggccgag agcccaaggg tcgggagtgg tcggctaccg cgctgaagcg gtcgctgatc      720
tcggaggcga tgctcgggta cgcgacgctg aacggtaaga ccgtccgaga cgacgacggc      780
gccccgctgg tgcgggccga gccgatcctg acgcgtgagc agctggaggc gctgcgcgcc      840
gagctcgtca agaccgaccg gaccaagccc gcagtggcta ctccgtcgct gctgctgcgg      900
gtgttgttct gcgcagtgtg cggtgagccc gcgtacaagt tcaccggtgg cggtaggaag      960
aacgctcgct accgctgccg gtcgtgggga tgggcgcagc ggtgcggcaa cggaacggtc     1020
gcgatggcgg agtgggatgc gttctgcgag gagcaggtgc tggatctgct cggtggctcg     1080
gagcgtctgg agaaagtctg ggtagcaggc tcggactcgg cagtcgaact cgcagaggtg     1140
aacgcagagc tggtggacct gacgtcgctg atcggttccc ccgcataccg ggtcggttct     1200
ccgcagcgcg aggcactgga tgctcgtatc gcggcactgg ccgcacggca ggaggagttg     1260
gaagggctgg aggctcgccc gtcgggttgg gagtggcgcg agactgggca gaggttcggt     1320
gactggtggc gggagcaggg taccgcggca aagaacacct ggctccggtc gatgaacgtt     1380
cggctgacgt tcgacgtccg cggtgggctg actcgcacga tcgacttcgg ggatctgcag     1440
gagtacgagc agcatctcag gctcggtagc gtggtcgaac ggctacacgc agggatgtcg     1500
tag                                                                   1503
```

<210> SEQ ID NO 69
<211> LENGTH: 507
<212> TYPE: PRT
<213> ORGANISM: Artificial Sequence
<220> FEATURE:
<223> OTHER INFORMATION: Synthetic Polypeptide

<400> SEQUENCE: 69

```
Met Tyr Pro Thr Phe Val Arg Val Leu Gly Arg Leu Arg Leu Ser Arg
1               5                   10                  15

Ser Thr Glu Glu Ser Thr Ser Ile Glu Arg Gln Arg Glu Ile Val Thr
            20                  25                  30

Ala Trp Ala Asp Ser Asn Gly His Thr Val Val Gly Trp Ala Glu Asp
        35                  40                  45

Val Asp Val Ser Gly Ala Ile Asp Pro Phe Asp Thr Pro Ser Leu Gly
    50                  55                  60

Val Trp Leu Asp Glu Arg Arg Gly Glu Trp Asp Ile Leu Cys Ala Trp
65                  70                  75                  80

Lys Leu Asp Arg Leu Gly Arg Asp Ala Ile Arg Leu Asn Lys Leu Phe
                85                  90                  95

Leu Trp Cys Gln Glu His Gly Lys Thr Val Thr Ser Cys Ser Glu Gly
            100                 105                 110

Ile Asp Leu Gly Thr Pro Val Gly Arg Leu Ile Ala Asn Val Ile Ala
```

```
            115                 120                 125
Phe Leu Ala Glu Gly Glu Arg Glu Ala Ile Arg Glu Arg Val Ala Ser
        130                 135                 140

Ser Lys Gln Lys Leu Arg Glu Ile Gly Arg Trp Gly Gly Lys Pro
145                 150                 155                 160

Pro Phe Gly Tyr Met Gly Val Arg Asn Pro Asp Gly Gln Gly His Ile
                165                 170                 175

Leu Val Val Asp Pro Val Ala Lys Pro Val Val Arg Arg Ile Val Glu
                180                 185                 190

Asp Ile Leu Glu Gly Lys Pro Leu Thr Arg Leu Cys Thr Glu Leu Thr
            195                 200                 205

Glu Glu Arg Tyr Leu Thr Pro Ala Glu Tyr Tyr Ala Thr Leu Lys Ala
        210                 215                 220

Gly Ala Pro Arg Gln Gln Ala Glu Glu Gly Val Thr Ala Lys Trp
225                 230                 235                 240

Arg Pro Thr Ala Val Arg Asn Leu Leu Arg Ser Lys Ala Leu Arg Gly
                245                 250                 255

His Ala His His Lys Gly Gln Thr Val Arg Asp Asp Gln Gly Arg Ala
                260                 265                 270

Ile Gln Leu Ala Glu Pro Leu Val Asp Ala Asp Glu Trp Glu Leu Leu
            275                 280                 285

Gln Glu Thr Leu Asp Gly Ile Ala Ala Asp Phe Ser Gly Arg Arg Val
        290                 295                 300

Glu Gly Ala Ser Pro Leu Ser Gly Val Ala Val Cys Met Thr Cys Asp
305                 310                 315                 320

Lys Pro Leu His His Asp Arg Tyr Leu Val Lys Arg Pro Tyr Gly Asp
                325                 330                 335

Tyr Pro Tyr Arg Tyr Tyr Arg Cys Arg Asp Arg His Gly Lys Asn Val
                340                 345                 350

Pro Ala Glu Thr Leu Glu Glu Leu Val Glu Asp Ala Phe Leu Gln Arg
            355                 360                 365

Val Gly Asp Phe Pro Val Arg Glu Arg Val Trp Val Gln Gly Asp Thr
        370                 375                 380

Asn Trp Ala Asp Leu Lys Glu Ala Val Ala Ala Tyr Asp Glu Leu Val
385                 390                 395                 400

Gln Ala Ala Gly Arg Ala Lys Ser Ala Thr Ala Arg Glu Arg Leu Gln
                405                 410                 415

Arg Gln Leu Asp Ile Leu Asp Glu Arg Ile Ala Glu Leu Glu Ser Ala
            420                 425                 430

Pro Asn Thr Glu Ala His Trp Glu Tyr Gln Pro Thr Gly Gly Thr Tyr
        435                 440                 445

Arg Asp Ala Trp Glu Asn Ser Asp Ala Asp Glu Arg Glu Leu Leu
450                 455                 460

Arg Arg Ser Gly Ile Val Val Ala Val His Ile Asp Gly Val Glu Gly
465                 470                 475                 480

Arg Arg Ser Lys His Asn Pro Gly Ala Leu His Phe Asp Ile Arg Val
                485                 490                 495

Pro His Glu Leu Thr Gln Arg Leu Ile Ala Pro
            500                 505

<210> SEQ ID NO 70
<211> LENGTH: 1524
<212> TYPE: DNA
<213> ORGANISM: Artificial Sequence
```

<220> FEATURE:
<223> OTHER INFORMATION: Synthetic Polynucleotide

<400> SEQUENCE: 70

```
atgtatccta ccttcgtgcg tgtgttgggt agactgcgtc tgtcgaggtc aacggaggaa      60
tccacctcga ttgagaggca aagggagatc gtcaccgcct gggccgattc taacggtcac     120
accgtcgtcg gatgggcaga ggacgtagac gtatcgggtg ccatcgaccc cttcgacacc     180
ccgtctctgg gggtgtggtt ggacgagcgc cggggcgagt gggacatcct gtgcgcctgg     240
aaactggacc gcctgggccg tgatgccatc cggctgaaca agctcttcct gtggtgccag     300
gagcacggca agacggtgac atcgtgcagt gagggaatcg acctcggcac gccggtcggc     360
cggctcatcg ccaacgtgat cgcattcctg gccgaggggg agcgggaggc catccgcgag     420
cgggtcgcat cctcgaagca gaagctgcgc gagatcggtc ggtggggtgg cggtaagccg     480
cccttcggat acatgggtgt ccgcaaccca gacggacagg gacacatcct tgtggtcgat     540
cccgtcgcaa agccagtcgt gcgccggatc gtggaggaca tcctggaggg caagccgctc     600
acgcggctct gcaccgagct gaccgaggag cggtacctga cccctgcgga gtactacgcc     660
accctcaagg ccggtgcccc gaggcagcag gccgaggagg gggaggtgac cgccaagtgg     720
cgtccgaccg ccgtcaggaa cctgctccgc agcaaagccc tccggggcca cgcccatcac     780
aagggccaga ccgtcagaga cgaccagggg agggctatcc agctcgctga gcccttgtc      840
gacgccgacg agtgggagtt gctgcaggaa accctggacg gtatcgccgc cgacttctcc     900
ggtcggcgcg tcgagggtgc cagcccgctc tccggtgtcg cagtctgcat gacgtgtgac     960
aagcccctgc accatgaccg gtatctggtg aagaggccct acggtgacta ccctaccgg     1020
tactaccggt gccgtgatcg gcacggcaag aacgtcccag ccgaaaccct ggaggagttg    1080
gtcgaggacg cattcctgca gcgcgtaggt gacttcccgg tgcgcgagcg ggtgtgggtc    1140
cagggtgaca ccaactgggc agacctgaag gaggcagtgg cagcgtatga cgaactggtg    1200
caggccgctg gccgtgccaa gtcggccacg gcgcgagagc gcctccagag gcaactggac    1260
atcctggacg agcggatcgc ggagctggag tccgcaccga acaccgaggc ccactgggag    1320
taccagccga ccggagggac ctaccgggac gcctgggaga actccgacgc cgacgagcgc    1380
cgcgagctac tgcggcggtc cgggatcgtc gtggcggtcc acatcgacgg cgtggaaggc    1440
cgacgctcca agcacaaccc cggagccctc cacttcgaca tccgggtccc gcacgaactg    1500
acacagagac tcatcgcccc atga                                            1524
```

<210> SEQ ID NO 71
<211> LENGTH: 500
<212> TYPE: PRT
<213> ORGANISM: Artificial Sequence
<220> FEATURE:
<223> OTHER INFORMATION: Synthetic Polypeptide

<400> SEQUENCE: 71

Met Arg Ala Leu Val Val Ile Arg Leu Ser Arg Val Thr Asp Ala Thr
1               5                   10                  15

Thr Ser Pro Glu Arg Gln Leu Glu Ser Cys Gln Gln Leu Cys Ala Gln
            20                  25                  30

Arg Gly Trp Asp Val Val Gly Val Ala Glu Asp Leu Asp Val Ser Gly
        35                  40                  45

Ala Val Asp Pro Phe Asp Arg Lys Arg Pro Asn Leu Ala Arg Trp
    50                  55                  60

```
Leu Ala Phe Glu Glu Gln Pro Phe Asp Val Ile Val Ala Tyr Arg Val
 65                  70                  75                  80

Asp Arg Leu Thr Arg Ser Ile Arg His Leu Gln Gln Leu Val His Trp
                 85                  90                  95

Ala Glu Asp His Lys Lys Leu Ile Val Ser Ala Thr Glu Ala His Phe
                100                 105                 110

Asp Thr Thr Thr Pro Phe Ala Ala Val Val Ile Ala Leu Met Gly Thr
                115                 120                 125

Val Ala Gln Met Glu Leu Glu Ala Ile Lys Glu Arg Asn Arg Ser Ala
        130                 135                 140

Ala His Phe Asn Ile Arg Ala Gly Lys Tyr Arg Gly Ser Leu Pro Pro
145                 150                 155                 160

Trp Gly Tyr Leu Pro Thr Arg Val Asp Gly Glu Trp Arg Leu Val Pro
                165                 170                 175

Asp Pro Val Gln Arg Glu Arg Ile Leu Glu Val Tyr His Arg Val Val
                180                 185                 190

Asp Asn His Glu Pro Leu His Leu Val Ala His Asp Leu Asn Arg Arg
                195                 200                 205

Gly Val Leu Ser Pro Lys Asp Tyr Phe Ala Lys Leu Gln Gly Arg Asp
210                 215                 220

Pro Gln Gly Arg Glu Trp Ser Ala Thr Ala Leu Lys Arg Ser Leu Ile
225                 230                 235                 240

Ser Glu Ala Met Leu Gly Tyr Ala Thr Leu Asn Gly Lys Thr Val Arg
                245                 250                 255

Asp Asp Asp Gly Ala Pro Leu Val Arg Ala Glu Pro Ile Leu Thr Arg
                260                 265                 270

Glu Gln Leu Glu Ala Leu Arg Ala Glu Leu Val Lys Thr Asp Arg Thr
                275                 280                 285

Lys Pro Ala Val Ser Thr Pro Ser Leu Leu Leu Arg Val Leu Phe Cys
290                 295                 300

Ala Val Cys Gly Glu Pro Ala Tyr Lys Phe Thr Gly Gly Gly Arg Arg
305                 310                 315                 320

Asn Ala Arg Tyr Arg Cys Arg Ser Trp Gly Trp Ala Gln Arg Cys Gly
                325                 330                 335

Asn Gly Thr Val Ala Met Ala Glu Trp Asp Ala Phe Cys Glu Glu Gln
                340                 345                 350

Val Leu Asp Leu Leu Gly Asp Ala Glu Arg Leu Glu Lys Val Trp Val
                355                 360                 365

Ala Gly Ser Asp Ser Ala Val Glu Leu Ala Glu Val Asn Ala Glu Leu
        370                 375                 380

Val Asp Leu Thr Ser Leu Ile Gly Ser Pro Ala Tyr Arg Val Gly Ser
385                 390                 395                 400

Pro Gln Arg Glu Ala Leu Asp Ala Arg Ile Ala Ala Leu Ala Ala Arg
                405                 410                 415

Gln Glu Glu Leu Glu Gly Leu Glu Ala Arg Pro Ser Gly Trp Glu Trp
                420                 425                 430

Arg Glu Thr Gly Gln Arg Phe Gly Asp Trp Arg Glu Gln Asp Thr
                435                 440                 445

Ser Gly Lys Asn Thr Trp Leu Arg Ser Met Asn Val Arg Leu Thr Phe
        450                 455                 460

Asp Val Arg Gly Gly Leu Thr Arg Thr Ile Asp Phe Gly Asp Leu Gln
465                 470                 475                 480

Glu Tyr Glu Gln His Leu Arg Leu Gly Ser Val Val Glu Arg Leu His
```

485                 490                 495

Thr Gly Met Ser
        500

<210> SEQ ID NO 72
<211> LENGTH: 1515
<212> TYPE: DNA
<213> ORGANISM: Artificial Sequence
<220> FEATURE:
<223> OTHER INFORMATION: Synthetic Polynucleotide

<400> SEQUENCE: 72

```
atgagagctc tcgtcgtgat ccgcttgtcc cgcgtcaccg atgctacgac ctcaccggag      60
cgtcagctgg agtcttgccg gcagctctgc gcccagcgcg gttgggacgt cgtcggtgta     120
gcggaggatc tggacgtctc cggagcagtc gatccgttcg accggaagcg cagaccgaac     180
ctggcacggt ggctagcatt cgaggagcaa ccgttcgacg tcatcgtggc gtaccgggtg     240
gaccggttga cccgctcgat ccggcatctt cagcagctgg tccactgggc ggaggaccac     300
aagaagctgg tcgtctccgc gaccgaagcc cacttcgaca cgacgacgcc gttcgcggcg     360
gtcgtcatcg cgcttatggg aacggtggcg cagatggaat tagaagcgat caaagagcgg     420
aaccgttcgg ctgcacattt caatattcgc gccgggaaat accgcggttc cctgccgccg     480
tggggttacc tgcctacgcg cgtggacggg gagtggcggc tggtgccgga cccggtgcag     540
cgcgagcgca tcctcgaggt gtatcaccgc gtcgtcgaca ccacgagcc gctgcacctg     600 gtggcacacg acctgaaccg cgtggtgtc ctgtcgccga aggactactt cgcaaagctg     660
caaggtcgcg agccgcaggg gcgggagtgg tcggctaccg cactgaagcg ctcgctgatc     720
tccgaggcga tgctcgggta cgcgactctg aacggtaaga ccgtccgaga cgacgacgga     780
gccccgctgg tgcgggctgc gccgatcctg accgtgagc agctggaggc gctgcgcgcc     840
gagctcgtca agaccgaccg gaccaagccc gcagtgtcta ccccgtcgct gctgctgcgg     900
gtgctgttct gcgcagtgtg cggtgagccc gcatacaagt tcgcaggtgg aggacgcaag     960
cacccgcgct accgctgccg ctcgatgggt ttcccgaagc actgcggtaa cggtacggtc    1020
gcaatggccg agtgggacgc attctgcgag gagcaggtgc tggatctgct cggggacgca    1080
gagcgtctgg agaaagtctg ggtagctggc tcggactcag cagtagaact cgcagaggtg    1140
aacgcagagc tggtggacct gacgtcgctg atcggttccc cggcgtaccg ggccggttct    1200
ccgcagcgcg aggcgctgga tgctcgtatc gcggcgctgg ccgcgcggca ggaggagttg    1260
gaagggctag aggctcgccc gtcgggctgg gagtggcgcg aaaccgggca gaggttcggg    1320
gactggtggc gggatcagga caccgcgggt aagaacacct ggctccggtc gatgaacgtt    1380
cggctgacgt tcgacgtccg aggcggcctg actcgtacga tcgacttcgg ggatctgcag    1440
gagtatgagc agcatctgag gctgggcgcg gctctagacc tcgtaaacgc agaaaagccc    1500
cctacgggcc gctag                                                     1515
```

<210> SEQ ID NO 73
<211> LENGTH: 500
<212> TYPE: PRT
<213> ORGANISM: Artificial Sequence
<220> FEATURE:
<223> OTHER INFORMATION: Synthetic Polypeptide

<400> SEQUENCE: 73

Met Arg Ala Leu Val Val Ile Arg Leu Ser Arg Val Thr Asp Ala Thr
1               5                   10                  15

```
Thr Ser Pro Glu Arg Gln Leu Glu Ser Cys Gln Gln Leu Cys Ala Gln
            20                  25                  30

Arg Gly Trp Asp Val Val Gly Val Ala Glu Asp Leu Asp Val Ser Gly
            35                  40                  45

Ala Val Asp Pro Phe Asp Arg Lys Arg Pro Asn Leu Ala Arg Trp
50                      55                  60

Leu Ala Phe Glu Glu Gln Pro Phe Asp Val Ile Val Ala Tyr Arg Val
65                  70                  75                  80

Asp Arg Leu Thr Arg Ser Ile Arg His Leu Gln Gln Leu Val His Trp
                85                  90                  95

Ala Glu Asp His Lys Lys Leu Val Val Ser Ala Thr Glu Ala His Phe
                100                 105                 110

Asp Thr Thr Thr Pro Phe Ala Ala Val Val Ile Ala Leu Met Gly Thr
            115                 120                 125

Val Ala Gln Met Glu Leu Glu Ala Ile Lys Glu Arg Asn Arg Ser Ala
    130                 135                 140

Ala His Phe Asn Ile Arg Ala Gly Lys Tyr Arg Gly Ser Leu Pro Pro
145                 150                 155                 160

Trp Gly Tyr Leu Pro Thr Arg Val Asp Gly Glu Trp Arg Leu Val Pro
                165                 170                 175

Asp Pro Val Gln Arg Glu Arg Ile Leu Glu Val Tyr His Arg Val Val
            180                 185                 190

Asp Asn His Glu Pro Leu His Leu Val Ala His Asp Leu Asn Arg Arg
        195                 200                 205

Gly Val Leu Ser Pro Lys Asp Tyr Phe Ala Gln Leu Gln Gly Arg Glu
    210                 215                 220

Pro Gln Gly Arg Glu Trp Ser Ala Thr Ala Leu Lys Arg Ser Met Ile
225                 230                 235                 240

Ser Glu Ala Met Leu Gly Tyr Ala Thr Leu Asn Gly Lys Thr Val Arg
                245                 250                 255

Asp Asp Asp Gly Ala Pro Leu Val Arg Ala Glu Pro Ile Leu Thr Arg
            260                 265                 270

Glu Gln Leu Glu Ala Leu Arg Ala Glu Leu Val Lys Thr Ser Arg Ala
        275                 280                 285

Lys Pro Ala Val Ser Thr Pro Ser Leu Leu Leu Arg Val Leu Phe Cys
    290                 295                 300

Ala Val Cys Gly Glu Pro Ala Tyr Lys Phe Ala Gly Gly Arg Lys
305                 310                 315                 320

His Pro Arg Tyr Arg Cys Arg Ser Met Gly Phe Pro Lys His Cys Gly
                325                 330                 335

Asn Gly Thr Val Ala Met Ala Glu Trp Asp Ala Phe Cys Glu Glu Gln
            340                 345                 350

Val Leu Asp Leu Leu Gly Asp Ala Glu Arg Leu Glu Lys Val Trp Val
        355                 360                 365

Ala Gly Ser Asp Ser Ala Val Glu Leu Ala Glu Val Asn Ala Glu Leu
    370                 375                 380

Val Asp Leu Thr Ser Leu Ile Gly Ser Pro Ala Tyr Arg Ala Gly Ser
385                 390                 395                 400

Pro Gln Arg Glu Ala Leu Asp Ala Arg Ile Ala Ala Leu Ala Ala Arg
                405                 410                 415

Gln Glu Glu Leu Glu Gly Leu Glu Ala Arg Pro Ser Gly Trp Glu Trp
            420                 425                 430
```

```
Arg Glu Thr Gly Gln Arg Phe Gly Asp Trp Trp Arg Glu Gln Asp Thr
            435                 440                 445

Ala Ala Lys Asn Thr Trp Leu Arg Ser Met Asn Val Arg Leu Thr Phe
        450                 455                 460

Asp Val Arg Gly Leu Thr Arg Thr Ile Asp Phe Gly Asp Leu Gln
465             470                 475                 480

Glu Tyr Glu Gln His Leu Arg Leu Gly Ser Val Val Glu Arg Leu His
                485                 490                 495

Thr Gly Met Ser
            500
```

<210> SEQ ID NO 74
<211> LENGTH: 1503
<212> TYPE: DNA
<213> ORGANISM: Artificial Sequence
<220> FEATURE:
<223> OTHER INFORMATION: Synthetic Polynucleotide

<400> SEQUENCE: 74

```
atgagagcac tggtggtcat ccgactgagt agggtcacag acgcaacaac aagccccgag      60
aggcagctgg aatcatgtca gcagctgtgc gcacagcgag gatgggacgt ggtcggagtg     120
gcagaggatc tggacgtgag cggcgctgtc gatccattcg acagaaagcg gaggcccaac     180
ctggcaaggt ggctggcttt cgaggaacag ccctttgatg tgatcgtcgc ctacagagtg     240
gacaggctga cacgctctat cgacatctg cagcagctgg tgcattgggc cgaggaccac      300
aagaaactgg tggtcagtgc aactgaagcc cacttcgata ccacaactcc ttttgccgct     360
gtggtcatcg cactgatggg caccgtggcc cagatggagc tggaagctat caaggagcga     420
aaccggagtg cagcccattt caatattcgg gccgggaaat acagaggatc actgccccct     480
tggggctatc tgcctacccg ggtggatggg gagtggagac tggtgccaga ccccgtccag     540
agagagagga ttctggaagt gtaccacagg gtggtcgata ccacgaaacc actgcatctg     600
gtcgcccacg acctgaatag cgcgcggcgtg ctgagcccaa agattatttt tgctcagctg     660
cagggaaggg agccacaggg acgagaatgg tccgctaccg ccctgaagcg gagcatgatc     720
agtgaggcta tgctgggcta cgcaactctg aatgggaaaa ccgtccggga cgatgacgga     780
gcaccactgg tgagggctga gcctattctg acacgcgagc agctggaagc tctgcgggca     840
gaactggtga aaacctccag agccaaacct gccgtgagca ccccaagcct gctgctgagg     900
gtgctgttct gcgccgtctg tggggagcca gcatacaagt ttgccggcgg gggaagaaaa     960
catccccgct atcgatgccg gtctatggga ttccctaagc actgtggaaa cggcactgtg    1020
gctatggccg agtgggacgc ctttttgtgag gaacaggtgc tggatctgct gggagacgcc    1080
gagaggctga aaaagtgtg gtcgctggc agcgactccg ctgtggagct ggcagaagtc     1140
aatgccgagc tggtggatct gacctccctg atcggatctc ctgcatatag gcaggctca     1200
ccacagcgag aagctctgga cgcacgaatt gctgcactgg cagctcgaca ggaggaactg    1260
gagggggctgg aagcacgacc tagcggatgg gagtggcgag aaacaggcca gcggtttggg    1320
gattggtgga gagagcagga cacagcagcc aagaacactt ggctgagaag tatgaatgtc    1380
aggctgactt tcgatgtgcg cggcgggctg acccgaacaa tcgattttgg cgacctgcag    1440
gagtatgaac agcacctgag actggggagc gtggtcgaaa gactgcacac tgggatgtca    1500
tag                                                                  1503
```

<210> SEQ ID NO 75

<211> LENGTH: 507
<212> TYPE: PRT
<213> ORGANISM: Artificial Sequence
<220> FEATURE:
<223> OTHER INFORMATION: Synthetic Polypeptide

<400> SEQUENCE: 75

```
Met Glu Thr Met Pro Gln Pro Leu Arg Ala Leu Val Gly Ala Arg Val
1               5                   10                  15

Ser Val Val Gln Gly Pro Gln Lys Val Ser Gln Ala Gln Leu Glu
            20                  25                  30

Thr Ala Arg Lys Trp Ala Glu Ala Gln Gly His Glu Ile Val Gly Thr
            35                  40                  45

Phe Glu Asp Leu Gly Val Ser Ala Ser Val Arg Pro Asp Glu Arg Pro
    50                  55                  60

Asp Leu Gly Lys Trp Leu Thr Asp Glu Gly Ala Ser Lys Trp Asp Val
65                  70                  75                  80

Ile Val Trp Ser Lys Met Asp Arg Ala Phe Arg Ser Thr Lys His Cys
                85                  90                  95

Val Asp Phe Ala Gln Trp Ala Glu Glu Arg Gln Lys Val Val Met Phe
            100                 105                 110

Ala Glu Asp Asn Leu Arg Leu Asp Tyr Arg Pro Gly Ala Ala Lys Gly
        115                 120                 125

Ile Asp Ala Met Met Ala Glu Leu Phe Val Tyr Leu Gly Ser Phe Phe
130                 135                 140

Ala Gln Leu Glu Leu Asn Arg Phe Lys Ser Arg Ala Gln Asp Ser His
145                 150                 155                 160

Arg Val Leu Arg Gln Thr Asp Arg Trp Ala Ser Gly Leu Pro Pro Leu
                165                 170                 175

Gly Tyr Lys Thr Val Pro His Pro Ser Gly Lys Gly Phe Gly Leu Asp
            180                 185                 190

Thr Asp Glu Asp Thr Lys Ala Val Leu Tyr Asp Met Ala Gly Lys Leu
        195                 200                 205

Leu Asp Gly Trp Ser Leu Ile Gly Ile Ala Lys Asp Leu Asn Asp Arg
210                 215                 220

Gly Val Leu Gly Ser Arg Ser Arg Ala Arg Leu Ala Lys Gly Lys Pro
225                 230                 235                 240

Ile Asp Gln Ala Pro Trp Asn Val Ser Thr Val Lys Asp Ala Leu Thr
                245                 250                 255

Asn Leu Lys Thr Gln Gly Ile Lys Met Thr Gly Lys Gly Lys His Ala
            260                 265                 270

Lys Pro Val Leu Asp Asp Lys Gly Glu Gln Ile Val Leu Ala Pro Pro
        275                 280                 285

Thr Phe Asp Trp Asp Thr Trp Lys Gln Ile Gln Asp Ala Val Ala Leu
290                 295                 300

Arg Glu Gln Ala Pro Arg Ser Arg Val His Thr Lys Asn Pro Met Leu
305                 310                 315                 320

Gly Ile Gly Ile Cys Gly Lys Cys Gly Ala Thr Leu Ala Gln Gln His
                325                 330                 335

Ser Arg Lys Lys Ser Asp Lys Ser Val Val Tyr Arg Tyr Arg Cys
            340                 345                 350

Ser Arg Thr Pro Val Asn Cys Asp Gly Val Phe Ile Val Ala Asp Glu
        355                 360                 365

Ala Asp Thr Leu Leu Glu Glu Ala Phe Leu Tyr Glu Trp Ala Asp Gln
370                 375                 380
```

```
Pro Val Thr Arg Arg Val Phe Val Pro Gly Glu Asp His Thr Tyr Glu
385                 390                 395                 400

Leu Glu Gln Ile Asn Glu Thr Ile Ala Arg Leu Arg Arg Glu Ser Asp
            405                 410                 415

Ala Gly Leu Ile Val Ser Asp Glu Asp Glu Arg Ile Tyr Leu Glu Arg
        420                 425                 430

Met Arg Ser Leu Ile Thr Arg Arg Thr Lys Leu Glu Ala Met Pro Arg
    435                 440                 445

Arg Ser Ala Gly Trp Val Glu Glu Thr Thr Gly Gln Thr Tyr Gly Glu
    450                 455                 460

Ala Trp Glu Thr Glu Asp His Gln Gln Leu Leu Lys Asp Ala Lys Val
465                 470                 475                 480

Lys Phe Ile Leu Tyr Ser Asn Lys Pro Arg Asn Ile Glu Val Val Val
                485                 490                 495

Pro Gln Asp Arg Val Ala Val Asp Leu Ala Ile
            500                 505

<210> SEQ ID NO 76
<211> LENGTH: 1524
<212> TYPE: DNA
<213> ORGANISM: Artificial Sequence
<220> FEATURE:
<223> OTHER INFORMATION: Synthetic Polynucleotide

<400> SEQUENCE: 76
atggagacaa tgcctcagcc actgagggct ctggtgggag ctagagtgag tgtggtgcag      60
gggcctcaga aagtgtcaca gcaggcccag ctggagacag ctagaaagtg ggccgaggct     120
cagggccacg aaatcgtggg gacttttgaa gatctgggcg tgagcgcttc cgtgaggcca     180
gatgagcgcc ccgacctggg gaagtggctg acagatgaag gagccagcaa atgggacgtg     240
attgtgtggt ccaagatgga tcgcgccttc cggtctacca acattgcgt ggactttgcc      300 cagtgggctg aggaaagaca gaaggtggtc atgttcgccg aggataacct gcggctggac     360
tacagacctg gagccgctaa aggcatcgac gccatgatgg ctgagctgtt tgtgtatctg     420 gggagttttct ttgcccagct ggaactgaat aggttcaagt cccgcgctca ggattctcac    480
agagtgctga gcagactga cagatgggct agcggactgc ccctctgggc tacaaaacc      540 gtgccccatc cttccggcaa gggtttggga ctggacacag atgaggacac taaagccgtg     600
ctgtatgata tggctgggaa gctgctggac ggatggtccc tgatcggcat tgccaaagat     660
ctgaacgacc gcggggtgct gggatctcgg agtagagcca ggctggctaa aggcaagcct     720
atcgatcagg ccccatggaa cgtgtctacc gtgaaggacg ctctgaccaa tctgaaaaca     780
cagggaatta agatgacagg caaagggaag cacgccaaac cagtgctgga cgataaggga     840
gagcagatcg tgctggctcc accaactttc gattgggaca cctggaaaca gattcaggat     900
gctgtggctc tgaggaaca ggctcctcgc agcgggtgc acactaaaaa cccaatgctg        960
ggaatcggca tttgcggcaa gtgtggagct accctggctc agcagcattc acgcaaaaag    1020
tcagataaga gcgtggtgta ccgctactat cggtgcagca gaacacccgt gaattgtgac    1080
ggcgtgttca tcgtggccga tgaggctgac actctgctgg aggaagcctt tctgtacgaa    1140
tgggctgatc agcccgtgac ccggagagtg ttcgtgcctg gggaggacca cacctatgag    1200
ctggaacaga tcaatgagac aattgcccgg ctgaggcgcg aaagtgacgc tggactgatc    1260
gtgtcagatg aggacgaaag aatctacctg gagagaatgc ggagcctgat cactcggaga    1320
```

```
accaagctgg aagctatgcc aaggaggagt gctggatggg tggaggaaac cacagggcag    1380
acatacggag aggcctggga gactgaagat catcagcagc tgctgaaaga cgctaaagtg    1440
aagtttatcc tgtattccaa caagccaagg aatattgaag tggtggtgcc acaggatagg    1500
gtggctgtgg acctggctat ttga                                          1524
```

```
<210> SEQ ID NO 77
<211> LENGTH: 522
<212> TYPE: PRT
<213> ORGANISM: Artificial Sequence
<220> FEATURE:
<223> OTHER INFORMATION: Synthetic Polypeptide

<400> SEQUENCE: 77
```

```
Met Ala Gln Pro Leu Arg Ala Leu Val Gly Ala Arg Val Ser Val Val
1               5                   10                  15

Gln Gly Pro Gln Lys Val Ser His Ile Ala Gln Gln Glu Thr Gly Ala
            20                  25                  30

Lys Trp Val Ala Glu Gln Gly His Thr Val Val Gly Ser Phe Lys Asp
        35                  40                  45

Leu Asp Val Ser Ala Thr Val Ser Pro Phe Glu Arg Pro Asp Leu Gly
    50                  55                  60

Pro Trp Leu Ser Pro Glu Leu Glu Gly Glu Trp Asp Ile Leu Val Phe
65                  70                  75                  80

Ser Lys Ile Asp Arg Met Phe Arg Ser Arg Asp Cys Val Lys Phe
                85                  90                  95

Ala Glu Trp Ala Glu Ala His Gly Lys Ile Leu Val Phe Ala Glu Asp
            100                 105                 110

Asn Met Thr Leu Asn Tyr Arg Asp Lys Asp Arg Ser Gly Ser Leu Glu
        115                 120                 125

Ser Met Met Ser Glu Leu Phe Ile Tyr Ile Gly Ser Phe Phe Ala Gln
    130                 135                 140

Leu Glu Leu Asn Arg Phe Lys Ser Arg Ala Arg Asp Ser His Arg Val
145                 150                 155                 160

Leu Arg Gly Met Asp Arg Trp Ala Ser Gly Val Pro Pro Leu Gly Phe
                165                 170                 175

Arg Ile Val Asp His Pro Ser Gly Lys Gly Lys Gly Leu Asp Thr Asp
            180                 185                 190

Pro Glu Gly Lys Ala Ile Leu Glu Asp Met Ala Ala Lys Leu Leu Asp
        195                 200                 205

Gly Trp Ser Phe Ile Arg Ile Ala Gln Asp Leu Asn Gln Arg Lys Val
    210                 215                 220

Leu Thr Asn Met Asp Lys Ala Lys Ile Ala Lys Gly Lys Pro Pro His
225                 230                 235                 240

Pro Asn Pro Trp Thr Val Asn Thr Val Ile Glu Ser Leu Thr Ser Pro
                245                 250                 255

Arg Thr Gln Gly Ile Lys Met Thr Lys His Gly Thr Arg Gly Gly Ser
            260                 265                 270

Lys Ile Gly Thr Thr Val Leu Asp Ala Glu Gly Asn Pro Ile Arg Leu
        275                 280                 285

Ala Pro Pro Thr Phe Asp Pro Ala Thr Trp Lys Gln Ile Gln Glu Ala
    290                 295                 300

Ala Ala Arg Arg Gln Gly Asn Arg Arg Ser Lys Thr Tyr Thr Ala Asn
305                 310                 315                 320

Pro Met Leu Gly Val Gly His Cys Gly Ala Cys Gly Ala Ser Leu Ala
```

```
                    325                 330                 335
Gln Gln Phe Thr His Arg Lys Leu Ala Asp Gly Thr Glu Val Thr Tyr
        340                 345                 350

Arg Thr Tyr Arg Cys Gly Arg Thr Pro Leu Asn Cys Asn Gly Ile Ser
        355                 360                 365

Met Arg Gly Asp Glu Ala Asp Gly Leu Leu Glu Gln Leu Phe Leu Glu
        370                 375                 380

Gln Tyr Gly Ser Gln Pro Val Thr Glu Lys Val Phe Val Pro Gly Glu
385                 390                 395                 400

Asp His Ser Glu Glu Leu Glu Gln Val Arg Ala Thr Ile Asp Arg Leu
                405                 410                 415

Arg Arg Glu Ser Asp Ala Gly Leu Ile Ala Thr Ala Glu Asp Glu Arg
                420                 425                 430

Ile Tyr Phe Glu Arg Met Lys Ser Leu Ile Asp Arg Arg Thr Arg Leu
        435                 440                 445

Glu Ala Gln Pro Arg Arg Ala Ser Gly Trp Val Thr Gln Glu Thr Asp
450                 455                 460

Lys Thr Asn Ala Asp Glu Trp Thr Lys Ala Ser Thr Pro Asp Glu Arg
465                 470                 475                 480

Arg Arg Leu Leu Met Lys Gln Gly Ile Arg Phe Glu Leu Val Arg Gly
                485                 490                 495

Lys Pro Asp Pro Glu Val Arg Leu Phe Thr Pro Gly Ile Pro Glu
        500                 505                 510

Gly Glu Pro Leu Pro Glu Pro Ser Pro Arg
        515                 520
```

<210> SEQ ID NO 78
<211> LENGTH: 1572
<212> TYPE: DNA
<213> ORGANISM: Artificial Sequence
<220> FEATURE:
<223> OTHER INFORMATION: Synthetic Polynucleotide

<400> SEQUENCE: 78

```
atggcacagc cactgagggc actggtcgga gcacgggtca gcgtcgtcca ggggccacag      60
aaagtctccc acatcgcaca gcaggagact ggagcaaagt gggtggcaga gcagggacac     120
accgtggtcg gaagcttcaa agacctggac gtgagcgcca ccgtctctcc ttttgaacgc     180
ccagatctgg accctggct gtcccctgag ctggaagggg agtgggacat cctggtgttc     240
agcaagattg ataggatgtt tagatccact cgggactgcg tgaagttcgc agaatgggca     300
gaggcccatg aaaaatcct ggtctttgcc gaggacaaca tgaccctgaa ttaccgcgac     360
aaggatcgaa gcggatccct ggaatctatg atgagtgagc tgttcatcta tattgggtct     420
ttctttgctc agctggagct gaacaggttc aagagtcgcg cacgagattc acaccgcgtg     480
ctgcgaggca tggacagatg ggcatctgga gtgccacctc tgggcttccg gatcgtcgac     540
catcccagtg ggaagggcaa aggactggac acagatcctg aaggcaaggc tattctggag     600
gacatggccg ctaaactgct ggatggatgg agctttatcc gcattgcaca ggatctgaac     660
cagaggaagg tgctgactaa tatggacaag gccaaaatcg ctaagggcaa ccaccccac     720 cccaacccett ggacagtgaa tactgtcatc gagtcactga ccagcccccg cacacaggga     780
attaagatga ctaaacatgg gaccaggggc ggatccaaga tcggcaccac agtgctggat     840
gccgagggaa atcctattcg gctggcacct ccaaccttcg acccagccac atggaagcag     900
atccaggaag cagcagctag gagacaggga aaccggcgca gtaaaactta caccgccaat     960
```

```
cctatgctgg gagtgggaca ctgcggagca tgtggagcct cactggctca gcagtttacc    1020
catagaaagc tggctgatgg caccgaggtc acatacagga cttatagatg cggacggaca    1080
ccactgaact gtaatggaat ttctatgcgg ggggacgaag ctgatggcct gctggaacag    1140
ctgttcctgg agcagtacgg gtcacagcca gtgaccgaaa aggtgtttgt ccccggcgag    1200
gaccacagcg aggaactgga acaggtcagg gccacaatcg acagactgcg aagggagagt    1260
gatgctgggc tgatcgctac tgcagaagat gagcggatct acttcgagcg catgaaatcc    1320
ctgattgaca gacggacaag gctggaagct cagccacgcc gagcatctgg ctgggtgacc    1380
caggagacag acaagactaa cgccgatgaa tggacaaaag ctagcactcc cgatgagagg    1440
agacggctgc tgatgaagca ggggatccga ttcgagctgg tgcggggcaa accagacccc    1500
gaagtcagac tgttcacccc cggcgaaatc cccgaaggcg agcccctgcc cgagccctcc    1560
cccagatgat aa                                                       1572
```

<210> SEQ ID NO 79
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 79

```
gcggtctcca tcgggatctg cacatcgagc agcatgccga ccag              44
```

<210> SEQ ID NO 80
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 80

```
gcggtctcca tcgggatctg cagatcgagc agcatgccga ccag              44
```

<210> SEQ ID NO 81
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 81

```
gcggtctcca tcgggatctg cccatcgagc agcatgccga ccag              44
```

<210> SEQ ID NO 82
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 82

```
gcggtctcca tcgggatctg ctcatcgagc agcatgccga ccag              44
```

<210> SEQ ID NO 83
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 83
gcggtctcca tcgggatctg ctgatcgagc agcatgccga ccag                44

<210> SEQ ID NO 84
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 84
gcggtctcca tcgggatctg cttatcgagc agcatgccga ccag                44

<210> SEQ ID NO 85
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 85
ggcttgtcga cgacggcacc ctccgtcgtc aggatcat                       38

<210> SEQ ID NO 86
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 86
ggcttgtcga cgacggcagc ctccgtcgtc aggatcat                       38

<210> SEQ ID NO 87
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 87
ggcttgtcga cgacggcccc ctccgtcgtc aggatcat                       38

<210> SEQ ID NO 88
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 88
ggcttgtcga cgacggctcc ctccgtcgtc aggatcat                       38

<210> SEQ ID NO 89
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 89
ggcttgtcga cgacggctgc ctccgtcgtc aggatcat                       38

<210> SEQ ID NO 90
<211> LENGTH: 38

<212> TYPE: DNA
<213> ORGANISM: Artificial Sequence
<220> FEATURE:
<223> OTHER INFORMATION: Synthetic Polynucleotide

<400> SEQUENCE: 90
ggcttgtcga cgacggcttc ctccgtcgtc aggatcat                    38

<210> SEQ ID NO 91
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 91
gtggtttgtc tggtcaacca ccgcacgctc agtggtgtac ggtacaaacc ca    52

<210> SEQ ID NO 92
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 92
gtggtttgtc tggtcaacca ccgcaggctc agtggtgtac ggtacaaacc ca    52

<210> SEQ ID NO 93
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 93
gtggtttgtc tggtcaacca ccgcccgctc agtggtgtac ggtacaaacc ca    52

<210> SEQ ID NO 94
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 94
gtggtttgtc tggtcaacca ccgctcgctc agtggtgtac ggtacaaacc ca    52

<210> SEQ ID NO 95
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 95
gtggtttgtc tggtcaacca ccgctggctc agtggtgtac ggtacaaacc ca    52

<210> SEQ ID NO 96
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 96
gtggtttgtc tggtcaacca ccgcttgctc agtggtgtac ggtacaaacc ca        52

<210> SEQ ID NO 97
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 97
cggtattcgg cgcgatccgc ggcacgaaga acatcaccct gaacatcg        48

<210> SEQ ID NO 98
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 98
cggtattcgg cgcgatccgc ggcaggaaga acatcaccct gaacatcg        48

<210> SEQ ID NO 99
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 99
cggtattcgg cgcgatccgc ggcccgaaga acatcaccct gaacatcg        48

<210> SEQ ID NO 100
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 100
cggtattcgg cgcgatccgc ggctcgaaga acatcaccct gaacatcg        48

<210> SEQ ID NO 101
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 101
cggtattcgg cgcgatccgc ggctggaaga acatcaccct gaacatcg        48

<210> SEQ ID NO 102
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 102
cggtattcgg cgcgatccgc ggcttgaaga acatcaccct gaacatcg        48

<210> SEQ ID NO 103
<211> LENGTH: 48
<212> TYPE: DNA
<213> ORGANISM: Artificial Sequence

```
<220> FEATURE:
<223> OTHER INFORMATION: Synthetic Polynucleotide

<400> SEQUENCE: 103
agagcatcgg agcctttcgg gggatgtgat gttcgagacg aagaacat         48

<210> SEQ ID NO 104
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 104
agagcatcgg agcctttcgg gggatgtgat gttcgagagg aagaacat         48

<210> SEQ ID NO 105
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 105
agagcatcgg agcctttcgg gggatgtgat gttcgagccg aagaacat         48

<210> SEQ ID NO 106
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 106
agagcatcgg agcctttcgg gggatgtgat gttcgagtcg aagaacat         48

<210> SEQ ID NO 107
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 107
agagcatcgg agcctttcgg gggatgtgat gttcgagtgg aagaacat         48

<210> SEQ ID NO 108
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 108
agagcatcgg agcctttcgg gggatgtgat gttcgagttg aagaacat         48

<210> SEQ ID NO 109
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 109
cggtattcgg cgcgatccgc ggcacgaaga acatcaccct gaacatcg         48
```

<210> SEQ ID NO 110
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 110
cggtattcgg cgcgatccgc ggcaggaaga acatcaccct gaacatcg            48

<210> SEQ ID NO 111
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 111
cggtattcgg cgcgatccgc ggcccgaaga acatcaccct gaacatcg            48

<210> SEQ ID NO 112
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 112
cggtattcgg cgcgatccgc ggctcgaaga acatcaccct gaacatcg            48

<210> SEQ ID NO 113
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 113
cggtattcgg cgcgatccgc ggctggaaga acatcaccct gaacatcg            48

<210> SEQ ID NO 114
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 114
cggtattcgg cgcgatccgc ggcttgaaga acatcaccct gaacatcg            48

<210> SEQ ID NO 115
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 115
gtattggggg aacgcgatat tcgagacgta gaacatcacc ttcaccaaat tc        52

<210> SEQ ID NO 116
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 116
gtattggggg aacgcgatat tcgagaggta gaacatcacc ttcaccaaat tc    52

<210> SEQ ID NO 117
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 117
gtattggggg aacgcgatat tcgagccgta gaacatcacc ttcaccaaat tc    52

<210> SEQ ID NO 118
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 118
gtattggggg aacgcgatat tcgagtcgta gaacatcacc ttcaccaaat tc    52

<210> SEQ ID NO 119
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 119
gtattggggg aacgcgatat tcgagtggta gaacatcacc ttcaccaaat tc    52

<210> SEQ ID NO 120
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 120
gtattggggg aacgcgatat tcgagttgta gaacatcacc ttcaccaaat tc    52

<210> SEQ ID NO 121
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 121
tgggtgaacg caaagatggg gacctcgatg ccgagctcgt cgca    44

<210> SEQ ID NO 122
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 122
tgggtgaacg caaagatggg gagctcgatg ccgagctcgt cgca    44

<210> SEQ ID NO 123

```
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 123
tgggtgaacg caaagatggg gccctcgatg ccgagctcgt cgca                          44

<210> SEQ ID NO 124
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 124
tgggtgaacg caaagatggg gtcctcgatg ccgagctcgt cgca                          44

<210> SEQ ID NO 125
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 125
tgggtgaacg caaagatggg gtgctcgatg ccgagctcgt cgca                          44

<210> SEQ ID NO 126
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 126
tgggtgaacg caaagatggg gttctcgatg ccgagctcgt cgca                          44

<210> SEQ ID NO 127
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 127
ttgtcaaagt ctaaagatgg ggacctcaat attcatgctt tgcgaa                        46

<210> SEQ ID NO 128
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 128
ttgtcaaagt ctaaagatgg ggagctcaat attcatgctt tgcgaa                        46

<210> SEQ ID NO 129
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 129
```
ttgtcaaagt ctaaagatgg ggccctcaat attcatgctt tgcgaa         46

<210> SEQ ID NO 130
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 130
ttgtcaaagt ctaaagatgg ggtcctcaat attcatgctt tgcgaa         46

<210> SEQ ID NO 131
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 131
ttgtcaaagt ctaaagatgg ggtgctcaat attcatgctt tgcgaa         46

<210> SEQ ID NO 132
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 132
ttgtcaaagt ctaaagatgg ggttctcaat attcatgctt tgcgaa         46

<210> SEQ ID NO 133
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 133
tgggtgaacg caaagatggg gacctcgatg ccgagctcgt cgca           44

<210> SEQ ID NO 134
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 134
tgggtgaacg caaagatggg gagctcgatg ccgagctcgt cgca            44

<210> SEQ ID NO 135
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 135
tgggtgaacg caaagatggg gccctcgatg ccgagctcgt cgca            44

<210> SEQ ID NO 136
<211> LENGTH: 44
<212> TYPE: DNA

<213> ORGANISM: Artificial Sequence
<220> FEATURE:
<223> OTHER INFORMATION: Synthetic Polynucleotide

<400> SEQUENCE: 136
tgggtgaacg caaagatggg gtcctcgatg ccgagctcgt cgca          44

<210> SEQ ID NO 137
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 137
tgggtgaacg caaagatggg gtgctcgatg ccgagctcgt cgca          44

<210> SEQ ID NO 138
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 138
tgggtgaacg caaagatggg gttctcgatg ccgagctcgt cgca          44

<210> SEQ ID NO 139
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 139
ttcgcaaagc ctcaaaatcg ggacctcgat attcatgctt tgtgaa          46

<210> SEQ ID NO 140
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 140
ttcgcaaagc ctcaaaatcg ggagctcgat attcatgctt tgtgaa          46

<210> SEQ ID NO 141
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 141
ttcgcaaagc ctcaaaatcg ggccctcgat attcatgctt tgtgaa          46

<210> SEQ ID NO 142
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 142
ttcgcaaagc ctcaaaatcg ggtcctcgat attcatgctt tgtgaa          46

<210> SEQ ID NO 143
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 143
ttcgcaaagc ctcaaaatcg ggtgctcgat attcatgctt tgtgaa          46

<210> SEQ ID NO 144
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 144
gtgcgggtgc cagggcgtgc ccacgggctc cccgggcgcg tactcc          46

<210> SEQ ID NO 145
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 145
gtgcgggtgc cagggcgtgc ccaggggctc cccgggcgcg tactcc          46

<210> SEQ ID NO 146
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 146
gtgcgggtgc cagggcgtgc ccccgggctc cccgggcgcg tactcc          46

<210> SEQ ID NO 147
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 147
gtgcgggtgc cagggcgtgc cctcgggctc cccgggcgcg tactcc          46

<210> SEQ ID NO 148
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 148
gtgcgggtgc cagggcgtgc cctggggctc cccgggcgcg tactcc          46

<210> SEQ ID NO 149
<211> LENGTH: 46
<212> TYPE: DNA
<213> ORGANISM: Artificial Sequence
<220> FEATURE:

<223> OTHER INFORMATION: Synthetic Polynucleotide

<400> SEQUENCE: 149
gtgcgggtgc cagggcgtgc ccttgggctc cccgggcgcg tactcc                          46

<210> SEQ ID NO 150
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 150
gtgccccaac tggggtaacc tacgagttct ctcagttggg gg                              42

<210> SEQ ID NO 151
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 151
gtgccccaac tggggtaacc taggagttct ctcagttggg gg                              42

<210> SEQ ID NO 152
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 152
gtgccccaac tggggtaacc tccgagttct ctcagttggg gg                              42

<210> SEQ ID NO 153
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 153
gtgccccaac tggggtaacc ttcgagttct ctcagttggg gg                              42

<210> SEQ ID NO 154
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 154
gtgccccaac tggggtaacc ttggagttct ctcagttggg gg                              42

<210> SEQ ID NO 155
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 155
gtgccccaac tggggtaacc tttgagttct ctcagttggg gg                              42

```
<210> SEQ ID NO 156
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 156

Tyr Xaa Arg Val Ser
1               5

<210> SEQ ID NO 157
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Asp or Glu
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa is Ser or Thr
<220> FEATURE:
<221> NAME/KEY: misc_feature
<222> LOCATION: (6)..(9)
<223> OTHER INFORMATION: Xaa can be any naturally occurring amino acid

<400> SEQUENCE: 157

Xaa Xaa Xaa Xaa Gly Xaa Xaa Xaa Xaa Arg
1               5                   10

<210> SEQ ID NO 158
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Leu or Met
<220> FEATURE:
<221> NAME/KEY: misc_feature
<222> LOCATION: (4)..(4)
<223> OTHER INFORMATION: Xaa is Leu or Ile
<220> FEATURE:
<221> NAME/KEY: misc_feature
<222> LOCATION: (5)..(5)
<223> OTHER INFORMATION: Xaa can be any naturally occurring amino acid

<400> SEQUENCE: 158

Xaa Asp Arg Xaa Xaa Arg
1               5

<210> SEQ ID NO 159
<211> LENGTH: 26
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
```

```
<222> LOCATION: (1)..(1)
<223> OTHER INFORMATION: Xaa is Glu or Gln
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (15)..(17)
<223> OTHER INFORMATION: Xaa can be any naturally occurring amino acid
<220> FEATURE:
<221> NAME/KEY: misc_feature
<222> LOCATION: (19)..(21)
<223> OTHER INFORMATION: Xaa can be any naturally occurring amino acid
<220> FEATURE:
<221> NAME/KEY: misc_feature
<222> LOCATION: (23)..(25)
<223> OTHER INFORMATION: Xaa can be any naturally occurring amino acid

<400> SEQUENCE: 159

Xaa Xaa Glu Arg Xaa Xaa Ile Xaa Glu Arg Xaa Xaa Xaa Gly Xaa Xaa
1               5                   10                  15

Xaa Ala Xaa Xaa Xaa Gly Xaa Xaa Xaa Gly
            20                  25

<210> SEQ ID NO 160
<211> LENGTH: 605
<212> TYPE: PRT
<213> ORGANISM: Artificial Sequence
<220> FEATURE:
<223> OTHER INFORMATION: Synthetic Polypeptide

<400> SEQUENCE: 160

Met Asp Thr Tyr Ala Gly Ala Tyr Asp Arg Gln Ser Arg Glu Arg Glu
1               5                   10                  15

Asn Ser Ser Ala Ala Ser Pro Ala Thr Gln Arg Ser Ala Asn Glu Asp
            20                  25                  30

Lys Ala Ala Asp Leu Gln Arg Glu Val Glu Arg Asp Gly Gly Arg Phe
        35                  40                  45

Arg Phe Val Gly His Phe Ser Glu Ala Pro Gly Thr Ser Ala Phe Gly
    50                  55                  60

Thr Ala Glu Arg Pro Glu Phe Glu Arg Ile Leu Asn Glu Cys Arg Ala
65                  70                  75                  80

Gly Arg Leu Asn Met Ile Ile Val Tyr Asp Val Ser Arg Phe Ser Arg
                85                  90                  95

Leu Lys Val Met Asp Ala Ile Pro Ile Val Ser Glu Leu Leu Ala Leu
            100                 105                 110

Gly Val Thr Ile Val Ser Thr Gln Glu Gly Val Phe Arg Gln Gly Asn
        115                 120                 125

Val Met Asp Leu Ile His Leu Ile Met Arg Leu Asp Ala Ser His Lys
    130                 135                 140

Glu Ser Ser Leu Lys Ser Ala Lys Ile Leu Asp Thr Lys Asn Leu Gln
145                 150                 155                 160
```

-continued

```
Arg Glu Leu Gly Gly Tyr Val Gly Gly Lys Ala Pro Tyr Gly Phe Glu
            165                 170                 175

Leu Val Ser Glu Thr Lys Glu Ile Thr Arg Asn Gly Arg Met Val Asn
        180                 185                 190

Val Val Ile Asn Lys Leu Ala His Ser Thr Thr Pro Leu Thr Gly Pro
        195                 200                 205

Phe Glu Phe Glu Pro Asp Val Ile Arg Trp Trp Arg Glu Ile Lys
    210                 215                 220

Thr His Lys His Leu Pro Phe Lys Pro Gly Ser Gln Ala Ala Ile His
225                 230                 235                 240

Pro Gly Ser Ile Thr Gly Leu Cys Lys Arg Met Asp Ala Asp Ala Val
                245                 250                 255

Pro Thr Arg Gly Glu Thr Ile Gly Lys Lys Thr Ala Ser Ser Ala Trp
                260                 265                 270

Asp Pro Ala Thr Val Met Arg Ile Leu Arg Asp Pro Arg Ile Ala Gly
            275                 280                 285

Phe Ala Ala Glu Val Ile Tyr Lys Lys Pro Asp Gly Thr Pro Thr
    290                 295                 300

Thr Lys Ile Glu Gly Tyr Arg Ile Gln Arg Asp Pro Ile Thr Leu Arg
305                 310                 315                 320

Pro Val Glu Leu Asp Cys Gly Pro Ile Ile Glu Pro Ala Glu Trp Tyr
                325                 330                 335

Glu Leu Gln Ala Trp Leu Asp Gly Arg Gly Arg Gly Lys Gly Leu Ser
            340                 345                 350

Arg Gly Gln Ala Ile Leu Ser Ala Met Asp Lys Leu Tyr Cys Glu Cys
        355                 360                 365

Gly Ala Val Met Thr Ser Lys Arg Gly Glu Glu Ser Ile Lys Asp Ser
370                 375                 380

Tyr Arg Cys Arg Arg Lys Val Val Asp Pro Ser Ala Pro Gly Gln
385                 390                 395                 400

His Glu Gly Thr Cys Asn Val Ser Met Ala Ala Leu Asp Lys Phe Val
                405                 410                 415

Ala Glu Arg Ile Phe Asn Lys Ile Arg His Ala Glu Gly Asp Glu Glu
            420                 425                 430

Thr Leu Ala Leu Leu Trp Glu Ala Ala Arg Arg Phe Gly Lys Leu Thr
        435                 440                 445

Glu Ala Pro Glu Lys Ser Gly Glu Arg Ala Asn Leu Val Ala Glu Arg
    450                 455                 460

Ala Asp Ala Leu Asn Ala Leu Glu Glu Leu Tyr Glu Asp Arg Ala Ala
465                 470                 475                 480

Gly Ala Tyr Asp Gly Pro Val Gly Arg Lys His Phe Arg Lys Gln Gln
                485                 490                 495

Ala Ala Leu Thr Leu Arg Gln Gln Gly Ala Glu Arg Leu Ala Glu
            500                 505                 510

Leu Glu Ala Ala Glu Ala Pro Lys Leu Pro Leu Asp Gln Trp Phe Pro
        515                 520                 525

Glu Asp Ala Asp Ala Asp Pro Thr Gly Pro Lys Ser Trp Trp Gly Arg
    530                 535                 540

Ala Ser Val Asp Asp Lys Arg Val Phe Val Gly Leu Phe Val Asp Lys
545                 550                 555                 560

Ile Val Val Thr Lys Ser Thr Thr Gly Arg Gly Gln Gly Thr Pro Ile
                565                 570                 575

Glu Lys Arg Ala Ser Ile Thr Trp Ala Lys Pro Pro Thr Asp Asp Asp
```

```
                  580                 585                 590
Glu Asp Asp Ala Gln Asp Gly Thr Glu Asp Val Ala Ala
        595                 600                 605

<210> SEQ ID NO 161
<211> LENGTH: 1818
<212> TYPE: DNA
<213> ORGANISM: Artificial Sequence
<220> FEATURE:
<223> OTHER INFORMATION: Synthetic Polynucleotide

<400> SEQUENCE: 161
gtggacacgt acgcgggtgc ttacgaccgt cagtcgcgcg agcgcgagaa ttcgagcgca      60
gcaagcccag cgacacagcg tagcgccaac gaagacaagg cggccgacct tcagcgcgaa     120
gtcgagcgcg acggggccg gttcaggttc gtcgggcatt tcagcgaagc gccgggcacg      180
tcggcgttcg ggacggcgga gcgcccggag ttcgaacgca tcctgaacga atgccgcgcc     240
gggcggctca acatgatcat tgtctatgac gtgtcgcgct tctcgcgcct gaaggtcatg     300
gacgcgattc cgattgtctc ggaattgctc gccctgggcg tgacgattgt ttccactcag     360
gaaggcgtct tccggcaggg aaacgtcatg gacctgattc acctgattat gcggctcgac     420
gcgtcgcaca aagaatcttc gctgaagtcg gcgaagattc tcgacacgaa gaaccttcag     480
cgcgaattgg gcgggtacgt cggcgggaag gcgccttacg gcttcgagct tgtttcggag     540
acgaaggaga tcacgcgcaa cggccgaatg gtcaatgtcg tcatcaacaa gcttgcgcac     600
tcgaccactc cccttaccgg acccttcgag ttcgagcccg acgtaatccg gtggtggtgg     660
cgtgagatca agacgcacaa acaccttccc ttcaagccgg gcagtcaagc cgccattcac     720
ccgggcagca tcacgggggct ttgtaagcgc atggacgctg acgccgtgcc gacccggggc     780
gagacgattg ggaagaagac cgcttcaagc gcctgggacc cggcaaccgt tatgcgaatc     840
cttcgggacc cgcgtattgc gggcttcgcc gctgaggtga tctacaagaa gaagccggac     900
ggcacgccga ccacgaagat tgagggttac cgcattcagc gcgacccgat cacgctccgg     960
ccggtcgagc ttgattgcgg accgatcatc gagcccgctg agtggtatga gcttcaggcg    1020
tggttggacg gcaggggcg cggcaagggg ctttcccggg ggcaagccat tctgtccgcc    1080
atggacaagc tgtactgcga gtgtggcgcc gtcatgactt cgaagcgcgg ggaagaatcg    1140
atcaaggact cttaccgctg ccgtcgccgg aaggtggtcg acccgtccgc acctgggcag    1200
cacgaaggca cgtgcaacgt cagcatggcg gcactcgaca agttcgttgc ggaacgcatc    1260
ttcaacaaga tcaggcacgc cgaaggcgac gaagagacgt tggcgcttct gtgggaagcc    1320
gcccgacgct tcggcaagct cactgaggcg cctgagaaga gcggcgaacg ggcgaacctt    1380
gttgcggagc gcgccgacgc cctgaacgcc cttgaagagc tgtacgaaga ccgcgcggca    1440
ggcgcgtacg acgacccgt tggcaggaag cacttccgga agcaacaggc agcgctgacg    1500
ctccggcagc aagggcgga agagcggctt gccgaacttg aagccgccga agccccgaag    1560
cttccccttg accaatggtt ccccgaagac gccgacgctg acccgaccgg ccctaagtcg    1620 tggtggggc gcgcgtcagt agacgacaag cgcgtgttcg tcgggctctt cgtagacaag    1680
atcgttgtca cgaagtcgac tacgggcagg ggcagggaa cgcccatcga gaagcgcgct    1740
tcgatcacgt gggcgaagcc gccgaccgac gacgacgaag acgacgccca ggacggcacg    1800
gaagacgtag cggcgtag                                                  1818
```